(12) United States Patent
Davies et al.

(10) Patent No.: US 8,912,395 B2
(45) Date of Patent: Dec. 16, 2014

(54) GENERATION OF PLANTS WITH ALTERED PROTEIN, FIBER, OR OIL CONTENT

(75) Inventors: John P. Davies, Portland, OR (US); Hein Tsoeng (Medard) Ng, Charlottesville, VA (US); D. Ry Wagner, Pleasant Hill, OR (US)

(73) Assignee: Agrigenetics, Inc., Indianapolis, IN (US)

( * ) Notice: Subject to any disclaimer, the term of this patent is extended or adjusted under 35 U.S.C. 154(b) by 404 days.

(21) Appl. No.: 13/328,782

(22) Filed: Dec. 16, 2011

(65) Prior Publication Data

US 2012/0090050 A1    Apr. 12, 2012

Related U.S. Application Data

(62) Division of application No. 11/940,248, filed on Nov. 14, 2004, now Pat. No. 8,106,253.

(60) Provisional application No. 60/866,053, filed on Nov. 15, 2006.

(51) Int. Cl.
   C12N 15/82       (2006.01)
   C12N 15/09       (2006.01)
   C12N 15/00       (2006.01)
   C07K 14/415      (2006.01)

(52) U.S. Cl.
   CPC ........ *C12N 15/8242* (2013.01); *C12N 15/8245* (2013.01); *C12N 15/8251* (2013.01); *C07K 14/415* (2013.01); *C12N 15/8247* (2013.01)
   USPC ........ 800/281; 800/278; 800/287; 435/320.1; 435/468; 536/23.1; 536/23.6

(58) Field of Classification Search
   None
   See application file for complete search history.

(56) References Cited

U.S. PATENT DOCUMENTS

| | | | |
|---|---|---|---|
| 5,322,783 A | 6/1994 | Tomes et al. | |
| 5,538,880 A | 7/1996 | Lundquist et al. | |
| 5,550,318 A | 8/1996 | Adams et al. | |
| 5,563,055 A | 10/1996 | Townsend et al. | |
| 5,610,042 A | 3/1997 | Chang et al. | |
| 5,639,790 A | 6/1997 | Voelker et al. | |
| 5,704,160 A | 1/1998 | Bergquist et al. | |
| 5,952,544 A | 9/1999 | Browse et al. | |
| 6,229,033 B1 | 5/2001 | Knowlton | |
| 6,248,939 B1 | 6/2001 | Leto et al. | |
| 6,750,046 B2 | 6/2004 | Moloney et al. | |
| 7,566,816 B2 * | 7/2009 | Lightner et al. | 800/298 |
| 2003/0046723 A1 | 3/2003 | Heard et al. | |
| 2004/0019927 A1 | 1/2004 | Sherman et al. | |
| 2004/0025202 A1 | 2/2004 | Laurie et al. | |
| 2004/0216190 A1 * | 10/2004 | Kovalic | 800/289 |
| 2006/0048240 A1 | 3/2006 | Alexandrov et al. | |
| 2006/0107345 A1 | 5/2006 | Alexandrov et al. | |
| 2006/0150283 A1 | 7/2006 | Alexandrov et al. | |
| 2006/0277630 A1 | 12/2006 | Lightner et al. | |

FOREIGN PATENT DOCUMENTS

| | | |
|---|---|---|
| EP | 1033405 | 9/2000 |
| WO | WO 94/11516 | 5/1994 |
| WO | WO 95/06128 | 3/1995 |
| WO | WO 98/37755 | 9/1998 |
| WO | WO 2004/035798 | 4/2004 |
| WO | WO 2004/093528 | 11/2004 |
| WO | WO 2004/093532 | 11/2004 |
| WO | WO 2005/047516 | 11/2004 |
| WO | WO 2005/107437 | 11/2005 |
| WO | WO 2007/053482 | 5/2007 |

OTHER PUBLICATIONS

Anoop et al., "Modulation of citrate metabolism alters aluminum tolerance in yeast and transgenic canola overexpressing a mitochondrial citrate synthase," *Plant Physiol.*, 132:2205-2217, 2003.

Bateman et al., "Pfam 3.1: 1313 multiple alignments and profile HMMs match the majority of proteins," *Nucleic Acids Res.*, 27:260-262, 1999.

Beisson et al., "Arabidopsis genes involved in acyl lipid metabolism. A 2003 census of the candidates, a study of the distribution of expressed sequence tags in organs, and a web-based database," *Plant Physiol.*, 132:681-697, 2003.

Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, 2003.

Browse et al., "Fluxes through the prokaryotic and eukaryotic pathways of lipid synthesis in the '16:3' plant *Arabidopsis thaliana*," *Biochem J.* 235:25-31, 1986.

Chapple and Carpita, "Plant cell walls as targets for biotechnology," *Current Opinion in Plant Biology*, 1:179-185, 1998.

Christensen et al., *9th International Conference on Arabidopsis Research*, Univ. of Wisconsin-Madison, Jun. 24-28, Abstract 165, 1998.

Christou et al., "Inheritance and expression of foreign genes in transgenic soybean plants," *Proc. Natl. Acad. Sci. USA*, 86:7500-7504, 1989.

Colbert et al., "High-throughput screening for induced point mutations," *Plant Physiol.* 126:480-484, 2001.

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701, 1989.

Dehesh et al., "Overexpression of 3-ketoacyl-acyl-carrier protein synthase IIIs in plants reduces the rate of lipid synthesis," *Plant Physiol.*, 125:1103-1114, 2001.

Douglas et al., "Nutritional evaluation of low phytate and high protein corns," *Poultry Sci.* 79:1586-1591, 2000.

(Continued)

*Primary Examiner* — Brent T Page
(74) *Attorney, Agent, or Firm* — Marcia I. Rosenfeld; Klarquist Sparkman, LLP.

(57) ABSTRACT

The present invention is directed to plants that display an improved oil quantity phenotype or an improved meal quality phenotype due to altered expression of an IMQ nucleic acid. The invention is further directed to methods of generating plants with an improved oil quantity phenotype or improved meal quality phenotype.

7 Claims, No Drawings

(56) References Cited

OTHER PUBLICATIONS

Eastmond and Graham, "Re-examining the role of glyoxylate cycle in oilseeds," *Trends Plant Sci.*, 6(2):72-77, 2001.

Eccleston and Ohlrogge, "Expression of lauroyl-acyl carrier protein thioesterase in *Brassica napus* seeds induces pathways for both fatty acid oxidation and biosynthesis and implies a set point for triacylglycerol accumulation," *Plant Cell.* 10:613-621, 1998.

Edwards et al., "Protein and energy evaluation of soybean meals processed from genetically modified high-protein soybeans," *Poultry Sci.* 79:525-527, 1999.

Everett et al., "Genetic engineering of sunflower (*Helianthus annuus* L.)," Bio/Technology, 5:1201, 1987.

Falco et al., "Transgenic canola and soybean seeds with increased lysine," *Bio/Technology*, 13:577-582, 1995.

Fatland et al., "Molecular biology of cytosolic acetyl-CoA generation," *Biochem. Soc. Trans.*, 28(6):593-595, 2000.

Fatland et al., "Reverse genetic characterization of cytosolic acetyl-CoA generation by ATP-citrate lyase in *Arabidopsis*," *Plant Cell*, 17:182-203, 2005.

Feldmann et al., "A Dwarf Mutant of *Arabidopsis* Generated by T-DNA Insertion Mutagenesis," *Science*, 243:1351-1354, 1989.

Focks and Benning, "*wrinkled1*: A novel, low-seed-oil mutant of *Arabidopsis* with a deficiency in the seed-specific regulation of carbohydrate metabolism," *Plant Physiol.*, 118:91-101, 1998.

Fridborg et al., "The *Arabidopsis* dwarf mutant *shi* exhibits reduced gibberellin responses conferred by overexpression of a new putative zinc finger protein," *Plant Cell*, 11:1019-1032, 1999.

Girke et al., "Microarray analysis of developing *Arabidopsis* seeds," Plant Physiol., 124:1570-1581, 2000.

Hayashi et al., "Activation of a plant gene by T-DNA tagging: auxin-independent growth in vitro," *Science*, 258:1350-1353, 1992.

Honig and Rackis, "Determination of the total pepsin-pancreatin indigestible content (dietary fiber) of soybean products, wheat bran, and corn bran," *J. Agri. Food Chem.*, 27:1262-1266, 1979.

Jako et al., "Seed-specific over-expression of an *Arabidopsis* cDNA encoding a diacylglycerol acyltransferase enhances seed oil content and seed weight," *Plant Physiol.*, 126(2):861-74, 2001.

James and Dooner, "Isolation of EMS-induced mutants in *Arabidopsis* altered in seed fatty acid composition," *Theor. Appl. Genet.*, 80:241-245, 1990.

Kardailsky et al., "Activation tagging of the floral inducer FT," *Science*, 286:1962-1965, 1999.

Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.

Katavic et al., "Utility of the *Arabidopsis FAE1* and yeast *SLC1-1* genes for improvements in erucic acid and oil content in rapeseed," *Biochem. Soc. Trans.*, 28(6):935-937, 2000.

Klein et al., "High velocity microprojectiles for delivering nucleic acids into living cells," *Nature*, 327:70-73, 1987.

Larson et al., "Acyl CoA profiles of transgenic plants that accumulate medium-chain fatty acids indicate inefficient storage lipid synthesis in developing oilseeds," *Plant J.*, 32:519-527, 2002.

Lemieux et al., "Mutants of *Arabidopsis* with alterations in seed lipid fatty acid composition," *Theor. Appl. Genet.*, 80:234-240, 1990.

Lin et al., "The Pex16p Homolog SSE1 and Storage Organelle Formation in *Arabidopsis* Seeds," *Science*, 284:328-330, 1999.

Lionneton et al., "Development of an AFLP-based linkage map and localization of QTLs for seed fatty acid content in condiment mustard (*Brassica juncea*)," *Genome*, 45:1203-15, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nature Biotechnology*, 18:455-457, 2000.

Mekhedov et al., "Toward a Functional Catalog of the Plant Genome. A Survey of Genes for Lipid Biosynthesis," *Plant Physiology*, 122:389-401, 2000.

Moire et al., "Impact of Unusual Fatty Acid Synthesis on Futile Cycling through β-Oxidation and on Gene Expression in Transgenic Plants," *Plant Physiology*, 134:432-442, 2004.

Moore et al., "Chromatography of Amino Acids on Sulfonated Polystyrene Resins," *Anal. Chem.*, 30:1185-1190, 1958.

Mulder et al., "The InterPro Database, 2003 brings increased coverage and new features," *Nucleic Acids Res.*, 31:315-318, 2003.

Neuhaus et al., "Nonphotosynthetic Metabolism in Plastids," *Annu. Rev. Plant Physiol. Plant Mol.*, 51:111-140, 2000.

O'Hara et al., "Fatty Acid and Lipid Biosynthetic Genes Are Expressed at Constant Molar Ratios But Different Absolute Levels during Embryogenesis," *Plant Physiology*, 129:310-320, 2002.

Okuley et al., "*Arabidopsis* FAD2 gene encodes the enzyme that is essential for polyunsaturated lipid synthesis," *Plant Cell*, 6:147-158, 1994.

Parsons et al., "Nutritional evaluation of soybean meals varying in oligosaccharide content," *Poultry Sci.*, 79:1127-1131, 2000.

Pritchard et al., "Germination and storage reserve mobilization are regulated independently in *Arabidopsis*," the *Plant Journal*, 31(5):639-647, 2002.

Rangasamy and Ratledge, "Genetic enhancement of fatty acid synthesis by targeting rat liver ATP:citrate lyase into plastids of tobacco," *Plant Physiol.*, 122:1231-1238, 2000.

Rangasamy et al., "Compartmentation of ATP:Citrate Lyase in Plants," *Plant Physiology*, 122:1225-1230, 2000.

Ratledge et al., "Correlation of ATP/Citrate Lyase Activity with Lipid Accumulation in Developing Seeds of *Brassica napus* L.," Lipids, 32(1):7-12, 1997.

Rawsthorne, Stephen, "Carbon flux and fatty acid synthesis in plants," *Progress in Lipid Research*, 41:182-196, 2002.

Ruuska et al., "Contrapuntal Networks of Gene Expression during *Arabidopsis* Seed Filling," *The Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schaffer et al., "The late elongated hypocotyl mutation of *Arabidopsis* disrupts circadian rhythms and the photoperiodic control of flowering," *Cell*, 93:1219-1229, 1998.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of an acyl-CoA synthetase from *Arabidopsis thaliana*," *Biochem Soc. Trans.*, 28(6):957-958, 2000.

Shewry, "Seed storage proteins: structures and biosynthesis," *Plant Cell*, 7:945-956, 1995.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in Brassicaceae oilseeds," *Biochem. Soc. Trans.*, 28(6):595-598, 2000.

Weigel et al., "Activation tagging in *Arabidopsis*," *Plant Physiology*, 122:1003-1013, 2000.

White et al., "A new set of *Arabidopsis* expressed sequence tags from developing seeds. The metabolic pathway from carbohydrates to seed oil," *Plant Physiol.*, 124:1582-1594, 2000.

Wilson et al., "A Dissociation insertion causes a semidominant mutation that increases expression of Tiny, an *Arabidopsis* gene related to APETALA2," *Plant Cell*, 8:659-671, 1996.

Yadav et al., "Cloning of higher plant omega-3 fatty acid desaturases," *Plant Physiol.*, 103:467-476, 1993.

Zou et al., "Modification of Seed Oil Content and Acyl Composition in the Brassicaceae by Expression of a Yeast *sn*-2 Acyltransferase Gene," *The Plant Cell*, 9:909-923, 1997.

\* cited by examiner

GENERATION OF PLANTS WITH ALTERED PROTEIN, FIBER, OR OIL CONTENT

CROSS REFERENCE TO RELATED APPLICATIONS

This is a divisional of U.S. patent application Ser. No. 11/940,248, filed Nov. 14, 2007 now U.S. Pat. No. 8,106,253, which claims the benefit of U.S. Provisional Application No. 60/866,053, filed Nov. 15, 2006, both of which are incorporated herein by reference in their entirety.

FIELD OF THE DISCLOSURE

The present disclosure is related to transgenic plants with altered oil, protein, and/or fiber content, as well as methods of making plants having altered oil, protein, and/or fiber content and producing oil from such plants.

INCORPORATION-BY-REFERENCE OF MATERIAL SUBMITTED AS AN ASCII TEXT FILE

A Sequence Listing is submitted herewith as an ASCII compliant text file named "Sequence_Listing.txt", created on Dec. 15, 2011, and having a size of 295 kilobytes, as permitted under 37 CFR 1.821(c). The material in the aforementioned file is hereby incorporated by reference in its entirety.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952, 544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80, 234-240; James and Dooner, 1990, *Theor. Appl. Genet.* 80, 241-245). T-DNA mutagenesis screens (Feldmann et al., 1989, *Science* 243: 1351-1354) that detected altered fatty acid composition identified the omega 3 desaturase (FAD3) and delta-12 desaturase (FAD2) genes (U.S. Pat. No. 5,952,544; Yadav et al., 1993, *Plant Physiol.* 103, 467-476; Okuley et al., 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, *9th International Conference on Arabidopsis Research*, Univ. of Wisconsin-Madison, June 24-28, Abstract 165).

SUMMARY

Provided herein are transgenic plants having an Improved Seed Quality phenotype. Transgenic plants with an Improved Seed Quality phenotype may include an improved oil quantity and/or an improved meal quality. Transgenic plants with improved meal quality have an Improved Meal Quality (IMQ) phenotype and transgenic plants with improved oil quantity have an Improved Oil Quantity (IOQ) phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Examples of the disclosed transgenic plant are produced by a method that comprises introducing into progenitor cells of the plant a plant transformation vector comprising an IMQ nucleotide sequence that encodes, or is complementary to a sequence that encodes, an IMQ polypeptide, and growing the transformed progenitor cells to produce a transgenic plant, wherein the IMQ polynucleotide sequence is expressed, causing an IOQ phenotype and/or and IMQ phenotype in the transgenic plant. In some specific, non-limiting examples, the method produces transgenic plants wherein expression of the IMQ polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. In some embodiments of the method, the method employs candidate gene/QTL methodology or TILLING methodology.

Also provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "IMQ phenotype" refers to plants, or any part of a plant (for example, seeds, or meal produced from seeds), with an altered protein and/or fiber content (phenotype). As provided herein, altered protein and/or fiber content includes either an increased or decreased level of protein and/or fiber content in plants, seeds or seed meal. Any combination of these changes can lead to an IMQ phenotype. For example, in one specific non-limiting example, an IMQ phenotype can refer to increased protein and decreased fiber content. In another specific non-limiting example, an IMQ phenotype can refer to unchanged protein and decreased fiber content. In yet another specific non-limiting example, an IMQ phenotype can refer to increased protein and unchanged fiber content. It is also provided that any combination of these changes can lead to an increase in the AME (available metabolizable energy) from the seed or meal generated from the seed. An IMQ phenotype also includes an improved seed quality (ISQ) phenotype or an improved seed meal quality phenotype.

As used herein, the term "IOQ phenotype" refers to plants, or any part of a plant (for example, seeds), with an altered oil content (phenotype). As provided herein, altered oil content includes an increased, for example a high, oil content in plants or seeds. In some embodiments, a transgenic plant can express both an IOQ phenotype and an IMQ phenotype. In specific, non-limiting examples, a transgenic plant having a combination of an IOQ phenotype and an IMQ phenotype can lead to an increase in the AME (available metabolizable energy) from the seed or meal generated from the seed. An IOQ phenotype also includes an improved seed quality (ISQ) phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a transgenic plant with an increase in AME includes transgenic plants with altered seed protein and/or fiber content and without a decrease in seed oil content (seed oil content remains unchanged or is increased), resulting in an increase in the value of animal feed derived from the seed.

As used herein, the term "content" refers to the type and relative amount of, for instance, a seed or seed meal component.

As used herein, the term "fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include an IMQ nucleic acid sequence, or a fragment, derivative (variant), or ortholog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type plant is also a control plant. In another embodiment, a wild-type plant is a non-transgenic plant.

As used herein, the term "modified" regarding a plant trait, refers to a change in the phenotype of a transgenic plant (for example, a transgenic plant with any combination of an altered oil content, an altered protein content, and/or an altered fiber content) in any part of the transgenic plant, for example the seeds, relative to a similar non-transgenic plant. As used herein, the term "altered" refers to either an increase or a decrease of a plant trait or phenotype (for example, oil content, protein content, and/or fiber content) in a transgenic plant, relative to a similar non-transgenic plant. In one specific, non-limiting example, a transgenic plant with a modified trait includes a plant with an increased oil content, increased protein content, and/or decreased fiber content relative to a similar non-transgenic plant. In another specific, non-limiting example, a transgenic plant with a modified trait includes unchanged oil content, increased protein content, and/or decreased fiber content relative to a similar non-transgenic plant. In yet another specific, non-limiting example, a transgenic plant with a modified trait includes an increased oil content, increased protein content, and/or unchanged fiber content relative to a similar non-transgenic plant. Specific, non-limiting examples of a change in phenotype include an IMQ phenotype or an IOQ phenotype.

An "interesting phenotype (trait)" with reference to a transgenic plant refers to an observable or measurable phenotype demonstrated by a T1 and/or subsequent generation plant, which is not displayed by the corresponding non-transgenic plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such transgenic plants may have an improved phenotype, such as an IMQ phenotype or an IOQ phenotype.

The phrase "altered oil content phenotype" refers to a measurable phenotype of a genetically modified (transgenic) plant, where the plant displays a statistically significant increase or decrease in overall oil content (i.e., the percentage of seed mass that is oil), as compared to the similar, but non-modified (non-transgenic) plant. A high oil phenotype refers to an increase in overall oil content. The phrase "altered protein content phenotype" refers to measurable phenotype of a genetically modified plant, where the plant displays a statistically significant increase or decrease in overall protein content (i.e., the percentage of seed mass that is protein), as compared to the similar, but non-modified plant. A high protein phenotype refers to an increase in overall protein content. The phrase "altered fiber content phenotype" refers to measurable phenotype of a genetically modified plant, where the plant displays a statistically significant increase or decrease in overall fiber content (i.e., the percentage of seed mass that is fiber), as compared to the similar, but non-modified plant. A low fiber phenotype refers to decrease in overall fiber content.

As used herein, a "mutant" polynucleotide sequence or gene differs from the corresponding wild-type polynucleotide sequence or gene either in terms of sequence or expression, where the difference contributes to a modified or altered plant phenotype or trait. Relative to a plant or plant line, the term "mutant" refers to a plant or plant line which has a modified or altered plant phenotype or trait, where the modified or altered phenotype or trait is associated with the modified or altered expression of a wild-type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a transgenic plant cell having an IMQ phenotype and/or an IOQ phenotype. The transgenic plant cell comprises a transformation vector comprising an IMQ nucleotide sequence that encodes or is complementary to a sequence that encodes an IMQ polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are transgenic plants having an Improved Seed Quality phenotype. Transgenic plants with an Improved Seed Quality phenotype may include an improved oil quantity and/or an improved meal quality. Transgenic plants with improved meal quality have an IMQ phenotype and transgenic plants with improved oil quantity have an IOQ phenotype. The IMQ phenotype in a transgenic plant may include altered protein and/or fiber content in any part of the transgenic plant, for example in the seeds. The IOQ phenotype in a transgenic plant may include altered oil content in any part of the transgenic plant, for example in the seeds. In particular embodiments, a transgenic plant may include an IOQ phenotype and/or an IMQ phenotype. In some embodiments of a transgenic plant, the IMQ phenotype may be an increase in protein content in the seed and/or a decrease in the fiber content of the seed. In other embodiments of a transgenic plant, the IOQ phenotype is an increase in the oil content of the seed (a high oil phenotype). Also provided is seed meal derived from the seeds of transgenic plants, wherein the seeds have altered protein content and/or altered fiber content. Further provided is oil derived from the seeds of transgenic plants, wherein the seeds have altered oil content. Any of these changes can lead to an increase in the AME from the seed or seed meal from transgenic plants, relative to control, non-transgenic, or wild-type plants. Also provided herein is meal, feed, or food produced from any part of the transgenic plant with an IMQ phenotype and/or IOQ phenotype.

In certain embodiments, the disclosed transgenic plants comprise a transformation vector comprising an IMQ nucleotide sequence that encodes or is complementary to a sequence that encodes an "IMQ" polypeptide. In particular embodiments, expression of an IMQ polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes an IMQ polypeptide. The disclosure also provides feed, meal, grain, or seed comprising the IMQ polypeptide, or an ortholog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods (see, for example, WO 2007/053482 and WO 2005/107437, which are incorporated herein by reference in their entirety).

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

*Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species.

*Agrobacterium*-mediated genetic transformation of plants involves several steps. The first step, in which the virulent *Agrobacterium* and plant cells are first brought into contact with each other, is generally called "inoculation." Following the inoculation, the *Agrobacterium* and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880, U.S. Pat. No. 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin), methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, and U.S. Pat. No. 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (*Plant J.* 4:833-840, 1993) and Misawa et al., (*Plant J.* 6:481-489, 1994) for norflurazon tolerance; a polynucleotide molecule encoding acetohydroxyacid synthase (AHAS, also known as ALS) described in Sathasiivan et al. (*Nucl. Acids Res.* 18:2188-2193, 1990) for tolerance to sulfonylurea herbicides; and the bar gene described in DeBlock, et al., (*EMBO J.* 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., *Scientia Sinica* 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Improved Oil Quantity Phenotype and/or Improved Meal Quality Phenotype An *Arabidopsis* activation tagging screen (ACTTAG) was used to identify the association between 1) ACTTAG plant lines with an altered protein, fiber and/or oil content (phenotype, for example, see columns 4, 5 and 6, respectively, of Table 1, below) and 2) the nucleic acid sequences identified in column 3 of Tables 2 and 3, wherein each nucleic acid sequence is provided with a gene alias or an IMQ designation (IMQ#; see column 1 in Tables 1, 2, and 3). Briefly, and as further described in the Examples, a large number of *Arabidopsis* plants were mutated with the pSKI015 vector, which comprises a T-DNA from the Ti plasmid of *Agrobacterium tumefaciens*, a viral enhancer element, and a selectable marker gene (Weigel et al., 2000, *Plant Physiology*, 122: 1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

Quantitative determination of fatty acid (FA) content (column 7, Table 1) in T2 seeds was performed using the following methods. A sample of 15 to 20 T2 seeds from each line tested. This sample generally contained plants with homozygous insertions, no insertions, and hemizygous insertions in a standard 1:1:2 ratios. The seed sample was massed on UMT-2 ultra-microbalance (Mettler-Toledo Co., Ohio, USA) and then transferred to a glass extraction vial. Lipids were extracted from the seeds and trans-esterified in 500 µl 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 µl of water and 400 µl of hexane were added to each vial, which was then shaken vigorously and allowed to phase separate. Reaction vials were loaded directly onto gas chromatography (GC) for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 ul of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Peaks were initially identified by comparison with standards. Integration and quantification were performed automatically, but all analyses were subsequently examined manually to verify correct peak identification and acceptable signal to noise ratio before inclusion of the derived results in the study.

The association of an IMQ nucleic acid sequence with an IMQ phenotype or an IOQ phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed IMQ nucleic acid sequences and/or polypeptides may be employed in the development of transgenic plants having an improved seed quality phenotype, including an IMQ phenotype and/or an IOQ phenotype. IMQ nucleic acid sequences may be used in the generation of transgenic plants, such as oilseed crops, that provide improved oil yield from oilseed processing and result in an increase in the quantity of oil recovered from seeds of the transgenic plant. IMQ nucleic acid sequences may also be used in the generation of transgenic plants, such as feed grain crops, that provide an IMQ phenotype resulting in increased energy for animal feeding, for example, seeds or seed meal with an altered protein and/or fiber content, resulting in an increase in AME. IMQ nucleic acid sequences may further be used to increase the oil content of specialty oil crops, in order to augment yield and/or recovery of desired unusual fatty acids. Transgenic plants that have been genetically modified to express IMQ polypeptides can be used in the production of seeds, wherein the transgenic plants are grown, and oil and seed meal are obtained from plant parts (e.g. seed) using standard methods.

IMO Nucleic Acids and Polypeptides

The IMQ designation for each of the IMQ nucleic acid sequences discovered in the activation tagging screen described herein are listed in column 1 of Tables 1-3, below. The disclosed IMQ polypeptides are listed in column 5 of Table 2 and column 4 of Table 3. As used herein, the term "IMQ polypeptide" refers to any polypeptide that when expressed in a plant causes an IMQ phenotype and/or an IOQ phenotype in any part of the plant, for example the seeds. In one embodiment, an IMQ polypeptide refers to a full-length IMQ protein, or a fragment, derivative (variant), or ortholog thereof that is "functionally active," such that the protein fragment, derivative, or ortholog exhibits one or more or the functional activities associated with one or more of the disclosed full-length IMQ polypeptides, for example, the amino acid sequences provided in the GenBank entry referenced in column 5 of Table 2, which correspond to the amino acid sequences set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof. In one preferred embodiment, a functionally active IMQ polypeptide causes an IMQ phenotype and/or an IOQ phenotype in a transgenic plant. In another embodiment, a functionally active IMQ polypeptide causes an altered oil, protein, and/or fiber content phenotype (for example, an altered seed meal content phenotype) when mis-expressed in a plant. In other preferred embodiments, mis-expression of the IMQ polypeptide causes a high oil (such as, increased oil), high protein (such as, increased protein), and/or low fiber (such as, decreased fiber) phenotype in a plant. In another embodiment, mis-expression of the IMQ polypeptide causes an improved AME of meal. In yet another embodiment, a functionally active IMQ polypeptide can rescue defective (including deficient) endogenous IMQ activity when expressed in a plant or in plant cells; the rescuing polypeptide may be from the same or from a different species as the species with the defective polypeptide activity. The disclosure also provides feed, meal, grain, food, or seed comprising the IMQ polypeptide, or a fragment, derivative (variant), or ortholog thereof.

In another embodiment, a functionally active fragment of a full length IMQ polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or a naturally occurring ortholog thereof) retains one or more of the biological properties associated with the full-length IMQ polypeptide, such as signaling activity, binding activity, catalytic activity, or cellular or extra-cellular localizing activity. An IMQ fragment preferably comprises an IMQ domain, such as a C- or N-terminal or catalytic domain, among others, and preferably comprises at least 10, preferably at least 20, more preferably at least 25, and most preferably at least 50 contiguous amino acids of an IMQ protein. Functional domains of IMQ genes are listed in column 8 of Table 2 and can be identified using the PFAM program (Bateman A et al., 1999, *Nucleic Acids Res.* 27:260-262) or INTERPRO (Mulder et al., 2003, *Nucleic Acids Res.* 31, 315-318) program. Functionally active variants of full-length IMQ polypeptides, or fragments thereof, include polypeptides with amino acid insertions, deletions, or substitutions that retain one of more of the biological properties associated with the full-length IMQ polypeptide. In some cases, variants are generated that change the post-translational processing of an IMQ polypeptide. For instance, variants may have altered protein transport or protein localization characteristics, or altered protein half-life, compared to the native polypeptide.

As used herein, the term "IMQ nucleic acid" refers to any polynucleotide that when expressed in a plant causes an IMQ phenotype and/or an IOQ phenotype in any part of the plant, for example the seeds. In one embodiment, an IMQ polynucleotide encompasses nucleic acids with the sequence provided in or complementary to the GenBank entry referenced in column 3 of Table 2, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, as well as functionally active fragments, derivatives, or orthologs thereof. An IMQ nucleic acid of this disclosure may be DNA, derived from genomic DNA or cDNA, or RNA. Genomic sequences of the genes listed in Table 2 are known and available in public databases such as GenBank.

In one embodiment, a functionally active IMQ nucleic acid encodes or is complementary to a nucleic acid that encodes a functionally active IMQ polypeptide. A functionally active IMQ nucleic acid also includes genomic DNA that serves as a template for a primary RNA transcript (i.e., an mRNA precursor) that requires processing, such as splicing, before encoding the functionally active IMQ polypeptide. An IMQ nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed IMQ polypeptide, or an intermediate form. An IMQ polynucleotide can also include heterologous coding sequences, for example, sequences that encode a marker included to facilitate the purification of the fused polypeptide, or a transformation marker. In another embodiment, a functionally active IMQ nucleic acid is capable of being used in the generation of loss-of-function IMQ phenotypes, for instance, via antisense suppression, co-suppression, etc. The disclosure also provides feed, meal, grain, food, or seed comprising a nucleic acid sequence that encodes an IMQ polypeptide.

In one preferred embodiment, an IMQ nucleic acid used in the disclosed methods comprises a nucleic acid sequence that encodes, or is complementary to a sequence that encodes, an IMQ polypeptide having at least 50%, 60%, 70%, 75%, 80%, 85%, 90%, 95%, 97%, 98%, or 99% sequence identity to a disclosed IMQ polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100.

In another embodiment, an IMQ polypeptide comprises a polypeptide sequence with at least 50% or 60% identity to a disclosed IMQ polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100) and may have at least 70%, 80%, 85%, 90%, 95%, 97%, 98%, or 99% sequence identity to a disclosed IMQ polypeptide sequence. In a further embodiment, an IMQ polypeptide comprises 50%, 60%, 70%, 80%, 85%, 90%, 95%, 97%, 98%, or 99% sequence identity to a disclosed IMQ polypeptide sequence, and may include a conserved protein domain of the IMQ polypeptide (such as the protein domain(s) listed in column 8 of Table 2). In another embodiment, an IMQ polypeptide comprises a polypeptide sequence with at least 50%, 60%, 70%, 80%, 85%, 90%, 95%, 97%, 98%, or 99% sequence identity to a functionally active fragment of the polypeptide referenced in column 5 of Table 2. In yet another embodiment, an IMQ polypeptide comprises a polypeptide sequence with at least 50%, 60%, 70%, 80%, 90%, 95%, 97%, 98%, or 99% identity to the polypeptide sequence of the GenBank entry referenced in column 5 of Table 2 over its entire length and comprises a conserved protein domain(s) listed in column 8 of Table 2.

In another aspect, an IMQ polynucleotide sequence is at least 50% to 60% identical over its entire length to a disclosed IMQ nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and may comprise at least 70%, 80%, 85%, 90%, 95%, 97%, 98%, or 99% sequence identity to the disclosed IMQ sequence, or a functionally active fragment thereof, or complementary sequences. In another embodiment, a disclosed IMQ nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99, or nucleic acid sequences that are complementary to such an IMQ sequence, and nucleic acid sequences that have substantial sequence homology to a such IMQ sequences. As used herein, the phrase "substantial sequence homology" refers to those nucleic acid sequences that have slight or inconsequential sequence variations from such IMQ sequences, i.e., the sequences function in substantially the same manner and encode an IMQ polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.,* 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed IMQ nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99). The stringency of hybridization can be controlled by temperature, ionic strength, pH, and the presence of denaturing agents such as formamide during hybridization and washing. Conditions routinely used are well known (see, e.g., *Current Protocol in Molecular Biology,* Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding an IMQ polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs of a disclosed *Arabidopsis* IMQ nucleic acid sequence. Representative putative orthologs of each of the disclosed *Arabidopsis* IMQ genes are identified in column 3 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen and Bork, 1998, *Proc. Natl. Acad. Sci.,* 95:5849-5856; Huynen et al., 2000, *Genome Research,* 10:1204-1210).

Programs for multiple sequence alignment, such as CLUSTAL (Thompson J D et al., 1994, *Nucleic Acids Res.* 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* IMQ coding sequence may be used as a probe. IMQ ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73 SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, or SEQ ID NO: 99 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known IMQ polypeptides are used for ortholog isolation (see, e.g., Harlow and Lane, 1988, 1999, *Antibodies: A Laboratory Manual*, Cold Spring Harbor Laboratory Press, New York). Western blot analysis can determine that an IMQ ortholog (i.e., a protein orthologous to a disclosed IMQ polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which IMQ nucleic acid and/or polypeptide sequences have been identified.

IMQ nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel et al., 1991, *Methods Enzymol.* 204:125-39), may be used to introduce desired changes into a cloned nucleic acid.

In general, the methods disclosed herein involve incorporating the desired form of the IMQ nucleic acid into a plant expression vector for transformation of plant cells, and the IMQ polypeptide is expressed in the host plant. Transformed plants and plant cells expressing an IMQ polypeptide express an IMQ phenotype and/or an IOQ phenotype and, in one specific, non-limiting example, may have high (increased) oil, high (increased) protein, and/or low (decreased) fiber content.

An "isolated" IMQ nucleic acid molecule is other than in the form or setting in which it is found in nature, and is identified and separated from least one contaminant nucleic acid molecule with which it is ordinarily associated in the natural source of the IMQ nucleic acid. However, an isolated IMQ nucleic acid molecule includes IMQ nucleic acid molecules contained in cells that ordinarily express IMQ where, for example, the nucleic acid molecule is in a chromosomal location different from that of natural cells.

Generation of Genetically Modified Plants with an Improved Oil Quantity Phenotype and/or an Improved Meal Quality Phenotype The disclosed IMQ nucleic acids and polypeptides may be used in the generation of transgenic plants having a modified or altered oil, protein, and/or fiber content phenotype. As used herein, an "altered oil content (phenotype)" may refer to altered oil content in any part of the plant. In a preferred embodiment, altered expression of the IMQ gene in a plant is used to generate plants with a high oil content (phenotype). As used herein, an "altered protein content (phenotype)" may refer to altered protein content in any part of the plant. In a preferred embodiment, altered expression of the IMQ gene in a plant is used to generate plants with a high (or increased) protein content (phenotype). As used herein, an "altered fiber content (phenotype)" may refer to altered fiber content in any part of the plant. In a preferred embodiment, altered expression of the IMQ gene in a plant is used to generate plants with a low (or decreased) fiber content (phenotype). The altered oil, protein, and/or fiber content is often observed in seeds. Examples of a transgenic plant include plants comprising a plant transformation vector with a nucleotide sequence that encodes or is complementary to a sequence that encodes an IMQ polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, or SEQ ID NO: 100, or an ortholog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the IMQ nucleic acid sequence (or an ortholog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annuus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species may also be a source of unique fatty acids. In other embodiments, any plant expressing the IMQ nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an IMQ polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.*, 91:694-701), sunflower (Everett et al., 1987, *Bio/Technology*, 5:1201), soybean (Christou et al., 1989, *Proc. Natl. Acad. Sci USA*, 86:7500-7504; Kline et al., 1987, *Nature*, 327:70), wheat, rice and oat.

Expression (including transcription and translation) of an IMQ nucleic acid sequence may be regulated with respect to the level of expression, the tissue type(s) where expression takes place and/or developmental stage of expression. A number of heterologous regulatory sequences (e.g., promoters and enhancers) are available for controlling the expression of an IMQ nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci.* (*U.S.A.*) 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.*, 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci.* (*U.S.A.*) 84:6624-6628, 1987), the sucrose synthase promoter (Yang et al., *Proc. Natl. Acad. Sci.* (*U.S.A.*) 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol Biol.*, 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol Bio.*, 21:625-640).

In one preferred embodiment, expression of the IMQ nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219, 1991), globulin (Belanger and Kriz, *Genet.*, 129: 863-872, 1991, GenBank Accession No. L22295), gamma zein Z 27 (Lopes et al., *Mol Gen Genet.*, 247:603-613, 1995), L3 oleosin promoter (U.S. Pat. No. 6,433,252), phaseolin (Bustos et al., *Plant Cell*, 1(9):839-853, 1989), arcelin5 (U.S. Application No. 2003/0046727), a soybean 7S promoter, a 7Sα promoter (U.S. Application No. 2003/0093828), the soybean 7Sα' beta conglycinin promoter, a 7S α' promoter (Beachy et al., *EMBO J.*, 4:3047, 1985; Schuler et al., *Nucleic Acid Res.*, 10(24):8225-8244, 1982), soybean trypsin inhibitor (Riggs et al., *Plant Cell* 1(6):609-621, 1989), ACP (Baerson et al., *Plant Mol. Biol.*, 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Application No. 2003/229918) and *Zea mays* L3 oleosin promoter (Hong et al., *Plant Mol. Biol.*, 34(3):549-555, 1997). Also included are the zeins, which are a group of storage proteins found in corn endosperm. Genomic clones for zein genes have been isolated (Pedersen et al., *Cell*, 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, *Mol. Gen. Genet.* 225:121-8; Baumlein et al., 1992, *Plant J.* 2:233-9), *V. faba* usp (Fiedler et al., 1993, *Plant Mol. Biol.* 22:669-79), pea convicilin (Bown et al., 1988, *Biochem. J.* 251:717-26), pea lectin (dePater et al., 1993, *Plant Cell* 5:877-86), *P. vulgaris* beta phaseolin (Bustos et al., 1991, *EMBO J.* 10:1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3,"Yoshihara and Takaiwa, 1996, *Plant Cell Physiol.* 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley B-hordeins (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus* napin, 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus* oleosin (Keddie et al., 1994, *Plant Mol. Biol.* 24:327-40), *Arabidopsis* oleosin (Plant et al., 1994, *Plant Mol. Biol.* 25:193-205), *Arabidopsis* FAE1 (Rossak et al., 2001, *Plant Mol. Biol.* 46:717-25), *Canavalia* gladiata conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378, 619; 5,391,725; 5,428,147; 5,447,858; 5,608,144; 5,608,144; 5,614,399; 5,633,441; 5,633,435; and 4,633,436.

In yet another aspect, in some cases it may be desirable to inhibit the expression of the endogenous IMQ nucleic acid sequence in a host cell. Exemplary methods for practicing this aspect of the invention include, but are not limited to antisense suppression (Smith, et al., 1988, *Nature*, 334:724-726; van der Krol et al., 1988, *BioTechniques*, 6:958-976); co-suppression (Napoli, et al., 1990, *Plant Cell*, 2:279-289); ribozymes (PCT Publication WO 97/10328); and combinations of sense and antisense (Waterhouse, et al., 1998, *Proc. Natl. Acad. Sci. USA*, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA*, 85:8805-8809), a partial cDNA sequence including fragments of 5' coding sequence, (Cannon et al., 1990, *Plant Mol. Biol.*, 15:39-47), or 3' non-coding sequences (Ch'ng et al., 1989, *Proc. Natl. Acad. Sci. USA*, 86:10006-10010). Cosuppression techniques may use the entire cDNA sequence (Napoli et al., 1990, *Plant Cell*, 2:279-289; van der Krol et al., 1990, *Plant Cell*, 2:291-299), or a partial cDNA sequence (Smith et al., 1990, *Mol. Gen. Genetics*, 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Improved Oil Quantity Phenotype and/or Improved Meal Quality Phenotype Additional methods are disclosed herein of generating a plant having an IMQ and/or an IOQ phenotype, wherein a plant is identified that has an allele in its IMQ nucleic acid sequence that results in an IMQ phenotype and/or an IOQ phenotype, compared to plants lacking the allele. The plant can generate progeny, wherein the progeny inherit the allele and have an IMQ phenotype and/or an IOQ phenotype. For example, provided herein is a method of identifying plants that have mutations in the endogenous IMQ nucleic acid sequence that confer an IMQ phenotype and/or an IOQ phenotype and generating progeny of these plants with an IMQ and/or IOQ phenotype that are not genetically modified. In some embodiments, the plants have an IMQ phenotype with an altered protein and/or fiber content or seed meal content, or an IOQ phenotype, with an altered oil content.

In one method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the IMQ nucleic acid sequence is used to identify whether a mutated plant has a mutation in the IMQ nucleic acid sequence. Plants having IMQ mutations may then be tested for altered oil, protein, and/or fiber content, or alternatively, plants may be tested for altered oil, protein, and/or fiber content, and then PCR amplification and sequencing of the IMQ nucleic acid sequence is used to determine whether a plant having altered oil, protein, and/or fiber content has a mutated IMQ nucleic acid sequence. TILLING can identify mutations that may alter the expression of specific genes or the activity of proteins encoded by these genes (see Colbert et al., 2001, *Plant Physiol.* 126:480-484; McCallum et al., 2000, *Nature Biotechnology* 18:455-457).

In another method, a candidate gene/Quantitative Trait Locus (QTLs) approach can be used in a marker-assisted breeding program to identify alleles of or mutations in the IMQ nucleic acid sequence or orthologs of the IMQ nucleic acid sequence that may confer altered oil, protein, and/or fiber content (see Bert et al., *Theor Appl Genet.*, 2003 June; 107 (1):181-9; and Lionneton et al., *Genome*, 2002 December; 45(6):1203-15). Thus, in a further aspect of the disclosure, an IMQ nucleic acid is used to identify whether a plant with altered oil, protein, and/or fiber content has a mutation an endogenous IMQ nucleic acid sequence or has a particular allele that causes altered oil, protein, and/or fiber content.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with an IMQ Phenotype and/or an IOQ Phenotype by Transformation with an Activation Tagging Construct This Example describes the generation of transgenic plants with altered oil, protein, and/or fiber content.

Mutants were generated using the activation tagging "ACT-TAG" vector, pSKI015 (GI#6537289; Weigel D et al., 2000, *Plant Physiology*, 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A fiber content predicting calibration was developed by measuring crude fiber content in a set of seed samples. Fiber content of in a known mass of seed was determined using the method of Honig and Rackis, (1979, *J. Agri. Food Chem.*, 27: 1262-1266). Digestible protein content of in a known mass of seed was determined by quantifying the individual amino acids liberated by an acid hydrolysis Steine and Moore (1958, *Anal. Chem.*, 30:1185-1190). The quantification was performed by the Amino Quant (Agilent). The undigested protein remaining associated with the non digestible fraction is measured by the same method described for the whole seed homogenate. Digestible protein content is determined by subtracting the amount of undigested protein associated with the non digestible fraction from the total amount of protein in the seed sample.

Seed oil, protein, digestible protein and fiber values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Promoters within 9 kb of the enhancers in the ACTTAG element are considered to be within "activation space." Genes with T-DNA inserts within coding sequences were not considered to be within "activation space." The ACTTAG lines with the above average oil and protein values, and below average fiber values were identified and are listed in column 3 of Table 1.

TABLE 1

| 1. Gene alias | 2. Tair | 3. ACTTAG Line | 4. Relative Seed Protein Content | 5. Relative Seed Fiber Content | 6. Relative Seed Oil Content | 7. GC FA |
|---|---|---|---|---|---|---|
| IMQ21.1 | At1g05230 | W000032537 | 114.20% | 100.35% | 79.63% | |
| IMQ21.1 | At1g05230 | W000032537 | 114.20% | 100.35% | 79.63% | |
| IMQ21.2 | At1g05240 | W000032537 | 114.20% | 100.35% | 79.63% | |
| IMQ21.3 | At1g05250 | W000032537 | 114.20% | 100.35% | 79.63% | |
| IMQ21.4 | At1g05260 | W000032537 | 114.20% | 100.35% | 79.63% | |
| IMQ22.1 | At1g10140 | W000181281 | 106.75% | 91.28% | 94.79% | |
| IMQ22.2 | At1g10150 | W000181281 | 106.75% | 91.28% | 94.79% | |
| IMQ22.3 | At1g10155 | W000181281 | 106.75% | 91.28% | 94.79% | |
| IMQ23.1 | At1g13630 | W000189711 | 156.76% | 98.48% | 62.78% | |
| IMQ23.2 | At1g13640 | W000189711 | 156.76% | 98.48% | 62.78% | |
| IMQ23.3 | At1g13650 | W000189711 | 156.76% | 98.48% | 62.78% | |
| IMQ23.3 | At1g13650 | W000189711 | 156.76% | 98.48% | 62.78% | |
| IMQ24.1 | At1g25400 | W000092974 | 113.43% | 93.89% | 92.75% | |
| IMQ24.2 | At1g25410 | W000092974 | 113.43% | 93.89% | 92.75% | |
| IMQ24.3 | At1g25420 | W000092974 | 113.43% | 93.89% | 92.75% | |
| IMQ24.3 | At1g25420 | W000092974 | 113.43% | 93.89% | 92.75% | |
| IMQ24.3 | At1g25420 | W000092974 | 113.43% | 93.89% | 92.75% | |
| IMQ25.1 | At1g27630 | W000156857 | 115.45% | 91.17% | 93.30% | |
| IMQ25.2 | At1g27640 | W000156857 | 115.45% | 91.17% | 93.30% | |
| IMQ25.3 | At1g27650 | W000156857 | 115.45% | 91.17% | 93.30% | |
| IMQ25.4 | At1g27660 | W000156857 | 115.45% | 91.17% | 93.30% | 94.87% |
| IMQ26.1 | At1g34160 | W000181882 | 106.61% | 89.49% | 95.13% | |
| IMQ26.2 | At1g34170 | W000181882 | 106.61% | 89.49% | 95.13% | |
| IMQ26.2 | At1g34170 | W000181882 | 106.61% | 89.49% | 95.13% | |
| IMQ26.3 | At1g34180 | W000181882 | 106.61% | 89.49% | 95.13% | |
| IMQ27.1 | At1g45160 | W000144884 | 99.69% | 99.35% | 106.43% | |
| IMQ27.2 | At1g45170 | W000144884 | 99.69% | 99.35% | 106.43% | |
| IMQ27.3 | At1g45180 | W000144884 | 99.69% | 99.35% | 106.43% | |
| IMQ28.1 | At1g52140 | W000160181 | 111.10% | 92.26% | 96.12% | |
| IMQ28.2 | At1g52150 | W000160181 | 111.10% | 92.26% | 96.12% | |
| IMQ28.2 | At1g52150 | W000160181 | 111.10% | 92.26% | 96.12% | |
| IMQ29.1 | At1g58410 | W000050532 | 100.73% | 91.01% | 101.59% | 108.07% |
| IMQ29.1 | At1g58410 | W000050532 | 100.73% | 91.01% | 101.59% | |
| IMQ29.1 | At1g58410 | W000050532 | 100.73% | 91.01% | 101.59% | |
| IMQ29.2 | At1g58420 | W000050532 | 100.73% | 91.01% | 101.59% | |
| IMQ29.3 | At1g58430 | W000050532 | 100.73% | 91.01% | 101.59% | |
| IMQ30.1 | At1g75670 | W000161468 | 114.49% | 91.60% | 93.46% | |
| IMQ30.1 | At1g75670 | W000161468 | 114.49% | 91.60% | 93.46% | |
| IMQ30.2 | At1g75680 | W000161468 | 114.49% | 91.60% | 93.46% | |
| IMQ30.3 | At1g75690 | W000161468 | 114.49% | 91.60% | 93.46% | |
| IMQ30.4 | At1g75700 | W000161468 | 114.49% | 91.60% | 93.46% | |
| IMQ31.1 | At1g77730 | W000032887 | 115.30% | 99.58% | 80.09% | |
| IMQ31.2 | At1g77740 | W000032887 | 115.30% | 99.58% | 80.09% | |
| IMQ32.1 | At1g78100 | W000060346 | 116.83% | 90.96% | 88.40% | |
| IMQ32.2 | At1g78110 | W000060346 | 116.83% | 90.96% | 88.40% | |
| IMQ32.3 | At1g78120 | W000060346 | 116.83% | 90.96% | 88.40% | |
| IMQ33.1 | At2g17036 | W000176513 | 138.95% | 98.90% | 78.13% | |
| IMQ33.2 | At2g17040 | W000176513 | 138.95% | 98.90% | 78.13% | |
| IMQ34.1 | At2g31460 | W000137133 | 135.45% | 89.55% | 82.65% | |
| IMQ34.2 | At2g31470 | W000137133 | 135.45% | 89.55% | 82.65% | |

TABLE 2

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ21.1 | At1g05230 | gi\|30679180 | SEQ ID NO: 1 | gi\|30679181 | SEQ ID NO: 2 | DNA binding/ transcription factor | IPR002913 Lipid-binding START; IPR001356 Homeobox |
| IMQ21.1 | At1g05230 | gi\|30679175 | SEQ ID NO: 3 | gi\|15220448 | SEQ ID NO: 4 | DNA binding/ transcription factor | IPR002913 Lipid-binding START; IPR001356 Homeobox |
| IMQ21.2 | At1g05240 | gi\|30679186 | SEQ ID NO: 5 | gi\|18390498 | SEQ ID NO: 6 | peroxidase | IPR002016 Haem peroxidase, plant/fungal/bacterial; IPR000823 Plant peroxidase |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ21.3 | At1g05250 | gi\|30679195 | SEQ ID NO: 7 | gi\|18390500 | SEQ ID NO: 8 | peroxidase | IPR002016 Haem peroxidase, plant/fungal/bacterial; IPR000823 Plant peroxidase |
| IMQ21.4 | At1g05260 | gi\|30679199 | SEQ ID NO: 9 | gi\|15220463 | SEQ ID NO: 10 | RCI3 (RARE COLD INDUCIBLE GENE 3); peroxidase | IPR002016 Haem peroxidase, plant/fungal/bacterial; IPR000823 Plant peroxidase |
| IMQ22.1 | At1g10140 | gi\|42561890 | SEQ ID NO: 11 | gi\|18391115 | SEQ ID NO: 12 | unknown protein | |
| IMQ22.2 | At1g10150 | gi\|42561891 | SEQ ID NO: 13 | gi\|18391117 | SEQ ID NO: 14 | ATPP2-A10 | |
| IMQ22.3 | At1g10155 | gi\|22329463 | SEQ ID NO: 15 | gi\|22329464 | SEQ ID NO: 16 | unknown protein | |
| IMQ23.1 | At1g13630 | gi\|18394018 | SEQ ID NO: 17 | gi\|15222912 | SEQ ID NO: 18 | unknown protein | IPR002885 Pentatricopeptide repeat |
| IMQ23.2 | At1g13640 | gi\|30683391 | SEQ ID NO: 19 | gi\|18394020 | SEQ ID NO: 20 | inositol or phosphatidylinositol kinase/ phosphotransferase, alcohol group as acceptor | IPR000403 Phosphatidylinositol 3- and 4-kinase, catalytic; IPR000626 Ubiquitin |
| IMQ23.3 | At1g13650 | gi\|30683401 | SEQ ID NO: 21 | gi\|30683402 | SEQ ID NO: 22 | unknown protein | |
| IMQ23.3 | At1g13650 | gi\|30683399 | SEQ ID NO: 23 | gi\|15222916 | SEQ ID NO: 24 | unknown protein | |
| IMQ24.1 | At1g25400 | gi\|30689203 | SEQ ID NO: 25 | gi\|18395663 | SEQ ID NO: 26 | unknown protein | |
| IMQ24.2 | At1g25410 | gi\|18395666 | SEQ ID NO: 27 | gi\|15222583 | SEQ ID NO: 28 | ATIPT6; ATP binding/ adenylate dimethylallyltransferase/ tRNA isopentenyltransferase | IPR002648 Isopentenyl transferase; IPR002627 tRNA isopentenyltransferase; IPR011593 Isopentenyl transferase-like |
| IMQ24.3 | At1g25420 | gi\|42571640 | SEQ ID NO: 29 | gi\|42571641 | SEQ ID NO: 30 | expressed protein | IPR005061 Protein of unknown function DUF292, eukaryotic |
| IMQ24.3 | At1g25420 | gi\|42571638 | SEQ ID NO: 31 | gi\|42571639 | SEQ ID NO: 32 | expressed protein | IPR005061 Protein of unknown function DUF292, eukaryotic |
| IMQ24.3 | At1g25420 | gi\|30689214 | SEQ ID NO: 33 | gi\|18395668 | SEQ ID NO: 34 | expressed protein | IPR005061 Protein of unknown function DUF292, eukaryotic |
| IMQ25.1 | At1g27630 | gi\|30690014 | SEQ ID NO: 35 | gi\|15217663 | SEQ ID NO: 36 | cyclin-dependent protein kinase | IPR005258 Cyclin ccl1; IPR006671 Cyclin, N-terminal |
| IMQ25.2 | At1g27640 | gi\|18396427 | SEQ ID NO: 37 | gi\|15217664 | SEQ ID NO: 38 | unknown protein | |
| IMQ25.3 | At1g27650 | gi\|30690022 | SEQ ID NO: 39 | gi\|15217666 | SEQ ID NO: 40 | RNA binding/nucleic acid binding | IPR000571 Zinc finger, CCCH-type; IPR000504 RNA-binding region RNP-1 (RNA recognition motif); IPR009145 U2 auxiliary factor small subunit |
| IMQ25.4 | At1g27660 | gi\|42562353 | SEQ ID NO: 41 | gi\|15217667 | SEQ ID NO: 42 | transcription factor | IPR001092 Basic helix-loop-helix dimerisation region bHLH |
| IMQ26.1 | At1g34160 | gi\|18399159 | SEQ ID NO: 43 | gi\|15218513 | SEQ ID NO: 44 | unknown protein | IPR002885 Pentatricopeptide repeat |
| IMQ26.2 | At1g34170 | gi\|79356538 | SEQ ID NO: 45 | gi\|79356539 | SEQ ID NO: 46 | ARF13; transcription factor | IPR010525 Auxin response factor; IPR003340 Transcriptional factor B3 |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ26.2 | At1g34170 | gi\|79319168 | SEQ ID NO: 47 | gi\|79319169 | SEQ ID NO: 48 | ARF13 | IPR010525 Auxin response factor; IPR003340 Transcriptional factor B3 |
| IMQ26.3 | At1g34180 | gi\|30693015 | SEQ ID NO: 49 | gi\|18399166 | SEQ ID NO: 50 | ANAC016; transcription factor | IPR003441 No apical meristem (NAM) protein |
| IMQ27.1 | At1g45160 | gi\|30693922 | SEQ ID NO: 51 | gi\|15219539 | SEQ ID NO: 52 | kinase | IPR000719 Protein kinase; IPR008271 Serine/threonine protein kinase, active site; IPR000687 Protein of unknown function RIO1 |
| IMQ27.2 | At1g45170 | gi\|79360074 | SEQ ID NO: 53 | gi\|79360075 | SEQ ID NO: 54 | unknown protein | |
| IMQ27.3 | At1g45180 | gi\|30693927 | SEQ ID NO: 55 | gi\|15220067 | SEQ ID NO: 56 | protein binding/ ubiquitin-protein ligase/ zinc ion binding | IPR001841 Zinc finger, RING-type; IPR001965 Zinc finger, PHD-type |
| IMQ28.1 | At1g52140 | gi\|30695146 | SEQ ID NO: 57 | gi\|18403871 | SEQ ID NO: 58 | unknown protein | |
| IMQ28.2 | At1g52150 | gi\|30695148 | SEQ ID NO: 59 | gi\|30695149 | SEQ ID NO: 60 | ATHB-15 (INCURVATA 4); DNA binding/ transcription factor | IPR002913 Lipid-binding START; IPR001356 Homeobox; IPR004827 Basic-leucine zipper (bZIP) transcription factor |
| IMQ28.2 | At1g52150 | gi\|30695147 | SEQ ID NO: 61 | gi\|15218158 | SEQ ID NO: 62 | ATHB-15 (INCURVATA 4); DNA binding/ transcription factor | IPR002913 Lipid-binding START; IPR001356 Homeobox; IPR004827 Basic-leucine zipper (bZIP) transcription factor |
| IMQ29.1 | At1g58410 | gi\|18406289 | SEQ ID NO: 63 | gi\|15217959 | SEQ ID NO: 64 | ATP binding | IPR000767 Disease resistance protein; IPR001611 Leucine-rich repeat; IPR002182 NB-ARC; IPR011072 Protein kinase PKN/PRK1, effector |
| IMQ29.1 | At1g58410 | gi\|79583692 | SEQ ID NO: 65 | gi\|79583693 | SEQ ID NO: 66 | ATP binding | IPR000767 Disease resistance protein; IPR001611 Leucine-rich repeat; IPR002182 NB-ARC |
| IMQ29.1 | At1g58410 | gi\|79320239 | SEQ ID NO: 67 | gi\|79320240 | SEQ ID NO: 68 | ATP binding | IPR000767 Disease resistance protein; IPR001611 Leucine-rich repeat; IPR002182 NB-ARC |
| IMQ29.2 | At1g58420 | gi\|30696259 | SEQ ID NO: 69 | gi\|18406291 | SEQ ID NO: 70 | unknown protein | |
| IMQ29.3 | At1g58430 | gi\|30696261 | SEQ ID NO: 71 | gi\|15217963 | SEQ ID NO: 72 | RXF26; carboxylic ester hydrolase/hydrolase, acting on ester bonds | IPR001087 Lipolytic enzyme, G-D-S-L |
| IMQ30.1 | At1g75670 | gi\|42572114 | SEQ ID NO: 73 | gi\|42572115 | SEQ ID NO: 74 | unknown protein | IPR007830 RNA polymerase Rpa43 subunit |
| IMQ30.1 | At1g75670 | gi\|30699111 | SEQ ID NO: 75 | gi\|18410907 | SEQ ID NO: 76 | unknown protein | IPR007830 RNA polymerase Rpa43 subunit |
| IMQ30.2 | At1g75680 | gi\|30699112 | SEQ ID NO: 77 | gi\|15222328 | SEQ ID NO: 78 | hydrolase, hydrolyzing O-glycosyl compounds | IPR001701 Glycoside hydrolase, family 9 |
| IMQ30.3 | At1g75690 | gi\|30699113 | SEQ ID NO: 79 | gi\|15222330 | SEQ ID NO: 80 | unknown protein | IPR001305 DnaJ central region |

TABLE 2-continued

| 1. Gene alias | 2. Tair | 3. Nucleic Acid seq. GI# | 4. SEQ ID NO | 5. Polypeptide seq. GI# | 6. SEQ ID NO | 7. Putative biochemical function/protein name | 8. Conserved protein domain |
|---|---|---|---|---|---|---|---|
| IMQ30.4 | At1g75700 | gi\|18410915 | SEQ ID NO: 81 | gi\|15222332 | SEQ ID NO: 82 | unknown protein | IPR004345 TB2/DP1 and HVA22 related protein; IPR005296 IBV 3C protein |
| IMQ31.1 | At1g77730 | gi\|18411662 | SEQ ID NO: 83 | gi\|15217449 | SEQ ID NO: 84 | unknown protein | IPR001849 Pleckstrin-like; IPR000648 Oxysterol-binding protein |
| IMQ31.2 | At1g77740 | gi\|18411668 | SEQ ID NO: 85 | gi\|15217451 | SEQ ID NO: 86 | 1-phosphatidylinositol-4-phosphate 5-kinase | IPR002498 Phosphatidylinositol-4-phosphate 5-kinase; IPR003409 MORN motif |
| IMQ32.1 | At1g78100 | gi\|30699306 | SEQ ID NO: 87 | gi\|18411823 | SEQ ID NO: 88 | unknown protein | IPR001810 Cyclin-like F-box |
| IMQ32.2 | At1g78110 | gi\|42563307 | SEQ ID NO: 89 | gi\|15218227 | SEQ ID NO: 90 | unknown protein | |
| IMQ32.3 | At1g78120 | gi\|18411834 | SEQ ID NO: 91 | gi\|15218228 | SEQ ID NO: 92 | unknown protein | IPR001440 TPR repeat; IPR005687 Mitochondrial import translocase, subunit Tom70 |
| IMQ33.1 | At2g17036 | gi\|18398290 | SEQ ID NO: 93 | gi\|18398291 | SEQ ID NO: 94 | unknown protein | IPR001810 Cyclin-like F-box; IPR005174 Protein of unknown function DUF295 |
| IMQ33.2 | At2g17040 | gi\|30679858 | SEQ ID NO: 95 | gi\|18398293 | SEQ ID NO: 96 | ANAC036; transcription factor | IPR003441 No apical meristem (NAM) protein |
| IMQ34.1 | At2g31460 | gi\|18402675 | SEQ ID NO: 97 | gi\|15225088 | SEQ ID NO: 98 | unknown protein | IPR005508 Protein of unknown function DUF313 |
| IMQ34.2 | At2g31470 | gi\|18402677 | SEQ ID NO: 99 | gi\|15225089 | SEQ ID NO: 100 | unknown protein | IPR006527 F-box protein interaction domain; IPR001810 Cyclin-like F-box |

TABLE 3

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ21.1 | At1g05230 | gi\|30679180 | gi\|30679181 | gi\|30679175 | gi\|15220448 | *Arabidopsis thaliana* |
| | | | | gi\|42567019 | gi\|22328861 | *Arabidopsis thaliana* |
| | | | | gi\|1173621 | gi\|1173622 | *Phalaenopsis* sp. SM9108 |
| | | | | gi\|50928892 | gi\|50928893 | *Oryza sativa* (japonica cultivar-group) |
| IMQ21.1 | At1g05230 | gi\|30679175 | gi\|15220448 | gi\|30679180 | gi\|30679181 | *Arabidopsis thaliana* |
| | | | | gi\|42567019 | gi\|22328861 | *Arabidopsis thaliana* |
| | | | | gi\|1173621 | gi\|1173622 | *Phalaenopsis* sp. SM9108 |
| | | | | gi\|50928892 | gi\|50928893 | *Oryza sativa* (japonica cultivar-group) |
| IMQ21.2 | At1g05240 | gi\|30679186 | gi\|18390498 | gi\|30679195 | gi\|18390500 | *Arabidopsis thaliana* |
| | | | | gi\|30685217 | gi\|15242237 | *Arabidopsis thaliana* |
| | | | | gi\|30678297 | gi\|15232058 | *Arabidopsis thaliana* |
| | | | | gi\|7259218 | gi\|7259219 | *Spinacia oleracea* |
| IMQ21.3 | At1g05250 | gi\|30679195 | gi\|18390500 | gi\|30679186 | gi\|18390498 | *Arabidopsis thaliana* |
| | | | | gi\|30685217 | gi\|15242237 | *Arabidopsis thaliana* |
| | | | | gi\|30678297 | gi\|15232058 | *Arabidopsis thaliana* |
| | | | | gi\|7259218 | gi\|7259219 | *Spinacia oleracea* |
| IMQ21.4 | At1g05260 | gi\|30679199 | gi\|15220463 | gi\|50261254 | gi\|50261255 | *Capsella bursa-pastoris* |
| | | | | gi\|30686383 | gi\|15233153 | *Arabidopsis thaliana* |
| | | | | gi\|30681721 | gi\|15237128 | *Arabidopsis thaliana* |
| IMQ22.1 | At1g10140 | gi\|42561890 | gi\|18391115 | gi\|30696259 | gi\|18406291 | *Arabidopsis thaliana* |
| | | | | gi\|50933830 | gi\|50933831 | *Oryza sativa* (japonica cultivar-group) |
| | | | | gi\|45860990 | gi\|50872457 | *Oryza sativa* (japonica cultivar-group) |
| IMQ22.2 | At1g10150 | gi\|42561891 | gi\|18391117 | gi\|30696298 | gi\|18406365 | *Arabidopsis thaliana* |
| | | | | gi\|50933834 | gi\|50933835 | *Oryza sativa* (japonica cultivar-group) |
| | | | | gi\|37514985 | gi\|40539064 | *Oryza sativa* (japonica cultivar-group) |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ22.3 | At1g10155 | gi|22329463 | gi|22329464 | gi|18397840 | gi|15221633 | *Arabidopsis thaliana* |
| | | | | gi|6850933 | gi|6850934 | *Cicer arietinum* |
| | | | | gi|4995204 | gi|4995205 | *Glycine max* |
| IMQ23.1 | At1g13630 | gi|18394018 | gi|15222912 | gi|37535403 | gi|37535404 | *Oryza sativa* (japonica cultivar-group) |
| | | | | gi|18403403 | gi|15228763 | *Arabidopsis thaliana* |
| | | | | gi|18391375 | gi|15221282 | *Arabidopsis thaliana* |
| IMQ23.2 | At1g13640 | gi|30683391 | gi|18394020 | gi|30678087 | gi|18395629 | *Arabidopsis thaliana* |
| | | | | gi|30689401 | gi|18395825 | *Arabidopsis thaliana* |
| | | | | gi|42570678 | gi|42570679 | *Arabidopsis thaliana* |
| IMQ23.3 | At1g13650 | gi|30683401 | gi|30683402 | gi|30683399 | gi|15222916 | *Arabidopsis thaliana* |
| | | | | gi|30678078 | gi|30678079 | *Arabidopsis thaliana* |
| | | | | gi|42570676 | gi|42570677 | *Arabidopsis thaliana* |
| | | | | gi|23496321 | gi|23496344 | *Plasmodium falciparum* 3D7 |
| IMQ23.3 | At1g13650 | gi|30683399 | gi|15222916 | gi|30683401 | gi|30683402 | *Arabidopsis thaliana* |
| | | | | gi|30678078 | gi|30678079 | *Arabidopsis thaliana* |
| | | | | gi|42570676] | gi|42570677 | *Arabidopsis thaliana* |
| | | | | gi|23496321 | gi|23496344 | *Plasmodium falciparum* 3D7 |
| IMQ24.1 | At1g25400 | gi|30689203 | gi|18395663 | gi|30697678 | gi|18409031 | *Arabidopsis thaliana* |
| IMQ24.2 | At1g25410 | gi|18395666 | gi|15222583 | gi|18409036 | gi|15221410 | *Arabidopsis thaliana* |
| | | | | gi|74038586 | gi|74038587 | *Brassica rapa* subsp. *pekinensis* |
| | | | | gi|18402143 | gi|15230294 | *Arabidopsis thaliana* |
| IMQ24.3 | At1g25420 | gi|42571640 | gi|42571641 | gi|42571638 | gi|42571639 | *Arabidopsis thaliana* |
| | | | | gi|30689214 | gi|18395668 | *Arabidopsis thaliana* |
| | | | | gi|34911297 | gi|34911298 | *Oryza sativa* (japonica cultivar-group) |
| | | | | gi|16191725 | gi|56784451 | *Oryza sativa* (japonica cultivar-group) |
| IMQ24.3 | At1g25420 | gi|42571638 | gi|42571639 | gi|42571640 | gi|42571641 | *Arabidopsis thaliana* |
| | | | | gi|30689214 | gi|18395668 | *Arabidopsis thaliana* |
| | | | | gi|34911297 | gi|34911298 | *Oryza sativa* (japonica cultivar-group) |
| | | | | gi|16191725 | gi|56784451 | *Oryza sativa* (japonica cultivar-group) |
| IMQ24.3 | At1g25420 | gi|30689214 | gi|18395668 | gi|42571640 | gi|42571641 | *Arabidopsis thaliana* |
| | | | | gi|42571638 | gi|42571639 | *Arabidopsis thaliana* |
| | | | | gi|16191725 | gi|56784451 | *Oryza sativa* (japonica cultivar-group) |
| | | | | gi|42571740 | gi|42571741 | *Arabidopsis thaliana* |
| IMQ25.1 | At1g27630 | gi|30690014 | gi|15217663 | gi|30694714 | gi|30694715 | *Arabidopsis thaliana* |
| | | | | gi|77548247 | gi|77548754 | *Oryza sativa* (japonica cultivar-group) |
| | | | | gi|30684821 | gi|30684822 | *Arabidopsis thaliana* |
| IMQ25.2 | At1g27640 | gi|18396427 | gi|15217664 | gi|214833 | gi|214834 | *Xenopus laevis* |
| IMQ25.3 | At1g27650 | gi|30690022 | gi|15217666 | gi|30694150 | gi|15239067 | *Arabidopsis thaliana* |
| | | | | gi|42573546 | gi|42573547 | *Arabidopsis thaliana* |
| | | | | gi|13278054 | gi|13278055 | *Mus musculus* |
| | | | | gi|3850815 | gi|3850816 | *Oryza sativa* |
| IMQ25.4 | At1g27660 | gi|42562353 | gi|15217667 | gi|55769700 | gi|55769701 | *Oryza sativa* (japonica cultivar-group) |
| | | | | gi|58532108 | gi|21741062 | *Oryza sativa* (japonica cultivar-group) |
| | | | | gi|30696593 | gi|18407276 | *Arabidopsis thaliana* |
| IMQ26.1 | At1g34160 | gi|18399159 | gi|15218513 | gi|77552765 | gi|77554579 | *Oryza sativa* (japonica cultivar-group) |
| | | | | gi|54695179 | gi|54695180 | *Physcomitrella patens* |
| | | | | gi|45935109 | gi|45935146 | *Ipomoea trifida* |
| IMQ26.2 | At1g34170 | gi|79356538 | gi|79356539 | gi|42562509 | gi|42562510 | *Arabidopsis thaliana* |
| | | | | gi|18399246 | gi|15218610 | *Arabidopsis thaliana* |
| | | | | gi|18399735 | gi|15219635 | *Arabidopsis thaliana* |
| IMQ26.2 | At1g34170 | gi|79319168 | gi|79319169 | gi|42562509 | gi|42562510 | *Arabidopsis thaliana* |
| | | | | gi|18399735 | gi|15219635 | *Arabidopsis thaliana* |
| | | | | gi|18399246 | gi|15218610 | *Arabidopsis thaliana* |
| IMQ26.3 | At1g34180 | gi|30693015 | gi|18399166 | gi|30693016 | gi|18399168 | *Arabidopsis thaliana* |
| | | | | gi|21105741 | gi|21105742 | *Petunia* x *hybrida* |
| | | | | gi|21105739 | gi|21105740 | *Petunia* x *hybrida* |
| IMQ27.1 | At1g45160 | gi|30693922 | gi|15219539 | gi|30684701 | gi|30684702 | *Arabidopsis thaliana* |
| | | | | gi|50918242 | gi|50918243 | *Oryza sativa* (japonica cultivar-group) |
| | | | | gi|30697658 | gi|15241795 | *Arabidopsis thaliana* |
| IMQ27.2 | At1g45170 | gi|79360074 | gi|79360075 | gi|42562572 | gi|42562573 | *Arabidopsis thaliana* |
| | | | | gi|30694183 | gi|18422277 | *Arabidopsis thaliana* |
| | | | | gi|2764573 | gi|2764574 | *Pisum sativum* |
| IMQ27.3 | At1g45180 | gi|30693927 | gi|15220067 | gi|22327533 | gi|15239131 | *Arabidopsis thaliana* |
| | | | | gi|42569056 | gi|15226553 | *Arabidopsis thaliana* |
| | | | | gi|42570792 | gi|42570793 | *Arabidopsis thaliana* |
| | | | | gi|50929180 | gi|50929181 | *Oryza sativa* (japonica cultivar-group) |
| IMQ28.1 | At1g52140 | gi|30695146 | gi|18403871 | gi|30684002 | gi|15228179 | *Arabidopsis thaliana* |
| | | | | gi|12003387 | gi|12003388 | *Nicotiana tabacum* |
| | | | | gi|18417331 | gi|15233454 | *Arabidopsis thaliana* |
| IMQ28.2 | At1g52150 | gi|30695148 | gi|30695149 | gi|30695147 | gi|15218158 | *Arabidopsis thaliana* |
| | | | | gi|60327628 | gi|60327629 | *Populus trichocarpa* |
| | | | | gi|60327630 | gi|60327631 | *Populus trichocarpa* |
| IMQ28.2 | At1g52150 | gi|30695147 | gi|15218158 | gi|30695148 | gi|30695149 | *Arabidopsis thaliana* |
| | | | | gi|60327628 | gi|60327629 | *Populus trichocarpa* |
| | | | | gi|60327630 | gi|60327631 | *Populus trichocarpa* |

TABLE 3-continued

| 1. Gene alias | 2. Tair | 3. Nucleic Acid seq. GI# | 4. Polypeptide seq. GI# | 5. Orthologous Genes: Nucleic Acid/Polypeptide seq. GI# | | |
|---|---|---|---|---|---|---|
| | | | | Nucleic Acid GI# | Polypeptide GI# | Species |
| IMQ29.1 | At1g58410 | gi|18406289 | gi|15217959 | gi|18406284 | gi|15217957 | *Arabidopsis thaliana* |
| | | | | gi|42562806 | gi|15218003 | *Arabidopsis thaliana* |
| | | | | gi|79320239 | gi|79320240 | *Arabidopsis thaliana* |
| | | | | gi|79583692 | gi|79583693 | *Arabidopsis thaliana* |
| | | | | gi|18406280 | gi|15217954 | *Arabidopsis thaliana* |
| IMQ29.1 | At1g58410 | gi|79583692 | gi|79583693 | gi|42562806 | gi|15218003 | *Arabidopsis thaliana* |
| | | | | gi|79320239 | gi|79320240 | *Arabidopsis thaliana* |
| | | | | gi|30696274 | gi|22330316 | *Arabidopsis thaliana* |
| | | | | gi|22330305 | gi|22330306 | *Arabidopsis thaliana* |
| | | | | gi|30696285 | gi|30696286 | *Arabidopsis thaliana* |
| IMQ29.1 | At1g58410 | gi|79320239 | gi|79320240 | gi|42562806 | gi|15218003 | *Arabidopsis thaliana* |
| | | | | gi|79583692 | gi|79583693 | *Arabidopsis thaliana* |
| | | | | gi|30696274 | gi|22330316 | *Arabidopsis thaliana* |
| | | | | gi|22330305 | gi|22330306 | *Arabidopsis thaliana* |
| | | | | gi|30696285 | gi|30696286 | *Arabidopsis thaliana* |
| IMQ29.2 | At1g58420 | gi|30696259 | gi|18406291 | gi|42561890 | gi|18391115 | *Arabidopsis thaliana* |
| | | | | gi|50933830 | gi|50933831 | *Oryza sativa* (japonica cultivar-group) |
| | | | | gi|30698165 | gi|30698166 | *Arabidopsis thaliana* |
| IMQ29.3 | At1g58430 | gi|30696261 | gi|15217963 | gi|18402698 | gi|15225096 | *Arabidopsis thaliana* |
| | | | | gi|18402315 | gi|15227734 | *Arabidopsis thaliana* |
| | | | | gi|18402293 | gi|15227723 | *Arabidopsis thaliana* |
| IMQ30.1 | At1g75670 | gi|42572114 | gi|42572115 | gi|30699111 | gi|18410907 | *Arabidopsis thaliana* |
| | | | | gi|55741413 | gi|55741414 | *Oryza sativa* (japonica cultivar-group) |
| | | | | gi|34898425 | gi|34898426 | *Oryza sativa* (japonica cultivar-group) |
| | | | | gi|66828550 | gi|66828551 | *Dictyostelium discoideum* |
| IMQ30.1 | At1g75670 | gi|30699111 | gi|18410907 | gi|42572114 | gi|42572115 | *Arabidopsis thaliana* |
| | | | | gi|55741413 | gi|55741414 | *Oryza sativa* (japonica cultivar-group) |
| | | | | gi|34898425 | gi|34898426 | *Oryza sativa* (japonica cultivar-group) |
| | | | | gi|66828550 | gi|66828551 | *Dictyostelium discoideum* |
| IMQ30.2 | At1g75680 | gi|30699112 | gi|15222328 | gi|18394803 | gi|15223718 | *Arabidopsis thaliana* |
| | | | | gi|50725787 | gi|50725801 | *Oryza sativa* (japonica cultivar-group) |
| | | | | gi|46849602 | gi|53791781 | *Oryza sativa* (japonica cultivar-group) |
| IMQ30.3 | At1g75690 | gi|30699113 | gi|15222330 | gi|4732090 | gi|4732091 | *Zea mays* |
| | | | | gi|68433925 | gi|68433926 | *Danio rerio* |
| | | | | gi|13430173 | gi|13430174 | *Castanea sativa* |
| IMQ30.4 | At1g75700 | gi|18410915 | gi|15222332 | gi|18394804 | gi|18394805 | *Arabidopsis thaliana* |
| | | | | gi|30694082 | gi|18422223 | *Arabidopsis thaliana* |
| | | | | gi|50919650 | gi|50919651 | *Oryza sativa* (japonica cultivar-group) |
| IMQ31.1 | At1g77730 | gi|18411662 | gi|15217449 | gi|42572842 | gi|42572843 | *Arabidopsis thaliana* |
| | | | | gi|42570130 | gi|42570131 | *Arabidopsis thaliana* |
| | | | | gi|30680661 | gi|30680662 | *Arabidopsis thaliana* |
| IMQ31.2 | At1g77740 | gi|18411668 | gi|15217451 | gi|30687626 | gi|15219152 | *Arabidopsis thaliana* |
| | | | | gi|50918122 | gi|50918123 | *Oryza sativa* (japonica cultivar-group) |
| | | | | gi|8885991 | gi|8885992 | *Nicotiana rustica* |
| IMQ32.1 | At1g78100 | gi|30699306 | gi|18411823 | gi|42562235 | gi|15219845 | *Arabidopsis thaliana* |
| | | | | gi|18844754 | gi|55297493 | *Oryza sativa* (japonica cultivar-group) |
| | | | | gi|50931860 | gi|50931861 | *Oryza sativa* (japonica cultivar-group) |
| IMQ32.2 | At1g78110 | gi|42563307 | gi|15218227 | gi|18395090 | gi|15219847 | *Arabidopsis thaliana* |
| | | | | gi|50899793 | gi|50899794 | *Oryza sativa* (japonica cultivar-group) |
| | | | | gi|50912868 | gi|50912869 | *Oryza sativa* (japonica cultivar-group) |
| IMQ32.3 | At1g78120 | gi|18411834 | gi|15218228 | gi|42568787 | gi|15238361 | *Arabidopsis thaliana* |
| | | | | gi|18416178 | gi|15238058 | *Arabidopsis thaliana* |
| | | | | gi|37694873 | gi|72255609 | *Brassica rapa* |
| IMQ33.1 | At2g17036 | gi|18398290 | gi|18398291 | gi|42569091 | gi|18398287 | *Arabidopsis thaliana* |
| | | | | gi|18424314 | gi|15238601 | *Arabidopsis thaliana* |
| | | | | gi|42562951 | gi|42562952 | *Arabidopsis thaliana* |
| IMQ33.2 | At2g17040 | gi|30679858 | gi|18398293 | gi|66394519 | gi|66394520 | *Glycine max* |
| | | | | gi|54291125 | gi|54291129 | *Oryza sativa* (japonica cultivar-group) |
| | | | | gi|30678001 | gi|30678002 | *Arabidopsis thaliana* |
| IMQ34.1 | At2g31460 | gi|18402675 | gi|15225088 | gi|18401417 | gi|15225878 | *Arabidopsis thaliana* |
| | | | | gi|18402662 | gi|15224674 | *Arabidopsis thaliana* |
| | | | | gi|18408901 | gi|15229174 | *Arabidopsis thaliana* |
| IMQ34.2 | At2g31470 | gi|18402677 | gi|15225089 | gi|18403984 | gi|15229553 | *Arabidopsis thaliana* |
| | | | | gi|18424999 | gi|15239182 | *Arabidopsis thaliana* |
| | | | | gi|18408857 | gi|15229145 | *Arabidopsis thaliana* |

Example 2

Analysis of the *Arabidopsis* IMO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318.), PSORT (Nakai K, and Horton P, 1999, *Trends Biochem. Sci.* 24:34-6), and/or CLUSTAL (Thompson J D et al., 1994, *Nucleic Acids Res.* 22:4673-4680). Conserved domains for each protein are listed in column 8 of Table 2.

Example 3

To test whether over-expression of the genes identified in Tables 1-3 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value $\leq 0.05$. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

Example 4

To test whether over-expression of the genes identified in Tables 1-4 alter the seed composition phenotype, protein, digestible protein, oil, and fiber content in seeds from transgenic plants expressing these genes is compared with protein, digestible protein, oil and fiber content in seeds from non-transgenic control plants. Any one of the genes identified in Tables 1-4 is used to transform *Brassica napus* (canola). To do this, the genes are cloned into plant transformation vectors behind the strong constitutive CsVMV promoter and the seed specific phaseolin promoter. These constructs (which include a gene encoding a selection agent) are transformed into canola plants.

Transformation of canola is accomplished via *Agrobacterium*-mediated transformation. Seeds are surface-sterilized with 10% commercial bleach for 10 minutes and rinsed 3 times with sterile distilled water. The seeds are then placed on one half concentration of MS basal medium (Murashige and Skoog, *Physiol. Plant.* 15:473-497, 1962) and maintained under growth regime set at 25° C., and a photoperiod of 16 hrs light/8 hrs dark.

Hypocotyl segments (3-5 mm) are excised from 5-7 day old seedlings and placed on callus induction medium K1D1 (MS medium with 1 mg/l kinetin and 1 mg/l 2,4-D) for 3 days as pre-treatment. The segments are then transferred into a petri plate, treated with *Agrobacterium* Z7075 or LBA4404 strain containing pDAB721. The *Agrobacterium* is grown overnight at 28° C. in the dark on a shaker at 150 rpm and subsequently re-suspended in the culture medium.

After 30 minute treatment of the hypocotyl segments with *Agrobacterium*, these are placed back on the callus induction medium for 3 days. Following co-cultivation, the segments are placed on K1D1TC (callus induction medium containing 250 mg/l Carbenicillin and 300 mg/l Timentin) for one week of recovery. Alternately, the segments are placed directly on selection medium K1D1H1 (above medium with 1 mg/l selection agent, for example an herbicide). Carbenicillin and Timentin are antibiotics used to kill the *Agrobacterium*. The selection agent is used to allow the growth of the transformed cells.

Callus samples from independent events are tested by PCR. All the samples tested are positive for the presence of the transformed gene, whereas the non-transformed controls are negative. Callus samples are confirmed to express the appropriate protein as determined by ELISA.

Callused hypocotyl segments are then placed on B3Z1H1 (MS medium, 3 mg/l benzylamino purine, 1 mg/l Zeatin, 0.5 gm/l MES [2-(N-morpholino) ethane sulfonic acid], 5 mg/l silver nitrate, 1 mg/l selection agent, Carbenicillin and Timentin) shoot regeneration medium. After shoots start to regenerate (approximately 3 weeks), hypocotyl segments

TABLE 4

| 1. Gene | 2. TAIR | 3. Construct | 4. ANOVA Protein | 5. ANOVA Oil | 6. ANOVA Digestible Protein | 7. ANOVA Fiber | 8. Protein | 9. Oil | 10. Digestible Protein | 11. Fiber |
|---|---|---|---|---|---|---|---|---|---|---|
| IMQ25.3 | At1g27650 | CsVMV::At1g27650 | 0.000 | 0.052 | 0.010 | 0.003 | 89.8% | 103.7% | 95.9% | 105.1% |
| IMQ25.3 | At1g27650 | Pru::At1g27650 | 0.004 | 0.126 | 0.024 | 0.266 | 94.0% | 102.4% | 98.0% | 100.9% |
| IMQ29.1 | At1g58410 | CsVMV::At1g58410 | 0.012 | 0.005 | 0.279 | 0.775 | 104.4% | 96.7% | 101.2% | 99.7% |
| IMQ29.1 | At1g58410 | Pru::At1g58410 | 0.993 | 0.805 | 0.090 | 0.025 | 100.1% | 99.6% | 101.5% | 97.9% |
| IMQ29.2 | At1g58420 | CsVMV::At1g58420 | 0.000 | 0.011 | 0.689 | 0.145 | 95.93% | 103.73% | 99.60% | 98.73% |
| IMQ30.3 | At1g75690 | Pru::At1g75690 | 0.051 | 0.007 | 0.851 | 0.326 | 96.0% | 104.9% | 99.9% | 99.0% | along with the shoots are transferred to B3Z1H3 medium (MS medium, 3 mg/l benzylamino purine, 1 mg/l Zeatin, 0.5 gm/l MES [2-(N-morpholino) ethane sulfonic acid], 5 mg/l silver nitrate, 3 mg/l selection agent, Carbenicillin and Timentin) for 3 weeks.

Shoots are excised from the hypocotyl segments and transferred to shoot elongation medium MESH10 (MS, 0.5 gm/l MES, 10 mg/l selection agent, Carbenicillin, Timentin) for 2-4 weeks. The elongated shoots are cultured for root induction on MSI.1 (MS with 0.1 mg/l Indolebutyric acid). Once the plants have a well established root system, these are transplanted into soil. The plants are acclimated under controlled environmental conditions in the Conviron for 1-2 weeks before transfer to the greenhouse. The transformed T0 plants self-pollinate in the greenhouse to obtain T1 seed. Transgenic plants are selected at the T1 generation based on resistance to a selection agent. T2 seed (from T1 plants) is harvested and sown in soil. T2 plants are grown to maturity, allowed to self-fertilize and set seed. T3 seed (from the T2 plants) is harvested in bulk for each line. Seed oil, protein, digestible protein, and fiber values are measured as discussed in Example 1.

It is claimed:

1. A method of producing an improved meal quality phenotype in a plant, said method comprising:
   a) introducing into progenitor cells of the plant a plant transformation vector comprising a nucleotide sequence that encodes an IMQ polypeptide comprising the amino acid sequence set forth in SEQ ID NO: 70;
   b) growing the transformed progenitor cells to produce a transgenic plant, wherein the nucleotide sequence is expressed, and the transgenic plant exhibits an improved meal quality phenotype relative to control plants; and
   c) measuring the improved meal quality phenotype in the transgenic plant relative to the control plants,
   thereby producing the improved meal quality phenotype in the plant.

2. The method of claim 1, wherein the IMQ polypeptide is encoded by a nucleic acid comprising the sequence set forth in SEQ ID NO: 69.

3. A method of generating a plant having an improved meal quality phenotype comprising:
   identifying a plant that has an allele in its IMQ gene, wherein the IMQ gene comprises the nucleic acid sequence set forth as SEQ ID NO: 69, which allele results in improved meal quality phenotype, compared to a control plant lacking the allele;
   generating progeny of said identified plant, wherein the generated progeny inherit the allele and have the improved meal quality phenotype; and
   measuring the improved meal quality phenotype in the progeny comprising the allele relative to the control plant lacking the allele,
   thereby generating a plant having an improved meal quality phenotype.

4. The method of claim 3 that employs candidate gene/QTL methodology to identify the plant.

5. The method of claim 3 that employs TILLING methodology to identify the plant.

6. The method of claim 1, wherein the IMQ polypeptide consists of the amino acid sequence set forth in SEQ ID NO: 70.

7. The method of claim 1, wherein the nucleotide sequence is operably linked to a constitutive, inducible, or regulatable promoter sequence.

* * * * *

SEQUENCE LISTING

```
<160> NUMBER OF SEQ ID NOS: 100

<210> SEQ ID NO 1
<211> LENGTH: 2888
<212> TYPE: DNA
<213> ORGANISM: Arabidopsis thaliana

<400> SEQUENCE: 1
agtgtccctc tcgcaccatt taatttcatt gcaccctctc aattctctct gtcattactc      60
tctcatctct cttcctccaa gatttgcacc tacctttcaa accttttgct cgccaacaaa     120
accgcgcttc acaaaaccat cagcggtttt ccgagaaaca aatctcagac cagacaccgc     180
tctactcttc tctctctctc cctctagggt ttcgtcgctt cttcctatat cccagttcag     240
agatgaaacc ttcaagaaaa caataaagag gaaagattaa agggtttgct ttcagtttcc     300
ggagtataag aaaagatgtt cgagccaaat atgctgcttg cggctatgaa caacgcagac     360
agcaataacc acaactacaa ccatgaagac aacaataatg aaggatttct tcgggacgat     420
gaattcgaca gtccgaatac taaatcggga agtgagaatc aagaaggagg atcaggaaac     480
gaccaagatc ctcttcatcc taacaagaag aaacgatatc atcgacacac ccaacttcag     540
atccaggaga tggaagcgtt cttcaaagag tgtcctcacc cagatgacaa gcaaaggaaa     600
cagctaagcc gtgaattgaa tttggaacct cttcaggtca aattctggtt ccaaaacaaa     660
cgtacccaaa tgaagaatca tcacgagcgg catgagaact cacatcttcg ggcggagaac     720
gaaaagcttc gaaacgacaa cctaagatat cgagaggctc ttgcaaatgc ttcgtgtcct     780
aattgtggtg gtccaacagc tatcggagaa atgtcattcg acgaacacca actccgtctc     840
gaaaatgctc gattaaggga agatcgac cgtatatccg caatcgcagc taaatacgta     900
ggcaagccag tctcaaacta tccacttatg tctcctcctc ctcttcctcc acgtccacta     960
gaactcgcca tgggaaatat tggaggagaa gctatggaa acaatccaaa cgatctcctt    1020
aagtccatca ctgcaccaac agaatctgac aaacctgtca tcatcgactt atccgtggct    1080
gcaatggaag agctcatgag gatggttcaa gtagacgagc ctctgtggaa gagtttggtt    1140
ttagacgaag aagaatatgc aaggaccttt cctagaggga tcggacctag accggctgga    1200
tatagatcag aagcttcgcg agaaagcgcg gttgtgatca tgaatcatgt taacatcgtt    1260
gagattctca tggatgtgaa tcaatggtcg acgattttcg cggggatggt ttctagagca    1320
atgacattag cggtttttatc gacaggagtt gcaggaaact ataatggagc tcttcaagtg    1380
atgagtgcag agtttcaagt tccatctcca ttagtcccaa cacgtgaaac ctatttcgca    1440
cgttactgta aacaacaagg agatggttcg tgggcggttg tcgatatttc gttggatagt    1500
ctccaaccaa atccccggc tagatgcagg cggcgagctc caggatgttt gattcaagaa    1560
ttgccaaatg gatattctaa ggtgacttgg gtggagcatg tggaagttga tgacagagga    1620
```

```
gttcataact tatacaaaca catggttagt actggtcatg cctttggtgc taaacgctgg    1680
gtagccattc ttgaccgcca atgcgagcgg ttagctagtg tcatggctac aaacatttcc    1740
tctggagaag ttgcgtgat aaccaaccaa gaagggagga ggagtatgct gaaattggca    1800
gagcggatgg ttataagctt ttgtgcagga gtgagtgctt caaccgctca cacgtggact    1860
acattgtccg gtacaggagc tgaagatgtt agagtgatga ctaggaagag tgtggatgat    1920
ccaggaaggc ctcctggtat tgttcttagt gcagccactt cttttttggat ccctgttcct    1980 ccaaagcgag tctttgactt cctcagagac gagaattcaa gaaatgagtg ggatattctg    2040
tctaatggag gagttgtgca agaaatggca catattgcta acgggaggga taccggaaac    2100
tgtgtttctc ttcttcgggt aaatagtgca aactctagcc agagcaatat gctgatccta    2160
caagagagct gcactgatcc tacagcttcc tttgtgatct atgctccagt cgatattgta    2220
gctatgaaca tagtgcttaa tggaggtgat ccagactatg tggctctgct tccatcaggt    2280
tttgctattc ttcctgatgg taatgccaat agtggagccc ctggaggaga tggagggtcg    2340
ctcttgactg ttgcttttca gattctggtt gactcagttc ctacggctaa gctgtctctt    2400
ggctctgttg caactgtcaa caatctaata gcttgcactg ttgagagaat caaagcttca    2460
atgtcttgtg agactgcttg aaaaccatcc attaggaaat aacaaaatgg tgatgatgga    2520
aaaaagagag agatttcagt ttgagaaaag cggaggagtc aagatcgaac ctcacaagag    2580
aataccattg agtgtttgtt agtgttaagt tttggtctgc ttatttgatg aaactaagca    2640
gtgaaaaact ttttacttga aagtgaatat gtagatggtt ttacgaggtt cgggaatttg    2700
acttcccctg tcacatactg aattagacaa aaacaaaaac taggttagaa agaatgcttt    2760
cggatttctt tttgtgttac agttactgtt tttctttcct tcttgtggtt agatggacca    2820
tcatcaggaa tttggagttt gtctttcttt tgtataaata tcttatacaa gtattttggt    2880
acttttgt                                                             2888
```

```
<210> SEQ ID NO 2
<211> LENGTH: 721
<212> TYPE: PRT
<213> ORGANISM: Arabidopsis thaliana

<400> SEQUENCE: 2

Met Phe Glu Pro Asn Met Leu Leu Ala Ala Met Asn Asn Ala Asp Ser
1               5                   10                  15

Asn Asn His Asn Tyr Asn His Glu Asp Asn Asn Asn Glu Gly Phe Leu
            20                  25                  30

Arg Asp Asp Glu Phe Asp Ser Pro Asn Thr Lys Ser Gly Ser Glu Asn
        35                  40                  45

Gln Glu Gly Gly Ser Gly Asn Asp Gln Asp Pro Leu His Pro Asn Lys
    50                  55                  60

Lys Lys Arg Tyr His Arg His Thr Gln Leu Gln Ile Gln Glu Met Glu
65                  70                  75                  80

Ala Phe Phe Lys Glu Cys Pro His Pro Asp Asp Lys Gln Arg Lys Gln
                85                  90                  95

Leu Ser Arg Glu Leu Asn Leu Glu Pro Leu Gln Val Lys Phe Trp Phe
            100                 105                 110

Gln Asn Lys Arg Thr Gln Met Lys Asn His His Glu Arg His Glu Asn
        115                 120                 125

Ser His Leu Arg Ala Glu Asn Glu Lys Leu Arg Asn Asp Asn Leu Arg
    130                 135                 140
```

-continued

```
Tyr Arg Glu Ala Leu Ala Asn Ala Ser Cys Pro Asn Cys Gly Gly Pro
145                 150                 155                 160

Thr Ala Ile Gly Glu Met Ser Phe Asp Glu His Gln Leu Arg Leu Glu
            165                 170                 175

Asn Ala Arg Leu Arg Glu Glu Ile Asp Arg Ile Ser Ala Ile Ala Ala
        180                 185                 190

Lys Tyr Val Gly Lys Pro Val Ser Asn Tyr Pro Leu Met Ser Pro Pro
    195                 200                 205

Pro Leu Pro Pro Arg Pro Leu Glu Leu Ala Met Gly Asn Ile Gly Gly
210                 215                 220

Glu Ala Tyr Gly Asn Asn Pro Asn Asp Leu Leu Lys Ser Ile Thr Ala
225                 230                 235                 240

Pro Thr Glu Ser Asp Lys Pro Val Ile Ile Asp Leu Ser Val Ala Ala
            245                 250                 255

Met Glu Glu Leu Met Arg Met Val Gln Val Asp Glu Pro Leu Trp Lys
            260                 265                 270

Ser Leu Val Leu Asp Glu Glu Tyr Ala Arg Thr Phe Pro Arg Gly
        275                 280                 285

Ile Gly Pro Arg Pro Ala Gly Tyr Arg Ser Glu Ala Ser Arg Glu Ser
290                 295                 300

Ala Val Val Ile Met Asn His Val Asn Ile Val Glu Ile Leu Met Asp
305                 310                 315                 320

Val Asn Gln Trp Ser Thr Ile Phe Ala Gly Met Val Ser Arg Ala Met
            325                 330                 335

Thr Leu Ala Val Leu Ser Thr Gly Val Ala Gly Asn Tyr Asn Gly Ala
            340                 345                 350

Leu Gln Val Met Ser Ala Glu Phe Gln Val Pro Ser Pro Leu Val Pro
        355                 360                 365

Thr Arg Glu Thr Tyr Phe Ala Arg Tyr Cys Lys Gln Gln Gly Asp Gly
        370                 375                 380

Ser Trp Ala Val Val Asp Ile Ser Leu Asp Ser Leu Gln Pro Asn Pro
385                 390                 395                 400

Pro Ala Arg Cys Arg Arg Arg Ala Ser Gly Cys Leu Ile Gln Glu Leu
            405                 410                 415

Pro Asn Gly Tyr Ser Lys Val Thr Trp Val Glu His Val Glu Val Asp
        420                 425                 430

Asp Arg Gly Val His Asn Leu Tyr Lys His Met Val Ser Thr Gly His
        435                 440                 445

Ala Phe Gly Ala Lys Arg Trp Val Ala Ile Leu Asp Arg Gln Cys Glu
    450                 455                 460

Arg Leu Ala Ser Val Met Ala Thr Asn Ile Ser Ser Gly Glu Val Gly
465                 470                 475                 480

Val Ile Thr Asn Gln Glu Gly Arg Arg Ser Met Leu Lys Leu Ala Glu
            485                 490                 495

Arg Met Val Ile Ser Phe Cys Ala Gly Val Ser Ala Thr Ala His
        500                 505                 510

Thr Trp Thr Thr Leu Ser Gly Thr Gly Ala Glu Asp Val Arg Val Met
        515                 520                 525

Thr Arg Lys Ser Val Asp Asp Pro Gly Arg Pro Gly Ile Val Leu
    530                 535                 540

Ser Ala Ala Thr Ser Phe Trp Ile Pro Val Pro Pro Lys Arg Val Phe
545                 550                 555                 560

Asp Phe Leu Arg Asp Glu Asn Ser Arg Asn Glu Trp Asp Ile Leu Ser
```

```
                      565                 570                 575
Asn Gly Gly Val Val Gln Glu Met Ala His Ile Ala Asn Gly Arg Asp
                580                 585                 590

Thr Gly Asn Cys Val Ser Leu Leu Arg Val Asn Ser Ala Asn Ser Ser
            595                 600                 605

Gln Ser Asn Met Leu Ile Leu Gln Glu Ser Cys Thr Asp Pro Thr Ala
        610                 615                 620

Ser Phe Val Ile Tyr Ala Pro Val Asp Ile Val Ala Met Asn Ile Val
625                 630                 635                 640

Leu Asn Gly Gly Asp Pro Asp Tyr Val Ala Leu Leu Pro Ser Gly Phe
                645                 650                 655

Ala Ile Leu Pro Asp Gly Asn Ala Asn Ser Gly Ala Pro Gly Gly Asp
            660                 665                 670

Gly Gly Ser Leu Leu Thr Val Ala Phe Gln Ile Leu Val Asp Ser Val
        675                 680                 685

Pro Thr Ala Lys Leu Ser Leu Gly Ser Val Ala Thr Val Asn Asn Leu
    690                 695                 700

Ile Ala Cys Thr Val Glu Arg Ile Lys Ala Ser Met Ser Cys Glu Thr
705                 710                 715                 720

Ala

<210> SEQ ID NO 3
<211> LENGTH: 2679
<212> TYPE: DNA
<213> ORGANISM: Arabidopsis thaliana

<400> SEQUENCE: 3
```

| | | | | | |
|---|---|---|---|---|---|
| gtatgatctt | caagaagaaa | gataaacgac | tccgaagaaa | gatttaagtt | attgttgttc | 60 |
| atacaaaaag | aagggtttgc | tttcagtttc | cggagtataa | gaaaagatgt | tcgagccaaa | 120 |
| tatgctgctt | gcggctatga | acaacgcaga | cagcaataac | cacaactaca | accatgaaga | 180 |
| caacaataat | gaaggatttc | ttcgggacga | tgaattcgac | agtccgaata | ctaaatcggg | 240 |
| aagtgagaat | caagaaggag | gatcaggaaa | cgaccaagat | cctcttcatc | ctaacaagaa | 300 |
| gaaacgatat | catcgacaca | cccaacttca | gatccaggag | atggaagcgt | tcttcaaaga | 360 |
| gtgtcctcac | ccagatgaca | agcaaaggaa | acagctaagc | cgtgaattga | atttggaacc | 420 |
| tcttcaggtc | aaattctggt | tccaaaacaa | acgtacccaa | atgaagaatc | atcacgagcg | 480 |
| gcatgagaac | tcacatcttc | gggcggagaa | cgaaaagctt | cgaaacgaca | acctaagata | 540 |
| tcgagaggct | cttgcaaatg | cttcgtgtcc | taattgtggt | ggtccaacag | ctatcggaga | 600 |
| aatgtcattc | gacgaacacc | aactccgtct | cgaaaatgct | cgattaaggg | aagagatcga | 660 |
| ccgtatatcc | gcaatcgcag | ctaaatacgt | aggcaagcca | gtctcaaaact | atccacttat | 720 |
| gtctcctcct | cctcttcctc | cacgtccact | agaactcgcc | atgggaaata | ttggaggaga | 780 |
| agcttatgga | aacaatccaa | acgatctcct | taagtccatc | actgcaccaa | cagaatctga | 840 |
| caaacctgtc | atcatcgact | atccgtggc | tgcaatggaa | gagctcatga | ggatggttca | 900 |
| agtagacgag | cctctgtgga | agagtttggt | tttagacgaa | gagaatatg | caaggacctt | 960 |
| tcctagaggg | atcggaccta | gaccggctgg | atatagatca | gaagcttcgc | gagaaagcgc | 1020 |
| ggttgtgatc | atgaatcatg | ttaacatcgt | tgagattctc | atggatgtga | atcaatggtc | 1080 |
| gacgattttc | gcggggatgg | tttctagagc | aatgacatta | gcggttttat | cgacaggagt | 1140 |
| tgcaggaaac | tataatggag | ctcttcaagt | gatgagtgca | gagtttcaag | ttccatctcc | 1200 |

```
attagtccca acacgtgaaa cctatttcgc acgttactgt aaacaacaag gagatggttc   1260
gtgggcggtt gtcgatattt cgttggatag tctccaacca aatccccgg  ctagatgcag   1320
gcggcgagct tcaggatgtt tgattcaaga attgccaaat ggatattcta aggtgacttg   1380
ggtggagcat gtggaagttg atgacagagg agttcataac ttatacaaac acatggttag   1440
tactggtcat gccttttggtg ctaaacgctg ggtagccatt cttgaccgcc aatgcgagcg   1500
gttagctagt gtcatggcta caaacatttc ctctggagaa gttggcgtga taaccaacca   1560
agaagggagg aggagtatgc tgaaattggc agagcggatg ttataagct  tttgtgcagg   1620
agtgagtgct tcaaccgctc acacgtggac tacattgtcc ggtacaggag ctgaagatgt   1680
tagagtgatg actaggaaga gtgtggatga tccaggaagg cctcctggta ttgttcttag   1740
tgcagccact tcttttttgga tccctgttcc tccaaagcga gtctttgact tcctcagaga   1800
cgagaattca agaaatgagt gggatattct gtctaatgga ggagttgtgc aagaaatggc   1860
acatattgct aacgggaggg ataccggaaa ctgtgtttct cttcttcggg taaatagtgc   1920
aaactctagc cagagcaata tgctgatcct acaagagagc tgcactgatc ctacagcttc   1980
ctttgtgatc tatgctccag tcgatattgt agctatgaac atagtgctta atggaggtga   2040
tccagactat gtggctctgc ttccatcagg ttttgctatt cttcctgatg gtaatgccaa   2100
tagtggagcc cctggaggag atggagggtc gctcttgact gttgctttttc agattctggt   2160
tgactcagtt cctacggcta agctgtctct ggctctgtt  gcaactgtca acaatctaat   2220
agcttgcact gttgagagaa tcaaagcttc aatgtcttgt gagactgctt gaaaaccatc   2280
cattaggaaa taacaaaatg gtgatgatgg aaaaaagaga gagatttcag tttgagaaaa   2340
gcggaggagt caagatcgaa cctcacaaga gaataccatt gagtgtttgt tagtgttaag   2400
ttttggtctg cttatttgat gaaactaagc agtgaaaaac tttttacttg aaagtgaata   2460
tgtagatggt tttacgaggt tcgggaattt gacttcccct gtcacatact gaattagaca   2520
aaaacaaaaa ctaggttaga aagaatgctt tcggatttct ttttgtgtta cagttactgt   2580
ttttctttcc ttcttgtggt tagatggacc atcatcagga atttggagtt tgtctttctt   2640
ttgtataaat atcttataca agtattttgg tacttttgt                          2679
```

<210> SEQ ID NO 4
<211> LENGTH: 721
<212> TYPE: PRT
<213> ORGANISM: Arabidopsis thaliana

<400> SEQUENCE: 4

```
Met Phe Glu Pro Asn Met Leu Leu Ala Ala Met Asn Asn Ala Asp Ser
1               5                   10                  15

Asn Asn His Asn Tyr Asn His Glu Asp Asn Asn Asn Glu Gly Phe Leu
            20                  25                  30

Arg Asp Asp Glu Phe Asp Ser Pro Asn Thr Lys Ser Gly Ser Glu Asn
        35                  40                  45

Gln Glu Gly Gly Ser Gly Asn Asp Gln Asp Pro Leu His Pro Asn Lys
    50                  55                  60

Lys Lys Arg Tyr His Arg His Thr Gln Leu Gln Ile Gln Glu Met Glu
65                  70                  75                  80

Ala Phe Phe Lys Glu Cys Pro His Pro Asp Asp Lys Gln Arg Lys Gln
                85                  90                  95

Leu Ser Arg Glu Leu Asn Leu Glu Pro Leu Gln Val Lys Phe Trp Phe
            100                 105                 110
```

```
Gln Asn Lys Arg Thr Gln Met Lys Asn His His Glu Arg His Glu Asn
            115                 120                 125
Ser His Leu Arg Ala Glu Asn Glu Lys Leu Arg Asn Asp Asn Leu Arg
    130                 135                 140
Tyr Arg Glu Ala Leu Ala Asn Ala Ser Cys Pro Asn Cys Gly Gly Pro
145                 150                 155                 160
Thr Ala Ile Gly Glu Met Ser Phe Asp Glu His Gln Leu Arg Leu Glu
                165                 170                 175
Asn Ala Arg Leu Arg Glu Glu Ile Asp Arg Ile Ser Ala Ile Ala Ala
            180                 185                 190
Lys Tyr Val Gly Lys Pro Val Ser Asn Tyr Pro Leu Met Ser Pro Pro
    195                 200                 205
Pro Leu Pro Pro Arg Pro Leu Glu Leu Ala Met Gly Asn Ile Gly Gly
210                 215                 220
Glu Ala Tyr Gly Asn Asn Pro Asn Asp Leu Leu Lys Ser Ile Thr Ala
225                 230                 235                 240
Pro Thr Glu Ser Asp Lys Pro Val Ile Ile Asp Leu Ser Val Ala Ala
                245                 250                 255
Met Glu Glu Leu Met Arg Met Val Gln Val Asp Glu Pro Leu Trp Lys
            260                 265                 270
Ser Leu Val Leu Asp Glu Glu Tyr Ala Arg Thr Phe Pro Arg Gly
    275                 280                 285
Ile Gly Pro Arg Pro Ala Gly Tyr Arg Ser Glu Ala Ser Arg Glu Ser
            290                 295                 300
Ala Val Val Ile Met Asn His Val Asn Ile Val Glu Ile Leu Met Asp
305                 310                 315                 320
Val Asn Gln Trp Ser Thr Ile Phe Ala Gly Met Val Ser Arg Ala Met
                325                 330                 335
Thr Leu Ala Val Leu Ser Thr Gly Val Ala Gly Asn Tyr Asn Gly Ala
            340                 345                 350
Leu Gln Val Met Ser Ala Glu Phe Gln Val Pro Ser Pro Leu Val Pro
    355                 360                 365
Thr Arg Glu Thr Tyr Phe Ala Arg Tyr Cys Lys Gln Gln Gly Asp Gly
370                 375                 380
Ser Trp Ala Val Val Asp Ile Ser Leu Asp Ser Leu Gln Pro Asn Pro
385                 390                 395                 400
Pro Ala Arg Cys Arg Arg Ala Ser Gly Cys Leu Ile Gln Glu Leu
                405                 410                 415
Pro Asn Gly Tyr Ser Lys Val Thr Trp Val Glu His Val Glu Val Asp
            420                 425                 430
Asp Arg Gly Val His Asn Leu Tyr Lys His Met Val Ser Thr Gly His
    435                 440                 445
Ala Phe Gly Ala Lys Arg Trp Val Ala Ile Leu Asp Arg Gln Cys Glu
450                 455                 460
Arg Leu Ala Ser Val Met Ala Thr Asn Ile Ser Ser Gly Glu Val Gly
465                 470                 475                 480
Val Ile Thr Asn Gln Glu Gly Arg Arg Ser Met Leu Lys Leu Ala Glu
                485                 490                 495
Arg Met Val Ile Ser Phe Cys Ala Gly Val Ser Ala Ser Thr Ala His
            500                 505                 510
Thr Trp Thr Thr Leu Ser Gly Thr Gly Ala Glu Asp Val Arg Val Met
    515                 520                 525
Thr Arg Lys Ser Val Asp Asp Pro Gly Arg Pro Pro Gly Ile Val Leu
```

Ser Ala Ala Thr Ser Phe Trp Ile Pro Val Pro Lys Arg Val Phe
545                 550                 555                 560

Asp Phe Leu Arg Asp Glu Asn Ser Arg Asn Glu Trp Asp Ile Leu Ser
                565                 570                 575

Asn Gly Gly Val Val Gln Glu Met Ala His Ile Ala Asn Gly Arg Asp
            580                 585                 590

Thr Gly Asn Cys Val Ser Leu Leu Arg Val Asn Ser Ala Asn Ser Ser
        595                 600                 605

Gln Ser Asn Met Leu Ile Leu Gln Glu Ser Cys Thr Asp Pro Thr Ala
    610                 615                 620

Ser Phe Val Ile Tyr Ala Pro Val Asp Ile Val Ala Met Asn Ile Val
625                 630                 635                 640

Leu Asn Gly Gly Asp Pro Asp Tyr Val Ala Leu Leu Pro Ser Gly Phe
                645                 650                 655

Ala Ile Leu Pro Asp Gly Asn Ala Asn Ser Gly Ala Pro Gly Gly Asp
            660                 665                 670

Gly Gly Ser Leu Leu Thr Val Ala Phe Gln Ile Leu Val Asp Ser Val
        675                 680                 685

Pro Thr Ala Lys Leu Ser Leu Gly Ser Val Ala Thr Val Asn Asn Leu
    690                 695                 700

Ile Ala Cys Thr Val Glu Arg Ile Lys Ala Ser Met Ser Cys Glu Thr
705                 710                 715                 720

Ala

<210> SEQ ID NO 5
<211> LENGTH: 1258
<212> TYPE: DNA
<213> ORGANISM: Arabidopsis thaliana

<400> SEQUENCE: 5
atctccaaag ctcgttctca ccttacttgg caaacactca acgaagaaag gagagagaga     60
cggtaatggc gatcaagaac attctcgccc ttgtggttct tcttagcgtg gttggagttt    120
ctgtcgccat tccacagttg cttgacctcg actactaccg gtctaagtgt cccaaggcag    180
aggaaattgt tcgtggtgtc acagtacaat atgtttctcg ccagaaaacc cttgccgcta    240
aacttctaag gatgcatttc catgattgtt tcgtcagagg atgtgatggt tccgttcttc    300
tgaaatctgc aaagaatgat gcggaaagag acgctgtccc caacctgacc ctgaaaggtt    360
atgaagtggt ggatgcggcc aagacagcgc tggagaggaa gtgtcctaat ctcatttctt    420
gcgctgatgt tcttgccttg gtcgccagag atgccgtggc agtgatcggg ggaccatggt    480
ggccggttcc attgggccgc agggatggac gcatctcgaa attgaacgat gcattgctaa    540
atttaccatc tcctttcgcc gacataaaga cgctgaagaa gaactttgcc aacaagggtc    600
ttaacgctaa agaccttgtg gttctctcag ggggtcacac cattggaatc tctagttgcg    660
ctctcgtcaa cagtcgtctc tacaacttca caggaaaggg cgattctgac ccatccatga    720
accctagcta cgtgagggaa ttgaagagaa agtgcccgcc tacagatttc agaacctcac    780
tgaacatgga cccaggcagt gcgttgacat tcgacactca ctacttcaag gtcgtggctc    840
agaagaaagg gctcttcaca tctgactcta cgcttctcga tgacattgag accaaaaact    900
acgttcagac tcaggccatt ctccctcctg tgttttcttc tttcaataaa gatttctccg    960
attccatggt caaacttggt ttcgtccaaa ttcttaccgg caaaaatggt gagatcagga   1020

```
agagatgcgc ttccctaac taatttggat cgatcagacc gggtttcgga tgattttgag    1080
tctacacgtt tttctctgct tatttctttt cttttcttt tttctttcac ggaagtttga    1140
gctttggtgt tgtcttcttc tgtttcttcc atgaataatt gttttttgtt gagtaacttt    1200
acatttgtat tctttacggt gactgtgttt tgtaatggaa aaagtttgtt tcgaattc     1258
```

```
<210> SEQ ID NO 6
<211> LENGTH: 325
<212> TYPE: PRT
<213> ORGANISM: Arabidopsis thaliana

<400> SEQUENCE: 6

Met Ala Ile Lys Asn Ile Leu Ala Leu Val Val Leu Leu Ser Val Val
1               5                   10                  15

Gly Val Ser Val Ala Ile Pro Gln Leu Leu Asp Leu Asp Tyr Tyr Arg
            20                  25                  30

Ser Lys Cys Pro Lys Ala Glu Glu Ile Val Arg Gly Val Thr Val Gln
        35                  40                  45

Tyr Val Ser Arg Gln Lys Thr Leu Ala Ala Lys Leu Leu Arg Met His
    50                  55                  60

Phe His Asp Cys Phe Val Arg Gly Cys Asp Gly Ser Val Leu Leu Lys
65                  70                  75                  80

Ser Ala Lys Asn Asp Ala Glu Arg Asp Ala Val Pro Asn Leu Thr Leu
                85                  90                  95

Lys Gly Tyr Glu Val Val Asp Ala Ala Lys Thr Ala Leu Glu Arg Lys
            100                 105                 110

Cys Pro Asn Leu Ile Ser Cys Ala Asp Val Leu Ala Leu Val Ala Arg
        115                 120                 125

Asp Ala Val Ala Val Ile Gly Gly Pro Trp Trp Pro Val Pro Leu Gly
    130                 135                 140

Arg Arg Asp Gly Arg Ile Ser Lys Leu Asn Asp Ala Leu Leu Asn Leu
145                 150                 155                 160

Pro Ser Pro Phe Ala Asp Ile Lys Thr Leu Lys Lys Asn Phe Ala Asn
                165                 170                 175

Lys Gly Leu Asn Ala Lys Asp Leu Val Val Leu Ser Gly Gly His Thr
            180                 185                 190

Ile Gly Ile Ser Ser Cys Ala Leu Val Asn Ser Arg Leu Tyr Asn Phe
        195                 200                 205

Thr Gly Lys Gly Asp Ser Asp Pro Ser Met Asn Pro Ser Tyr Val Arg
    210                 215                 220

Glu Leu Lys Arg Lys Cys Pro Pro Thr Asp Phe Arg Thr Ser Leu Asn
225                 230                 235                 240

Met Asp Pro Gly Ser Ala Leu Thr Phe Asp Thr His Tyr Phe Lys Val
                245                 250                 255

Val Ala Gln Lys Lys Gly Leu Phe Thr Ser Asp Ser Thr Leu Leu Asp
            260                 265                 270

Asp Ile Glu Thr Lys Asn Tyr Val Gln Thr Gln Ala Ile Leu Pro Pro
        275                 280                 285

Val Phe Ser Ser Phe Asn Lys Asp Phe Ser Asp Ser Met Val Lys Leu
    290                 295                 300

Gly Phe Val Gln Ile Leu Thr Gly Lys Asn Gly Glu Ile Arg Lys Arg
305                 310                 315                 320

Cys Ala Phe Pro Asn
                325
```

<210> SEQ ID NO 7
<211> LENGTH: 1346
<212> TYPE: DNA
<213> ORGANISM: Arabidopsis thaliana

<400> SEQUENCE: 7

```
ccttacttgg caaacactca acgaagaaag gagagagaga cggtaatggc gatcaagaac      60
attctcgccc ttgtggttct tcttagcgtg gttggagttt ctgtcgccat tccacagttg     120
cttgacctcg actactaccg gtctaagtgt cccaaggcag aggaaattgt tcgtggtgtc     180
acagtacaat atgtttctcg ccagaaaacc cttgccgcta aacttctaag gatgcatttc     240
catgattgtt tcgtcagagg atgtgatggt tccgttcttc tgaaatctgc aaagaatgat     300
gcggaaagag acgctgtccc caacctgacc ctgaaaggtt atgaagtggt ggatgcggcc     360
aagacagcgc tggagaggaa gtgtcctaat ctcatttctt gcgctgatgt tcttgccttg     420
gtcgccagag atgccgtggc agtgatcggg ggaccatggt ggccggttcc attgggccgc     480
agggatggac gcatctcgaa attgaacgat gcattgctaa atttaccatc tcctttcgcc     540
gacataaaga cgctgaagaa gaactttgcc aacaagggtc ttaacgctaa agaccttgtg     600
gttctctcag ggggtcacac cattggaatc tctagttgcg ctctcgtcaa cagtcgtctc     660
tacaacttca caggaaaggg cgattctgac ccatccatga accctagcta cgtgagggaa     720
ttgaagagaa agtgcccgcc tacagatttc agaacctcac tgaacatgga cccaggcagt     780
gcgttgacat cgacactca ctacttcaag gtcgtggctc agaagaaagg gctcttcaca     840
tctgactcta cgcttctcga tgacattgag accaaaaact acgttcagac tcaggccatt     900
ctccctcctg tgttttcttc tttcaataaa gatttctccg attccatggt caaacttggt     960
ttcgtccaaa ttcttaccgg caaaaatggt gagatcagga agagatgcgc cttccctaac    1020
taatttggat cgatcagacc gggtttcgga tgattttgag tctacacgtt tttctctgct    1080
tattttcttt cttttctttt tttctttcac ggaagtttga gctttggtgt tgtcttcttc    1140
tgtttcttcc atgaataatt gttttttgtt gagtaacttt acatttgtat tctttacggt    1200
gactgtgttt tgtaatggaa aaagtttgtt tcgaattcat ccgttaaacg taaacctaaa    1260
ttaaacaaaa attataattg gaaagcaaaa cattttgtaa gcttcgtggt gttttttacta   1320
tgaattaata tttatgtttg tttttc                                         1346
```

<210> SEQ ID NO 8
<211> LENGTH: 325
<212> TYPE: PRT
<213> ORGANISM: Arabidopsis thaliana

<400> SEQUENCE: 8

```
Met Ala Ile Lys Asn Ile Leu Ala Leu Val Val Leu Leu Ser Val Val
1               5                   10                  15

Gly Val Ser Val Ala Ile Pro Gln Leu Leu Asp Leu Asp Tyr Tyr Arg
            20                  25                  30

Ser Lys Cys Pro Lys Ala Glu Glu Ile Val Arg Gly Val Thr Val Gln
        35                  40                  45

Tyr Val Ser Arg Gln Lys Thr Leu Ala Ala Lys Leu Leu Arg Met His
    50                  55                  60

Phe His Asp Cys Phe Val Arg Gly Cys Asp Gly Ser Val Leu Leu Lys
65                  70                  75                  80

Ser Ala Lys Asn Asp Ala Glu Arg Asp Ala Val Pro Asn Leu Thr Leu
                85                  90                  95
```

Lys Gly Tyr Glu Val Val Asp Ala Ala Lys Thr Ala Leu Glu Arg Lys
            100                 105                 110

Cys Pro Asn Leu Ile Ser Cys Ala Asp Val Leu Ala Leu Val Ala Arg
        115                 120                 125

Asp Ala Val Ala Val Ile Gly Gly Pro Trp Trp Pro Val Pro Leu Gly
130                 135                 140

Arg Arg Asp Gly Arg Ile Ser Lys Leu Asn Asp Ala Leu Leu Asn Leu
145                 150                 155                 160

Pro Ser Pro Phe Ala Asp Ile Lys Thr Leu Lys Asn Phe Ala Asn
            165                 170                 175

Lys Gly Leu Asn Ala Lys Asp Leu Val Val Leu Ser Gly Gly His Thr
        180                 185                 190

Ile Gly Ile Ser Ser Cys Ala Leu Val Asn Ser Arg Leu Tyr Asn Phe
    195                 200                 205

Thr Gly Lys Gly Asp Ser Asp Pro Ser Met Asn Pro Ser Tyr Val Arg
210                 215                 220

Glu Leu Lys Arg Lys Cys Pro Pro Thr Asp Phe Arg Thr Ser Leu Asn
225                 230                 235                 240

Met Asp Pro Gly Ser Ala Leu Thr Phe Asp Thr His Tyr Phe Lys Val
            245                 250                 255

Val Ala Gln Lys Lys Gly Leu Phe Thr Ser Asp Ser Thr Leu Leu Asp
        260                 265                 270

Asp Ile Glu Thr Lys Asn Tyr Val Gln Thr Gln Ala Ile Leu Pro Pro
    275                 280                 285

Val Phe Ser Ser Phe Asn Lys Asp Phe Ser Asp Ser Met Val Lys Leu
            290                 295                 300

Gly Phe Val Gln Ile Leu Thr Gly Lys Asn Gly Glu Ile Arg Lys Arg
305                 310                 315                 320

Cys Ala Phe Pro Asn
            325

<210> SEQ ID NO 9
<211> LENGTH: 1208
<212> TYPE: DNA
<213> ORGANISM: Arabidopsis thaliana

<400> SEQUENCE: 9

```
acacaacata atcctcccaa acagagagag tctcaaaaat taaaccaaca aatttaaaga      60
tgaattgctt gatagctata gctctttcag tctctttctt tcttgtggga attgttggac     120
cgatccaagc tcaattgcag atgaatttct atgccaattc ttgtcctaat gctgaaaaga     180
ttgttcaaga ttttgtttca aaccacgttt ctaatgctcc ttctcttgct gctgctctca     240
ttagaatgca tttccatgac tgttttgtcc gaggttgtga tggatcagtg cttataaact     300
caacgtcagg aaacgcagag agagacgcga ctcctaacct aacggttcga gggtttggct     360
tcatcgacgc aattaaatct gtgcttgaag ctcaatgccc tggaattgtc tcttgcgctg     420
atattatcgc tctagcttct cgcgacgctg tcgttttcac cggaggaccg aattggagtg     480
taccgaccgg aagaagagac gggaggatat caaacgcagc ggaggcatta gccaacattc     540
ctcctccaac cagtaatatc accaatcttc agacactctt tgcaaaccaa ggacttgatc     600
ttaaggacct cgttttacta tccggggctc acactattgg tgtatctcac tgctcgtctt     660
tcacaaaccg tctctacaat tttacgggtc gtggaggcca agatccggct ttggacagcg     720
agtacgcagc caatctcaag tctagaaaat gtcctagcct caacgataac aagaccatcg     780
```

-continued

```
tagagatgga tccagggagc cgcaaaacat tgatctaag ttattaccag ctcgtactca    840
agcgtagagg tctgtttcaa tcagactctg ctctcaccac taaccccaca acactttcaa    900
acataaaccg gatcttgacg ggttcggtgg ggagtttctt ctctgagttt gccaagtcaa    960
tggagaaaat gggtcggatc aatgtcaaga ctggttcagc tggagtggtt aggaggcaat   1020
gttccgttgc aaatagttaa ggggtggaaa tgtaaaagat tgggagctt gtgggggtag   1080 ttgtgataat aattaataag gatgattgtg aatttatgat gtggcctttt gggatttgtg   1140
tgtatggatt ttgttacaga cttcgtcaat aaagaaataa aaagatttta ctgcttttt    1200 tttaacat                                                            1208
```

<210> SEQ ID NO 10
<211> LENGTH: 326
<212> TYPE: PRT
<213> ORGANISM: Arabidopsis thaliana

<400> SEQUENCE: 10

```
Met Asn Cys Leu Ile Ala Ile Ala Leu Ser Val Ser Phe Phe Leu Val
  1               5                  10                  15

Gly Ile Val Gly Pro Ile Gln Ala Gln Leu Gln Met Asn Phe Tyr Ala
             20                  25                  30

Asn Ser Cys Pro Asn Ala Glu Lys Ile Val Gln Asp Phe Val Ser Asn
         35                  40                  45

His Val Ser Asn Ala Pro Ser Leu Ala Ala Ala Leu Ile Arg Met His
     50                  55                  60

Phe His Asp Cys Phe Val Arg Gly Cys Asp Gly Ser Val Leu Ile Asn
 65                  70                  75                  80

Ser Thr Ser Gly Asn Ala Glu Arg Asp Ala Thr Pro Asn Leu Thr Val
                 85                  90                  95

Arg Gly Phe Gly Phe Ile Asp Ala Ile Lys Ser Val Leu Glu Ala Gln
            100                 105                 110

Cys Pro Gly Ile Val Ser Cys Ala Asp Ile Ile Ala Leu Ala Ser Arg
        115                 120                 125

Asp Ala Val Val Phe Thr Gly Gly Pro Asn Trp Ser Val Pro Thr Gly
    130                 135                 140

Arg Arg Asp Gly Arg Ile Ser Asn Ala Ala Glu Ala Leu Ala Asn Ile
145                 150                 155                 160

Pro Pro Pro Thr Ser Asn Ile Thr Asn Leu Gln Thr Leu Phe Ala Asn
                165                 170                 175

Gln Gly Leu Asp Leu Lys Asp Leu Val Leu Leu Ser Gly Ala His Thr
            180                 185                 190

Ile Gly Val Ser His Cys Ser Ser Phe Thr Asn Arg Leu Tyr Asn Phe
        195                 200                 205

Thr Gly Arg Gly Gly Gln Asp Pro Ala Leu Asp Ser Glu Tyr Ala Ala
    210                 215                 220

Asn Leu Lys Ser Arg Lys Cys Pro Ser Leu Asn Asp Asn Lys Thr Ile
225                 230                 235                 240

Val Glu Met Asp Pro Gly Ser Arg Lys Thr Phe Asp Leu Ser Tyr Tyr
                245                 250                 255

Gln Leu Val Leu Lys Arg Arg Gly Leu Phe Gln Ser Asp Ser Ala Leu
            260                 265                 270

Thr Thr Asn Pro Thr Leu Ser Asn Ile Asn Arg Ile Leu Thr Gly
        275                 280                 285
```

Ser Val Gly Ser Phe Phe Ser Glu Phe Ala Lys Ser Met Glu Lys Met
        290                 295                 300

Gly Arg Ile Asn Val Lys Thr Gly Ser Ala Gly Val Val Arg Arg Gln
305                 310                 315                 320

Cys Ser Val Ala Asn Ser
                325

<210> SEQ ID NO 11
<211> LENGTH: 747
<212> TYPE: DNA
<213> ORGANISM: Arabidopsis thaliana

<400> SEQUENCE: 11
aaacccacca ttcaaacaaa acacaaaaac aacaaaaaaa ccatttcccc aaaaaaaaaa      60
aaacaaaaac agaggatgaa acaaaaccag agcaagttct tgagaataat ctcaacacct     120
ctaagagctt taggcaaggc acgtgatttc tacgtgagaa gcatcaccgg ttgcgcagct     180
cgtactcaat attcctcctc cgcctccgtc tccgctcctt ttccaagaag ccggagctcc     240
tcctccgccg ccttctcctc ctccgcatca tcccggagaa ccaccgattt cgggatagat     300
gaagattaca gcgagctagt gagagctgcg tcggtgagga gtttagggca caagaatgag     360
atagacatgt tgatacaaga gaagctgcaa cagcagaagc aacagaagca aggagggttg     420
cctaagagct cgagtgctgg gatggcgagg atagaggaag aggaagaaac agaggaagga     480
tctgtgaatc cgaaggtgaa gaagactaag aaagtctctg atcttttgta tcctcgtagc     540
aaatcttacg ccgttactac tagtaccccct atcttgtaac ttctcttctt cttttttctt     600
cttcttaatt ttagtatttt gtggattgat tatcattttt ctagctcgat ttttcgtgca     660
ctgtgaaata ctattttctt agcttgattt taataatttt gtggattgat tagaaataaa     720
taactaaacc tactctagct tcgaatc                                        747

<210> SEQ ID NO 12
<211> LENGTH: 167
<212> TYPE: PRT
<213> ORGANISM: Arabidopsis thaliana

<400> SEQUENCE: 12

Met Lys Gln Asn Gln Ser Lys Phe Leu Arg Ile Ile Ser Thr Pro Leu
1               5                   10                  15

Arg Ala Leu Gly Lys Ala Arg Asp Phe Tyr Val Arg Ser Ile Thr Gly
                20                  25                  30

Cys Ala Arg Thr Gln Tyr Ser Ser Ser Ala Ser Val Ser Ala Pro
            35                  40                  45

Phe Pro Arg Ser Arg Ser Ser Ser Ala Ala Phe Ser Ser Ser Ala
        50                  55                  60

Ser Ser Arg Arg Thr Thr Asp Phe Gly Ile Asp Glu Asp Tyr Ser Glu
65                  70                  75                  80

Leu Val Arg Ala Ala Ser Val Arg Ser Leu Gly His Lys Asn Glu Ile
                85                  90                  95

Asp Met Leu Ile Gln Glu Lys Leu Gln Gln Gln Lys Gln Gln Lys Gln
            100                 105                 110

Gly Gly Leu Pro Lys Ser Ser Ser Ala Gly Met Ala Arg Ile Glu Glu
        115                 120                 125

Glu Glu Glu Thr Glu Glu Gly Ser Val Asn Pro Lys Val Lys Lys Thr
    130                 135                 140

Lys Lys Val Ser Asp Leu Leu Tyr Pro Arg Ser Lys Ser Tyr Ala Val

| 145 | | | 150 | | | | 155 | | | | 160 | |

Thr Thr Ser Thr Pro Ile Leu
            165

<210> SEQ ID NO 13
<211> LENGTH: 1791
<212> TYPE: DNA
<213> ORGANISM: Arabidopsis thaliana

<400> SEQUENCE: 13

```
cgttttgttg tttatccaac ttgtcattca tcgatgtctc tctcttccag cctttcttga    60
atctctcacc tctcacgcca atttcatttt catgcatcgc tatttcccct tatcttcttc   120
ttcttcttct tatctcccaa ctaaattatc tgtctccatt catgttatta tggtcaacaa   180
cagaatctga atcccatttc ccattttccg gatcacaata actaacaaac cctagatttc   240
tatctatagt ccttcgatct gtttctgtgt ctccttaaag ctgtgatttt tgcaattggg   300
gtttgtgaga ttcgatcaat taattgtgtt tgttgaatgg accttcttcg attgagagaa   360
aagggtatat ttttatctca gagaagaagg aaatggctga ttttatggc gatctctgga    420
gtttctggct atggagctta caaggtttat catttgccat ctgttgccag aaaaaggaag   480
cgtcttttta agcttttcgg agccattgtc tctgtagctg aattgatctc tgattcagct   540
gagaccttaa gtatggtatc acgagacgtg aaggattttc tcaattcaga ttcagatgaa   600
atccctaaca gcttgaagca gatcgcgaag atcacaactt cgaatgagtt tacggattcg   660
cttttctaggg tttctcaggc tgtgactatt ggtgccttc gtgggtacaa atccgaatcg   720
tctattggtg attcaggaat tgagaaatca tcagactcga gtgttgttga tagagtgatt   780
gataaggttt tctcagaggc tggaactggt tttgtttcag ttgttgttgg tagctttgct   840
aagaatcttg ttcttggatt ttactctggt aaggtagaga gtggtgtgaa atgtgagggt   900
tctgattctt ctgagacacc tagatgggtg actttgcttg gtgatgacaa gtgtagagag   960
cttttagctg attgtattga gagattcacc agcactgcaa ttggtgtgta tcttgacaag  1020
acgatggata tcaatactta tgatcaaatc tttgaaggct tgacgaatcc gaaacatcag  1080
gatagtgtca aggacgttct tgtttcggtt tgtaacggtg ctctcgagac tattgttagg  1140
acatctcacg acgtgtttac atcttcaagg tctaagaatg tgatagaaga gatcgaagat  1200
gatgatttca agagtaatgg ttccgcgaga agcaagatgg tttcggaatc aggagatggg  1260
gtcaagagta atgggtggac tgaggctatt gcaactacat ggcagttcc gagcaatcgg  1320
aggtttatgt tgatgtaac aggaagagta acactagaaa cgacgagatc aatcatcgca  1380
tttataatgg tgaagacatt tcaagggttc agaaaaagta tcaatgtggt tcatgaagag  1440
gttacagaca gaggacgcca agcagttgaa tatgttggag ccaaatcttc tgttataatc  1500
actgtatgcc ttgcgttgta cttgcacatc ataagcggct gtgttcggaa ttctcccata  1560
ggcgtaagcc agcatttta gttcttcaga tgaagaagag atcatcgatt tggttggata  1620
taggataata tttgttaggt acacaagatt tatcagctcg ttgtttatag ttggagctga  1680
gaatattgta aagattgtgt gcgtgtatta gcacaacttg attcttattg atggatcatg  1740
gatcttatat atatatacat attggaaaag gttccttgggc attgatcttt g          1791
```

<210> SEQ ID NO 14
<211> LENGTH: 414
<212> TYPE: PRT
<213> ORGANISM: Arabidopsis thaliana

```
<400> SEQUENCE: 14

Met Asp Leu Leu Arg Leu Arg Glu Lys Gly Ile Phe Leu Ser Gln Arg
1               5                   10                  15

Arg Arg Lys Trp Leu Ile Phe Met Ala Ile Ser Gly Val Ser Gly Tyr
            20                  25                  30

Gly Ala Tyr Lys Val Tyr His Leu Pro Ser Val Ala Lys Arg Lys
        35                  40                  45

Arg Leu Phe Lys Leu Phe Gly Ala Ile Val Ser Val Ala Glu Leu Ile
    50                  55                  60

Ser Asp Ser Ala Glu Thr Leu Ser Met Val Ser Arg Asp Val Lys Asp
65                  70                  75                  80

Phe Leu Asn Ser Asp Ser Asp Glu Ile Pro Asn Ser Leu Lys Gln Ile
                85                  90                  95

Ala Lys Ile Thr Thr Ser Asn Glu Phe Thr Asp Ser Leu Ser Arg Val
            100                 105                 110

Ser Gln Ala Val Thr Ile Gly Ala Phe Arg Gly Tyr Lys Ser Glu Ser
        115                 120                 125

Ser Ile Gly Asp Ser Gly Ile Glu Lys Ser Ser Asp Ser Ser Val Val
    130                 135                 140

Asp Arg Val Ile Asp Lys Val Phe Ser Glu Ala Gly Thr Gly Phe Val
145                 150                 155                 160

Ser Val Val Gly Ser Phe Ala Lys Asn Leu Val Leu Gly Phe Tyr
                165                 170                 175

Ser Gly Lys Val Glu Ser Gly Val Lys Cys Glu Gly Ser Asp Ser Ser
            180                 185                 190

Glu Thr Pro Arg Trp Val Thr Leu Leu Gly Asp Asp Lys Cys Arg Glu
        195                 200                 205

Leu Leu Ala Asp Cys Ile Glu Arg Phe Thr Ser Thr Ala Ile Gly Val
    210                 215                 220

Tyr Leu Asp Lys Thr Met Asp Ile Asn Thr Tyr Asp Gln Ile Phe Glu
225                 230                 235                 240

Gly Leu Thr Asn Pro Lys His Gln Asp Ser Val Lys Asp Val Leu Val
                245                 250                 255

Ser Val Cys Asn Gly Ala Leu Glu Thr Ile Val Arg Thr Ser His Asp
            260                 265                 270

Val Phe Thr Ser Ser Arg Ser Lys Asn Val Ile Glu Glu Ile Glu Asp
        275                 280                 285

Asp Asp Phe Lys Ser Asn Gly Ser Ala Arg Ser Lys Met Val Ser Glu
    290                 295                 300

Ser Gly Asp Gly Val Lys Ser Asn Gly Trp Thr Glu Ala Ile Ala Thr
305                 310                 315                 320

Thr Leu Ala Val Pro Ser Asn Arg Arg Phe Met Phe Asp Val Thr Gly
                325                 330                 335

Arg Val Thr Leu Glu Thr Thr Arg Ser Ile Ile Ala Phe Ile Met Val
            340                 345                 350

Lys Thr Phe Gln Gly Phe Arg Lys Ser Ile Asn Val Val His Glu Glu
        355                 360                 365

Val Thr Asp Arg Gly Arg Gln Ala Val Glu Tyr Val Gly Ala Lys Ser
    370                 375                 380

Ser Val Ile Ile Thr Val Cys Leu Ala Leu Tyr Leu His Ile Ile Ser
385                 390                 395                 400

Gly Cys Val Arg Asn Ser Pro Ile Gly Val Ser Gln His Phe
                405                 410
```

<210> SEQ ID NO 15
<211> LENGTH: 555
<212> TYPE: DNA
<213> ORGANISM: Arabidopsis thaliana

<400> SEQUENCE: 15

```
atgtctgtcc aaaaagctgt caagagttct cactacgagg cagaatccaa catggaacaa      60
gatattgtta gaaaagcatg ggtctttaag ccaagtggtc ttaatttcat atggggaggt     120
gattctcggt attgggtcat ccctaacgaa gacaggacgc ctgctgaact aaagaaagtg     180
agttggttag aagtaaccgg ttcgtacgac aagatagaac aggcaaaaac ataccgaatt     240
ggttttaaaa tctcgttcac agctgatgca accggatggg accaagctcc agttttcatg     300
tcagcaaaaa ttggaaagaa agggaggaca atttggaaga ggatcaaatc ggttaacaat     360
aactttgaca aactcaaagg cggaaccgga ccggttaaca taccagatga gactgatggt     420
cggtttgaga tctttgtaag tcccaaggta gcaataaacc aagacaccaa gctccaattt     480
ggtttgtatg aagtgtggac cggaaaatgg aaaacaggct tgttgatcta tgaagctttt     540
gttgaagaag tgtaa                                                      555
```

<210> SEQ ID NO 16
<211> LENGTH: 184
<212> TYPE: PRT
<213> ORGANISM: Arabidopsis thaliana

<400> SEQUENCE: 16

```
Met Ser Val Gln Lys Ala Val Lys Ser Ser His Tyr Glu Ala Glu Ser
1               5                   10                  15
Asn Met Glu Gln Asp Ile Val Arg Lys Ala Trp Val Phe Lys Pro Ser
            20                  25                  30
Gly Leu Asn Phe Ile Trp Gly Gly Asp Ser Arg Tyr Trp Val Ile Pro
        35                  40                  45
Asn Glu Asp Arg Thr Pro Ala Glu Leu Lys Lys Val Ser Trp Leu Glu
    50                  55                  60
Val Thr Gly Ser Tyr Asp Lys Ile Glu Pro Gly Lys Thr Tyr Arg Ile
65                  70                  75                  80
Gly Phe Lys Ile Ser Phe Thr Ala Asp Ala Thr Gly Trp Asp Gln Ala
                85                  90                  95
Pro Val Phe Met Ser Ala Lys Ile Gly Lys Lys Gly Arg Thr Ile Trp
            100                 105                 110
Lys Arg Ile Lys Ser Val Asn Asn Asn Phe Asp Lys Leu Lys Gly Gly
        115                 120                 125
Thr Gly Pro Val Asn Ile Pro Asp Glu Thr Asp Gly Arg Phe Glu Ile
    130                 135                 140
Phe Val Ser Pro Lys Val Ala Ile Asn Gln Asp Thr Lys Leu Gln Phe
145                 150                 155                 160
Gly Leu Tyr Glu Val Trp Thr Gly Lys Trp Lys Thr Gly Leu Leu Ile
                165                 170                 175
Tyr Glu Ala Phe Val Glu Glu Val
            180
```

<210> SEQ ID NO 17
<211> LENGTH: 2295
<212> TYPE: DNA
<213> ORGANISM: Arabidopsis thaliana

<400> SEQUENCE: 17

```
atggacgatg agtcattacc cacaaccaat tccacttccg atcacagagg cttctataaa    60
gagattctct ttgggatgaa gaagattggg ttccgcgagt ttcttcacgg gtatcacttt   120
cgaggtttgg tttcggaatt gaggcatgtt catgtcgaag aaatcatgga tgaattgatg   180
tctgaaagct cagatctttc tgtttggttt ttcaaagagc tgagagatat ctatgcgttt   240
cgtcattcga gttttccac attgttggtt tcacatgttt tagctggtca aagacgtttc   300
aaagagcttc aagtgattct ggaacaattg cttcaagaag aaggcacatt gagaatggtt   360
gatgattctc tttatatctt gaaaaagatg aaggatcaga acttgaatgt gtcgacacag   420
tcgtacaact ccgttttgta tcattttaga gagacggata agatgtggga tgtgtacaag   480
gaaatcaagg ataagaacga gcacacgtac tcaacagttg tagatggttt gtgtaggcaa   540
caaaagctag aggatgcagt tttgttcctt cgaacttcag agtggaagga tattggtccc   600
tctgtagttt ctttcaatag tataatgtca ggttactgta aattgggttt tgtagatatg   660
gcgaagtcgt ttttctgtac agttttgaaa tgtgggttgg ttcctagtgt atatagtcac   720
aatatactca tcaatggact ctgtctagtt ggttctatcg cagaagcttt agagttggct   780
agtgacatga ataagcatgg agtggaacct gattctgtga catacaatat tcttgcgaaa   840
gggtttcatc ttctcggtat gatcagtggg gcttgggagg taattcgaga tatgttggat   900
aaaggattga gtcctgatgt tattacatac acaattttac tatgtggaca atgtcagtta   960
ggaaatattg acatgggttt agtattgctg aaggatatgt tgtcgagggg atttgagtta  1020
aacagtatca tcccatgcag tgtaatgctc agtggtttat gtaaaacagg aagaatagat  1080
gaagctttgt cgttattcaa tcaaatgaaa gccgatggtc tgagccctga tcttgtagca  1140
tattctattg tgattcatgg cctctgcaag ttaggaaaat ttgatatggc tctttggctt  1200
tacgacgaga tgtgtgacaa aagaattctt ccgaattcga ggactcatgg tgctcttttg  1260
ctcggtttat gtcagaaagg gatgttactt gaggcaagat cgcttttgga ttctctgatt  1320
tcaagtggag agacactgga tattgttctg tacaatatcg taattgacgg gtatgcaaag  1380
tctggttgca ttgaggaggc gttagagtta ttcaaagtag tcattgagac tgggataact  1440
cctagcgttg caacttttaa ttctttgata tacgggtatt gcaaaaccca gaatatagct  1500
gaggctagaa aaatcttaga tgtcatcaag ttatatggat tggctccaag tgttgtgagt  1560
tatacaactc tgatggatgc atatgcaaat tgtggaaata ccaaaagcat agatgaattg  1620
cgcagggaaa tgaaagcaga aggaatccca ccaaccaatg tcacgtactc agtgattttt  1680
aaaggacttt gcagaggctg gaaacatgaa aattgcaacc atgtactcag ggaaaggata  1740
ttcgaaaaat gcaagcaggg actcagggac atggaatctg aaggtatacc tccagatcag  1800
atcacatata atacaattat tcagtatcta tgcagagtta acatttatc tggagcattt  1860
gtgtttctcg aaataatgaa atctcgaaat cttgatgctt catctgctac ttataatatt  1920
ctaatcgaca gcctttgtgt ctacggttac ataaggaaag ctgacagttt tatctattcg  1980
ctccaggagc agaatgttag tttgtccaaa tttgcttata ccacactgat caaggcacat  2040
tgtgtaaagg gtgaccctga aatggcagtg aagctatttc atcaactgct gcacagagga  2100
ttcaatgttt ccattaggga ctatagcgcg gtgatcaacc gtttgtgtag agacatttg   2160
gtaaacgaga gcaaattctt cttctgtcta atgttatccc agggtatttc gcctgactta  2220
gacatttgtg aagtgatgat caagtcagat gaattgcttt cctggacaat caaatggggt  2280
ttgttgcctg attag                                                   2295
```

<210> SEQ ID NO 18
<211> LENGTH: 764
<212> TYPE: PRT
<213> ORGANISM: Arabidopsis thaliana

<400> SEQUENCE: 18

```
Met Asp Asp Glu Ser Leu Pro Thr Thr Asn Ser Thr Ser Asp His Arg
1               5                   10                  15

Gly Phe Tyr Lys Glu Ile Leu Phe Gly Met Lys Lys Ile Gly Phe Arg
            20                  25                  30

Glu Phe Leu His Gly Tyr His Phe Arg Gly Leu Val Ser Glu Leu Arg
        35                  40                  45

His Val His Val Glu Glu Ile Met Asp Glu Leu Met Ser Glu Ser Ser
    50                  55                  60

Asp Leu Ser Val Trp Phe Lys Glu Leu Arg Asp Ile Tyr Ala Phe
65                  70                  75                  80

Arg His Ser Ser Phe Ser Thr Leu Leu Val Ser His Val Leu Ala Gly
                85                  90                  95

Gln Arg Arg Phe Lys Glu Leu Gln Val Ile Leu Glu Gln Leu Leu Gln
            100                 105                 110

Glu Glu Gly Thr Leu Arg Met Val Asp Asp Ser Leu Tyr Ile Leu Lys
        115                 120                 125

Lys Met Lys Asp Gln Asn Leu Asn Val Ser Thr Gln Ser Tyr Asn Ser
130                 135                 140

Val Leu Tyr His Phe Arg Glu Thr Asp Lys Met Trp Asp Val Tyr Lys
145                 150                 155                 160

Glu Ile Lys Asp Lys Asn Glu His Thr Tyr Ser Thr Val Val Asp Gly
                165                 170                 175

Leu Cys Arg Gln Gln Lys Leu Glu Asp Ala Val Leu Phe Leu Arg Thr
            180                 185                 190

Ser Glu Trp Lys Asp Ile Gly Pro Ser Val Val Ser Phe Asn Ser Ile
        195                 200                 205

Met Ser Gly Tyr Cys Lys Leu Gly Phe Val Asp Met Ala Lys Ser Phe
    210                 215                 220

Phe Cys Thr Val Leu Lys Cys Gly Leu Val Pro Ser Val Tyr Ser His
225                 230                 235                 240

Asn Ile Leu Ile Asn Gly Leu Cys Leu Val Gly Ser Ile Ala Glu Ala
                245                 250                 255

Leu Glu Leu Ala Ser Asp Met Asn Lys His Gly Val Glu Pro Asp Ser
            260                 265                 270

Val Thr Tyr Asn Ile Leu Ala Lys Gly Phe His Leu Leu Gly Met Ile
        275                 280                 285

Ser Gly Ala Trp Glu Val Ile Arg Asp Met Leu Asp Lys Gly Leu Ser
    290                 295                 300

Pro Asp Val Ile Thr Tyr Thr Ile Leu Leu Cys Gly Gln Cys Gln Leu
305                 310                 315                 320

Gly Asn Ile Asp Met Gly Leu Val Leu Lys Asp Met Leu Ser Arg
                325                 330                 335

Gly Phe Glu Leu Asn Ser Ile Ile Pro Cys Ser Val Met Leu Ser Gly
            340                 345                 350

Leu Cys Lys Thr Gly Arg Ile Asp Glu Ala Leu Ser Leu Phe Asn Gln
        355                 360                 365

Met Lys Ala Asp Gly Leu Ser Pro Asp Leu Val Ala Tyr Ser Ile Val
```

```
                  370                 375                 380
Ile His Gly Leu Cys Lys Leu Gly Lys Phe Asp Met Ala Leu Trp Leu
385                 390                 395                 400

Tyr Asp Glu Met Cys Asp Lys Arg Ile Leu Pro Asn Ser Arg Thr His
                405                 410                 415

Gly Ala Leu Leu Leu Gly Leu Cys Gln Lys Gly Met Leu Leu Glu Ala
                420                 425                 430

Arg Ser Leu Leu Asp Ser Leu Ile Ser Ser Gly Glu Thr Leu Asp Ile
                435                 440                 445

Val Leu Tyr Asn Ile Val Ile Asp Gly Tyr Ala Lys Ser Gly Cys Ile
    450                 455                 460

Glu Glu Ala Leu Glu Leu Phe Lys Val Val Ile Glu Thr Gly Ile Thr
465                 470                 475                 480

Pro Ser Val Ala Thr Phe Asn Ser Leu Ile Tyr Gly Tyr Cys Lys Thr
                485                 490                 495

Gln Asn Ile Ala Glu Ala Arg Lys Ile Leu Asp Val Ile Lys Leu Tyr
                500                 505                 510

Gly Leu Ala Pro Ser Val Val Ser Tyr Thr Thr Leu Met Asp Ala Tyr
                515                 520                 525

Ala Asn Cys Gly Asn Thr Lys Ser Ile Asp Glu Leu Arg Arg Glu Met
530                 535                 540

Lys Ala Glu Gly Ile Pro Pro Thr Asn Val Thr Tyr Ser Val Ile Phe
545                 550                 555                 560

Lys Gly Leu Cys Arg Gly Trp Lys His Glu Asn Cys Asn His Val Leu
                565                 570                 575

Arg Glu Arg Ile Phe Glu Lys Cys Lys Gln Gly Leu Arg Asp Met Glu
                580                 585                 590

Ser Glu Gly Ile Pro Pro Asp Gln Ile Thr Tyr Asn Thr Ile Ile Gln
                595                 600                 605

Tyr Leu Cys Arg Val Lys His Leu Ser Gly Ala Phe Val Phe Leu Glu
                610                 615                 620

Ile Met Lys Ser Arg Asn Leu Asp Ala Ser Ala Thr Tyr Asn Ile
625                 630                 635                 640

Leu Ile Asp Ser Leu Cys Val Tyr Gly Tyr Ile Arg Lys Ala Asp Ser
                645                 650                 655

Phe Ile Tyr Ser Leu Gln Glu Gln Asn Val Ser Leu Ser Lys Phe Ala
                660                 665                 670

Tyr Thr Thr Leu Ile Lys Ala His Cys Val Lys Gly Asp Pro Glu Met
                675                 680                 685

Ala Val Lys Leu Phe His Gln Leu Leu His Arg Gly Phe Asn Val Ser
690                 695                 700

Ile Arg Asp Tyr Ser Ala Val Ile Asn Arg Leu Cys Arg Arg His Leu
705                 710                 715                 720

Val Asn Glu Ser Lys Phe Phe Phe Cys Leu Met Leu Ser Gln Gly Ile
                725                 730                 735

Ser Pro Asp Leu Asp Ile Cys Glu Val Met Ile Lys Ser Asp Glu Leu
                740                 745                 750

Leu Ser Trp Thr Ile Lys Trp Gly Leu Leu Pro Asp
                755                 760

<210> SEQ ID NO 19
<211> LENGTH: 2481
<212> TYPE: DNA
<213> ORGANISM: Arabidopsis thaliana
```

<400> SEQUENCE: 19

```
aaaaaagcgt cgttgagagg ttagagacga aggaaggagg cagaggatag agagatagcg      60
aggctaatgg atcagtgact cactgagtca gattttaccg attcattgcc tccattgaag     120
cctctttct cagattctac gcttcactgt ctcttctcca tgtgcgtctc ctcctcctcc      180
gtttcttcag atcttgcttt ccggtgacgg ttttaatctt cttctctctg gtaacacgta     240
taaagcatgg cttacctgat gtagacatgt agtgttaggc taaagactcc tcttttcact    300
tctgtcttgt tgagtttgtg ttggtttaag gctttaagcc aaaggcgttg ttggtctgac     360
aagatggcaa tggcggtgtt taaggctcct ctaaaagggg aatttcatgg ggctagaaag    420
atggaaggga agcaatataa gcaccatctg cttcagcaac agtctacagg gagaagacgt    480
gtgttcgtgc aaaccgatac tggctgtgtg ttgggagttg agttggatcg taatgacaat    540
gttcatactg tgaagaaaag gcttcagatt gcgtttaact ttcctactga ggaaagctct    600
ttgacctttg gggatatggt gttgaagaat gacttgagtg ctgtgaggaa tgattctccg    660
cttctcttaa agcgtaactt aatgcacaga agctcttcta ctccgtgtct ttcacctact    720
gggaatgatc tgcagaggaa agatcgaagt ggtcctattg agatacttag tcactcgccc    780
tgttttctgt ctttgaagca aacagcgaat gacattgtta aggcgatgaa gatgggtgtt    840
gaaccaatcc ctgttaatgg tgggcttgga ggggcatact attttaggga tgaaaagggt    900
caaagtgttg ctattgtcaa gcctacggat gaagagccgt ttgcccctaa caatcctaaa    960
ggcttcgtag ggaaagcgct tgggcagcct ggtttaaagc cttctgtgcg ggttggggaa   1020
accgggttta gagaagttgc tgcatacctt cttgattatg atcactttgc taatgttcct   1080
cctacggctc ttgtgaagat aacacactct gttttcaatg tcaatgatgg aatggatggg   1140
aacaaatctc gtgagaagaa gaagctggtc agcagcaaga ttgcttcgtt ccagaagttt   1200
gtacctcatg atttttgatgc cagtgatcac gggacttcaa gcttccctgt cgcttctgtg   1260
caccgcattg ggattttgga cataaggatt ctcaacacag accggcatgg tggaaatctt   1320
ttggtgaaga agcttgatga tggtggtgtt gggaggtttg gtcaagtgga gcttattcca   1380
atagatcatg gtctttgctt accagaaaca ctcgaagatc cttacttcga atggattcat   1440
tggcctcagg cttcaatacc tttctctgaa gaagaacttg actacataca aagtcttgat   1500
ccagtgaaag attgtgaaat gcttcgaaga gagcttccga tgattcgaga ggcttgtctc   1560
agggttctag ttctctgtac cgttttcctt aaagaagctg ctgttttgg actttgtctt    1620
gcagagatcg gtgagatgat gactcgaaa tttcgtgcag agaagagga accaagtgaa    1680
ctagaaatgt tgtgtatcga agccaagaga ttaaccactg aacaagacgt tttgtctccc   1740
aagtcagatg gagaaggaga gacagagttt cagtttgata tagactacaa tgagctagac   1800
tcggtttatg gctctgagac agaaaccgat gagttcttcg ccaagaaccc attttcaaac   1860
ggacgttctt cacttggaga gctcaaagag agcattgctg aagaagaaga agatgacgaa   1920
gaggaggcaa aacttactct atctctctca aagctttcca catcaatgaa gaacaatcta   1980
agcaacacca tgggatccgg atacctgaaa cctccgaaag acaaccaaac cgacaaagca   2040
ttggtaagtc acaagagcgc gaacgtgcag ctcccgctta gcgtaaactt tgtgaagtta   2100
gccgacatga aagaagttga atgggttgtg ttcttggaga ggtttcagga gttgctttac   2160
tcggcttttg cagaacgcaa gaccatgacg ttgaggaaca cacagagact tggtacatcg   2220
tgcaagtttt gagatcatac gagttcacat aagagaagac caaagatttc acttttacga   2280
```

```
gttttgaagc aattacttgt tagctacgtt aagattagtt tacttttgta gcgaccacga    2340
gcacttgcaa tgtgaagaaa tgtttatttt gcctgtaaat attctttacc attttttttt    2400
ccctaacttc catttccttc ttttgtttca aatcgttttg cattgtcttt acaagaataa    2460
gttgaatgaa aatagttgcc t                                              2481
```

<210> SEQ ID NO 20
<211> LENGTH: 622
<212> TYPE: PRT
<213> ORGANISM: Arabidopsis thaliana

<400> SEQUENCE: 20

```
Met Ala Met Ala Val Phe Lys Ala Pro Leu Lys Gly Glu Phe His Gly
1               5                   10                  15

Ala Arg Lys Met Glu Gly Lys Gln Tyr Lys His His Leu Leu Gln Gln
            20                  25                  30

Gln Ser Thr Gly Arg Arg Val Phe Val Gln Thr Asp Thr Gly Cys
        35                  40                  45

Val Leu Gly Val Glu Leu Asp Arg Asn Asp Asn Val His Thr Val Lys
    50                  55                  60

Lys Arg Leu Gln Ile Ala Phe Asn Phe Pro Thr Glu Glu Ser Ser Leu
65                  70                  75                  80

Thr Phe Gly Asp Met Val Leu Lys Asn Asp Leu Ser Ala Val Arg Asn
                85                  90                  95

Asp Ser Pro Leu Leu Leu Lys Arg Asn Leu Met His Arg Ser Ser Ser
            100                 105                 110

Thr Pro Cys Leu Ser Pro Thr Gly Asn Asp Leu Gln Arg Lys Asp Arg
        115                 120                 125

Ser Gly Pro Ile Glu Ile Leu Ser His Ser Pro Cys Phe Leu Ser Leu
    130                 135                 140

Lys Gln Thr Ala Asn Asp Ile Val Lys Ala Met Lys Met Gly Val Glu
145                 150                 155                 160

Pro Ile Pro Val Asn Gly Gly Leu Gly Gly Ala Tyr Tyr Phe Arg Asp
                165                 170                 175

Glu Lys Gly Gln Ser Val Ala Ile Val Lys Pro Thr Asp Glu Glu Pro
            180                 185                 190

Phe Ala Pro Asn Asn Pro Lys Gly Phe Val Gly Lys Ala Leu Gly Gln
        195                 200                 205

Pro Gly Leu Lys Pro Ser Val Arg Val Gly Glu Thr Gly Phe Arg Glu
    210                 215                 220

Val Ala Ala Tyr Leu Leu Asp Tyr Asp His Phe Ala Asn Val Pro Pro
225                 230                 235                 240

Thr Ala Leu Val Lys Ile Thr His Ser Val Phe Asn Val Asn Asp Gly
                245                 250                 255

Met Asp Gly Asn Lys Ser Arg Glu Lys Lys Leu Val Ser Ser Lys
            260                 265                 270

Ile Ala Ser Phe Gln Lys Phe Val Pro His Asp Phe Ala Ser Asp
        275                 280                 285

His Gly Thr Ser Ser Phe Pro Val Ala Ser Val His Arg Ile Gly Ile
    290                 295                 300

Leu Asp Ile Arg Ile Leu Asn Thr Asp Arg His Gly Gly Asn Leu Leu
305                 310                 315                 320

Val Lys Lys Leu Asp Asp Gly Val Gly Arg Phe Gly Gln Val Glu
                325                 330                 335
```

```
Leu Ile Pro Ile Asp His Gly Leu Cys Leu Pro Glu Thr Leu Glu Asp
            340                 345                 350

Pro Tyr Phe Glu Trp Ile His Trp Pro Gln Ala Ser Ile Pro Phe Ser
        355                 360                 365

Glu Glu Glu Leu Asp Tyr Ile Gln Ser Leu Asp Pro Val Lys Asp Cys
    370                 375                 380

Glu Met Leu Arg Arg Glu Leu Pro Met Ile Arg Glu Ala Cys Leu Arg
385                 390                 395                 400

Val Leu Val Leu Cys Thr Val Phe Leu Lys Glu Ala Ala Val Phe Gly
                405                 410                 415

Leu Cys Leu Ala Glu Ile Gly Glu Met Met Thr Arg Glu Phe Arg Ala
            420                 425                 430

Gly Glu Glu Glu Pro Ser Glu Leu Glu Met Leu Cys Ile Glu Ala Lys
        435                 440                 445

Arg Leu Thr Thr Glu Gln Asp Val Leu Ser Pro Lys Ser Asp Gly Glu
    450                 455                 460

Gly Glu Thr Glu Phe Gln Phe Asp Ile Asp Tyr Asn Glu Leu Asp Ser
465                 470                 475                 480

Val Tyr Gly Ser Glu Thr Glu Thr Asp Glu Phe Phe Ala Lys Asn Pro
                485                 490                 495

Phe Ser Asn Gly Arg Ser Ser Leu Gly Glu Leu Lys Glu Ser Ile Ala
            500                 505                 510

Glu Glu Glu Asp Asp Glu Glu Ala Lys Leu Thr Leu Ser Leu
        515                 520                 525

Ser Lys Leu Ser Thr Ser Met Lys Asn Leu Ser Asn Thr Met Gly
530                 535                 540

Ser Gly Tyr Leu Lys Pro Pro Lys Asp Asn Gln Thr Asp Lys Ala Leu
545                 550                 555                 560

Val Ser His Lys Ser Ala Asn Val Gln Leu Pro Leu Ser Val Asn Phe
                565                 570                 575

Val Lys Leu Ala Asp Met Lys Glu Val Glu Trp Val Val Phe Leu Glu
            580                 585                 590

Arg Phe Gln Glu Leu Leu Tyr Ser Ala Phe Ala Glu Arg Lys Thr Met
        595                 600                 605

Thr Leu Arg Asn Thr Gln Arg Leu Gly Thr Ser Cys Lys Phe
    610                 615                 620

<210> SEQ ID NO 21
<211> LENGTH: 1189
<212> TYPE: DNA
<213> ORGANISM: Arabidopsis thaliana

<400> SEQUENCE: 21
cagagcaaaa aaacactagt taagagattc aggttacctt caagttacaa attgagacaa      60
tcttgttctt tgtttgttag attaccttct attcttgatt gtgttttccg aagatttttt     120
agaaccaatc cacttgtttt tcctaataca ggggtggtgt tttcgtggtg gtaaaaggat     180
aaaatttctt gagaatgcct gcatacattt ctgaggagaa gttgttcttc aacaagaaac     240
ctttcggatc caaatctca gacaacaacg aaattgaaga acttgatcaa gagaatttgg     300
ttgtgacaag acaagaagtt aatgatgatt ccaaagtggc accgagagat gtagtagcta     360
catcaacaag tgtctctaag aaggctttaa ccttgggaga tatttatca ttggaggatt     420 cccaaagccc acccaacaaa acaacactaa tggacctgaa gaaaacatg gtccatcata     480 acccacatct ggagataaca gaggaatcag aagcagacaa ctcttgtgat gacaacaatc     540
```

```
tcttgaaaag gaatctccca aatggtttcg gggaaataag tttctgtgaa gcaaagtcga      600
gtttagatta tattacttac tgtggaccac tctcaggctc cgaaaacctc tctattcgtt      660
ctgatggaac cagcgcaagc tcttttgctc tcccaatact gcaatcggag tggaacagca      720
gtcctgtaag aatggggaaa gctgaggaga cgcaacttcg aatggtgata gctgaggaga      780
gaaaagttcg aaaggataaa gctgagaaga cacaacttcg aaaggagaaa gctgaggagt      840
cacaacttcg agaggtgaaa gctgaggaga ctcaacttcg aatggtgaaa gctgaggaga      900
ctcaacttcg aaaggagaaa gctgaggaaa cacaacttcg aatggtgata gctgaggaga      960
gacaacttcg aaaggagaaa gatgagaaga gacaacttcg aaaggggaag aaaggatgga     1020
gacattactc ttctcttctc tgttgtagat tctgatggat tctatcagag gattttttaac     1080 ctttttaggc tttgcattca atatacaaag accgttcgaa taagaacaga aaatagtggt     1140
ttttctgtaa tgtattattt cgtagacctc aaatacttta tattcaatt                1189
```

<210> SEQ ID NO 22
<211> LENGTH: 286
<212> TYPE: PRT
<213> ORGANISM: Arabidopsis thaliana

<400> SEQUENCE: 22

```
Met Pro Ala Tyr Ile Ser Glu Glu Lys Leu Phe Phe Asn Lys Lys Pro
1               5                   10                  15

Phe Gly Ser Lys Ile Ser Asp Asn Asn Glu Ile Glu Glu Leu Asp Gln
                20                  25                  30

Glu Asn Leu Val Val Thr Arg Gln Glu Val Asn Asp Asp Ser Lys Val
            35                  40                  45

Ala Pro Arg Asp Val Val Ala Thr Ser Thr Ser Val Ser Lys Lys Ala
        50                  55                  60

Leu Thr Leu Gly Asp Ile Leu Ser Leu Glu Asp Ser Gln Ser Pro Pro
65                  70                  75                  80

Asn Lys Asn Asn Thr Asn Gly Pro Glu Glu Asn Met Val His His Asn
                85                  90                  95

Pro His Leu Glu Ile Thr Glu Glu Ser Glu Ala Asp Asn Ser Cys Asp
                100                 105                 110

Asp Asn Asn Leu Leu Lys Arg Asn Leu Pro Asn Gly Phe Gly Glu Ile
            115                 120                 125

Ser Phe Cys Glu Ala Lys Ser Ser Leu Asp Tyr Ile Thr Tyr Cys Gly
        130                 135                 140

Pro Leu Ser Gly Ser Glu Asn Leu Ser Ile Arg Ser Asp Gly Thr Ser
145                 150                 155                 160

Ala Ser Ser Phe Ala Leu Pro Ile Leu Gln Ser Glu Trp Asn Ser Ser
                165                 170                 175

Pro Val Arg Met Gly Lys Ala Glu Glu Thr Gln Leu Arg Met Val Ile
                180                 185                 190

Ala Glu Glu Arg Lys Val Arg Lys Asp Lys Ala Glu Lys Thr Gln Leu
            195                 200                 205

Arg Lys Glu Lys Ala Glu Glu Ser Gln Leu Arg Glu Val Lys Ala Glu
        210                 215                 220

Glu Thr Gln Leu Arg Met Val Lys Ala Glu Glu Thr Gln Leu Arg Lys
225                 230                 235                 240

Glu Lys Ala Glu Glu Thr Gln Leu Arg Met Val Ile Ala Glu Glu Arg
                245                 250                 255
```

Gln Leu Arg Lys Glu Lys Asp Glu Lys Arg Gln Leu Arg Lys Gly Lys
                260                 265                 270

Lys Gly Trp Arg His Tyr Ser Ser Leu Leu Cys Cys Arg Phe
            275                 280                 285

<210> SEQ ID NO 23
<211> LENGTH: 1579
<212> TYPE: DNA
<213> ORGANISM: Arabidopsis thaliana

<400> SEQUENCE: 23

| | | | | | |
|---|---|---|---|---|---|
| cagagcaaaa | aaacactagt | taagagattc | aggttaccct | caagttacaa | attgagacaa | 60 |
| tcttgttctt | tgtttgttag | attaccttct | attcttgatt | gtgttttccg | aagattttt | 120 |
| agaaccaatc | cacttgtttt | tcctaataca | ggggtggtgt | tttcgtggtg | gtaaaaggat | 180 |
| aaaatttctt | gagaatgcct | gcatacattt | ctgaggtttg | gtttgtaatt | atttgcaaaa | 240 |
| tcaaacggca | ataaactgtt | tttcattgtt | tttgttatta | tatatgctca | aattaaatgc | 300 |
| agagattttg | gttgctgaaa | ctcattgaca | tttcaacgat | ttttttggat | tcttgtacta | 360 |
| tatgttttc | tattggataa | acagtaaaac | catctcgctt | tagattctag | tataattcat | 420 |
| tctttgacga | atactcttat | ttagattcta | gttgttagag | acattgacat | gtgactccat | 480 |
| ggctttatac | atcaataaaa | taatccagtt | gttatgaaat | aatccaatta | tttaatgatc | 540 |
| ttcatgttag | gatatatgtt | aaggtgtaat | agtttaatgg | aaagcttgtg | taacttacga | 600 |
| tgcaggagaa | gttgttcttc | aacaagaaac | ctttcggatc | caaatctca | gacaacaacg | 660 |
| aaattgaaga | acttgatcaa | gagaatttgg | ttgtgacaag | acaagaagtt | aatgatgatt | 720 |
| ccaaagtggc | accgagagat | gtagtagcta | catcaacaag | tgtctctaag | aaggctttaa | 780 |
| ccttgggaga | tattttatca | ttggaggatt | cccaaagccc | acccaacaaa | acaacacta | 840 |
| atggacctga | agaaaacatg | gtccatcata | cccacatct | ggagataaca | gaggaatcag | 900 |
| aagcagacaa | ctcttgtgat | gacaacaatc | tcttgaaaag | gaatctccca | aatggtttcg | 960 |
| gggaaataag | tttctgtgaa | gcaaagtcga | gtttagatta | tattacttac | tgtggaccac | 1020 |
| tctcaggctc | cgaaaaccct | tctattcgtt | ctgatggaac | cagcgcaagc | tcttttgctc | 1080 |
| tcccaatact | gcaatcggag | tggaacagca | gtcctgtaag | aatggggaaa | gctgaggaga | 1140 |
| cgcaacttcg | aatggtgata | gctgaggaga | gaaaagttcg | aaaggataaa | gctgagaaga | 1200 |
| cacaacttcg | aaaggagaaa | gctgaggagt | cacaacttcg | agaggtgaaa | gctgaggaga | 1260 |
| ctcaacttcg | aatggtgaaa | gctgaggaga | ctcaacttcg | aaaggagaaa | gctgaggaaa | 1320 |
| cacaacttcg | aatggtgata | gctgaggaga | gacaacttcg | aaaggagaaa | gatgagaaga | 1380 |
| gacaacttcg | aaaggggaag | aaaggatgga | gacattactc | ttctcttctc | tgttgtagat | 1440 |
| tctgatggat | tctatcagag | gattttaac | ctttttaggc | tttgcattca | atatacaaag | 1500 |
| accgttcgaa | taagaacaga | aaatagtggt | ttttctgtaa | tgtattattt | cgtagacctc | 1560 |
| aaatactta | tattcaatt | | | | | 1579 |

<210> SEQ ID NO 24
<211> LENGTH: 281
<212> TYPE: PRT
<213> ORGANISM: Arabidopsis thaliana

<400> SEQUENCE: 24

Met Gln Glu Lys Leu Phe Phe Asn Lys Lys Pro Phe Gly Ser Lys Ile
1               5                   10                  15

```
Ser Asp Asn Asn Glu Ile Glu Glu Leu Asp Gln Glu Asn Leu Val Val
            20                  25                  30

Thr Arg Gln Glu Val Asn Asp Asp Ser Lys Val Ala Pro Arg Asp Val
        35                  40                  45

Val Ala Thr Ser Thr Ser Val Ser Lys Lys Ala Leu Thr Leu Gly Asp
50                  55                  60

Ile Leu Ser Leu Glu Asp Ser Gln Ser Pro Pro Asn Lys Asn Asn Thr
65                  70                  75                  80

Asn Gly Pro Glu Glu Asn Met Val His His Asn Pro His Leu Glu Ile
                85                  90                  95

Thr Glu Glu Ser Glu Ala Asp Asn Ser Cys Asp Asp Asn Asn Leu Leu
            100                 105                 110

Lys Arg Asn Leu Pro Asn Gly Phe Gly Glu Ile Ser Phe Cys Glu Ala
        115                 120                 125

Lys Ser Ser Leu Asp Tyr Ile Thr Tyr Cys Gly Pro Leu Ser Gly Ser
    130                 135                 140

Glu Asn Leu Ser Ile Arg Ser Asp Gly Thr Ser Ala Ser Ser Phe Ala
145                 150                 155                 160

Leu Pro Ile Leu Gln Ser Glu Trp Asn Ser Ser Pro Val Arg Met Gly
                165                 170                 175

Lys Ala Glu Glu Thr Gln Leu Arg Met Val Ile Ala Glu Glu Arg Lys
            180                 185                 190

Val Arg Lys Asp Lys Ala Glu Lys Thr Gln Leu Arg Lys Glu Lys Ala
        195                 200                 205

Glu Glu Ser Gln Leu Arg Glu Val Lys Ala Glu Thr Gln Leu Arg
    210                 215                 220

Met Val Lys Ala Glu Glu Thr Gln Leu Arg Lys Glu Lys Ala Glu Glu
225                 230                 235                 240

Thr Gln Leu Arg Met Val Ile Ala Glu Glu Arg Gln Leu Arg Lys Glu
                245                 250                 255

Lys Asp Glu Lys Arg Gln Leu Arg Lys Gly Lys Lys Gly Trp Arg His
            260                 265                 270

Tyr Ser Ser Leu Leu Cys Cys Arg Phe
    275                 280

<210> SEQ ID NO 25
<211> LENGTH: 1269
<212> TYPE: DNA
<213> ORGANISM: Arabidopsis thaliana

<400> SEQUENCE: 25
ctctcttttt ctctctttac tatttcttc cttaccaaat atagcaacaa caaaaaaacg      60
ttttctgtga tggaggtccc gattataaac agaataggcg attttgacat ggggataaac     120
tcgataaacg acccgtcgta tttatctcga gctttggcag tctccggtgt cggaaagtta     180
catcaagctt atagtttttg gaatgggggc gccttattgc tacttgcatt ttttgcttca     240
tttacatcgt taactacaag aatcaagact ttagtcttta gattaagaaa tgtaaacgtg     300
tctctacctt cccaaactct tttatgtaat tacgacagcg actccgattg gtctttctcg     360
tcagactctt cagacgaaga gaaagatgag gacgataaca aagaagatga ctcggtcaat     420
ggcgattcac gcgttcaaag atttggttat taccatgatg atgatgataa gggtattagt     480
ggaagtgtcc cctggttgcg gcggtgcagt ggtagcttcg gagatttgtt agatttaggc     540
tcaagcggag tcgtgaagct ttgggacaat cttgatttca acggagaagg aagtccggtg     600
```

-continued

```
gcttcttttt tcagcaaatg cggctcatac tcgttattgt catcggcggt tttattagcg    660
gcggagaaga aaggatccga cggcttggaa gtgagtgcgt gggatgcacg cgttggtttt    720
ggggtgcccg cgttgctcgc ggaatggaag cagccgggaa ggttactcgg gaagatcatt    780
agggttgacg taggtgacgt ggacaagatc tacgtcggtg atgacgtcga aggagagatt    840
actgtgggag acatgaggat ggttaacggt gcgttgacgg aactgacgga atcagaggtt    900
gagaggatgg tgagaagacg cagacgccgt cattgaggct gacggtgccg ttggggagat    960
gtattgatga taaatgattg attggcatgg tagggtctaa taaagactga aaagttcaac   1020
gcaaatgcaa gtgacgaaca ttttttttatt tttgtaaata atttgtctgt cttgtatttt   1080
tttcaattta ggttttcaat tttttggcaa aaaaagaaag aaagaaatct cttattttgt   1140
tcttcgaaat aaagaaattc aacctcctgt tgtcgtgtat tttggatttc atgttgtaag   1200
tagacttgga aatgtaaggt aactctattt tttttggtta attattacat taataataat   1260
gtttaaatt                                                           1269
```

<210> SEQ ID NO 26
<211> LENGTH: 288
<212> TYPE: PRT
<213> ORGANISM: Arabidopsis thaliana

<400> SEQUENCE: 26

```
Met Glu Val Pro Ile Ile Asn Arg Ile Gly Asp Phe Asp Met Gly Ile
1               5                   10                  15

Asn Ser Ile Asn Asp Pro Ser Tyr Leu Ser Arg Ala Leu Ala Val Ser
                20                  25                  30

Gly Val Gly Lys Leu His Gln Ala Tyr Ser Phe Trp Lys Trp Gly Ala
            35                  40                  45

Leu Leu Leu Leu Ala Phe Phe Ala Ser Phe Thr Ser Leu Thr Thr Arg
        50                  55                  60

Ile Lys Thr Leu Val Phe Arg Leu Arg Asn Val Asn Val Ser Leu Pro
65                  70                  75                  80

Ser Gln Thr Leu Leu Cys Asn Tyr Asp Ser Asp Ser Asp Trp Ser Phe
                85                  90                  95

Ser Ser Asp Ser Ser Asp Glu Glu Lys Asp Glu Asp Asn Lys Glu
            100                 105                 110

Asp Asp Ser Val Asn Gly Asp Ser Arg Val Gln Arg Phe Gly Tyr Tyr
        115                 120                 125

His Asp Asp Asp Lys Gly Ile Ser Gly Ser Val Pro Trp Leu Arg
    130                 135                 140

Arg Cys Ser Gly Ser Phe Gly Asp Leu Leu Asp Leu Gly Ser Ser Gly
145                 150                 155                 160

Val Val Lys Leu Trp Asp Asn Leu Asp Phe Asn Gly Glu Gly Ser Pro
                165                 170                 175

Val Ala Ser Phe Phe Ser Lys Cys Gly Ser Tyr Ser Leu Leu Ser Ser
            180                 185                 190

Ala Val Leu Leu Ala Ala Glu Lys Lys Gly Ser Asp Gly Leu Glu Val
        195                 200                 205

Ser Ala Trp Asp Ala Arg Val Gly Phe Gly Val Pro Ala Leu Leu Ala
    210                 215                 220

Glu Trp Lys Gln Pro Gly Arg Leu Leu Gly Lys Ile Ile Arg Val Asp
225                 230                 235                 240

Val Gly Asp Val Asp Lys Ile Tyr Val Gly Asp Val Glu Gly Glu
                245                 250                 255
```

Ile Thr Val Gly Asp Met Arg Met Val Asn Gly Ala Leu Thr Glu Leu
            260                 265                 270

Thr Glu Ser Glu Val Glu Arg Met Val Arg Arg Arg Arg Arg His
        275                 280                 285

<210> SEQ ID NO 27
<211> LENGTH: 1029
<212> TYPE: DNA
<213> ORGANISM: Arabidopsis thaliana

<400> SEQUENCE: 27

| | | | | | |
|---|---|---|---|---|---|
| atgcaacaac | tcatgacctt | gttatcacca | ccactctctc | attcttctct | ccttcccacc | 60 |
| gtcactacca | aattcgggtc | accacgatta | gtcactacgt | gcatgggcca | tgcagggcgt | 120 |
| aaaaatatca | aggataaggt | ggttctcatc | acaggtacaa | caggcacagg | caagtcacgc | 180 |
| ctctcagtcg | atcttgccac | ccgttttttt | cccgccgaga | tcataaactc | ggacaaaatg | 240 |
| caaatctaca | agggattcga | gattgtcaca | aatctaatcc | cactgcatga | gcaaggagga | 300 |
| gtcccgcacc | atcttctagg | tcagttccac | ccacaagacg | tgaactcac | ccctgcagag | 360 |
| ttccgttctt | tggcgacact | gtccatctct | aaactaattt | ctagcaagaa | actcccgatt | 420 |
| gtagttggtg | atccaactc | cttcaatcac | gctctactcg | ccgagcgttt | tgacccggat | 480 |
| attgatccat | tctctcccgg | atcgagtctt | tcaacgatct | gctctgacct | aaggtacaaa | 540 |
| tgttgcatct | tatgggttga | tgttttagag | ccggttctgt | tccaacactt | gtgcaatcgt | 600 |
| gtcgaccaaa | tgatcgagtc | gggattggtc | gagcagcttg | ccgaattgta | cgaccctgtt | 660 |
| gtagattcgg | gtcgacgact | aggggttcgg | aagacgatag | gagtagagga | gttcgaccga | 720 |
| tactttagag | tataccctaa | ggagatggac | aagggaattt | gggacttagc | gagaaaggcg | 780 |
| gcgtacgagg | agacagtgaa | ggggatgaaa | gagaggacat | gtcggttggt | gaagaagcag | 840 |
| aaagagaaga | tcatgaagct | gataagaggt | ggttgggaga | ttaagaggct | tgacgctacg | 900 |
| gcggcaatta | tggctgagct | gaatcaaagt | acggcaaagg | gagaaggaaa | gaatgggaga | 960 |
| gagatttggg | aaaaacacat | tgtggatgaa | agtgtcgaga | ttgtcaagaa | gttttttgttg | 1020 |
| gaagtttag | | | | | | 1029 |

<210> SEQ ID NO 28
<211> LENGTH: 342
<212> TYPE: PRT
<213> ORGANISM: Arabidopsis thaliana

<400> SEQUENCE: 28

Met Gln Gln Leu Met Thr Leu Leu Ser Pro Pro Leu Ser His Ser Ser
1               5                   10                  15

Leu Leu Pro Thr Val Thr Thr Lys Phe Gly Ser Pro Arg Leu Val Thr
            20                  25                  30

Thr Cys Met Gly His Ala Gly Arg Lys Asn Ile Lys Asp Lys Val Val
        35                  40                  45

Leu Ile Thr Gly Thr Thr Gly Thr Gly Lys Ser Arg Leu Ser Val Asp
    50                  55                  60

Leu Ala Thr Arg Phe Phe Pro Ala Glu Ile Ile Asn Ser Asp Lys Met
65                  70                  75                  80

Gln Ile Tyr Lys Gly Phe Glu Ile Val Thr Asn Leu Ile Pro Leu His
                85                  90                  95

Glu Gln Gly Gly Val Pro His His Leu Leu Gly Gln Phe His Pro Gln
            100                 105                 110

```
Asp Gly Glu Leu Thr Pro Ala Glu Phe Arg Ser Leu Ala Thr Leu Ser
        115                 120                 125

Ile Ser Lys Leu Ile Ser Lys Lys Leu Pro Ile Val Val Gly Gly
        130                 135                 140

Ser Asn Ser Phe Asn His Ala Leu Leu Ala Glu Arg Phe Asp Pro Asp
145                 150                 155                 160

Ile Asp Pro Phe Ser Pro Gly Ser Ser Leu Ser Thr Ile Cys Ser Asp
                165                 170                 175

Leu Arg Tyr Lys Cys Cys Ile Leu Trp Val Asp Val Leu Glu Pro Val
                180                 185                 190

Leu Phe Gln His Leu Cys Asn Arg Val Asp Gln Met Ile Glu Ser Gly
        195                 200                 205

Leu Val Glu Gln Leu Ala Glu Leu Tyr Asp Pro Val Val Asp Ser Gly
    210                 215                 220

Arg Arg Leu Gly Val Arg Lys Thr Ile Gly Val Glu Glu Phe Asp Arg
225                 230                 235                 240

Tyr Phe Arg Val Tyr Pro Lys Glu Met Asp Lys Gly Ile Trp Asp Leu
                245                 250                 255

Ala Arg Lys Ala Ala Tyr Glu Glu Thr Val Lys Gly Met Lys Glu Arg
                260                 265                 270

Thr Cys Arg Leu Val Lys Lys Gln Lys Glu Lys Ile Met Lys Leu Ile
        275                 280                 285

Arg Gly Gly Trp Glu Ile Lys Arg Leu Asp Thr Ala Ala Ile Met
    290                 295                 300

Ala Glu Leu Asn Gln Ser Thr Ala Lys Gly Glu Gly Lys Asn Gly Arg
305                 310                 315                 320

Glu Ile Trp Glu Lys His Ile Val Asp Glu Ser Val Glu Ile Val Lys
                325                 330                 335

Lys Phe Leu Leu Glu Val
            340

<210> SEQ ID NO 29
<211> LENGTH: 1299
<212> TYPE: DNA
<213> ORGANISM: Arabidopsis thaliana

<400> SEQUENCE: 29
atctccaacc tccaccgcat tgattcctct gcttccggtt caatgtcgct gctaaaccaa      60
ctcttcaacc gtgggatctt tggcgccaaa tgcaagacaa gcttgaactt ggcgatagct     120
cgaatgaaat tgctgcaaaa caagagagat atgcagctta acatatgaa gaaggagata     180 gctcacttct gcaagctgg acaagaaccc attgctcgaa ttcgggtttg atctcattct     240
gatttctgta tgttacttct tacaatcaac atcaatctct tatgttcttg tctgagattt     300
aggtggagca tgtgatcaga gaatgaatt tatgggcagc ttatgagata ttggagctat     360
tctgcgagtt tatacttgct cgtgttccaa ttcttgaaag tgaaaggaa tgcccgagag     420 agttgagaga ggctattgct agcattatct ttgctgctcc aaggtgctct gaagtacctg     480
atcttcttca aataaagaat ctgtttggta caaatatgg aaaagaattt atcatggttg     540
cttctgagct tcgtccggat tctggtgtca atcgtactat cattgagaag ctttctccta     600
ccagtccatc tggagcggca aggctcaaga tgttaaagga aattgcgcag gagtacagtt     660
tgaattggga ttcttctgcc acggaagcag agttcatgaa gagccatgaa gacctactgg     720
gtggagctaa gcaaatacat cgtcaagatg gtatctctga atctcgaccg tcccaacaag     780
```

```
gctacggtca gtcttcggtt tctagggaag ttgaaagtct gcctgcagag gccacacaga    840
gattccaaaa gcttcaagct caaaacccag tgagcaaaag catgccatca tctaagctga    900
cttcagcctt tcaagctcct cctgatacta gacggaatca gactgatgta atggagatag    960
ctcgagctgc cctagctagc gctgatcgtg caacagcagc tgctcgtgct gctgcgcaac   1020
tagtgaatgt ctcttatggg gctactacac ccacagtagc agcagaaggg aagcccttaa   1080
acttaatgta gttgccacgt cgtcatttgt gaataaaagc aactgtattt gcttcataca   1140
cagaaagaag gataacgatg ttttctttgg tacttcatag gtttggaaaa atgagtatgc   1200
taaagagtat tggtagatta tgctcgagtg ttgtgacctt aggttgattc aaaagacagt   1260
gatgtttaaa tgtgacatac agatataact ctgaagttt                         1299
```

<210> SEQ ID NO 30
<211> LENGTH: 255
<212> TYPE: PRT
<213> ORGANISM: Arabidopsis thaliana

<400> SEQUENCE: 30

Met Asn Leu Trp Ala Ala Tyr Glu Ile Leu Glu Leu Phe Cys Glu Phe
1               5                   10                  15

Ile Leu Ala Arg Val Pro Ile Leu Glu Ser Glu Lys Glu Cys Pro Arg
            20                  25                  30

Glu Leu Arg Glu Ala Ile Ala Ser Ile Ile Phe Ala Ala Pro Arg Cys
        35                  40                  45

Ser Glu Val Pro Asp Leu Leu Gln Ile Lys Asn Leu Phe Gly Thr Lys
50                  55                  60

Tyr Gly Lys Glu Phe Ile Met Val Ala Ser Glu Leu Arg Pro Asp Ser
65                  70                  75                  80

Gly Val Asn Arg Thr Ile Ile Glu Lys Leu Ser Pro Thr Ser Pro Ser
                85                  90                  95

Gly Ala Ala Arg Leu Lys Met Leu Lys Glu Ile Ala Gln Glu Tyr Ser
            100                 105                 110

Leu Asn Trp Asp Ser Ser Ala Thr Glu Ala Glu Phe Met Lys Ser His
        115                 120                 125

Glu Asp Leu Leu Gly Gly Ala Lys Gln Ile His Arg Gln Asp Gly Ile
130                 135                 140

Ser Glu Ser Arg Pro Ser Gln Gln Gly Tyr Gly Gln Ser Ser Val Ser
145                 150                 155                 160

Arg Glu Val Glu Ser Leu Pro Ala Glu Ala Thr Gln Arg Phe Gln Lys
                165                 170                 175

Leu Gln Ala Gln Asn Pro Val Ser Lys Ser Met Pro Ser Ser Lys Leu
            180                 185                 190

Thr Ser Ala Phe Gln Ala Pro Pro Asp Thr Arg Arg Asn Gln Thr Asp
        195                 200                 205

Val Met Glu Ile Ala Arg Ala Leu Ala Ser Ala Asp Arg Ala Thr
210                 215                 220

Ala Ala Ala Arg Ala Ala Ala Gln Leu Val Asn Val Ser Tyr Gly Ala
225                 230                 235                 240

Thr Thr Pro Thr Val Ala Ala Glu Gly Lys Pro Leu Asn Leu Met
                245                 250                 255

<210> SEQ ID NO 31
<211> LENGTH: 1421
<212> TYPE: DNA

<213> ORGANISM: Arabidopsis thaliana

<400> SEQUENCE: 31

```
ttcctctgct tccggttcaa tgtcgctgct aaaccaactc ttcaaccgtg ggatctttgg      60
cgccaaatgg tttcttcgtc ttcttctttt ctcttatacg ttgatttggg ttttgattga     120
agctagggtt tcttcaataa tttgatgcca tcgattactc ttttgcttca atttgaaatt     180
agagtttgtt atgctcttaa ttgtccataa aactgagaaa ttgaagtaaa tgttggcagc     240
aagacaagct tgaacttggc gatagctcga atgaaattgc tgcaaaacaa gagagatatg     300
cagcttaaac atatgaagaa ggagatagct cacttcttgc aagctggaca agaacccatt     360
gctcgaattc gggtttgatc tcattctgat ttctgtatgt tacttcttac aatcaacatc     420
aatctcttat gttcttgtct gagatttagg tggagcatgt gatcagagaa atgaatttat     480
gggcagctta tgagatattg gagctattct gcgagtttat acttgctcgt gttccaattc     540
ttgaaagtga aaaggaatgc ccgagagagt tgagagaggc tattgctagc attatctttg     600
ctgctccaag gtgctctgaa gtacctgatc ttcttcaaat aaagaatctg tttggtacaa     660
aatatggaaa agaatttatc atggttgctt ctgagcttcg tccggattct ggtgtcaatc     720
gtactatcat tgagaagctt tctcctacca gtccatctgg agcggcaagg ctcaagatgt     780
taaaggaaat tgcgcaggag tacagtttga attgggattc ttctgccacg gaagcagagt     840
tcatgaagag ccatgaagac ctactgggtg agctaagca aatacatcgt caagatggta     900
tctctgaatc tcgaccgtcc caacaaggct acggtcagtc ttcggtttct agggaagttg     960
aaagtctgcc tgcagaggcc acacagagat tccaaaagct tcaagctcaa aacccagtga    1020
gcaaaagcat gccatcatct aagctgactt cagcctttca agctcctcct gatactagac    1080
ggaatcagac tgatgtaatg gagatagctc gagctgccct agctagcgct gatcgtgcaa    1140
cagcagctgc tcgtgctgct gcgcaactag tgaatgtctc ttatggggct actacaccca    1200
cagtagcagc agaagggaag cccttaaact taatgtagtt gccacgtcgt catttgtgaa    1260
taaaagcaac tgtatttgct tcatacacag aaagaaggat aacgatgttt tctttggtac    1320
ttcataggtt tggaaaaatg agtatgctaa agagtattgg tagattatgc tcgagtgttg    1380
tgaccttagg ttgattcaaa agacagtgat gtttaaatgt g                       1421
```

<210> SEQ ID NO 32
<211> LENGTH: 255
<212> TYPE: PRT
<213> ORGANISM: Arabidopsis thaliana

<400> SEQUENCE: 32

```
Met Asn Leu Trp Ala Ala Tyr Glu Ile Leu Glu Leu Phe Cys Glu Phe
1               5                   10                  15

Ile Leu Ala Arg Val Pro Ile Leu Glu Ser Glu Lys Glu Cys Pro Arg
            20                  25                  30

Glu Leu Arg Glu Ala Ile Ala Ser Ile Phe Ala Ala Pro Arg Cys
        35                  40                  45

Ser Glu Val Pro Asp Leu Leu Gln Ile Lys Asn Leu Phe Gly Thr Lys
    50                  55                  60

Tyr Gly Lys Glu Phe Ile Met Val Ala Ser Glu Leu Arg Pro Asp Ser
65                  70                  75                  80

Gly Val Asn Arg Thr Ile Ile Glu Lys Leu Ser Pro Thr Ser Pro Ser
                85                  90                  95

Gly Ala Ala Arg Leu Lys Met Leu Lys Glu Ile Ala Gln Glu Tyr Ser
```

```
              100              105              110
Leu Asn Trp Asp Ser Ser Ala Thr Glu Ala Glu Phe Met Lys Ser His
        115                  120              125
Glu Asp Leu Leu Gly Gly Ala Lys Gln Ile His Arg Gln Asp Gly Ile
    130                  135              140
Ser Glu Ser Arg Pro Ser Gln Gln Gly Tyr Gly Gln Ser Ser Val Ser
145              150                  155                  160
Arg Glu Val Glu Ser Leu Pro Ala Glu Ala Thr Gln Arg Phe Gln Lys
            165                  170                  175
Leu Gln Ala Gln Asn Pro Val Ser Lys Ser Met Pro Ser Ser Lys Leu
        180                  185                  190
Thr Ser Ala Phe Gln Ala Pro Pro Asp Thr Arg Arg Asn Gln Thr Asp
        195                  200                  205
Val Met Glu Ile Ala Arg Ala Ala Leu Ala Ser Ala Asp Arg Ala Thr
    210                  215                  220
Ala Ala Ala Arg Ala Ala Ala Gln Leu Val Asn Val Ser Tyr Gly Ala
225                  230                  235                  240
Thr Thr Pro Thr Val Ala Ala Glu Gly Lys Pro Leu Asn Leu Met
                245                  250                  255

<210> SEQ ID NO 33
<211> LENGTH: 1305
<212> TYPE: DNA
<213> ORGANISM: Arabidopsis thaliana

<400> SEQUENCE: 33
atcttcttcg tttccttttt tcctcaatcg acgacgatca atctccaacc tccaccgcat      60
tgattcctct gcttccggtt caatgtcgct gctaaaccaa ctcttcaacc gtgggatctt     120
tggcgccaaa tgcaagacaa gcttgaactt ggcgatagct cgaatgaaat tgctgcaaaa     180
caagagagat atgcagctta acatatgaa gaaggagata gctcacttct tgcaagctgg     240
acaagaaccc attgctcgaa ttcgggtgga gcatgtgatc agagaaatga atttatgggc     300
agcttatgag atattggagc tattctgcga gtttatactt gctcgtgttc caattcttga     360
aagtgaaaag gaatgcccga gagagttgag agaggctatt gctagcatta tcttgctgc     420 tccaaggtgc tctgaagtac ctgatcttct tcaaataaag aatctgtttg gtacaaaata     480
tggaaaagaa tttatcatgg ttgcttctga gcttcgtccg gattctggtg tcaatcgtac     540
tatcattgag aagctttctc ctaccagtcc atctggagcg gcaaggctca agatgttaaa     600
ggaaattgcg caggagtaca gtttgaattg ggattcttct gccacggaag cagagttcat     660
gaagagccat gaagacctac tgggtggagc taagcaaata catcgtcaag atggtatctc     720
tgaatctcga ccgtcccaac aaggctacgg tcagtcttcg gtttctaggg aagttgaaag     780
tctgcctgca gaggccacac agagattcca aaagcttcaa gctcaaaacc cagtgagcaa     840
aagcatgcca tcatctaagc tgacttcagc ctttcaagct cctcctgata ctagacggaa     900
tcagactgat gtaatggaga tagctcgagc tgccctagct agcgctgatc gtgcaacagc     960
agctgctcgt gctgctgcgc aactagtgaa tgtctcttat ggggctacta cacccacagt    1020
agcagcagaa gggaagccct taaacttaat gtagttgcca cgtcgtcatt tgtgaataaa    1080
agcaactgta tttgcttcat acacagaaag aaggataacg atgttttctt tggtacttca    1140
taggtttgga aaaatgagta tgctaaagag tattggtaga ttatgctcga gtgttgtgac    1200
cttaggttga ttcaaaagac agtgatgttt aaatgtgaca tacagatata actctgaagt    1260
```
ttgttggttt tacaaaatct atgcagaaaa aacaacatta tcatg            1305

<210> SEQ ID NO 34
<211> LENGTH: 323
<212> TYPE: PRT
<213> ORGANISM: Arabidopsis thaliana

<400> SEQUENCE: 34

Met Ser Leu Leu Asn Gln Leu Phe Asn Arg Gly Ile Phe Gly Ala Lys
1               5                   10                  15

Cys Lys Thr Ser Leu Asn Leu Ala Ile Ala Arg Met Lys Leu Leu Gln
            20                  25                  30

Asn Lys Arg Asp Met Gln Leu Lys His Met Lys Lys Glu Ile Ala His
        35                  40                  45

Phe Leu Gln Ala Gly Gln Glu Pro Ile Ala Arg Ile Arg Val Glu His
    50                  55                  60

Val Ile Arg Glu Met Asn Leu Trp Ala Ala Tyr Glu Ile Leu Glu Leu
65                  70                  75                  80

Phe Cys Glu Phe Ile Leu Ala Arg Val Pro Ile Leu Glu Ser Glu Lys
                85                  90                  95

Glu Cys Pro Arg Glu Leu Arg Glu Ala Ile Ala Ser Ile Ile Phe Ala
            100                 105                 110

Ala Pro Arg Cys Ser Glu Val Pro Asp Leu Leu Gln Ile Lys Asn Leu
        115                 120                 125

Phe Gly Thr Lys Tyr Gly Lys Glu Phe Ile Met Val Ala Ser Glu Leu
    130                 135                 140

Arg Pro Asp Ser Gly Val Asn Arg Thr Ile Ile Glu Lys Leu Ser Pro
145                 150                 155                 160

Thr Ser Pro Ser Gly Ala Ala Arg Leu Lys Met Leu Lys Glu Ile Ala
                165                 170                 175

Gln Glu Tyr Ser Leu Asn Trp Asp Ser Ser Ala Thr Glu Ala Glu Phe
            180                 185                 190

Met Lys Ser His Glu Asp Leu Leu Gly Gly Ala Lys Gln Ile His Arg
        195                 200                 205

Gln Asp Gly Ile Ser Glu Ser Arg Pro Ser Gln Gly Tyr Gly Gln
    210                 215                 220

Ser Ser Val Ser Arg Glu Val Glu Ser Leu Pro Ala Glu Ala Thr Gln
225                 230                 235                 240

Arg Phe Gln Lys Leu Gln Ala Gln Asn Pro Val Ser Lys Ser Met Pro
                245                 250                 255

Ser Ser Lys Leu Thr Ser Ala Phe Gln Ala Pro Asp Thr Arg Arg
            260                 265                 270

Asn Gln Thr Asp Val Met Glu Ile Ala Arg Ala Ala Leu Ala Ser Ala
        275                 280                 285

Asp Arg Ala Thr Ala Ala Arg Ala Ala Gln Leu Val Asn Val
    290                 295                 300

Ser Tyr Gly Ala Thr Thr Pro Thr Val Ala Ala Glu Gly Lys Pro Leu
305                 310                 315                 320

Asn Leu Met

<210> SEQ ID NO 35
<211> LENGTH: 1527
<212> TYPE: DNA
<213> ORGANISM: Arabidopsis thaliana

<400> SEQUENCE: 35

```
aggtcgcaac accgcaatag atctttccc caagtttcag acaaacataa agcagcagag      60
aaaattttca gtttcaaag gcttttccc tcaccaagca aaatttggat atttgtcagc      120
aaaatctgca gctaaattgg gacttgtctt gttagttcaa agattgaaac ttttttggtt    180
aattgtttgg cggaagaaga tttacaatgg gagaggagca tccgagaaag cggtctagac    240
aacattttga agcggaggcg agaaacgtat cgttgtttga atccctcaa tgcgaaacct     300
ccaagtggta tttcagcagg gaagagattg agcgtttctc tccatccaga aagatggga    360
ttgatcttgt gaaggagtcg ttttacggt cttcgtattg caccttcctg caaagacttg    420
gcatgaagct tcatgtgtcc caggttacaa tatcatgtgc aatggtgatg tgccacaggt    480
tttacatgcg ccaatctcat gcaaaaatg actggcagac aatagcgact tccagtctgt    540
tcctcgcttg caaagctgaa gatgagccat gtcaactgtc cagtgtcgtt gtagcgtctt    600
atgaaataat ttatgagtgg gatccttctg cctcaattag aatccatcaa actgagtgtt    660
atcatgaatt taaagaaatt attttgtccg gggaaagtct tctgctgagc acaagtgctt    720
tccatttaga cattgaactt ccctacaaac ctctggctgc ggctttgaat agactgaacg    780
cttggcctga ccttgcaaca gctgcatgga attttgtgca tgactggatt cgaaccacac    840
tatgcttgca gtacaaaccc catgttattg caacagccac tgtgcaccta gctgctacgt    900
ttcagaatgc gaaagtaggc agcaggagag attggtggtt ggagtttgga gttacaacta    960
agctattaaa agaggtaatc caggagatgt gcacactgat agaagtggac agaaggagga   1020
atatgccacc tccacctcca cctccaagaa gagagttaag ttgggcaata cctgcagccg   1080
taaagccggt ccatatggct agagcttatc cgtttcacag ctacccttg cagtcctata    1140
gacaggctgg catctggtga gccattgttg agcagcatga agatgtaatc tctcttagag   1200
tcttgagttg gtttagcaat aaaagatttc cgtagagact catgagagag gcagtgtagc   1260
attatataga gatccgagtg aggtgcttct gtctaagtta agcgtctcat gtatgaccaa   1320
agtggattct ctcgagattc ttggtctctg ttctcgatag agagagatta tgtatagaag   1380
tgtcccattc acatgttata atactagctg actttatatc gtttgtatat ctggaatcta   1440
tgttttggt ttcttaaaa agtttaaagt tgttttgatt ttgactaatt ctctcattgt     1500
taagtaattt ggttttgat gaagtgc                                         1527
```

<210> SEQ ID NO 36
<211> LENGTH: 317
<212> TYPE: PRT
<213> ORGANISM: Arabidopsis thaliana

<400> SEQUENCE: 36

```
Met Gly Glu Glu His Pro Arg Lys Arg Ser Arg Gln His Phe Glu Ala
1               5                   10                  15

Glu Ala Arg Asn Val Ser Leu Phe Glu Ser Pro Gln Cys Glu Thr Ser
            20                  25                  30

Lys Trp Tyr Phe Ser Arg Glu Glu Ile Glu Arg Phe Ser Pro Ser Arg
        35                  40                  45

Lys Asp Gly Ile Asp Leu Val Lys Glu Ser Phe Leu Arg Ser Ser Tyr
    50                  55                  60

Cys Thr Phe Leu Gln Arg Leu Gly Met Lys Leu His Val Ser Gln Val
65                  70                  75                  80

Thr Ile Ser Cys Ala Met Val Met Cys His Arg Phe Tyr Met Arg Gln
                85                  90                  95
```

Ser His Ala Lys Asn Asp Trp Gln Thr Ile Ala Thr Ser Ser Leu Phe
                100                 105                 110

Leu Ala Cys Lys Ala Glu Asp Glu Pro Cys Gln Leu Ser Ser Val Val
            115                 120                 125

Val Ala Ser Tyr Glu Ile Ile Tyr Glu Trp Asp Pro Ser Ala Ser Ile
        130                 135                 140

Arg Ile His Gln Thr Glu Cys Tyr His Glu Phe Lys Glu Ile Ile Leu
145                 150                 155                 160

Ser Gly Glu Ser Leu Leu Ser Thr Ser Ala Phe His Leu Asp Ile
                165                 170                 175

Glu Leu Pro Tyr Lys Pro Leu Ala Ala Ala Leu Asn Arg Leu Asn Ala
            180                 185                 190

Trp Pro Asp Leu Ala Thr Ala Ala Trp Asn Phe Val His Asp Trp Ile
        195                 200                 205

Arg Thr Thr Leu Cys Leu Gln Tyr Lys Pro His Val Ile Ala Thr Ala
210                 215                 220

Thr Val His Leu Ala Ala Thr Phe Gln Asn Ala Lys Val Gly Ser Arg
225                 230                 235                 240

Arg Asp Trp Trp Leu Glu Phe Gly Val Thr Thr Lys Leu Leu Lys Glu
                245                 250                 255

Val Ile Gln Glu Met Cys Thr Leu Ile Glu Val Asp Arg Arg Arg Asn
            260                 265                 270

Met Pro Pro Pro Pro Pro Arg Arg Glu Leu Ser Trp Ala Ile
        275                 280                 285

Pro Ala Ala Val Lys Pro Val His Met Ala Arg Ala Tyr Pro Phe His
        290                 295                 300

Ser Tyr Pro Leu Gln Ser Tyr Arg Gln Ala Gly Ile Trp
305                 310                 315

<210> SEQ ID NO 37
<211> LENGTH: 444
<212> TYPE: DNA
<213> ORGANISM: Arabidopsis thaliana

<400> SEQUENCE: 37
atggatataa atcggaaac agagcaatac aaaagaaaag cagagataga gaaacacaca      60
aaggagccaa ataaacacag agacgaagca gtgctccaaa atagagctgg gaggcacaga   120
gaccgagccg taatagatca caaaagcgaa gaaagagaga gagaaagcgt acagaatgtt   180
acagagatga gtgggattga gatctgag ggtgagtggt cgccgccggt ggaaggaatt     240
accgacgagg agctgccgtc tcactcgccg atggatgatc tagggtttgc tttgttcgcg   300
agttggggga aaagacagag agacagaga atgggatctc ctgacataag gatttatatt   360
tttaatccga taaaaaagat aataataatg gaaactagaa tccggtttgg tctagaatgg   420
aaaccaagcg gttttggttc ttga                                           444

<210> SEQ ID NO 38
<211> LENGTH: 147
<212> TYPE: PRT
<213> ORGANISM: Arabidopsis thaliana

<400> SEQUENCE: 38

Met Asp Ile Lys Ser Glu Thr Glu Gln Tyr Lys Arg Lys Ala Glu Ile
1               5                   10                  15

Glu Lys His Thr Lys Glu Pro Asn Lys His Arg Asp Glu Ala Val Leu
            20                  25                  30

```
Gln Asn Arg Ala Gly Arg His Arg Asp Arg Ala Val Ile Asp His Lys
        35                  40                  45

Ser Glu Glu Arg Glu Arg Glu Ser Val Gln Asn Val Thr Glu Met Ser
 50                  55                  60

Gly Ile Glu Arg Ser Gly Glu Trp Ser Pro Pro Val Glu Gly Ile
 65                  70                  75                  80

Thr Asp Glu Glu Leu Pro Ser His Ser Pro Met Asp Asp Leu Gly Phe
                 85                  90                  95

Ala Leu Phe Ala Ser Trp Gly Arg Lys Thr Glu Arg Gln Arg Met Gly
            100                 105                 110

Ser Pro Asp Ile Arg Ile Tyr Ile Phe Asn Pro Ile Lys Lys Ile Ile
            115                 120                 125

Ile Met Glu Thr Arg Ile Arg Phe Gly Leu Glu Trp Lys Pro Ser Gly
    130                 135                 140

Phe Gly Ser
145
```

<210> SEQ ID NO 39
<211> LENGTH: 1381
<212> TYPE: DNA
<213> ORGANISM: Arabidopsis thaliana

<400> SEQUENCE: 39

```
attctctgtc tctctgtctt tctcccccaa ctcgcgaaca aagcaaaccc tagatcatcc      60
atcggcgagt gagacggcag ctcctcgtcg gtaattcctt ccaccggcgg cgaccactca     120
ccctcagatc tctcaatccc actcatctct gtaacattct ggtggaaatt ctgccatggc     180
ggagcatttg gcttcaatct ttggtactga gaaagacaga gtgaattgcc ctttctactt     240
caagattggc gcttgccgtc atggtgaccg gtgctcgcgt cttcacaacc gtcctaccat     300
ctccccaaca ctccttcttt caaacatgta ccaaaggcct gacatgatta ccctggtgt     360
tgacgctcag ggccaaccac tcgacccgcg taagattcag gagcactttg aggatttctt     420
tgaggatctt tttgaggagc ttggaaagtt tggcgagata gagagcctca catttgtga     480
caaccttgct gaccacatga ttggcaacgt atatgttcag tttaaggaag aggatcaggc     540
tgcagctgct ttgcaggctc tgcaaggtag gttctattca ggacgtccca tcattgctga     600
tttctctcct gtgacggatt ccgcgaagc cacgtgtagg cagtatgaag aaaacaactg     660
caaccgtggt gggtactgta atttcatgca tgtgaagctt gtttcgaggg aactaaggag     720
aaaactcttt gggagatatc ggcgatcata ccgcagagga agtagaagca ggagcagaag     780
caggagtatt agccccagga caagagaga taatgaccga cgtgatcctt ctcacaggga     840
attcagtcat cgggacagag atcgcgagtt ttaccgtcat ggaagtggaa aaaggagcag     900
tgagaggtcg gagaggcaag agagggacgg ttcaaggggt aggagacaag caagccctaa     960
acgaggaggg agcccgggtg gcgggaggga aggaagtgag gagaggaggg caaggattga    1020
gcaatggaac agagaacggg aggagaagga gagggagga gcataaaaac agttgtttac    1080
tcaaatcaca attgctgcta tgtggtttct gcgtctgctt ctctgcgttt attctgaaat    1140
cggtaaaatc tggtgatgga ttttcatttt ggctgttcta atttggaact tgaaatgagt    1200
ggaatcaact tctttagatt ataaaatgtt tggggttact ttcttgtagt tttgattagg    1260
aaaaaccgct ctgtcccctt gttattgatt tcaccagtg ttctttagaa ctttgtacta    1320
tcttctgttg gttaaaactt aaaagagttc tagtttaatt cgaagttgtc tattgttctt    1380
``` c                                                                              1381

<210> SEQ ID NO 40
<211> LENGTH: 296
<212> TYPE: PRT
<213> ORGANISM: Arabidopsis thaliana

<400> SEQUENCE: 40

Met Ala Glu His Leu Ala Ser Ile Phe Gly Thr Glu Lys Asp Arg Val
1               5                   10                  15

Asn Cys Pro Phe Tyr Phe Lys Ile Gly Ala Cys Arg His Gly Asp Arg
            20                  25                  30

Cys Ser Arg Leu His Asn Arg Pro Thr Ile Ser Pro Thr Leu Leu Leu
        35                  40                  45

Ser Asn Met Tyr Gln Arg Pro Asp Met Ile Thr Pro Gly Val Asp Ala
    50                  55                  60

Gln Gly Gln Pro Leu Asp Pro Arg Lys Ile Gln Glu His Phe Glu Asp
65                  70                  75                  80

Phe Phe Glu Asp Leu Phe Glu Glu Leu Gly Lys Phe Gly Glu Ile Glu
                85                  90                  95

Ser Leu Asn Ile Cys Asp Asn Leu Ala Asp His Met Ile Gly Asn Val
            100                 105                 110

Tyr Val Gln Phe Lys Glu Glu Asp Gln Ala Ala Ala Leu Gln Ala
        115                 120                 125

Leu Gln Gly Arg Phe Tyr Ser Gly Arg Pro Ile Ile Ala Asp Phe Ser
    130                 135                 140

Pro Val Thr Asp Phe Arg Glu Ala Thr Cys Arg Gln Tyr Glu Glu Asn
145                 150                 155                 160

Asn Cys Asn Arg Gly Gly Tyr Cys Asn Phe Met His Val Lys Leu Val
                165                 170                 175

Ser Arg Glu Leu Arg Arg Lys Leu Phe Gly Arg Tyr Arg Arg Ser Tyr
            180                 185                 190

Arg Arg Gly Ser Arg Ser Arg Ser Arg Ser Ile Ser Pro Arg
        195                 200                 205

Asn Lys Arg Asp Asn Asp Arg Arg Asp Pro Ser His Arg Glu Phe Ser
    210                 215                 220

His Arg Asp Arg Asp Arg Glu Phe Tyr Arg His Gly Ser Gly Lys Arg
225                 230                 235                 240

Ser Ser Glu Arg Ser Glu Arg Gln Glu Arg Asp Gly Ser Arg Gly Arg
                245                 250                 255

Arg Gln Ala Ser Pro Lys Arg Gly Gly Ser Pro Gly Gly Gly Arg Glu
            260                 265                 270

Gly Ser Glu Glu Arg Arg Ala Arg Ile Glu Gln Trp Asn Arg Glu Arg
        275                 280                 285

Glu Glu Lys Glu Glu Gly Gly Ala
    290                 295

<210> SEQ ID NO 41
<211> LENGTH: 1824
<212> TYPE: DNA
<213> ORGANISM: Arabidopsis thaliana

<400> SEQUENCE: 41
gaaactcttc aaaatcatc attcttttc atctttcttt acacacaaac acacatacac      60
acacatatat aatacagaga tcaggtataa taaatactta tatatatagc atcatcaact    120

```
ctcatacata tatggactct gctaatctcc atcagcttca agatcaatta cagcttgtgg      180
ggtcttcttc atcttcttct tccttagaca ataactctga cccttcttgc tatggagctt      240
catctgccca tcaatggagc ccaggaggta tttctttgaa tagtgtgagc ttgagtcata      300
attataacaa tgagatgtta aacacaagag ctcacaacaa caacaacaac aacaacacaa      360
gtgaatgtat gagtctctcc agcatccaca atcactcctt gatccaacaa caagactttc      420
ctttacaatg gcctcatgac caatcttcat atcaacatca tgaaggactt ctcaagatca      480
aagaagagct ttcctcatca actatctcag accatcaaga aggcatatcc aagttcacag      540
acatgttaaa tagtccagtg ataacaaact atttgaagat caatgaacat aaggactaca      600
ctgagaagct tcttctcaag agtatgtctt ctggattccc gatcaatgga gactatggta      660
gcagccttcc ctcttcttct tcttcctctt caccttcgtc tcagtcgcat agaggcaact      720
tcagtcagat ttacccaagc gtaaacatat cgagtttgag cgaatctcgg aagatgagca      780
tggacgacat gagtaacatc tcaagaccat ttgatataaa catgcaggtt tttgatggaa      840
gattgtttga aggaaatgta ttagttcctc cttttaacgc tcaagagatt agtagtcttg      900
ggatgagcag aggaagcctt ccttcttttg gcctcccttt tcatcatcat ctgcagcaaa      960
cacttcccca cctttcttct tccccctact catcaaatgg aatgttcagc aatgaacctc     1020
aaacaagtga agggaagagg cataacttct tgatggcaac aaaagcagga gaaaatgctt     1080
ccaagaaacc gcgcgtggaa tcacgctcct cttgcccacc cttcaaggtg aggaaagaaa     1140
agttaggaga cagaatagca gctctgcagc agttggtttc accctttggg aagacagata     1200
cagcatctgt gttaatggaa gcaattggat acatcaaatt cctacagagc cagatcgaga     1260
ctttaagcgt cccctacatg agagcatcta ggaaccgacc cggaaaagcc tcccagctgg     1320
tctcacaatc acaagaaggg gatgaggaag agacagagag tcttagaagc cgtgggctat     1380
gtctagtgcc gttatcatgc atgacttatg ttaccggaga tggtggggat ggaggaggcg     1440
gtgttggtac tggttttggg ccaacgccac ctggttttgg tggcggaact agccgtggaa     1500
cttaacaaac cgtaggacta tgatgagtac atttatcgga cttggaggta gagaataaga     1560
agaaatgtta aaggtggagt attagttctt taatctcttt tggttttggt ttattaattg     1620
aaatttcggt ttttgatagt ggagcaaagt tggtcgtcct gattagaaag aagtgttaca     1680
ggatagacca gctttgatcc atttaagatt agtagtgaga cttgacgata tgttctact     1740
tacatgatgg gctgtggggg ctacataaaa tatcaaatag ctttggatta ttttgttaaa     1800
tctcttttgt agataatgtg tcaa                                            1824
```

<210> SEQ ID NO 42
<211> LENGTH: 453
<212> TYPE: PRT
<213> ORGANISM: Arabidopsis thaliana

<400> SEQUENCE: 42

Met Asp Ser Ala Asn Leu His Gln Leu Gln Asp Gln Leu Gln Leu Val
1               5                   10                  15

Gly Ser Ser Ser Ser Ser Ser Ser Leu Asp Asn Asn Ser Asp Pro Ser
            20                  25                  30

Cys Tyr Gly Ala Ser Ser Ala His Gln Trp Ser Pro Gly Gly Ile Ser
        35                  40                  45

Leu Asn Ser Val Ser Leu Ser His Asn Tyr Asn Asn Glu Met Leu Asn
    50                  55                  60

Thr Arg Ala His Asn Asn Asn Asn Asn Asn Asn Thr Ser Glu Cys Met

```
              65                  70                  75                  80
Ser Leu Ser Ser Ile His Asn His Ser Leu Ile Gln Gln Gln Asp Phe
                    85                  90                  95

Pro Leu Gln Trp Pro His Asp Gln Ser Ser Tyr Gln His His Glu Gly
            100                 105                 110

Leu Leu Lys Ile Lys Glu Glu Leu Ser Ser Thr Ile Ser Asp His
            115                 120                 125

Gln Glu Gly Ile Ser Lys Phe Thr Asp Met Leu Asn Ser Pro Val Ile
    130                 135                 140

Thr Asn Tyr Leu Lys Ile Asn Glu His Lys Asp Tyr Thr Glu Lys Leu
145                 150                 155                 160

Leu Leu Lys Ser Met Ser Ser Gly Phe Pro Ile Asn Gly Asp Tyr Gly
                165                 170                 175

Ser Ser Leu Pro Ser Ser Ser Ser Ser Ser Pro Ser Gln Ser
            180                 185                 190

His Arg Gly Asn Phe Ser Gln Ile Tyr Pro Ser Val Asn Ile Ser Ser
        195                 200                 205

Leu Ser Glu Ser Arg Lys Met Ser Met Asp Asp Met Ser Asn Ile Ser
    210                 215                 220

Arg Pro Phe Asp Ile Asn Met Gln Val Phe Asp Gly Arg Leu Phe Glu
225                 230                 235                 240

Gly Asn Val Leu Val Pro Pro Phe Asn Ala Gln Glu Ile Ser Ser Leu
                245                 250                 255

Gly Met Ser Arg Gly Ser Leu Pro Ser Phe Gly Leu Pro Phe His His
            260                 265                 270

His Leu Gln Gln Thr Leu Pro His Leu Ser Ser Ser Pro Thr His Gln
        275                 280                 285

Met Glu Met Phe Ser Asn Glu Pro Gln Thr Ser Glu Gly Lys Arg His
    290                 295                 300

Asn Phe Leu Met Ala Thr Lys Ala Gly Glu Asn Ala Ser Lys Lys Pro
305                 310                 315                 320

Arg Val Glu Ser Arg Ser Ser Cys Pro Pro Phe Lys Val Arg Lys Glu
                325                 330                 335

Lys Leu Gly Asp Arg Ile Ala Ala Leu Gln Gln Leu Val Ser Pro Phe
            340                 345                 350

Gly Lys Thr Asp Thr Ala Ser Val Leu Met Glu Ala Ile Gly Tyr Ile
        355                 360                 365

Lys Phe Leu Gln Ser Gln Ile Glu Thr Leu Ser Val Pro Tyr Met Arg
    370                 375                 380

Ala Ser Arg Asn Arg Pro Gly Lys Ala Ser Gln Leu Val Ser Gln Ser
385                 390                 395                 400

Gln Glu Gly Asp Glu Glu Thr Arg Asp Leu Arg Ser Arg Gly Leu
                405                 410                 415

Cys Leu Val Pro Leu Ser Cys Met Thr Tyr Val Thr Gly Asp Gly
            420                 425                 430

Asp Gly Gly Gly Gly Val Gly Thr Gly Phe Trp Pro Thr Pro Pro Gly
        435                 440                 445

Phe Gly Gly Gly Thr
    450

<210> SEQ ID NO 43
<211> LENGTH: 1677
<212> TYPE: DNA
<213> ORGANISM: Arabidopsis thaliana
```

<400> SEQUENCE: 43

```
atggctcgtg tttacatgga gacgatgata caaaaatgcg tcagcttctc ccaaatcaaa      60
caactccaat ctcacttcct caccgccggc catttccaat cttcctttct ccgttctcgt     120
cttctcgaac gctgcgcaat ctcaccattc ggagaccttt ccttcgccgt acaaattttc     180
cggtacatcc ctaaaccttt aaccaatgat tggaacgcaa tcatccgcgg attcgccgga     240
agttctcatc cttcacttgc gttttcatgg tatcgttcca tgttgcagca atcttcgtca     300
tcgtcggcta tatgtagagt cgatgctttg acttgttctt ttactcttaa agcttgtgca     360
cgtgcgcttt gttcttccgc tatggatcaa cttcattgtc agattaaccg tcggggatta     420
tccgctgatt cgcttctttg tactacgttg cttgatgctt actctaaaaa cggagattta     480
attagtgcgt ataagttgtt cgatgaaatg cctgtgagag atgttgcgtc gtggaacgcg     540
ttgatcgcgg ggttagtgtc tggtaatcga gcgagtgagg cgatggagtt gtataagaga     600
atggaaacgg aaggaattag aagaagtgaa gtaactgttg ttgctgcttt aggagcttgt     660
tctcatttgg gtgatgttaa ggaaggtgaa aatatcttcc atggatacag taacgataat     720
gtgattgtta gtaacgcggc tattgatatg tattcgaaat gcgggtttgt tgataaaagct    780
tatcaagtgt ttgaacaatt cactggtaag aagagtgttg ttacatggaa cactatgatt     840
acagggtttg cagtgcatgg agaagcacat agagcgttgg agattttgtga caagttggag    900
gataatggta ttaagcctga tgatgtctcg tacttagctg ctttaactgc gtgtagacat     960
gcggggttag tggagtatgg tttgtctgta ttcaataata tggcttgtaa gggcgttgag    1020
cgtaacatga agcactatgg ttgtgtggtt gatctgttaa gccgtgcagg aaggttgaga    1080
gaagctcacg atatcatatg ttcaatgtcg atgattccgg atcctgtttt gtggcagagc    1140
cttcttggag cttcggagat ttatagtgat gttgaaatgg ctgagattgc ttctagggaa    1200
ataaaggaaa tgggagttaa caatgatggt gattttgtgt tgctatcgaa tgtttatgct    1260
gcgcagggac ggtggaaaga tgtaggacga gtgagagatg tatggaaag caaacaagtg     1320
aagaaaattc caggtcttag ctacatagaa gccaaaggaa cgattcatga attctacaac    1380
agtgacaaga gccatgaaca gtggagagag atttatgaga agatcgatga gatcaggttc    1440
aagataagag aggatggtta cgtggcgcag acaggacttg tgttgcacga cataggagag    1500
gaagagaaag agaacgcttt gtgctatcac agcgagaaat tggcggtggc ctacggactg    1560
atgatgatgg atggtgcgga cgaggagagt ccgttcggtt tcataggttc aaagatggtt    1620
cttgctcttg cagagatttt tggtaacgtt acaaaattaa gagggtggca atttttaa      1677
```

<210> SEQ ID NO 44
<211> LENGTH: 558
<212> TYPE: PRT
<213> ORGANISM: Arabidopsis thaliana

<400> SEQUENCE: 44

```
Met Ala Arg Val Tyr Met Glu Thr Met Ile Gln Lys Cys Val Ser Phe
1               5                   10                  15

Ser Gln Ile Lys Gln Leu Gln Ser His Phe Leu Thr Ala Gly His Phe
            20                  25                  30

Gln Ser Ser Phe Leu Arg Ser Arg Leu Leu Glu Arg Cys Ala Ile Ser
        35                  40                  45

Pro Phe Gly Asp Leu Ser Phe Ala Val Gln Ile Phe Arg Tyr Ile Pro
    50                  55                  60
```

-continued

```
Lys Pro Leu Thr Asn Asp Trp Asn Ala Ile Ile Arg Gly Phe Ala Gly
 65                  70                  75                  80

Ser Ser His Pro Ser Leu Ala Phe Ser Trp Tyr Arg Ser Met Leu Gln
                 85                  90                  95

Gln Ser Ser Ser Ser Ala Ile Cys Arg Val Asp Ala Leu Thr Cys
            100                 105                 110

Ser Phe Thr Leu Lys Ala Cys Ala Arg Ala Leu Cys Ser Ser Ala Met
            115                 120                 125

Asp Gln Leu His Cys Gln Ile Asn Arg Arg Gly Leu Ser Ala Asp Ser
130                 135                 140

Leu Leu Cys Thr Thr Leu Leu Asp Ala Tyr Ser Lys Asn Gly Asp Leu
145                 150                 155                 160

Ile Ser Ala Tyr Lys Leu Phe Asp Glu Met Pro Val Arg Asp Val Ala
                165                 170                 175

Ser Trp Asn Ala Leu Ile Ala Gly Leu Val Ser Gly Asn Arg Ala Ser
            180                 185                 190

Glu Ala Met Glu Leu Tyr Lys Arg Met Glu Thr Glu Gly Ile Arg Arg
            195                 200                 205

Ser Glu Val Thr Val Val Ala Ala Leu Gly Ala Cys Ser His Leu Gly
210                 215                 220

Asp Val Lys Glu Gly Glu Asn Ile Phe His Gly Tyr Ser Asn Asp Asn
225                 230                 235                 240

Val Ile Val Ser Asn Ala Ala Ile Asp Met Tyr Ser Lys Cys Gly Phe
                245                 250                 255

Val Asp Lys Ala Tyr Gln Val Phe Glu Gln Phe Thr Gly Lys Lys Ser
            260                 265                 270

Val Val Thr Trp Asn Thr Met Ile Thr Gly Phe Ala Val His Gly Glu
            275                 280                 285

Ala His Arg Ala Leu Glu Ile Phe Asp Lys Leu Glu Asp Asn Gly Ile
            290                 295                 300

Lys Pro Asp Asp Val Ser Tyr Leu Ala Ala Leu Thr Ala Cys Arg His
305                 310                 315                 320

Ala Gly Leu Val Glu Tyr Gly Leu Ser Val Phe Asn Asn Met Ala Cys
                325                 330                 335

Lys Gly Val Glu Arg Asn Met Lys His Tyr Gly Cys Val Val Asp Leu
            340                 345                 350

Leu Ser Arg Ala Gly Arg Leu Arg Glu Ala His Asp Ile Ile Cys Ser
            355                 360                 365

Met Ser Met Ile Pro Asp Pro Val Leu Trp Gln Ser Leu Leu Gly Ala
370                 375                 380

Ser Glu Ile Tyr Ser Asp Val Glu Met Ala Glu Ile Ala Ser Arg Glu
385                 390                 395                 400

Ile Lys Glu Met Gly Val Asn Asn Asp Gly Asp Phe Val Leu Leu Ser
                405                 410                 415

Asn Val Tyr Ala Ala Gln Gly Arg Trp Lys Asp Val Gly Arg Val Arg
            420                 425                 430

Asp Asp Met Glu Ser Lys Gln Val Lys Lys Ile Pro Gly Leu Ser Tyr
            435                 440                 445

Ile Glu Ala Lys Gly Thr Ile His Glu Phe Tyr Asn Ser Asp Lys Ser
450                 455                 460

His Glu Gln Trp Arg Glu Ile Tyr Glu Lys Ile Asp Glu Ile Arg Phe
465                 470                 475                 480

Lys Ile Arg Glu Asp Gly Tyr Val Ala Gln Thr Gly Leu Val Leu His
```

```
                485                 490                 495
Asp Ile Gly Glu Glu Lys Glu Asn Ala Leu Cys Tyr His Ser Glu
                500                 505                 510

Lys Leu Ala Val Ala Tyr Gly Leu Met Met Met Asp Gly Ala Asp Glu
            515                 520                 525

Glu Ser Pro Phe Gly Phe Ile Gly Ser Lys Met Val Leu Ala Leu Ala
        530                 535                 540

Glu Ile Phe Gly Asn Val Thr Lys Leu Arg Gly Trp Gln Phe
545                 550                 555

<210> SEQ ID NO 45
<211> LENGTH: 1935
<212> TYPE: DNA
<213> ORGANISM: Arabidopsis thaliana

<400> SEQUENCE: 45
atggaaaata atggagaaat gaatgcacag cctgaattat cagttgatat aaccaagact    60
tatatgtatg agaaattatg gaacatatgt gctggacctt tgtgtgttct tccgaaacct   120
ggagaaaaag tttattactt tcctcaaggg cacatcgagc tcattgagaa ttctacaaga   180
gatgaattgg atcatatcag gccaattttt gatcttccat ctaagcttcg atgtcgtgtt   240
gtggctattg atcgtaaggt agacaaaaat acagatgaag tctatgctca gatttcgtta   300
atgcctgata caacagaagt tatgacccat aatactacta ggatactcg aagaccaata   360 gtttatttt ttagtaaaat tttaacggcg tctgacgtca gtttaagtgg tggattaatt   420
attcccaaac aatatgccat tgagtgtttt cctccgctgg atatgtccca accaatatcc   480
acacaaaatc ttgttgcaaa ggatctctat ggtcaagaat ggagtttcaa acatgtcttt   540
agaggtacac cgcagagaca tatgtttact agcggcggcg gctggagcgt atttgcaaca   600
acaaaaagat tgattgttgg ggatatattt gtactcctta gaggagagaa tggggagtta   660
cgatttggta ttaggcgagc aaagcatcaa caaggccaca taccttcatc agtaatatca   720
gcaaattgta tgcaacatgg agtaatagct tcagtagtga atgcttttaa aaccaaatgc   780
atgttcaatg tggtttataa gccaagttca agtcaatttg ttataagcta tgacaaattt   840
gttgatgcaa tgaacaataa ttacattgtt ggttcgagat ttaggatgca gtttgagggt   900
aaggattttt ctgaaaaaag atacgatggg acgattattg tgtaaatga catgtctcct   960 cattggaagg attcagaatg gcgaagccta aaagtgcaat gggacgagct ttcaccattt  1020
ctaagaccta atcaggtttc accttgggac atcgagcatc taattccttc gtcagatatc  1080
tctcaatcaa gtttgaaaaa gaaaaaacat tggcttcaat tgaatgaaat tggtgcaaca  1140
ttatcgaatc tttggacatg ccaagaaatt ggacaacgga gcatgaattc tcctataagt  1200
gttcctgagt ttagttatcc caatgcaatt gaagattcaa gtttctttc tggtttgcta  1260 ctgaatcact cactcctagc catacctaat gaaaactata acagcgacca aatgattcaa  1320
ccaaggaaag aagatataac aactgaagca accactagtt gcctcttgtt tggagttgat  1380
ctgaccaaag tatcaaagag caaagattcc atctgtccaa ttgaatcatg caaaaaatca  1440
gaaatttcaa aactcaaaaa tcaaaaagca accactagtt gcctcaagat aaaaagtttg  1500
accaaaccca acctctgaga tcaccaaaag aggtccaaag cacggaattc aattttacta  1560
gaagtcgtat taaagttcat atgcaaggtg tagccataag tagagctgtg gatttaactg  1620
ctatgcatgg atacaatcag ctgatacaaa aactggaaga actctttgat ctcaaagacg  1680
agttacgaac tcgcaatcaa tgggaaatag ttttttacaaa caatgaagga gctgagatgc  1740
```

```
ttgtcgggga tgatccatgg cctgagttct gcaatatggc gaaaagaata ttcatatgct    1800
caaaagagga gataaagaaa atgaagttga agaacaaatt ctttcaacct gaatcaaaag    1860
ctttaacatc ttcagacgta ccaccaaacg tcacagataa ctaacctttc ttataaagat    1920
aagagagctg aaaat                                                     1935
```

<210> SEQ ID NO 46
<211> LENGTH: 505
<212> TYPE: PRT
<213> ORGANISM: Arabidopsis thaliana

<400> SEQUENCE: 46

```
Met Glu Asn Asn Gly Glu Met Asn Ala Gln Pro Glu Leu Ser Val Asp
1               5                   10                  15

Ile Thr Lys Thr Tyr Met Tyr Glu Lys Leu Trp Asn Ile Cys Ala Gly
            20                  25                  30

Pro Leu Cys Val Leu Pro Lys Pro Gly Glu Lys Val Tyr Tyr Phe Pro
        35                  40                  45

Gln Gly His Ile Glu Leu Ile Glu Asn Ser Thr Arg Asp Glu Leu Asp
    50                  55                  60

His Ile Arg Pro Ile Phe Asp Leu Pro Ser Lys Leu Arg Cys Arg Val
65                  70                  75                  80

Val Ala Ile Asp Arg Lys Val Asp Lys Asn Thr Asp Glu Val Tyr Ala
                85                  90                  95

Gln Ile Ser Leu Met Pro Asp Thr Thr Glu Val Met Thr His Asn Thr
            100                 105                 110

Thr Met Asp Thr Arg Arg Pro Ile Val Tyr Phe Phe Ser Lys Ile Leu
        115                 120                 125

Thr Ala Ser Asp Val Ser Leu Ser Gly Gly Leu Ile Ile Pro Lys Gln
    130                 135                 140

Tyr Ala Ile Glu Cys Phe Pro Pro Leu Asp Met Ser Gln Pro Ile Ser
145                 150                 155                 160

Thr Gln Asn Leu Val Ala Lys Asp Leu Tyr Gly Gln Glu Trp Ser Phe
                165                 170                 175

Lys His Val Phe Arg Gly Thr Pro Gln Arg His Met Phe Thr Ser Gly
            180                 185                 190

Gly Gly Trp Ser Val Phe Ala Thr Thr Lys Arg Leu Ile Val Gly Asp
        195                 200                 205

Ile Phe Val Leu Leu Arg Gly Glu Asn Gly Glu Leu Arg Phe Gly Ile
    210                 215                 220

Arg Arg Ala Lys His Gln Gln Gly His Ile Pro Ser Ser Val Ile Ser
225                 230                 235                 240

Ala Asn Cys Met Gln His Gly Val Ile Ala Ser Val Val Asn Ala Phe
                245                 250                 255

Lys Thr Lys Cys Met Phe Asn Val Val Tyr Lys Pro Ser Ser Ser Gln
            260                 265                 270

Phe Val Ile Ser Tyr Asp Lys Phe Val Asp Ala Met Asn Asn Asn Tyr
        275                 280                 285

Ile Val Gly Ser Arg Phe Arg Met Gln Phe Glu Gly Lys Asp Phe Ser
    290                 295                 300

Glu Lys Arg Tyr Asp Gly Thr Ile Ile Gly Val Asn Asp Met Ser Pro
305                 310                 315                 320

His Trp Lys Asp Ser Glu Trp Arg Ser Leu Lys Val Gln Trp Asp Glu
                325                 330                 335
```

```
Leu Ser Pro Phe Leu Arg Pro Asn Gln Val Ser Pro Trp Asp Ile Glu
            340                 345                 350

His Leu Ile Pro Ser Ser Asp Ile Ser Gln Ser Ser Leu Lys Lys Lys
            355                 360                 365

Lys His Trp Leu Gln Leu Asn Glu Ile Gly Ala Thr Leu Ser Asn Leu
    370                 375                 380

Trp Thr Cys Gln Glu Ile Gly Gln Arg Ser Met Asn Ser Pro Ile Ser
385                 390                 395                 400

Val Pro Glu Phe Ser Tyr Pro Asn Ala Ile Glu Asp Ser Lys Phe Leu
                405                 410                 415

Ser Gly Leu Leu Leu Asn His Ser Leu Leu Ala Ile Pro Asn Glu Asn
            420                 425                 430

Tyr Asn Ser Asp Gln Met Ile Gln Pro Arg Lys Glu Asp Ile Thr Thr
            435                 440                 445

Glu Ala Thr Thr Ser Cys Leu Leu Phe Gly Val Asp Leu Thr Lys Val
    450                 455                 460

Ser Lys Ser Lys Asp Ser Ile Cys Pro Ile Glu Ser Cys Lys Lys Ser
465                 470                 475                 480

Glu Ile Ser Lys Leu Lys Asn Gln Lys Ala Thr Thr Ser Cys Leu Lys
                485                 490                 495

Ile Lys Ser Leu Thr Lys Pro Asn Leu
            500                 505

<210> SEQ ID NO 47
<211> LENGTH: 1857
<212> TYPE: DNA
<213> ORGANISM: Arabidopsis thaliana

<400> SEQUENCE: 47
atggaaaata atggagaaat gaatgcacag cctgaattat cagttgatat aaccaagact      60
tatatgtatg agaaattatg gaacatatgt gctggacctt tgtgtgttct tccgaaacct     120
ggagaaaaag tttattactt tcctcaaggg cacatcgagc tcattgagaa ttctacaaga     180
gatgaattgg atcatatcag gccaattttt gatcttccat ctaagcttcg atgtcgtgtt     240
gtggctattg atcgtaaggt agacaaaaat acagatgaag tctatgctca gatttcgtta     300
atgcctgata caacagaagt tatgacccat aatactacta ggatactcg aagaccaata      360
gtttattttt ttagtaaaat tttaacggcg tctgacgtca gtttaagtgg tggattaatt     420
attcccaaac aatatgccat tgagtgtttt cctccgctgg atatgtccca accaatatcc     480
acacaaaatc ttgttgcaaa ggatctctat ggtcaagaat ggagtttcaa acatgtcttt     540
agaggtacac cgcagagaca tatgtttact agcggcggcg gctggagcgt atttgcaaca     600
acaaaaagat tgattgttgg ggatatattt gtactcctta gaggagagaa tggggagtta     660
cgatttggta ttaggcgagc aaagcatcaa caaggccaca taccttcatc agtaatatca     720
gcaaattgta tgcaacatgg agtaatagct tcagtagtga atgcttttaa aaccaaatgc     780
atgttcaatg tggtttataa gccaaggatg cagtttgagg gtaaggattt ttctgaaaaa     840
agatacgatg gacgattat tggtgtaaat gacatgtctc ctcattggaa ggattcagaa      900
tggcgaagcc taaaagtgca atgggacgag ctttcaccat ttctaagacc taatcaggtt     960
tcaccttggg acatcgagca tctaattcct tcgtcagata tctctcaatc aagtttgaaa    1020
aagaaaaaac attggcttca attgaatgaa attggtgcaa cattatcgaa tctttggaca    1080
tgccaagaaa ttggacaacg gagcatgaat tctcctataa gtgttcctga gtttagttat    1140
```

```
cccaatgcaa ttgaagattc aaagtttctt tctggtttgc tactgaatca ctcactccta   1200
gccataccta atgaaaacta taacagcgac caaatgattc aaccaaggaa agaagatata   1260
acaactgaag caaccactag ttgcctcttg tttggagttg atctgaccaa agtatcaaag   1320
agcaaagatt ccatctgtcc aattgaatca tgcaaaaaat cagaaatttc aaaactcaaa   1380
aatcaaaaag caaccactag ttgcctcaag ataaaaagtt tgaccaaacc caacctctga   1440
gatcaccaaa agaggtccaa agcacggaat tcaattttac tagaagtcgt attaaagttc   1500
atatgcaagg tgtagccata agtagagctg tggatttaac tgctatgcat ggatacaatc   1560
agctgataca aaaactggaa gaactctttg atctcaaaga cgagttacga actcgcaatc   1620
aatgggaaat agtttttaca aacaatgaag gagctgagat gcttgtcggg gatgatccat   1680
ggcctgagtt ctgcaatatg gcgaaaagaa tattcatatg ctcaaaagag gagataaaga   1740
aaatgaagtt gaagaacaaa ttctttcaac ctgaatcaaa agctttaaca tcttcagacg   1800
taccaccaaa cgtcacagat aactaacctt tcttataaag ataagagagc tgaaaat      1857
```

<210> SEQ ID NO 48
<211> LENGTH: 479
<212> TYPE: PRT
<213> ORGANISM: Arabidopsis thaliana

<400> SEQUENCE: 48

```
Met Glu Asn Asn Gly Glu Met Asn Ala Gln Pro Glu Leu Ser Val Asp
1               5                   10                  15

Ile Thr Lys Thr Tyr Met Tyr Glu Lys Leu Trp Asn Ile Cys Ala Gly
            20                  25                  30

Pro Leu Cys Val Leu Pro Lys Pro Gly Glu Lys Val Tyr Tyr Phe Pro
        35                  40                  45

Gln Gly His Ile Glu Leu Ile Glu Asn Ser Thr Arg Asp Glu Leu Asp
    50                  55                  60

His Ile Arg Pro Ile Phe Asp Leu Pro Ser Lys Leu Arg Cys Arg Val
65                  70                  75                  80

Val Ala Ile Asp Arg Lys Val Asp Lys Asn Thr Asp Glu Val Tyr Ala
                85                  90                  95

Gln Ile Ser Leu Met Pro Asp Thr Thr Glu Val Met Thr His Asn Thr
            100                 105                 110

Thr Met Asp Thr Arg Arg Pro Ile Val Tyr Phe Phe Ser Lys Ile Leu
        115                 120                 125

Thr Ala Ser Asp Val Ser Leu Ser Gly Gly Leu Ile Ile Pro Lys Gln
    130                 135                 140

Tyr Ala Ile Glu Cys Phe Pro Pro Leu Asp Met Ser Gln Pro Ile Ser
145                 150                 155                 160

Thr Gln Asn Leu Val Ala Lys Asp Leu Tyr Gly Gln Glu Trp Ser Phe
                165                 170                 175

Lys His Val Phe Arg Gly Thr Pro Gln Arg His Met Phe Thr Ser Gly
            180                 185                 190

Gly Gly Trp Ser Val Phe Ala Thr Thr Lys Arg Leu Ile Val Gly Asp
        195                 200                 205

Ile Phe Val Leu Leu Arg Gly Glu Asn Gly Glu Leu Arg Phe Gly Ile
    210                 215                 220

Arg Arg Ala Lys His Gln Gln Gly His Ile Pro Ser Ser Val Ile Ser
225                 230                 235                 240

Ala Asn Cys Met Gln His Gly Val Ile Ala Ser Val Val Asn Ala Phe
```

|     |     |     |     |     | 245 |     |     |     |     | 250 |     |     |     |     | 255 |     |
| --- | --- | --- | --- | --- | --- | --- | --- | --- | --- | --- | --- | --- | --- | --- | --- | --- |

Lys Thr Lys Cys Met Phe Asn Val Val Tyr Lys Pro Arg Met Gln Phe
            260                 265                 270

Glu Gly Lys Asp Phe Ser Glu Lys Arg Tyr Asp Gly Thr Ile Ile Gly
        275                 280                 285

Val Asn Asp Met Ser Pro His Trp Lys Asp Ser Glu Trp Arg Ser Leu
    290                 295                 300

Lys Val Gln Trp Asp Glu Leu Ser Pro Phe Leu Arg Pro Asn Gln Val
305                 310                 315                 320

Ser Pro Trp Asp Ile Glu His Leu Ile Pro Ser Ser Asp Ile Ser Gln
                325                 330                 335

Ser Ser Leu Lys Lys Lys His Trp Leu Gln Leu Asn Glu Ile Gly
            340                 345                 350

Ala Thr Leu Ser Asn Leu Trp Thr Cys Gln Ile Gly Gln Arg Ser
            355                 360                 365

Met Asn Ser Pro Ile Ser Val Pro Glu Phe Ser Tyr Pro Asn Ala Ile
    370                 375                 380

Glu Asp Ser Lys Phe Leu Ser Gly Leu Leu Leu Asn His Ser Leu Leu
385                 390                 395                 400

Ala Ile Pro Asn Glu Asn Tyr Asn Ser Asp Gln Met Ile Gln Pro Arg
                405                 410                 415

Lys Glu Asp Ile Thr Thr Glu Ala Thr Thr Ser Cys Leu Leu Phe Gly
            420                 425                 430

Val Asp Leu Thr Lys Val Ser Lys Ser Lys Asp Ser Ile Cys Pro Ile
            435                 440                 445

Glu Ser Cys Lys Lys Ser Glu Ile Ser Lys Leu Lys Asn Gln Lys Ala
        450                 455                 460

Thr Thr Ser Cys Leu Lys Ile Lys Ser Leu Thr Lys Pro Asn Leu
465                 470                 475

<210> SEQ ID NO 49
<211> LENGTH: 2019
<212> TYPE: DNA
<213> ORGANISM: Arabidopsis thaliana

<400> SEQUENCE: 49

```
atccaaaatc tatctaccgc cgatcaaaaa accctagaat ttcttccact gttatgtaag      60
tttgatcttg ttgtctccac taagaggcga agagagaaag agggttttag gttgtgtgtt     120
ctgtttcaaa gggtttactt ctcgttgacc ccgatcgaga tggttgattc ttctcgtgat     180
tcgtgtttca agctggtaa gtttagtgct ccaggttttc gatttcaccc tactgatgaa      240
gagcttgtgg tttattatct taagaggaag atctgttgta aaaaacttcg agtcaatgcc     300
attggtgtcg ttgatgttta caagtcgat ccttctgaat tgcctggtct atcgatgttg      360
aagacgggag atagacagtg gttctttttc actccaagga ataggaagta tcctaacgca     420
gctaggtcaa gtagaggtac tgcaactggt tattggaagg cgacaggaaa ggatcgagtc     480
attgagtaca attcaagatc tgttggactc aagaagactc ttgttttcta tagaggtcgt     540
gctcctaatg gtgagagaac tgactgggtg atgcatgagt acactatgga tgaagaagag     600
ctagggagat gtaagaacgc taaggagtat tatgctcttt ataagcttta taagaagagt     660
ggggctggtc ctaagaatgg tgaacagtat ggtgctccgt tccaagaaga gaatggggtt     720
gatagtgata gtgaagatgc agatagtgtc gctgtaccgg attatcccgt ggtccgttat     780
gagaatggtc cttgtgtgga tgatactaaa ttttgcaatc ctgtcaaact tcagttagag     840
```

```
gatattgaga agcttctcaa tgaaatccca gatgcacccg gggttaacca aagacagttt      900
gatgagtttg ttggtgttcc acagggtaat agtgcagaag tgatacagag cacattgctg      960
aataattctt ctggagagta tattgaccct cggacgaatg gaatgttctt gccaaatggc     1020
cagctataca acagggactc gagttttcag tcccatttga attcatttga ggctacctct     1080
ggtatggcac ctcttctaga taatgagaag gaggagtaca ttgaaatgaa tgatcttctg     1140
atccctgagc tcggtgcttc ttcaacagag aaatccacag agttcttgaa ccatggtgaa     1200
tttggtgatg ttaatgaata cgaccaattg ttcaatgaca tatctgtttt tcagggaact     1260
tctacagatc tgtcttgtct gagtaatttt actaataaca catcaggcca agacagcaa      1320 ttactttatg aacagttcca gtaccagaca cctgagaacc agcttaataa ctacatgcat     1380
cctagtacca ctcttaatca gttcactgac aatatgtggt ttaaagatga tcaggctgct     1440
ctctatgttc aaccaccaca atcttcttct ggagcattca cttcacagtc aacaggtgtg     1500
atgcctgagt ctatgaatcc cactatgagt gtaaatcccc aatacaagga aggacaaaat     1560
ggtggtggaa caaggagcca gttctcatca gctctgtggg aattattgga atcaatacca     1620
tcaacaccag cctctgcctg tgagggtcct cttaaccaga cctttgtgcg tatgtctagc     1680
ttcagccgca tcaggttcaa tggaacgtca gtgactagta gaaaagtcac tgtagcaaag     1740
aagcgtatca gtaacagagg ttttcttctg ttatcaatta tgggtgcttt gtgtgctatc     1800
ttctgggtgt tcaaagccac cgttggagtt atgggaagac ctctcttgtc gtgacctaga     1860
ctcttgaatc ttgattcagc ataagttagc ctgatccaca tctttgatta tgtatagagt     1920
ttgaaagagt ttaattctta acaaaagatt tcttttttcc tggattctct gatggctttg     1980 aaatttgct tgcacttatc atattaagca gaattttg                              2019

<210> SEQ ID NO 50
<211> LENGTH: 564
<212> TYPE: PRT
<213> ORGANISM: Arabidopsis thaliana

<400> SEQUENCE: 50

Met Val Asp Ser Ser Arg Asp Ser Cys Phe Lys Ala Gly Lys Phe Ser
1               5                   10                  15

Ala Pro Gly Phe Arg Phe His Pro Thr Asp Glu Glu Leu Val Val Tyr
            20                  25                  30

Tyr Leu Lys Arg Lys Ile Cys Cys Lys Lys Leu Arg Val Asn Ala Ile
        35                  40                  45

Gly Val Val Asp Val Tyr Lys Val Asp Pro Ser Glu Leu Pro Gly Leu
    50                  55                  60

Ser Met Leu Lys Thr Gly Asp Arg Gln Trp Phe Phe Phe Thr Pro Arg
65                  70                  75                  80

Asn Arg Lys Tyr Pro Asn Ala Ala Arg Ser Ser Arg Gly Thr Ala Thr
                85                  90                  95

Gly Tyr Trp Lys Ala Thr Gly Lys Asp Arg Val Ile Glu Tyr Asn Ser
            100                 105                 110

Arg Ser Val Gly Leu Lys Lys Thr Leu Val Phe Tyr Arg Gly Arg Ala
        115                 120                 125

Pro Asn Gly Glu Arg Thr Asp Trp Val Met His Glu Tyr Thr Met Asp
    130                 135                 140

Glu Glu Glu Leu Gly Arg Cys Lys Asn Ala Lys Glu Tyr Tyr Ala Leu
145                 150                 155                 160
```

-continued

```
Tyr Lys Leu Tyr Lys Lys Ser Gly Ala Gly Pro Lys Asn Gly Glu Gln
            165                 170                 175
Tyr Gly Ala Pro Phe Gln Glu Glu Trp Val Asp Ser Asp Ser Glu
        180                 185                 190
Asp Ala Asp Ser Val Ala Val Pro Asp Tyr Pro Val Val Arg Tyr Glu
            195                 200                 205
Asn Gly Pro Cys Val Asp Asp Thr Lys Phe Cys Asn Pro Val Lys Leu
        210                 215                 220
Gln Leu Glu Asp Ile Glu Lys Leu Leu Asn Glu Ile Pro Asp Ala Pro
225                 230                 235                 240
Gly Val Asn Gln Arg Gln Phe Asp Glu Phe Val Gly Val Pro Gln Gly
                245                 250                 255
Asn Ser Ala Glu Val Ile Gln Ser Thr Leu Leu Asn Asn Ser Ser Gly
            260                 265                 270
Glu Tyr Ile Asp Pro Arg Thr Asn Gly Met Phe Leu Pro Asn Gly Gln
        275                 280                 285
Leu Tyr Asn Arg Asp Ser Ser Phe Gln Ser His Leu Asn Ser Phe Glu
        290                 295                 300
Ala Thr Ser Gly Met Ala Pro Leu Leu Asp Asn Glu Lys Glu Glu Tyr
305                 310                 315                 320
Ile Glu Met Asn Asp Leu Leu Ile Pro Glu Leu Gly Ala Ser Ser Thr
                325                 330                 335
Glu Lys Ser Thr Glu Phe Leu Asn His Gly Glu Phe Gly Asp Val Asn
            340                 345                 350
Glu Tyr Asp Gln Leu Phe Asn Asp Ile Ser Val Phe Gln Gly Thr Ser
        355                 360                 365
Thr Asp Leu Ser Cys Leu Ser Asn Phe Thr Asn Asn Thr Ser Gly Gln
        370                 375                 380
Arg Gln Gln Leu Leu Tyr Glu Gln Phe Gln Tyr Gln Thr Pro Glu Asn
385                 390                 395                 400
Gln Leu Asn Asn Tyr Met His Pro Ser Thr Thr Leu Asn Gln Phe Thr
                405                 410                 415
Asp Asn Met Trp Phe Lys Asp Asp Gln Ala Ala Leu Tyr Val Gln Pro
            420                 425                 430
Pro Gln Ser Ser Ser Gly Ala Phe Thr Ser Gln Ser Thr Gly Val Met
        435                 440                 445
Pro Glu Ser Met Asn Pro Thr Met Ser Val Asn Pro Gln Tyr Lys Glu
        450                 455                 460
Gly Gln Asn Gly Gly Thr Arg Ser Gln Phe Ser Ser Ala Leu Trp
465                 470                 475                 480
Glu Leu Leu Glu Ser Ile Pro Ser Thr Pro Ala Ser Ala Cys Glu Gly
                485                 490                 495
Pro Leu Asn Gln Thr Phe Val Arg Met Ser Ser Phe Ser Arg Ile Arg
            500                 505                 510
Phe Asn Gly Thr Ser Val Thr Ser Arg Lys Val Thr Val Ala Lys Lys
        515                 520                 525
Arg Ile Ser Asn Arg Gly Phe Leu Leu Leu Ser Ile Met Gly Ala Leu
        530                 535                 540
Cys Ala Ile Phe Trp Val Phe Lys Ala Thr Val Gly Val Met Gly Arg
545                 550                 555                 560
Pro Leu Leu Ser

<210> SEQ ID NO 51
```

<211> LENGTH: 3452
<212> TYPE: DNA
<213> ORGANISM: Arabidopsis thaliana

<400> SEQUENCE: 51

| | | | | | |
|---|---|---|---|---|---|
| atggcggaag | agaatcgtaa | ggatcgaggt | gtttcttcta | ctgttgcgat | tccttctggt | 60 |
| ttgaaccgga | tcaaaactcg | gttagcttcg | tcaggtccta | gacctgaaga | ttcctccgat | 120 |
| accgttctta | aacctccgtt | taatcggaat | cagaagacta | ttgttcctcg | tggtcatggt | 180 |
| agaaccactg | gctcttcgaa | acaagagcgt | aagggaacaa | aattgtcaag | gtggcttgct | 240 |
| tcctataaac | ccaagtattc | ttgtcaccct | ccaaaatatg | cttgctcgag | tacaacgagt | 300 |
| agtgaggaga | tcaagttaag | aggcaagaac | tctggtaaag | acgaagagaa | gatgattaag | 360 |
| atatctgaaa | ctaaccctcc | ctgttcaaag | tcaatgggta | taaagagctt | ttcccatgaa | 420 |
| ttaggaccaa | ggggtggtgt | tcaaactccc | taccctcgtc | cgcacagcta | taacgatctg | 480 |
| aaggaacttc | tgggctcact | tcactcaaga | tttgatgttg | ctaaagagac | tgtggataag | 540 |
| aagctggatg | tctttgtcag | agatgtcaaa | gaggctatgg | agaaaatgga | tccatcatgt | 600 |
| cctgaagatc | gagaaatggc | agagcagtta | cttgatgtgg | ctcgagcctg | tatggagatg | 660 |
| acatctgctc | aacttcgtgc | tacttgtgaa | tctattgtcc | aagacttaac | taggaaaagg | 720 |
| aaacagtgcc | aagcaggact | tgtgaagtgg | ttgttctctc | agttgctttt | tatattgact | 780 |
| cattgtacaa | gagttgtgat | gttttcagaag | gagactgagc | caattgatga | gagctccttt | 840 |
| cgcaaattta | aggaatgttt | agaacgcatc | cctgctttgg | aaacagattg | gggttctact | 900 |
| cctagagttg | atgattctgg | ttctggttat | cctgaatatc | aaagaaatga | agctgggcag | 960 |
| aaattcaaaa | gacgagacaa | agaatctttg | gagtcagaga | cagcacttga | ttatgtggta | 1020 |
| ccaaatgatc | atggcaataa | tgctgctaga | gaaggttatg | cagctgctaa | caagaatttt | 1080 |
| ccatcgcatg | aacctcaatt | tgatagtaaa | gtggtagaac | aaagatttta | tttgagcgat | 1140 |
| gagtatgaag | ataagatgtc | aaatgagcct | ggaaaagagt | taggcggatc | tgattatgta | 1200 |
| atctgcagga | tatgtgagga | ggaagttcct | ctcttccatc | tggaaccgca | ctcttacata | 1260 |
| tgtgcatacg | cagataaatg | tgaaataaat | tgtgtggatg | ttgatgagcg | ccttttgaaa | 1320 |
| ctggaggaga | tactggaaca | gataattgat | tcacgaagtt | taaattcctt | cactcaagct | 1380 |
| ggtggcttgg | aaaactctgt | tctgcggaaa | tctggagttg | catctgaagg | ttgttctccc | 1440 |
| aagataaacg | aatggcggaa | taaaggttta | gagggaatgt | ttgaggatct | gcacgagatg | 1500 |
| gacactgcct | tcatagacga | gtcttacaca | tatcctattc | accttaagag | ccatgtaggg | 1560 |
| gccaaatttt | gccatcatgc | cacttcatca | tcaacaggta | gcatcacgtc | agtatcttca | 1620 |
| acaaataccc | ccagaacaag | tcactttgac | tcctattggc | tagaacggca | ttgtccagag | 1680 |
| caagaggatc | ttcgactgat | gatggacctt | tctgatattg | cccgctgtgg | agcaagcaca | 1740 |
| gatttctcga | agagggggtc | ctgtgactat | ataatggcat | gcatgcaaga | catacaagct | 1800 |
| gtcttgaagc | agggcaagct | caaagcactt | gtaatagata | ctttcggggg | gcggatcgag | 1860 |
| aaacttctct | gcgagaaata | tttacatgct | cgtgaattga | ctgccgataa | aagttcggtg | 1920 |
| ggtaacatta | agagagtgaa | agatgtcttg | gagcatgcat | cggctactcc | acagttactg | 1980 |
| ctgaaagata | ggataagcat | cgatgacttt | gagatcatca | aaccaataag | tagaggtgcc | 2040 |
| tttggtaaag | tctttcttgc | acgcaaaaga | acaactggag | acttttttgc | aataaaggta | 2100 |
| ctcaaaaagt | tggatatgat | aaggaaaaat | gatatcgaga | ggatactaca | agagcgaaat | 2160 |
| atactaataa | ctgtcagata | cccctttttg | gttcgatttt | tttactcatt | cacctgcaga | 2220 |

-continued

```
gataatctct acttggtaat ggaatatctt aatggtggtg atctatactc tctgctccag    2280
aaagttggct gtcttgacga agaaattgct cgtatataca tcgcggaact ggttcttgca    2340
ttggagtacc tccattctct gaagattgtc caccgtgatc taaagcctga taacctgtta    2400
atcgcctata atgggcacat caagctaaca gactttgggc tttcaaagat tggtcttata    2460
aacaacacaa ttgatttatc tggccatgag tcagatgtat ccccaagaac aaattctcat    2520
cattttcaga agaaccaaga agaagaaaga attcggcatt cggctgttgg gacacctgac    2580
tacttggcac cagagattct tcttggaact gaacacggtt atgctgcgga ttggtggtct    2640
gctggaattg tcttgtttga attattaact ggaattccac ttttaccgc atcccgccca    2700 gagaaaatat ttgacaacat cctcaatggt aaaatgccct ggccagatgt tcctggtgaa    2760
atgtcttatg aagctcagga tttgattaac aggcttcttg tccatgagcc ggaaaagcga    2820 ctggggggcga acggtgctgc agaggtaaag tcgcatccct tttttcaagg agttgactgg    2880
gagaatcttg ctttgcaaaa ggctgctttt gttccgcaac ctgagagtat aaatgacaca    2940
agctatttcg tatcacgctt tagtgaaagc agttgcagcg atactgaaac tggtaacaac    3000
agtgggtcaa atccagattc aggagacgag ttggatgaat gcaccaacct ggagaagttt    3060
gattctccgc cttattatct ctcgctcatt aacttttctt tcaagaattt gtcacaattg    3120
gcttcaatca atcatgatgt gctattgcaa aaggatccag ctaaggagg aggagactca    3180 ccctttaaaa gccatggaac gtagagctct cctacaaccg tcaaggtgg ccttagtccg    3240 ctgttttctc tggtttgcgc cctgctttga ccgttgtagc tgctgctgct actatgctga    3300
aattgttacc tcaaggtctt tgggtaatta ttttcagttt tgtcataaat tgatttggaa    3360
ccatttcaaa tgcaaatcca agtatttatt gcgtggcaac aacacacata tacatgtgta    3420
taagcttgtg tgtattgagg ctgatggaaa ta                                  3452
```

<210> SEQ ID NO 52
<211> LENGTH: 1067
<212> TYPE: PRT
<213> ORGANISM: Arabidopsis thaliana

<400> SEQUENCE: 52

```
Met Ala Glu Glu Asn Arg Lys Asp Arg Gly Val Ser Ser Thr Val Ala
1               5                  10                  15

Ile Pro Ser Gly Leu Asn Arg Ile Lys Thr Arg Leu Ala Ser Ser Gly
            20                  25                  30

Pro Arg Pro Glu Asp Ser Ser Asp Thr Val Leu Lys Pro Pro Phe Asn
        35                  40                  45

Arg Asn Gln Lys Thr Ile Val Pro Arg Gly His Gly Arg Thr Thr Gly
    50                  55                  60

Ser Ser Lys Gln Glu Arg Lys Gly Thr Lys Leu Ser Arg Trp Leu Ala
65                  70                  75                  80

Ser Tyr Lys Pro Lys Tyr Ser Cys His Pro Lys Tyr Ala Cys Ser
            85                  90                  95

Ser Thr Thr Ser Ser Glu Glu Ile Lys Leu Arg Gly Lys Asn Ser Gly
            100                 105                 110

Lys Asp Glu Glu Lys Met Ile Lys Ile Ser Glu Thr Asn Pro Pro Cys
        115                 120                 125

Ser Lys Ser Met Gly Ile Lys Ser Phe Ser His Glu Leu Gly Pro Arg
    130                 135                 140

Gly Gly Val Gln Thr Pro Tyr Pro Arg Pro His Ser Tyr Asn Asp Leu
```

```
                145                 150                 155                 160
        Lys Glu Leu Leu Gly Ser Leu His Ser Arg Phe Asp Val Ala Lys Glu
                        165                 170                 175

Thr Val Asp Lys Lys Leu Asp Val Phe Val Arg Asp Val Lys Glu Ala
                        180                 185                 190

Met Glu Lys Met Asp Pro Ser Cys Pro Glu Asp Arg Glu Met Ala Glu
                        195                 200                 205

Gln Leu Leu Asp Val Ala Arg Ala Cys Met Glu Met Thr Ser Ala Gln
        210                 215                 220

Leu Arg Ala Thr Cys Glu Ser Ile Val Gln Asp Leu Thr Arg Lys Arg
        225                 230                 235                 240

Lys Gln Cys Gln Ala Gly Leu Val Lys Trp Leu Phe Ser Gln Leu Leu
                        245                 250                 255

Phe Ile Leu Thr His Cys Thr Arg Val Val Met Phe Gln Lys Glu Thr
                        260                 265                 270

Glu Pro Ile Asp Glu Ser Ser Phe Arg Lys Phe Lys Glu Cys Leu Glu
                        275                 280                 285

Arg Ile Pro Ala Leu Glu Thr Asp Trp Gly Ser Thr Pro Arg Val Asp
        290                 295                 300

Asp Ser Gly Ser Gly Tyr Pro Glu Tyr Gln Arg Asn Glu Ala Gly Gln
        305                 310                 315                 320

Lys Phe Lys Arg Arg Asp Lys Glu Ser Leu Glu Ser Glu Thr Ala Leu
                        325                 330                 335

Asp Tyr Val Val Pro Asn Asp His Gly Asn Asn Ala Ala Arg Glu Gly
                        340                 345                 350

Tyr Ala Ala Lys Gln Glu Phe Pro Ser His Glu Pro Gln Phe Asp
                        355                 360                 365

Ser Lys Val Val Glu Gln Arg Phe Tyr Leu Ser Asp Gly Tyr Glu Asp
                        370                 375                 380

Lys Met Ser Asn Glu Pro Gly Lys Glu Leu Gly Gly Ser Asp Tyr Val
        385                 390                 395                 400

Ile Cys Arg Ile Cys Glu Glu Val Pro Leu Phe His Leu Glu Pro
                        405                 410                 415

His Ser Tyr Ile Cys Ala Tyr Ala Asp Lys Cys Glu Ile Asn Cys Val
                        420                 425                 430

Asp Val Asp Glu Arg Leu Leu Lys Leu Glu Glu Ile Leu Glu Gln Ile
                        435                 440                 445

Ile Asp Ser Arg Ser Leu Asn Ser Phe Thr Gln Ala Gly Gly Leu Glu
        450                 455                 460

Asn Ser Val Leu Arg Lys Ser Gly Val Ala Ser Glu Gly Cys Ser Pro
        465                 470                 475                 480

Lys Ile Asn Glu Trp Arg Asn Lys Gly Leu Gly Met Phe Glu Asp
                        485                 490                 495

Leu His Glu Met Asp Thr Ala Phe Ile Asp Glu Ser Tyr Thr Tyr Pro
                        500                 505                 510

Ile His Leu Lys Ser His Val Gly Ala Lys Phe Cys His His Ala Thr
                        515                 520                 525

Ser Ser Ser Thr Gly Ser Ile Thr Ser Val Ser Thr Asn Thr Pro
        530                 535                 540

Arg Thr Ser His Phe Asp Ser Tyr Trp Leu Glu Arg His Cys Pro Glu
        545                 550                 555                 560

Gln Glu Asp Leu Arg Leu Met Met Asp Leu Ser Asp Ile Ala Arg Cys
                        565                 570                 575
```

```
Gly Ala Ser Thr Asp Phe Ser Lys Glu Gly Ser Cys Asp Tyr Ile Met
            580                 585                 590

Ala Cys Met Gln Asp Ile Gln Ala Val Leu Lys Gln Gly Lys Leu Lys
            595                 600                 605

Ala Leu Val Ile Asp Thr Phe Gly Gly Arg Ile Glu Lys Leu Leu Cys
610                 615                 620

Glu Lys Tyr Leu His Ala Arg Glu Leu Thr Ala Asp Lys Ser Ser Val
625                 630                 635                 640

Gly Asn Ile Lys Glu Ser Glu Asp Val Leu Glu His Ala Ser Ala Thr
                645                 650                 655

Pro Gln Leu Leu Leu Lys Asp Arg Ile Ser Ile Asp Asp Phe Glu Ile
            660                 665                 670

Ile Lys Pro Ile Ser Arg Gly Ala Phe Gly Lys Val Phe Leu Ala Arg
            675                 680                 685

Lys Arg Thr Thr Gly Asp Phe Phe Ala Ile Lys Val Leu Lys Lys Leu
            690                 695                 700

Asp Met Ile Arg Lys Asn Asp Ile Glu Arg Ile Leu Gln Glu Arg Asn
705                 710                 715                 720

Ile Leu Ile Thr Val Arg Tyr Pro Phe Leu Val Arg Phe Phe Tyr Ser
                725                 730                 735

Phe Thr Cys Arg Asp Asn Leu Tyr Leu Val Met Glu Tyr Leu Asn Gly
            740                 745                 750

Gly Asp Leu Tyr Ser Leu Leu Gln Lys Val Gly Cys Leu Asp Glu Glu
            755                 760                 765

Ile Ala Arg Ile Tyr Ile Ala Glu Leu Val Leu Ala Leu Glu Tyr Leu
770                 775                 780

His Ser Leu Lys Ile Val His Arg Asp Leu Lys Pro Asp Asn Leu Leu
785                 790                 795                 800

Ile Ala Tyr Asn Gly His Ile Lys Leu Thr Asp Phe Gly Leu Ser Lys
                805                 810                 815

Ile Gly Leu Ile Asn Asn Thr Ile Asp Leu Ser Gly His Glu Ser Asp
            820                 825                 830

Val Ser Pro Arg Thr Asn Ser His His Phe Gln Lys Asn Gln Glu Glu
            835                 840                 845

Glu Arg Ile Arg His Ser Ala Val Gly Thr Pro Asp Tyr Leu Ala Pro
850                 855                 860

Glu Ile Leu Leu Gly Thr Glu His Gly Tyr Ala Ala Asp Trp Trp Ser
865                 870                 875                 880

Ala Gly Ile Val Leu Phe Glu Leu Leu Thr Gly Ile Pro Pro Phe Thr
                885                 890                 895

Ala Ser Arg Pro Glu Lys Ile Phe Asp Asn Ile Leu Asn Gly Lys Met
            900                 905                 910

Pro Trp Pro Asp Val Pro Gly Glu Met Ser Tyr Glu Ala Gln Asp Leu
            915                 920                 925

Ile Asn Arg Leu Leu Val His Glu Pro Glu Lys Arg Leu Gly Ala Asn
930                 935                 940

Gly Ala Ala Glu Val Lys Ser His Pro Phe Phe Gln Gly Val Asp Trp
945                 950                 955                 960

Glu Asn Leu Ala Leu Gln Lys Ala Ala Phe Val Pro Gln Pro Glu Ser
                965                 970                 975

Ile Asn Asp Thr Ser Tyr Phe Val Ser Arg Phe Ser Glu Ser Ser Cys
            980                 985                 990
```

Ser Asp Thr Glu Thr Gly Asn Asn Ser Gly Ser Asn Pro Asp Ser Gly
               995       1000         1005

Asp Glu Leu Asp Glu Cys Thr Asn Leu Glu Lys Phe Asp Ser Pro
   1010         1015        1020

Pro Tyr Tyr Leu Ser Leu Ile Asn Phe Ser Phe Lys Asn Leu Ser
   1025         1030        1035

Gln Leu Ala Ser Ile Asn His Asp Val Leu Leu Gln Lys Asp Pro
   1040         1045        1050

Ala Lys Gly Gly Gly Asp Ser Pro Phe Lys Ser His Gly Thr
   1055         1060        1065

<210> SEQ ID NO 53
<211> LENGTH: 991
<212> TYPE: DNA
<213> ORGANISM: Arabidopsis thaliana

<400> SEQUENCE: 53

```
ttttatacat ttttaagaag cccacgaaaa gcccaaattt gaaaacttca atgggtttta      60
tcctgaaaat tccgattgga ttctccgatt gattccatga tgaaggcttc tttcaaggga     120
aagttcgatg tcgacaagag cggtagcgtt gcttcgctta ccttcaacgc cggcaatgct     180
aagctacgag ccaccatgac tgatgcttcc ttcgtcgccg gtcctagctt taatggtctc     240
tctctcgccg ttgagaagcc tggcttcttc atcatcgact acaacgtccc taaaaaggat     300
gttaggtttc agtttatgaa cactatcaga attgcagaga agcctttgaa tctgacttac     360
attcatatga gaggagataa ccggacgatt gttgacggga gttttgtgat tgatccagca     420
aacaagttgt ctgctaatta catggtgggt acaaagaatt gtaagctgaa gtatacttat     480
gttcatggag ggatagctac atttgagcct tgttatgacg tggctaagaa tatgtgggac     540
tttgcgattt ctcataaact ttatggtggt gataatctca aggcaactta tcagacttct     600
agtaagatgc ttggtttgga atggtcgaac aactctaaat caactggatc tttcaaggta     660
tgtgcatcaa tgaatctagc tgaggaattg aagccgccaa aactgaccgc agaaactaca     720
tggaacctgg aactttagct cccaaaaagt ctcaattctt tcggttgttt gatgtggatt     780
caaaagtctt gacagaggaa tctagaacat ttctagtcgt ttccttgttt atcattgtga     840
agactataat gaccacaaaa attgctattc tagtattagt gagtccaatt agtagtaaaa     900
gaatacccaa aaatgtagag tttgtcaacg aaggtgtttt tattcaacat ttcgagctaa     960
tactcacaaa tacatgaaga atttgcattt a                                    991
```

<210> SEQ ID NO 54
<211> LENGTH: 213
<212> TYPE: PRT
<213> ORGANISM: Arabidopsis thaliana

<400> SEQUENCE: 54

Met Met Lys Ala Ser Phe Lys Gly Lys Phe Asp Val Asp Lys Ser Gly
1      5        10        15

Ser Val Ala Ser Leu Thr Phe Asn Ala Gly Asn Ala Lys Leu Arg Ala
      20        25        30

Thr Met Thr Asp Ala Ser Phe Val Ala Gly Pro Ser Phe Asn Gly Leu
    35        40        45

Ser Leu Ala Val Glu Lys Pro Gly Phe Phe Ile Ile Asp Tyr Asn Val
  50        55        60

Pro Lys Lys Asp Val Arg Phe Gln Phe Met Asn Thr Ile Arg Ile Ala
65        70        75        80

```
Glu Lys Pro Leu Asn Leu Thr Tyr Ile His Met Arg Gly Asp Asn Arg
                 85                  90                  95

Thr Ile Val Asp Gly Ser Phe Val Ile Asp Pro Ala Asn Lys Leu Ser
            100                 105                 110

Ala Asn Tyr Met Val Gly Thr Lys Asn Cys Lys Leu Lys Tyr Thr Tyr
            115                 120                 125

Val His Gly Gly Ile Ala Thr Phe Glu Pro Cys Tyr Asp Val Ala Lys
        130                 135                 140

Asn Met Trp Asp Phe Ala Ile Ser His Lys Leu Tyr Gly Gly Asp Asn
145                 150                 155                 160

Leu Lys Ala Thr Tyr Gln Thr Ser Ser Lys Met Leu Gly Leu Glu Trp
                165                 170                 175

Ser Asn Asn Ser Lys Ser Thr Gly Ser Phe Lys Val Cys Ala Ser Met
            180                 185                 190

Asn Leu Ala Glu Glu Leu Lys Pro Pro Lys Leu Thr Ala Glu Thr Thr
            195                 200                 205

Trp Asn Leu Glu Leu
    210

<210> SEQ ID NO 55
<211> LENGTH: 2151
<212> TYPE: DNA
<213> ORGANISM: Arabidopsis thaliana

<400> SEQUENCE: 55
```

| | | | | |
|---|---|---|---|---|
| atgcagggag agagggctag tcttggttct ttatcaaagg ctttgaactt tgagcgcggt | | | | 60 |
| tctacgtcta gtaacgctgt ggtagatcag caaattcgtt gggagaatct tcacaattat | | | | 120 |
| ggtgataatg atttgcagga ttacatgagt tcagctgctg atacaaatcc tacttttgca | | | | 180 |
| aactcagttt atcatgagaa acggggcttg cagaggttta acattggtga ggctagctct | | | | 240 |
| agtgggacga agaacgaagg ggcaagtctc actgaacaat ggaagggaat tggaaggttt | | | | 300 |
| gaggaacaga ggaatgataa gcttgagttg agccctttgt tgtgcaacc atctaatgga | | | | 360 |
| agccgcgtgg ttcgtgatgt caatctaaat gcagaataca atgagcatct tgaggatatg | | | | 420 |
| aatccggtta cagttcatcc tggtcatttt gaggttaatg gacttaggtc tgagttttta | | | | 480 |
| ctagataaca gtgttagagc tggttcctct gttgatggac gtcgtgcatc ctgtaaaaga | | | | 540 |
| aaagctcttg atgcaagcgg tggtcagtcc tcttcaactg gaggtttccg tgagttccag | | | | 600 |
| cgtggagtat ccagttcttg gatctcaggt cctacgtatt acagcccagc aatgacagca | | | | 660 |
| aatgatttaa acatatctct tgatcatggt cgaaggggtt tggtatctag cgctgttcca | | | | 720 |
| aatctatctc ctcctaccat cacagagagc tctagtagaa attaccctgt ctgggttaat | | | | 780 |
| cccacatatc aacaagaaac cgtaagcaat tttgctccat ccttgaactc accagggctt | | | | 840 |
| atacctgcag atcaccagca gatcagcatg agatatggac atgcgttagg caattttgca | | | | 900 |
| tctcagaacc caaatgctcc tgctactcat atgccccctg tttcaagaaa tacatttcaa | | | | 960 |
| tggaacacaa gccccgtggc agcggttata tcatctagtt ctgctactcc tgttgacaga | | | | 1020 |
| aatgttattc atcgaaatgc aaccagacaa agaagtaata ctctagagat tcccttgttt | | | | 1080 |
| gtcccagctc ctgaactgag aaatgtggcc catggtcata ttagcagaaa tgcaagtggt | | | | 1140 |
| gctagacatg ttcatcgtc ttcatccagg acaagtgttc agccatcacc gtctagtcca | | | | 1200 |
| gcattgactc cttaccagaa taactcacta cataatcaaa gaagattatc tgaaaacttt | | | | 1260 |
| cgtaggtcat tgctttcttc ccttgttaca cagcagaggg ctgctcgttc attggcccat | | | | 1320 |

```
cctgcctctc caaatgagca cgtgcttcaa tctggtggtg ataacacctc tcaggtgcat   1380
aatcgagctt cctcgagagc aggtccaaga caagggcaag atgcaactgg catttctcat   1440
tctttgcgag gcttggcatc cacaagtcga ggaagaacca gaatgggggc atccgagatc   1500
cgtaacatct tggagcacat gcgtagagca gggaacttgc gtttggagga tgttatgctt   1560
ctcaatcagt ccataatgct aggtgcggct gatattcatg accgatatag agacatgcga   1620
cttgatgttg acaacatgac atatgaggag ctgttgtctc tagaagaacg gattggagat   1680
gtttgtaccg gtttgaacga ggaaaccata tcaaaccgat tgaagcagca gaagtacaaa   1740
agtagtacta gatcttcaca agaagtgaaa ccatgctgtg tttgtcagga ggaatataag   1800
gaagaagaag aaataggaag gctggaatgt ggacacgact tcatagtcaa atgcatcaaa   1860
gaatggctga agcagaagaa tctttgcccg atttgcaaaa caacaggatt aaacactgca   1920
aataagccac aaagataatg atcgaaagac tgttgggttc taaccatttg tcgaatcttc   1980
aataccattg aagcctcatc agaacactgc aggcaagttg gtgtctgctt ttggggttga   2040
ctgaagatag gaatgaaggg aaagtaactg aggggatag agagaacagg agaacctaag   2100
aaaaaacttt ggttcttctg aatttatttc tataagttaa ttttaccaat t           2151
```

<210> SEQ ID NO 56
<211> LENGTH: 645
<212> TYPE: PRT
<213> ORGANISM: Arabidopsis thaliana

<400> SEQUENCE: 56

```
Met Gln Gly Glu Arg Ala Ser Leu Gly Ser Leu Ser Lys Ala Leu Asn
1               5                   10                  15

Phe Glu Arg Gly Ser Thr Ser Ser Asn Ala Val Val Asp Gln Gln Ile
            20                  25                  30

Arg Trp Glu Asn Leu His Asn Tyr Gly Asp Asn Asp Leu Gln Asp Tyr
        35                  40                  45

Met Ser Ser Ala Ala Asp Thr Asn Pro Thr Phe Ala Asn Ser Val Tyr
    50                  55                  60

His Glu Lys Arg Gly Leu Gln Arg Phe Asn Ile Gly Glu Ala Ser Ser
65                  70                  75                  80

Ser Gly Thr Lys Asn Glu Gly Ala Ser Leu Thr Glu Gln Trp Lys Gly
                85                  90                  95

Ile Gly Arg Phe Glu Glu Gln Arg Asn Asp Lys Leu Glu Leu Ser Pro
            100                 105                 110

Leu Phe Val Gln Pro Ser Asn Gly Ser Arg Val Val Arg Asp Val Asn
        115                 120                 125

Leu Asn Ala Glu Tyr Asn Glu His Leu Glu Asp Met Asn Pro Val Thr
    130                 135                 140

Val His Pro Gly His Phe Glu Val Asn Gly Leu Arg Ser Glu Phe Leu
145                 150                 155                 160

Leu Asp Asn Ser Val Arg Ala Gly Ser Ser Val Asp Gly Arg Arg Ala
                165                 170                 175

Ser Cys Lys Arg Lys Ala Leu Asp Ala Ser Gly Gly Gln Ser Ser Ser
            180                 185                 190

Thr Gly Gly Phe Arg Glu Phe Gln Arg Gly Val Ser Ser Ser Trp Ile
        195                 200                 205

Ser Gly Pro Thr Tyr Tyr Ser Pro Ala Met Thr Ala Asn Asp Leu Asn
    210                 215                 220
```

```
Ile Ser Leu Asp His Gly Arg Arg Gly Leu Val Ser Ser Ala Val Pro
225                 230                 235                 240

Asn Leu Ser Pro Pro Thr Ile Thr Glu Ser Ser Arg Asn Tyr Pro
            245                 250                 255

Val Trp Val Asn Pro Thr Tyr Gln Gln Glu Thr Val Ser Asn Phe Ala
        260                 265                 270

Pro Ser Leu Asn Ser Pro Gly Leu Ile Pro Ala Asp His Gln Gln Ile
        275                 280                 285

Ser Met Arg Tyr Gly His Ala Leu Gly Asn Phe Ala Ser Gln Asn Pro
        290                 295                 300

Asn Ala Pro Ala Thr His Met Pro Pro Val Ser Arg Asn Thr Phe Gln
305                 310                 315                 320

Trp Asn Thr Ser Pro Val Ala Ala Val Ile Ser Ser Ser Ala Thr
                325                 330                 335

Pro Val Asp Arg Asn Val Ile His Arg Asn Ala Thr Arg Gln Arg Ser
                340                 345                 350

Asn Thr Leu Glu Ile Pro Leu Phe Val Pro Ala Pro Glu Leu Arg Asn
            355                 360                 365

Val Ala His Gly His Ile Ser Arg Asn Ala Ser Gly Ala Arg His Val
        370                 375                 380

Ala Ser Ser Ser Ser Arg Thr Ser Val Gln Pro Ser Pro Ser Ser Pro
385                 390                 395                 400

Ala Leu Thr Pro Tyr Gln Asn Asn Ser Leu His Asn Gln Arg Arg Leu
            405                 410                 415

Ser Glu Asn Phe Arg Arg Ser Leu Leu Ser Ser Leu Val Thr Gln Gln
                420                 425                 430

Arg Ala Ala Arg Ser Leu Ala His Pro Ala Ser Pro Asn Glu His Val
            435                 440                 445

Leu Gln Ser Gly Gly Asp Asn Thr Ser Gln Val His Asn Arg Ala Ser
    450                 455                 460

Ser Arg Ala Gly Pro Arg Gln Gly Gln Asp Ala Thr Gly Ile Ser His
465                 470                 475                 480

Ser Leu Arg Gly Leu Ala Ser Thr Ser Arg Gly Arg Thr Arg Met Gly
                485                 490                 495

Ala Ser Glu Ile Arg Asn Ile Leu Glu His Met Arg Arg Ala Gly Asn
            500                 505                 510

Leu Arg Leu Glu Asp Val Met Leu Leu Asn Gln Ser Ile Met Leu Gly
        515                 520                 525

Ala Ala Asp Ile His Asp Arg Tyr Arg Asp Met Arg Leu Asp Val Asp
530                 535                 540

Asn Met Thr Tyr Glu Glu Leu Leu Ser Leu Glu Glu Arg Ile Gly Asp
545                 550                 555                 560

Val Cys Thr Gly Leu Asn Glu Glu Thr Ile Ser Asn Arg Leu Lys Gln
            565                 570                 575

Gln Lys Tyr Lys Ser Ser Thr Arg Ser Ser Gln Glu Val Glu Pro Cys
        580                 585                 590

Cys Val Cys Gln Glu Glu Tyr Lys Glu Glu Glu Ile Gly Arg Leu
        595                 600                 605

Glu Cys Gly His Asp Phe His Ser Gln Cys Ile Lys Glu Trp Leu Lys
        610                 615                 620

Gln Lys Asn Leu Cys Pro Ile Cys Lys Thr Thr Gly Leu Asn Thr Ala
625                 630                 635                 640

Asn Lys Pro Gln Arg
```

<210> SEQ ID NO 57
<211> LENGTH: 891
<212> TYPE: DNA
<213> ORGANISM: Arabidopsis thaliana

<400> SEQUENCE: 57

```
ataagtaatc aaattccaaa aaaaataaaa taatacaaat ctctcttttt ctctctaaaa      60
aatcttgata tggatcaaaa cgtaccaata agcaagaagc tatggaacat cgtacgtttt     120
ctcttgtaca tgatccgcaa aggcgtctca aaaaacaaac tcatcgctga cttcaacgcc     180
actctcaaac gtggcaagaa cctcatgttc caccaacgtc gtcgtgtcca cgccggttcc     240
accgcctcag ccgctctaaa cgctacttca gccaccgcgt catcgcgaca agagtacgag     300
tttagctgca gcaacactcc aaactattca ttccctttct ctaatatggc tttcatgagg     360
aaaaagagtc acaataatct cttcacgtgt ggtcaaacgc ctcagacgct tgacgacgac     420
gtagccgccg ctagagccgt tcttgagctt cttaacggcg ttggagagaa aggaaacgtc     480
acgccggcag atttaacggt ggctttgtct ccttatttcc ccggttttgg acagactcca     540
ttggttagac cgttaagagt aacggactca ccgtttccgt taacgccgga aaatggtgat     600
gtggctaatg gacacgttga caaagcagct gatgatttta taagaagtt ttataagaac     660
ttgaatcagc agaaaaaaat gattgagttc agctaaatat taatccgaat tgtgtgtatc     720
ttcgtcatat ttctcttctt ccttaaatat ttttttaccc ttttttcttt ctttcttttt     780
tttctctcgt tttgtgctga ttaaaatcca aagatgtaat gatatttgg ggggttttta     840
ttttcgattc ctaacacaat tggatattat gaataaaaaa atatcatcgg t             891
```

<210> SEQ ID NO 58
<211> LENGTH: 208
<212> TYPE: PRT
<213> ORGANISM: Arabidopsis thaliana

<400> SEQUENCE: 58

```
Met Asp Gln Asn Val Pro Ile Ser Lys Lys Leu Trp Asn Ile Val Arg
1               5                   10                  15

Phe Leu Leu Tyr Met Ile Arg Lys Gly Val Ser Lys Asn Lys Leu Ile
            20                  25                  30

Ala Asp Phe Asn Ala Thr Leu Lys Arg Gly Lys Asn Leu Met Phe His
        35                  40                  45

Gln Arg Arg Arg Val His Ala Gly Ser Thr Ala Ser Ala Ala Leu Asn
    50                  55                  60

Ala Thr Ser Ala Thr Ala Ser Ser Arg Gln Glu Tyr Glu Phe Ser Cys
65                  70                  75                  80

Ser Asn Thr Pro Asn Tyr Ser Phe Pro Phe Ser Asn Met Ala Phe Met
                85                  90                  95

Arg Lys Lys Ser His Asn Asn Leu Phe Thr Cys Gly Gln Thr Pro Gln
            100                 105                 110

Thr Leu Asp Asp Asp Val Ala Ala Ala Arg Ala Val Leu Glu Leu Leu
        115                 120                 125

Asn Gly Val Gly Glu Lys Gly Asn Val Thr Pro Ala Asp Leu Thr Val
    130                 135                 140

Ala Leu Ser Pro Tyr Phe Pro Gly Phe Gly Gln Thr Pro Leu Val Arg
145                 150                 155                 160

Pro Leu Arg Val Thr Asp Ser Pro Phe Pro Leu Thr Pro Glu Asn Gly
```

165                 170                 175
Asp Val Ala Asn Gly His Val Asp Lys Ala Ala Asp Asp Phe Ile Lys
            180                 185                 190

Lys Phe Tyr Lys Asn Leu Asn Gln Gln Lys Lys Met Ile Glu Phe Ser
            195                 200                 205

<210> SEQ ID NO 59
<211> LENGTH: 3433
<212> TYPE: DNA
<213> ORGANISM: Arabidopsis thaliana

<400> SEQUENCE: 59

| | |
|---|---|
| acatctcttc ttcatcctct cttctacttt cctctttcct ctttccttct tcgaataaat | 60 |
| ttctagggtt tttcttttct ctaaagtttt cattttattt tcaatgagag ctcgaagaag | 120 |
| gagaatatgg gtttgagaac tgataatatt atggcttcgt tcgaggtgg aatcggggtt | 180 |
| tctaatggct gagtcaactc ggtgattctg tgttatagtc acgagcaaat ataaaaagt | 240 |
| ttgtaacttt cttgtttttt taggtgtgtg tgttcagaga aaaggtcgaa tcttttttcg | 300 |
| gtgtttgtaa aagggaaagt tgtaatctta aagtctgttt ttctttcttg tgttttggta | 360 |
| tttagctcat aaaagccgag gagtaatata aggatagg tttgtctttg tgtgcccttt | 420 |
| tgagattgca tgaagaaaaa aagcctctag tgtgttttga aggaaacaga attcgatatt | 480 |
| tatgcggtaa tgtgatttgt gaagctactc caagtgctta ggatttgaga tggcttagat | 540 |
| ttggtagttg ttcaagctgt ggagtttgtg gtggactaag aagctctctg tctcctttgt | 600 |
| ttagtatgtt gtggttatct tctgtttaga aggatttagt tattcatctg gaggggtag | 660 |
| tagggtcatt tgtgagattc tgtgattgtg aaataagaag agttttgctg aggagtaatg | 720 |
| gcaatgtctt gcaaggatgg taagttggga tgttttggata atgggaagta tgtgaggtat | 780 |
| acacctgaac aagttgaagc acttgagagg ctttatcatg actgtcctaa accgagttct | 840 |
| attcgccgtc agcagttgat cagagagtgt cctattctct ctaacattga gcctaaacag | 900 |
| atcaaagtgt ggtttcagaa ccgaagatgt agagagaaac aaaggaaaga ggcttcacgg | 960 |
| cttcaagctg tgaatcggaa gttgacggca atgaacaagc tcttgatgga ggagaatgac | 1020 |
| aggttgcaga agcaagtgtc acagctggtc catgaaaaca gctacttccg tcaacatact | 1080 |
| ccaaatcctt cactcccagc taaagacaca agctgtgaat cggtggtgac gagtggtcag | 1140 |
| caccaattgg catctcaaaa tcctcagaga gatgctagtc ctgcaggact tttgtccatt | 1200 |
| gcagaagaaa ctttagcaga gtttctttca aaggcaactg gaaccgctgt tgagtgggtt | 1260 |
| cagatgcctg gaatgaagcc tggtccggat tccattggaa tcatcgctat ttctcatggt | 1320 |
| tgcactggtg tggcagcacg cgcctgtggc ctagtgggtc ttgagcctac aagggttgca | 1380 |
| gagattgtca aggatcgtcc ttcgtggttc cgcgaatgtc gagctgttga agttatgaac | 1440 |
| gtgttgccaa ctgccaatgg tggaaccgtt gagctgcttt atatgcagct ctatgcacca | 1500 |
| actacattgg ccccaccacg cgatttctgg ctgttacgtt acacctctgt tttagaagat | 1560 |
| ggcagccttg tggtgtgcga gagatctctt aagagcactc aaaatggtcc tagtatgcca | 1620 |
| ctggttcaga atttttgtgag agcagagatg ctttccagtg gtacttgat acggccttgt | 1680 |
| gatggtggtg gctcaatcat acacatagtg gatcatatgg atttggaggc ttgtagcgtg | 1740 |
| cctgaggtct tgcgcccgct ctatgagtca cccaaagtac ttgcacagaa gacaacaatg | 1800 |
| gcggcactgc gtcagctcaa gcaaatagct caggaggtta ctcagactaa tagtagtgtt | 1860 |
| aatggggtggg gacggcgtcc tgctgcctta agagctctca gccagaggct aagcagaggc | 1920 |

```
ttcaatgaag ctgtaaatgg tttcactgat gaaggatggt cagtgatagg agatagcatg    1980
gatgatgtca caatcactgt aaactcttct ccagacaagc taatgggtct aaatcttaca    2040
tttgccaatg gctttgctcc tgtaagcaat gttgttttat gcgcaaaagc atcaatgctt    2100
ttacagaatg ttcctccggc gatcctgctt cggtttctga gggagcatag gtcagaatgg    2160
gctgacaaca acattgatgc gtatctagca gcagcagtta aagtagggcc ttgtagtgcc    2220
cgagttggag gatttggagg gcaggttata cttccacttg ctcatactat tgagcatgaa    2280
gagtttatgg aagtcatcaa attggaaggt cttggtcatt ccctgaaga tgcaatcgtt    2340
ccaagagata tcttccttct tcaactttgt agcggaatgg atgaaaatgc tgtaggaacc    2400
tgtgcggaac ttatatttgc tccaatcgat gcttcgtttg cggatgatgc acctctgctt    2460
ccttctggtt ttcgtattat ccctcttgat tccgcaaagc aggaagtatc tagcccaaac    2520
cgaaccttgg atcttgcttc ggcactggaa attggttcag ctggaacaaa agcctcaact    2580
gatcaatcag gaaactccac atgtgcaaga tctgtgatga caatagcatt tgagtttggt    2640
atcgagagcc atatgcaaga acatgtagca tccatggcta ggcagtatgt tcgaggtatc    2700
atatcatcgg tgcagagagt agcattggct ctttctcctt ctcatatcag ctcacaagtt    2760
ggtctacgca ctcctttggg tactcctgaa gcccaaacac ttgctcgttg gatttgccag    2820
agttacaggg gctacatggg tgttgagcta cttaaatcaa acagtgacgg caatgaatct    2880
attcttaaga atctttggca tcacactgat gctataatct gctgctcaat gaaggccttg    2940
cccgtcttca catttgcaaa ccaggcggga cttgacatgc tggagactac attagttgct    3000
cttcaagaca tctctttaga gaagatattt gatgacaatg gaagaaagac tctttgctct    3060
gagttcccac agatcatgca acagggcttc gcgtgccttc aaggcgggat atgtctctca    3120
agcatgggga gaccagtttc gtatgagaga gcagttgctt ggaaagtact caatgaagaa    3180
gaaaatgctc attgcatctg ctttgtgttc atcaattggt cctttgtgtg agatttattg    3240
tattttgtat tttcagacta agcttttgcc ttttggctgt attgtaaaac ggtcatgttg    3300
ttgttgttgt tgttgttgtt cttgatgttg ctgtgaacac gtaaaacagt gttttgtttc    3360
aaaactcaag aaatgcttgc ttaatttgta gtttgattaa gagtgataat gatgatcttt    3420
ttcttttctt gtt                                                        3433
```

<210> SEQ ID NO 60
<211> LENGTH: 837
<212> TYPE: PRT
<213> ORGANISM: Arabidopsis thaliana

<400> SEQUENCE: 60

```
Met Ala Met Ser Cys Lys Asp Gly Lys Leu Gly Cys Leu Asp Asn Gly
1               5                   10                  15

Lys Tyr Val Arg Tyr Thr Pro Glu Gln Val Glu Ala Leu Glu Arg Leu
            20                  25                  30

Tyr His Asp Cys Pro Lys Pro Ser Ser Ile Arg Arg Gln Gln Leu Ile
        35                  40                  45

Arg Glu Cys Pro Ile Leu Ser Asn Ile Glu Pro Lys Gln Ile Lys Val
    50                  55                  60

Trp Phe Gln Asn Arg Arg Cys Arg Glu Lys Gln Arg Lys Glu Ala Ser
65                  70                  75                  80

Arg Leu Gln Ala Val Asn Arg Lys Leu Thr Ala Met Asn Lys Leu Leu
                85                  90                  95
```

```
Met Glu Glu Asn Asp Arg Leu Gln Lys Gln Val Ser Gln Leu Val His
                100                 105                 110

Glu Asn Ser Tyr Phe Arg Gln His Thr Pro Asn Pro Ser Leu Pro Ala
            115                 120                 125

Lys Asp Thr Ser Cys Glu Ser Val Val Thr Ser Gly Gln His Gln Leu
        130                 135                 140

Ala Ser Gln Asn Pro Gln Arg Asp Ala Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Glu Trp Val Gln Met Pro Gly Met Lys Pro Gly Pro Asp Ser
            180                 185                 190

Ile Gly Ile Ile Ala Ile Ser His Gly Cys Thr Gly Val Ala Ala Arg
        195                 200                 205

Ala Cys Gly Leu Val Gly Leu Glu Pro Thr Arg Val Ala Glu Ile Val
210                 215                 220

Lys Asp Arg Pro Ser Trp Phe Arg Glu Cys Arg Ala Val Glu Val Met
225                 230                 235                 240

Asn Val Leu Pro Thr Ala Asn Gly Gly Thr Val Glu Leu Leu Tyr Met
                245                 250                 255

Gln Leu Tyr Ala Pro Thr Thr Leu Ala Pro Pro Arg Asp Phe Trp Leu
            260                 265                 270

Leu Arg Tyr Thr Ser Val Leu Glu Asp Gly Ser Leu Val Cys Glu
        275                 280                 285

Arg Ser Leu Lys Ser Thr Gln Asn Gly Pro Ser Met Pro Leu Val Gln
290                 295                 300

Asn Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Met Asp Leu
                325                 330                 335

Glu Ala Cys Ser Val Pro Glu Val Leu Arg Pro Leu Tyr Glu Ser Pro
            340                 345                 350

Lys Val Leu Ala Gln Lys Thr Thr Met Ala Ala Leu Arg Gln Leu Lys
        355                 360                 365

Gln Ile Ala Gln Glu Val Thr Gln Thr Asn Ser Ser Val Asn Gly Trp
370                 375                 380

Gly Arg Arg Pro Ala Ala Leu Arg Ala Leu Ser Gln Arg Leu Ser Arg
385                 390                 395                 400

Gly Phe Asn Glu Ala Val Asn Gly Phe Thr Asp Glu Gly Trp Ser Val
                405                 410                 415

Ile Gly Asp Ser Met Asp Val Thr Ile Thr Val Asn Ser Ser Pro
            420                 425                 430

Asp Lys Leu Met Gly Leu Asn Leu Thr Phe Ala Asn Gly Phe Ala Pro
        435                 440                 445

Val Ser Asn Val Val Leu Cys Ala Lys Ala Ser Met Leu Leu Gln Asn
450                 455                 460

Val Pro Pro Ala Ile Leu Leu Arg Phe Leu Arg Glu His Arg Ser Glu
465                 470                 475                 480

Trp Ala Asp Asn Asn Ile Asp Ala Tyr Leu Ala Ala Val Lys Val
                485                 490                 495

Gly Pro Cys Ser Ala Arg Val Gly Gly Phe Gly Gly Gln Val Ile Leu
            500                 505                 510

Pro Leu Ala His Thr Ile Glu His Glu Glu Phe Met Glu Val Ile Lys
```

```
            515                 520                 525
Leu Glu Gly Leu Gly His Ser Pro Glu Asp Ala Ile Val Pro Arg Asp
    530                 535                 540

Ile Phe Leu Leu Gln Leu Cys Ser Gly Met Asp Glu Asn Ala Val Gly
545                 550                 555                 560

Thr Cys Ala Glu Leu Ile Phe Ala Pro Ile Asp Ala Ser Phe Ala Asp
                565                 570                 575

Asp Ala Pro Leu Leu Pro Ser Gly Phe Arg Ile Ile Pro Leu Asp Ser
            580                 585                 590

Ala Lys Gln Glu Val Ser Ser Pro Asn Arg Thr Leu Asp Leu Ala Ser
        595                 600                 605

Ala Leu Glu Ile Gly Ser Ala Gly Thr Lys Ala Ser Thr Asp Gln Ser
    610                 615                 620

Gly Asn Ser Thr Cys Ala Arg Ser Val Met Thr Ile Ala Phe Glu Phe
625                 630                 635                 640

Gly Ile Glu Ser His Met Gln Glu His Val Ala Ser Met Ala Arg Gln
                645                 650                 655

Tyr Val Arg Gly Ile Ile Ser Ser Val Gln Arg Val Ala Leu Ala Leu
            660                 665                 670

Ser Pro Ser His Ile Ser Ser Gln Val Gly Leu Arg Thr Pro Leu Gly
        675                 680                 685

Thr Pro Glu Ala Gln Thr Leu Ala Arg Trp Ile Cys Gln Ser Tyr Arg
    690                 695                 700

Gly Tyr Met Gly Val Glu Leu Leu Lys Ser Asn Ser Asp Gly Asn Glu
705                 710                 715                 720

Ser Ile Leu Lys Asn Leu Trp His His Thr Asp Ala Ile Ile Cys Cys
                725                 730                 735

Ser Met Lys Ala Leu Pro Val Phe Thr Phe Ala Asn Gln Ala Gly Leu
            740                 745                 750

Asp Met Leu Glu Thr Thr Leu Val Ala Leu Gln Asp Ile Ser Leu Glu
        755                 760                 765

Lys Ile Phe Asp Asp Asn Gly Arg Lys Thr Leu Cys Ser Glu Phe Pro
    770                 775                 780

Gln Ile Met Gln Gln Gly Phe Ala Cys Leu Gln Gly Gly Ile Cys Leu
785                 790                 795                 800

Ser Ser Met Gly Arg Pro Val Ser Tyr Glu Arg Ala Val Ala Trp Lys
                805                 810                 815

Val Leu Asn Glu Glu Glu Asn Ala His Cys Ile Cys Phe Val Phe Ile
            820                 825                 830

Asn Trp Ser Phe Val
        835

<210> SEQ ID NO 61
<211> LENGTH: 3430
<212> TYPE: DNA
<213> ORGANISM: Arabidopsis thaliana

<400> SEQUENCE: 61
acatctcttc ttcatcctct cttctacttt cctctttcct ctttccttct tcgaataaat      60
ttctagggtt tttcttttct ctaaagtttt catttttatt tcaatgagag ctcgaagaag     120
gagaatatgg gtttgagaac tgataatatt atggcttcgt ttcgaggtgg aatcggggtt     180
tctaatggct gagtcaactc ggtgattctg tgttatagtc acgagcaaat ataaaaaagt     240
ttgtaacttt cttgtttttt taggtgtgtg tgttcagaga aaaggtcgaa tcttttttcg     300
```

```
gtgtttgtaa aagggaaagt tgtaatctta aagtctgttt ttctttcttg tgttttggta    360
tttagctcat aaaagccgag gagtaatata aaggataggt tttgtctttg tgtgcccttt    420
tgagattgca tgaagaaaaa aagcctctag tgtgttttga aggaaacaga attcgatatt    480
tatgcggtaa tgtgatttgt gaagctactc caagtgctta ggatttgaga tggcttagat    540
ttggtagttg ttcaagctgt ggagtttgtg gtggactaag aagctctctg tctcctttgt    600
ttagtatgtt gtggttatct tctgtttaga aggatttagt tattcatctg gaggggtag     660 tagggtcatt tgtgagattc tgtgattgtg aaataagaag agttttgctg aggagtaatg    720
gcaatgtctt gcaaggatgg taagttggga tgtttggata tgggaagta tgtgaggtat     780 acacctgaac aagttgaagc acttgagagg ctttatcatg actgtcctaa accgagttct    840
attcgccgtc agcagttgat cagagagtgt cctattctct ctaacattga gcctaaacag    900
atcaaagtgt ggtttcagaa ccgaagatgt agagagaaac aaaggaaaga ggcttcacgg    960
cttcaagctg tgaatcggaa gttgacggca atgaacaagc tcttgatgga ggagaatgac   1020
aggttgcaga agcaagtgtc acagctggtc catgaaaaca gctacttccg tcaacatact   1080
ccaaatcctt cactcccagc taaagacaca agctgtgaat cggtggtgac gagtggtcag   1140
caccaattgg catctcaaaa tcctcagaga gatgctagtc ctgcaggact tttgtccatt   1200
gcagaagaaa ctttagcaga gtttctttca aaggcaactg gaaccgctgt tgagtgggtt   1260
cagatgcctg gaatgaagcc tggtccggat tccattggaa tcatcgctat ttctcatggt   1320
tgcactggtg tggcagcacg cgcctgtggc ctagtgggtc ttgagcctac aagggttgca   1380
gagattgtca aggatcgtcc ttcgtggttc cgcgaatgtc gagctgttga agttatgaac   1440
gtgttgccaa ctgccaatgg tggaaccgtt gagctgcttt atatgcagct ctatgcacca   1500
actacattgg ccccaccacg cgatttctgg ctgttacgtt acacctctgt tttagaagat   1560
ggcagccttg tggtgtgcga gagatctctt aagagcactc aaaatggtcc tagtatgcca   1620
ctggttcaga attttgtgag agcagagatg ctttccagtg ggtacttgat acggccttgt   1680
gatggtggtg gctcaatcat acacatagtg gatcatatgg atttggaggc ttgtagcgtg   1740
cctgaggtct tgcgcccgct ctatgagtca cccaaagtac ttgcacagaa gacaacaatg   1800
gcggcactgc gtcagctcaa gcaaatagct caggaggtta ctcagactaa tagtagtgtt   1860
aatgggtggg gacggcgtcc tgctgcctta agagctctca gccagaggct aagcagaggc   1920
ttcaatgaag ctgtaaatgg tttcactgat gaaggatggt cagtgatagg agatagcatg   1980
gatgatgtca caatcactgt aaactcttct ccagacaagc taatgggtct aaatcttaca   2040
tttgccaatg gctttgctcc tgtaagcaat gttgttttat gcgcaaaagc atcaatgctt   2100
ttacagaatg ttcctccggc gatcctgctt cggtttctga gggagcatag gtcagaatgg   2160
gctgacaaca acattgatgc gtatctagca gcagcagtta aagtagggcc ttgtagtgcc   2220
cgagttggag gatttggagg gcaggttata cttccacttg ctcatactat tgagcatgaa   2280
gagtttatgg aagtcatcaa attggaaggt cttggtcatt cccctgaaga tgcaatcgtt   2340
ccaagagata tcttccttct tcaactttgt agcggaatgg atgaaaatgc tgtaggaacc   2400
tgtgcggaac ttatatttgc tccaatcgat gcttcgtttg cggatgatgc acctctgctt   2460
ccttctggtt ttcgtattat ccctcttgat tccgcaaagg aagtatctag cccaaaccga   2520
accttggatc ttgcttcggc actggaaatt ggttcagctg gaacaaaagc ctcaactgat   2580
caatcaggaa actccacatg tgcaagatct gtgatgacaa tagcatttga gtttggtatc   2640
```

-continued

```
gagagccata tgcaagaaca tgtagcatcc atggctaggc agtatgttcg aggtatcata    2700
tcatcggtgc agagagtagc attggctctt tctccttctc atatcagctc acaagttggt    2760
ctacgcactc ctttgggtac tcctgaagcc caaacacttg ctcgttggat ttgccagagt    2820
tacaggggct acatgggtgt tgagctactt aaatcaaaca gtgacggcaa tgaatctatt    2880
cttaagaatc tttggcatca cactgatgct ataatctgct gctcaatgaa ggccttgccc    2940
gtcttcacat ttgcaaacca ggcgggactt gacatgctgg agactacatt agttgctctt    3000
caagacatct ctttagagaa gatatttgat gacaatggaa gaaagactct ttgctctgag    3060
ttcccacaga tcatgcaaca gggcttcgcg tgccttcaag gcgggatatg tctctcaagc    3120
atggggagac cagtttcgta tgagagagca gttgcttgga aagtactcaa tgaagaagaa    3180
aatgctcatt gcatctgctt tgtgttcatc aattggtcct ttgtgtgaga tttattgtat    3240
tttgtatttt cagactaagc ttttgccttt tggctgtatt gtaaacggt catgttgttg     3300 ttgttgttgt tgttgttctt gatgttgctg tgaacacgta aaacagtgtt ttgtttcaaa    3360
actcaagaaa tgcttgctta atttgtagtt tgattaagag tgataatgat gatctttttc    3420
ttttcttgtt                                                           3430
```

<210> SEQ ID NO 62
<211> LENGTH: 836
<212> TYPE: PRT
<213> ORGANISM: Arabidopsis thaliana

<400> SEQUENCE: 62

```
Met Ala Met Ser Cys Lys Asp Gly Lys Leu Gly Cys Leu Asp Asn Gly
1               5                   10                  15

Lys Tyr Val Arg Tyr Thr Pro Glu Gln Val Glu Ala Leu Glu Arg Leu
            20                  25                  30

Tyr His Asp Cys Pro Lys Pro Ser Ser Ile Arg Arg Gln Gln Leu Ile
        35                  40                  45

Arg Glu Cys Pro Ile Leu Ser Asn Ile Glu Pro Lys Gln Ile Lys Val
    50                  55                  60

Trp Phe Gln Asn Arg Arg Cys Arg Glu Lys Gln Arg Lys Glu Ala Ser
65                  70                  75                  80

Arg Leu Gln Ala Val Asn Arg Lys Leu Thr Ala Met Asn Lys Leu Leu
                85                  90                  95

Met Glu Glu Asn Asp Arg Leu Gln Lys Gln Val Ser Gln Leu Val His
            100                 105                 110

Glu Asn Ser Tyr Phe Arg Gln His Thr Pro Asn Pro Ser Leu Pro Ala
        115                 120                 125

Lys Asp Thr Ser Cys Glu Ser Val Val Thr Ser Gly Gln His Gln Leu
    130                 135                 140

Ala Ser Gln Asn Pro Gln Arg Asp Ala Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Glu Trp Val Gln Met Pro Gly Met Lys Pro Gly Pro Asp Ser
            180                 185                 190

Ile Gly Ile Ile Ala Ile Ser His Gly Cys Thr Gly Val Ala Ala Arg
        195                 200                 205

Ala Cys Gly Leu Val Gly Leu Glu Pro Thr Arg Val Ala Glu Ile Val
    210                 215                 220

Lys Asp Arg Pro Ser Trp Phe Arg Glu Cys Arg Ala Val Glu Val Met
```

```
            225                 230                 235                 240
Asn Val Leu Pro Thr Ala Asn Gly Gly Thr Val Glu Leu Leu Tyr Met
                    245                 250                 255

Gln Leu Tyr Ala Pro Thr Thr Leu Ala Pro Pro Arg Asp Phe Trp Leu
                    260                 265                 270

Leu Arg Tyr Thr Ser Val Leu Glu Asp Gly Ser Leu Val Cys Glu
                275                 280                 285

Arg Ser Leu Lys Ser Thr Gln Asn Gly Pro Ser Met Pro Leu Val Gln
            290                 295                 300

Asn Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Met Asp Leu
                    325                 330                 335

Glu Ala Cys Ser Val Pro Glu Val Leu Arg Pro Leu Tyr Glu Ser Pro
                340                 345                 350

Lys Val Leu Ala Gln Lys Thr Thr Met Ala Ala Leu Arg Gln Leu Lys
            355                 360                 365

Gln Ile Ala Gln Glu Val Thr Gln Thr Asn Ser Ser Val Asn Gly Trp
        370                 375                 380

Gly Arg Arg Pro Ala Ala Leu Arg Ala Leu Ser Gln Arg Leu Ser Arg
385                 390                 395                 400

Gly Phe Asn Glu Ala Val Asn Gly Phe Thr Asp Glu Gly Trp Ser Val
                    405                 410                 415

Ile Gly Asp Ser Met Asp Val Thr Ile Thr Val Asn Ser Ser Pro
                420                 425                 430

Asp Lys Leu Met Gly Leu Asn Leu Thr Phe Ala Asn Gly Phe Ala Pro
            435                 440                 445

Val Ser Asn Val Val Leu Cys Ala Lys Ala Ser Met Leu Leu Gln Asn
        450                 455                 460

Val Pro Pro Ala Ile Leu Leu Arg Phe Leu Arg Glu His Arg Ser Glu
465                 470                 475                 480

Trp Ala Asp Asn Asn Ile Asp Ala Tyr Leu Ala Ala Val Lys Val
                    485                 490                 495

Gly Pro Cys Ser Ala Arg Val Gly Gly Phe Gly Gln Val Ile Leu
                500                 505                 510

Pro Leu Ala His Thr Ile Glu His Glu Glu Phe Met Glu Val Ile Lys
            515                 520                 525

Leu Glu Gly Leu Gly His Ser Pro Glu Asp Ala Ile Val Pro Arg Asp
        530                 535                 540

Ile Phe Leu Leu Gln Leu Cys Ser Gly Met Asp Glu Asn Ala Val Gly
545                 550                 555                 560

Thr Cys Ala Glu Leu Ile Phe Ala Pro Ile Asp Ala Ser Phe Ala Asp
                    565                 570                 575

Asp Ala Pro Leu Leu Pro Ser Gly Phe Arg Ile Ile Pro Leu Asp Ser
                580                 585                 590

Ala Lys Glu Val Ser Ser Pro Asn Arg Thr Leu Asp Leu Ala Ser Ala
            595                 600                 605

Leu Glu Ile Gly Ser Ala Gly Thr Lys Ala Ser Thr Asp Gln Ser Gly
        610                 615                 620

Asn Ser Thr Cys Ala Arg Ser Val Met Thr Ile Ala Phe Glu Phe Gly
625                 630                 635                 640

Ile Glu Ser His Met Gln Glu His Val Ala Ser Met Ala Arg Gln Tyr
                    645                 650                 655
```

-continued

```
Val Arg Gly Ile Ile Ser Ser Val Gln Arg Val Ala Leu Ala Leu Ser
            660                 665                 670
Pro Ser His Ile Ser Ser Gln Val Gly Leu Arg Thr Pro Leu Gly Thr
        675                 680                 685
Pro Glu Ala Gln Thr Leu Ala Arg Trp Ile Cys Gln Ser Tyr Arg Gly
    690                 695                 700
Tyr Met Gly Val Glu Leu Leu Lys Ser Asn Ser Asp Gly Asn Glu Ser
705                 710                 715                 720
Ile Leu Lys Asn Leu Trp His His Thr Asp Ala Ile Ile Cys Cys Ser
                725                 730                 735
Met Lys Ala Leu Pro Val Phe Thr Phe Ala Asn Gln Ala Gly Leu Asp
            740                 745                 750
Met Leu Glu Thr Thr Leu Val Ala Leu Gln Asp Ile Ser Leu Glu Lys
        755                 760                 765
Ile Phe Asp Asp Asn Gly Arg Lys Thr Leu Cys Ser Glu Phe Pro Gln
    770                 775                 780
Ile Met Gln Gln Gly Phe Ala Cys Leu Gln Gly Gly Ile Cys Leu Ser
785                 790                 795                 800
Ser Met Gly Arg Pro Val Ser Tyr Glu Arg Ala Val Ala Trp Lys Val
                805                 810                 815
Leu Asn Glu Glu Glu Asn Ala His Cys Ile Cys Phe Val Phe Ile Asn
            820                 825                 830
Trp Ser Phe Val
        835

<210> SEQ ID NO 63
<211> LENGTH: 2801
<212> TYPE: DNA
<213> ORGANISM: Arabidopsis thaliana

<400> SEQUENCE: 63
atggaacttg tgtcgtttgg agtagaaaag ctttgggacc gactgagcca agaatatgac      60
caatttaaag gagttgaaga tcaagtaact gagttaaaaa gtaacctaaa cttgttaaag     120 tcattttttga aagatgcaga tgccaagaaa catataagtg agatggtgcg acactgtgtg     180
gaagagatca aagatattgt ttatgacacg gaggacataa tcgaaacgtt tattctcaag     240
gaaaaagttg aaatgaaacg tggcatcatg aagcgtatca aagatttgc ttcgactata      300 atggatcgta gggaacttgc gtctgatatt ggaggaataa gtaagcggat ctccaaggtg     360
atacaggata tgcaaagttt tggagtacaa cagataatta ctgatggcag ccgttcttca     420
catccactac aagaaagaca agggagatg cggcacacgt tttctaggga ctccgaaaac      480
gattttgtgg aatgaagc aaatgttaag aaattggttg atatttggt ggagaaagat        540 gactatcaaa ttgtttcttt aaccgggatg ggtggtcttg gtaaaaccac ccttgctaga     600
caagttttta atcatgatgt tgtaaaagat cggtttgatg gattcgcatg ggtgagtgtt     660
tcgcaagagt ttactcggat atcggtgtgg caaacgatct tgcagaatct cacatctaaa     720
gagaggaaag atgaaatcca gaatatgaaa gaagctgacc ttcatgatga tctcttccga     780
ttgttggaat catctaaaac attaattgtg ctagatgaca tatggaaaga agaagattgg     840
gacttaatca agccaatatt tccacccaaa aaaggttgga aggtgctact tacttctcga     900
actgagagta tcgcgatgcg tggagataca acatatatta gctttaaacc aaaatgccta     960
tctatcccag acagttggac acttttccaa agcatagcaa tgccaaggaa agatacatcc    1020
```

-continued

```
gaatttaagg ttgatgagga aatggaaaat atgggtaaga agatgatcaa acattgtgga    1080
ggactatcat tggctgtcaa agtcttagga gggttgttag ctgcaaaata cacactgcat    1140
gattggaaaa gattatctga aatattggga tctcatatcg tggaaagaac tagcggtaac    1200
aacagttcta ttgatcatgt attgtctgtg agctttgaag aattgcctaa ttatttgaag    1260
cattgtttcc tatacctcgc ccactttcca gaagatcatg agatagacgt agagaagttg    1320
cattattatt gggctgcaga aggaatatct gaacgtaggc gttacgatgg agagaccatt    1380
cgagatactg gagatagcta catagaggag ttggtgagaa gaaatatggt tatttctgaa    1440
agggacgtta tgacttccag atttgaaact tgtcgtttgc atgacatgat gagagaaatt    1500
tgtttgttta aagccaaaga agagaacttc ctacaaattg tcagtaacca ctccccgaca    1560
tcaaaccctc aaactcttgg tgcttctcgc agatttgtct tacataatcc tactacatta    1620
catgttgaga gatataaaaa taatccaaaa cttcgatcgc tcgtggttgt ctatgatgat    1680
attggaaata aagatggat gctatcaggt tcaatcttta caagggtaaa acttctacgg    1740
gtgttagatc tcgttcaagc caagtttaaa ggagggaagt taccttctga cattggaaag    1800
ctcatccact taagatactt gagcttaaaa gatgccaagg tatctcatct accttcttct    1860
ctaagaaatc tagtcctgct aatctatttta gatatacgca cagatttcac ggatatattc    1920
gtgcccaatg tcttcatggg gatgagagaa ttgagatatc ttgaactacc cagatttatg    1980
catgagaaga caaagttgga gttgagtaat ctagaaaaat tggaggcctt agagaatttc    2040
tcaacaaaga gtagcagctt ggaggatctc cgtggtatgg tcaggttgag gactcttgtg    2100 atcatttaa gtgaggggac tagtctacaa actctatctg catcagtatg tggactgaga    2160
cacttggaaa attttaaaat aatggaaaac gctggcgtta acaggatggg agaagagaga    2220
atggtattgg atttcactta tctcaaaaag ctcaccttga gtatagagat gccaaggctt    2280
cctaaaatac aacaccttcc ttctcacctt acggtcttag atctatctta ctgttgtttg    2340
gaggaagatc caatgccgat tctagagaaa ttactcgagt taaaagattt aagtttagat    2400
tatctatctt tctccgggag gaaaatggtt tgctcggctg gtgggtttcc tcaattgcgt    2460
aagctagctt tggatgaaca agaggagtgg gaagagtgga tagtagaaga aggctccatg    2520
tcacggcttc atactctaag tatttggagt tcaacattaa aggagcttcc tgatgggctg    2580
cgattcatat attctttaaa gaatctgatc atgggaaaga gctggatgga gagattatcg    2640
gaacgaggag aagaatttta caaagttcaa aacattcctt ttattaaatt cagttcttaa    2700
ttcttattat aatctttga actctttgca ctgttttttgt atgggtgtct tttgttgtat    2760
aataacactt acagattttc ttgcaaaaat atattggttt t                       2801
```

<210> SEQ ID NO 64
<211> LENGTH: 899
<212> TYPE: PRT
<213> ORGANISM: Arabidopsis thaliana

<400> SEQUENCE: 64

```
Met Glu Leu Val Ser Phe Gly Val Glu Lys Leu Trp Asp Arg Leu Ser
1               5                   10                  15

Gln Glu Tyr Asp Gln Phe Lys Gly Val Glu Asp Gln Val Thr Glu Leu
            20                  25                  30

Lys Ser Asn Leu Asn Leu Leu Lys Ser Phe Leu Lys Asp Ala Asp Ala
        35                  40                  45

Lys Lys His Ile Ser Glu Met Val Arg His Cys Val Glu Glu Ile Lys
    50                  55                  60
```

```
Asp Ile Val Tyr Asp Thr Glu Asp Ile Ile Glu Thr Phe Ile Leu Lys
 65                  70                  75                  80

Glu Lys Val Glu Met Lys Arg Gly Ile Met Lys Arg Ile Lys Arg Phe
                 85                  90                  95

Ala Ser Thr Ile Met Asp Arg Arg Glu Leu Ala Ser Asp Ile Gly Gly
            100                 105                 110

Ile Ser Lys Arg Ile Ser Lys Val Ile Gln Asp Met Gln Ser Phe Gly
        115                 120                 125

Val Gln Gln Ile Ile Thr Asp Gly Ser Arg Ser His Pro Leu Gln
130                 135                 140

Glu Arg Gln Arg Glu Met Arg His Thr Phe Ser Arg Asp Ser Glu Asn
145                 150                 155                 160

Asp Phe Val Gly Met Glu Ala Asn Val Lys Lys Leu Val Gly Tyr Leu
                165                 170                 175

Val Glu Lys Asp Asp Tyr Gln Ile Val Ser Leu Thr Gly Met Gly Gly
            180                 185                 190

Leu Gly Lys Thr Thr Leu Ala Arg Gln Val Phe Asn His Asp Val Val
        195                 200                 205

Lys Asp Arg Phe Asp Gly Phe Ala Trp Val Ser Val Ser Gln Glu Phe
210                 215                 220

Thr Arg Ile Ser Val Trp Gln Thr Ile Leu Gln Asn Leu Thr Ser Lys
225                 230                 235                 240

Glu Arg Lys Asp Glu Ile Gln Asn Met Lys Glu Ala Asp Leu His Asp
                245                 250                 255

Asp Leu Phe Arg Leu Leu Glu Ser Ser Lys Thr Leu Ile Val Leu Asp
            260                 265                 270

Asp Ile Trp Lys Glu Glu Asp Trp Asp Leu Ile Lys Pro Ile Phe Pro
        275                 280                 285

Pro Lys Lys Gly Trp Lys Val Leu Leu Thr Ser Arg Thr Glu Ser Ile
290                 295                 300

Ala Met Arg Gly Asp Thr Thr Tyr Ile Ser Phe Lys Pro Lys Cys Leu
305                 310                 315                 320

Ser Ile Pro Asp Ser Trp Thr Leu Phe Gln Ser Ile Ala Met Pro Arg
                325                 330                 335

Lys Asp Thr Ser Glu Phe Lys Val Asp Glu Glu Met Glu Asn Met Gly
            340                 345                 350

Lys Lys Met Ile Lys His Cys Gly Gly Leu Ser Leu Ala Val Lys Val
        355                 360                 365

Leu Gly Gly Leu Leu Ala Ala Lys Tyr Thr Leu His Asp Trp Lys Arg
370                 375                 380

Leu Ser Glu Asn Ile Gly Ser His Ile Val Glu Arg Thr Ser Gly Asn
385                 390                 395                 400

Asn Ser Ser Ile Asp His Val Leu Ser Val Ser Phe Glu Glu Leu Pro
                405                 410                 415

Asn Tyr Leu Lys His Cys Phe Leu Tyr Leu Ala His Phe Pro Glu Asp
            420                 425                 430

His Glu Ile Asp Val Glu Lys Leu His Tyr Tyr Trp Ala Ala Glu Gly
        435                 440                 445

Ile Ser Glu Arg Arg Tyr Asp Gly Glu Thr Ile Arg Asp Thr Gly
450                 455                 460

Asp Ser Tyr Ile Glu Glu Leu Val Arg Arg Asn Met Val Ile Ser Glu
465                 470                 475                 480
```

```
Arg Asp Val Met Thr Ser Arg Phe Glu Thr Cys Arg Leu His Asp Met
                485                 490                 495

Met Arg Glu Ile Cys Leu Phe Lys Ala Lys Glu Glu Asn Phe Leu Gln
            500                 505                 510

Ile Val Ser Asn His Ser Pro Thr Ser Asn Pro Gln Thr Leu Gly Ala
            515                 520                 525

Ser Arg Arg Phe Val Leu His Asn Pro Thr Thr Leu His Val Glu Arg
            530                 535                 540

Tyr Lys Asn Asn Pro Lys Leu Arg Ser Leu Val Val Tyr Asp Asp
545                 550                 555                 560

Ile Gly Asn Arg Arg Trp Met Leu Ser Gly Ser Ile Phe Thr Arg Val
                565                 570                 575

Lys Leu Leu Arg Val Leu Asp Leu Val Gln Ala Lys Phe Lys Gly Gly
            580                 585                 590

Lys Leu Pro Ser Asp Ile Gly Lys Leu Ile His Leu Arg Tyr Leu Ser
            595                 600                 605

Leu Lys Asp Ala Lys Val Ser His Leu Pro Ser Ser Leu Arg Asn Leu
610                 615                 620

Val Leu Leu Ile Tyr Leu Asp Ile Arg Thr Asp Phe Thr Asp Ile Phe
625                 630                 635                 640

Val Pro Asn Val Phe Met Gly Met Arg Glu Leu Arg Tyr Leu Glu Leu
                645                 650                 655

Pro Arg Phe Met His Glu Lys Thr Lys Leu Glu Leu Ser Asn Leu Glu
            660                 665                 670

Lys Leu Glu Ala Leu Glu Asn Phe Ser Thr Lys Ser Ser Ser Leu Glu
            675                 680                 685

Asp Leu Arg Gly Met Val Arg Leu Arg Thr Leu Val Ile Ile Leu Ser
            690                 695                 700

Glu Gly Thr Ser Leu Gln Thr Leu Ser Ala Ser Val Cys Gly Leu Arg
705                 710                 715                 720

His Leu Glu Asn Phe Lys Ile Met Glu Asn Ala Gly Val Asn Arg Met
                725                 730                 735

Gly Glu Glu Arg Met Val Leu Asp Phe Thr Tyr Leu Lys Lys Leu Thr
            740                 745                 750

Leu Ser Ile Glu Met Pro Arg Leu Pro Lys Ile Gln His Leu Pro Ser
            755                 760                 765

His Leu Thr Val Leu Asp Leu Ser Tyr Cys Cys Leu Glu Glu Asp Pro
            770                 775                 780

Met Pro Ile Leu Glu Lys Leu Leu Glu Leu Lys Asp Leu Ser Leu Asp
785                 790                 795                 800

Tyr Leu Ser Phe Ser Gly Arg Lys Met Val Cys Ser Ala Gly Gly Phe
                805                 810                 815

Pro Gln Leu Arg Lys Leu Ala Leu Asp Glu Gln Glu Glu Trp Glu Glu
            820                 825                 830

Trp Ile Val Glu Glu Gly Ser Met Ser Arg Leu His Thr Leu Ser Ile
            835                 840                 845

Trp Ser Ser Thr Leu Lys Glu Leu Pro Asp Gly Leu Arg Phe Ile Tyr
850                 855                 860

Ser Leu Lys Asn Leu Ile Met Gly Lys Ser Trp Met Glu Arg Leu Ser
865                 870                 875                 880

Glu Arg Gly Glu Glu Phe Tyr Lys Val Gln Asn Ile Pro Phe Ile Lys
                885                 890                 895

Phe Ser Ser
```

<210> SEQ ID NO 65
<211> LENGTH: 3967
<212> TYPE: DNA
<213> ORGANISM: Arabidopsis thaliana

<400> SEQUENCE: 65

| | | | | | |
|---|---|---|---|---|---|
| cgtgtgctta | tccaaagacg | acgagaggag | tcccaagaag | tctagcggta | tcaatcaaat | 60 |
| ctcttcttac | tagaggagat | tccttggaac | catcaagagg | aagcattatg | gctggggaac | 120 |
| ttatttcgtt | tggtatacaa | aacctgtgga | acctactgag | tcaagaatgc | gagctatttc | 180 |
| agggagtcga | agatcaagta | actgaactaa | aaagggatct | aaacttgtta | agctcttttc | 240 |
| tgaaagatgc | agatgcaaag | aaacatacaa | gtgcggtggt | gaaaaactgt | gttgaagaga | 300 |
| tcaaggaaat | tatctatgat | ggagaggata | caatcgaaac | atttgttctt | gagcaaaacc | 360 |
| tgggaaaaac | aagtggtatc | aagaagagta | tcagaagact | tgcttgcatt | attccagatc | 420 |
| gaaggagata | tgcattaggt | atcggaggct | aagtaatag | gatctccaag | gtgatccgag | 480 |
| atatgcagag | ttttggagtg | caacaagcta | tcgttgatgg | tgggtataag | caacctcaag | 540 |
| gtgataaaca | aagggagatg | cgaccaagat | tttctaagga | cgacgatagc | gattttgtgg | 600 |
| ggttggaagc | aaatgttaag | aaattggttg | atatttggt | ggacgaagca | aacgttcaag | 660 |
| tggtttccat | aaccgggatg | ggtggtctag | gtaaaaccac | acttgctaaa | caggttttta | 720 |
| accatgagga | tgttaaacat | cagtttgatg | ggctctcatg | ggtgtgtgtt | tcacaagatt | 780 |
| ttacccgaat | gaatgtatgg | caaaagatct | tgagggacct | caaacccaaa | gaggaagaaa | 840 |
| agaaaatcat | ggagatgaca | caagatacac | tccaaggtga | actaattcga | ttgttggaaa | 900 |
| cgtctaagtc | attaattgtc | ctcgatgaca | tatgggaaaa | agaagattgg | gaactaatca | 960 |
| agccaatatt | tccaccgacc | aaaggttgga | aagtgttgct | tacttctcga | aacgagagtg | 1020 |
| tcgccatgcg | tagaaataca | tcatatatca | actttaaacc | agaatgccta | accactgaag | 1080 |
| acagttggac | actttttcag | aggatagccc | ttcctatgaa | agatgcagct | gaatttaaga | 1140 |
| ttgatgagga | aaaggaagag | ttgggtaagc | taatgatcaa | acactgtgga | gggttaccat | 1200 |
| tggccatcag | agtgttagga | ggtatgttag | ctgaaaaata | cacatcgcat | gattggagaa | 1260 |
| gattatctga | gaatattgga | tctcatctcg | tgggaggaag | aactaacttt | aatgacgaca | 1320 |
| acaacaatac | atgtaactat | gtattgtctc | taagctttga | agaattgcca | agttatttga | 1380 |
| agcattgttt | cctctacttg | gcccatttc | cagatgatta | tgagataaac | gtaaagaatt | 1440 |
| tgtcatatta | ctgggctgca | gaaggaatat | tccaacctag | gcattacgat | ggagaaatca | 1500 |
| ttcgagatgt | tggagatgtc | tacatagagg | agctggtgag | gaggaatatg | gtcatttccg | 1560 |
| aaagagatgt | aaagacttcg | agatttgaaa | cttgtcattt | gcatgacatg | atgagagaag | 1620 |
| tttgtttgtt | aaaagccaaa | gaagagaact | tcctacagat | taccagtagc | cgcacttcaa | 1680 |
| ctggaaactc | tctgtctatt | gtcacatctc | gcaggcttgt | ctaccaatat | cctattacat | 1740 |
| tagatgttga | gaaagatata | aacgatccaa | aacttcgatc | tctcgtggtt | gttgccaata | 1800 |
| cttatatgtt | ttggggaggt | tggagttgga | tgctgttagg | ttcaagcttt | ataaggttag | 1860 |
| aactactgag | ggtattagat | atccatagag | ccaagttgaa | aggagggaag | ttagcttctt | 1920 |
| ccattggaca | gctcatccac | ttaagatact | tgaacttaaa | gcatgctgag | gtaactcata | 1980 |
| taccttattc | actaggaaat | ctgaagttgt | tgatctatct | gaatttagtc | attttagtct | 2040 |
| ccggatctac | attggtgccc | aatgtcttga | aggagatgca | acaactgaga | taccttgcgt | 2100 |

| | | |
|---|---|---|
| taccaaaaga tatggggagg aagacaaaac tagaattgag taatctagta aaattggaga | 2160 | |
| ctttgaaaaa tttctcaaca aagaattgca gcttggagga tcttcgtggt atggtcaggc | 2220 | |
| tgagaacgct caccatcgaa ttacgtaagg agacgagtct agaaactcta gctgcatcta | 2280 | |
| taggcggatt gaaataccte gaaagccetta caataactga tcttggttct gagatgagga | 2340 | |
| cgaaggaagc gggaatcgta tttgatttcg tttatctcaa aacgctaacg ttgaaactgt | 2400 | |
| atatgcctag gctttctaaa gaacaacact tcccttctca ccttacaacc ttatatctac | 2460 | |
| aacattgtcg gttggaagag gatcccatgc cgattctaga gaagttgcat cagttgaaag | 2520 | |
| agcttgaatt aaggcgtaaa tctttcagtg gaaggaaat ggtttgctcg agcggtgggt | 2580 | |
| ttcctcaatt gcagaagctt tcaataaaag gactagagga atgggaagat tggaaagtag | 2640 | |
| aagaaagctc catgccagtt cttcatactc tcgatattcg ggattgtcga aaattaaagc | 2700 | |
| agcttcctga tgaacacctt cctctcacc ttacatccat atctctatttt ttttgttgtt | 2760 | |
| tggaggagga tccaatgccg actctagaga gattggttca cttgaaagag cttcaattat | 2820 | |
| tgtttagatc tttcagtggg aggataatgg tttgcgctgg cagtgggttt cctcaactgc | 2880 | |
| acaagctaaa attatctgaa ctagatgggt tggaagagtg gatagtagag gatggctcca | 2940 | |
| tgccacagct tcatactctg gaaattcgtc ggtgtccaaa gttaagaag cttcctaatg | 3000 | |
| ggtttccaca attgcagaat cttgagttaa atgagctaga ggaatgggaa gagtggatag | 3060 | |
| tagaggatgg ctccatgcca cttcttcata ctctaagaat ttggaattgt ccaaagttaa | 3120 | |
| agcagctgcc tgatggggttg cgatttatct attcattaaa gaatttgact gtaccaaaga | 3180 | |
| gatggaagaa gagattgtcg aaaggaggag aagattatta caagtccaa cacattcctt | 3240 | |
| ctgttgaatt ctactaggaa tgctctcagc aatcacagac tatgtatata tatgtacaca | 3300 | |
| taaagagctg cattgatggt gttcgatgaa ttgtctaact gtgactatcc ttgacgagat | 3360 | |
| atgtaatcat aagcctctgt ttccacccaa aatcaggtcg gaagatagtt gcaggtagga | 3420 | |
| agctaatcaa acaagacacc ttattttca cgacgagatg ttgaacccct gaagaatgtt | 3480 | |
| ggacaccatt ttgatggata aacatttttc ataggagaaa tgatacttta tgggagtgtt | 3540 | |
| gcggcgaagc tactgaacct ttttgaaagc ggtgttgcct atctttaaga gcgtcggagg | 3600 | |
| tgatataact gggagactct tgatgagatg ttggcctatc tggaatactt cccagttggg | 3660 | |
| agaccaacgg agatgaatac cgtcaacaat tcaccaacga cccatctcaa gagcttggac | 3720 | |
| acgagggaga aggttggtgc ctggttcaaa cagtggtgca tccaaaacgc aggccgtgta | 3780 | |
| gcattttgtt tcgggttcta catggccatg gcgaagaagg gtgaccagtt ggaaggtgca | 3840 | |
| tacaccctaa atactataaa ggtttataga agtgattgat ttattccatt caacgattta | 3900 | |
| caatatatat acacaagaga gacttgctga gcacacttat aatcaatgtg agtatataca | 3960 | |
| atattac | 3967 | |

<210> SEQ ID NO 66
<211> LENGTH: 1049
<212> TYPE: PRT
<213> ORGANISM: Arabidopsis thaliana

<400> SEQUENCE: 66

Met Ala Gly Glu Leu Ile Ser Phe Gly Ile Gln Asn Leu Trp Asn Leu
1               5                   10                  15

Leu Ser Gln Glu Cys Glu Leu Phe Gln Gly Val Glu Asp Gln Val Thr
            20                  25                  30

Glu Leu Lys Arg Asp Leu Asn Leu Leu Ser Ser Phe Leu Lys Asp Ala

```
                35                  40                  45
Asp Ala Lys Lys His Thr Ser Ala Val Val Lys Asn Cys Val Glu Glu
 50                  55                  60
Ile Lys Glu Ile Ile Tyr Asp Gly Glu Asp Thr Ile Glu Thr Phe Val
 65                  70                  75                  80
Leu Glu Gln Asn Leu Gly Lys Thr Ser Gly Ile Lys Lys Ser Ile Arg
                 85                  90                  95
Arg Leu Ala Cys Ile Ile Pro Asp Arg Arg Tyr Ala Leu Gly Ile
                100                 105                 110
Gly Gly Leu Ser Asn Arg Ile Ser Lys Val Ile Arg Asp Met Gln Ser
                115                 120                 125
Phe Gly Val Gln Gln Ala Ile Val Asp Gly Tyr Lys Gln Pro Gln
                130                 135                 140
Gly Asp Lys Gln Arg Glu Met Arg Pro Arg Phe Ser Lys Asp Asp
145                 150                 155                 160
Ser Asp Phe Val Gly Leu Glu Ala Asn Val Lys Lys Leu Val Gly Tyr
                165                 170                 175
Leu Val Asp Glu Ala Asn Val Gln Val Val Ser Ile Thr Gly Met Gly
                180                 185                 190
Gly Leu Gly Lys Thr Thr Leu Ala Lys Gln Val Phe Asn His Glu Asp
                195                 200                 205
Val Lys His Gln Phe Asp Gly Leu Ser Trp Val Cys Val Ser Gln Asp
210                 215                 220
Phe Thr Arg Met Asn Val Trp Gln Lys Ile Leu Arg Asp Leu Lys Pro
225                 230                 235                 240
Lys Glu Glu Glu Lys Lys Ile Met Glu Met Thr Gln Asp Thr Leu Gln
                245                 250                 255
Gly Glu Leu Ile Arg Leu Leu Glu Thr Ser Lys Ser Leu Ile Val Leu
                260                 265                 270
Asp Asp Ile Trp Glu Lys Glu Asp Trp Glu Leu Ile Lys Pro Ile Phe
                275                 280                 285
Pro Pro Thr Lys Gly Trp Lys Val Leu Leu Thr Ser Arg Asn Glu Ser
290                 295                 300
Val Ala Met Arg Arg Asn Thr Ser Tyr Ile Asn Phe Lys Pro Glu Cys
305                 310                 315                 320
Leu Thr Thr Glu Asp Ser Trp Thr Leu Phe Gln Arg Ile Ala Leu Pro
                325                 330                 335
Met Lys Asp Ala Ala Glu Phe Lys Ile Asp Glu Glu Lys Glu Glu Leu
                340                 345                 350
Gly Lys Leu Met Ile Lys His Cys Gly Gly Leu Pro Leu Ala Ile Arg
                355                 360                 365
Val Leu Gly Gly Met Leu Ala Glu Lys Tyr Thr Ser His Asp Trp Arg
                370                 375                 380
Arg Leu Ser Glu Asn Ile Gly Ser His Leu Val Gly Arg Thr Asn
385                 390                 395                 400
Phe Asn Asp Asp Asn Asn Thr Cys Asn Tyr Val Leu Ser Leu Ser
                405                 410                 415
Phe Glu Glu Leu Pro Ser Tyr Leu Lys His Cys Phe Leu Tyr Leu Ala
                420                 425                 430
His Phe Pro Asp Asp Tyr Glu Ile Asn Val Lys Asn Leu Ser Tyr Tyr
                435                 440                 445
Trp Ala Ala Glu Gly Ile Phe Gln Pro Arg His Tyr Asp Gly Glu Ile
                450                 455                 460
```

```
Ile Arg Asp Val Gly Asp Val Tyr Ile Glu Glu Leu Val Arg Arg Asn
465                 470                 475                 480

Met Val Ile Ser Glu Arg Asp Val Lys Thr Ser Arg Phe Glu Thr Cys
                485                 490                 495

His Leu His Asp Met Met Arg Glu Val Cys Leu Leu Lys Ala Lys Glu
            500                 505                 510

Glu Asn Phe Leu Gln Ile Thr Ser Ser Arg Thr Ser Thr Gly Asn Ser
            515                 520                 525

Leu Ser Ile Val Thr Ser Arg Arg Leu Val Tyr Gln Tyr Pro Ile Thr
530                 535                 540

Leu Asp Val Glu Lys Asp Ile Asn Asp Pro Lys Leu Arg Ser Leu Val
545                 550                 555                 560

Val Val Ala Asn Thr Tyr Met Phe Trp Gly Gly Trp Ser Trp Met Leu
                565                 570                 575

Leu Gly Ser Ser Phe Ile Arg Leu Glu Leu Leu Arg Val Leu Asp Ile
            580                 585                 590

His Arg Ala Lys Leu Lys Gly Gly Lys Leu Ala Ser Ser Ile Gly Gln
            595                 600                 605

Leu Ile His Leu Arg Tyr Leu Asn Leu Lys His Ala Glu Val Thr His
610                 615                 620

Ile Pro Tyr Ser Leu Gly Asn Leu Lys Leu Leu Ile Tyr Leu Asn Leu
625                 630                 635                 640

Val Ile Leu Val Ser Gly Ser Thr Leu Val Pro Asn Val Leu Lys Glu
                645                 650                 655

Met Gln Gln Leu Arg Tyr Leu Ala Leu Pro Lys Asp Met Gly Arg Lys
            660                 665                 670

Thr Lys Leu Glu Leu Ser Asn Leu Val Lys Leu Glu Thr Leu Lys Asn
            675                 680                 685

Phe Ser Thr Lys Asn Cys Ser Leu Glu Asp Leu Arg Gly Met Val Arg
690                 695                 700

Leu Arg Thr Leu Thr Ile Glu Leu Arg Lys Glu Thr Ser Leu Glu Thr
705                 710                 715                 720

Leu Ala Ala Ser Ile Gly Gly Leu Lys Tyr Leu Glu Ser Leu Thr Ile
                725                 730                 735

Thr Asp Leu Gly Ser Glu Met Arg Thr Lys Glu Ala Gly Ile Val Phe
            740                 745                 750

Asp Phe Val Tyr Leu Lys Thr Leu Thr Leu Lys Leu Tyr Met Pro Arg
            755                 760                 765

Leu Ser Lys Glu Gln His Phe Pro Ser His Leu Thr Thr Leu Tyr Leu
770                 775                 780

Gln His Cys Arg Leu Glu Glu Asp Pro Met Pro Ile Leu Glu Lys Leu
785                 790                 795                 800

His Gln Leu Lys Glu Leu Glu Leu Arg Arg Lys Ser Phe Ser Gly Lys
                805                 810                 815

Glu Met Val Cys Ser Ser Gly Gly Phe Pro Gln Leu Gln Lys Leu Ser
            820                 825                 830

Ile Lys Gly Leu Glu Glu Trp Glu Asp Trp Lys Val Glu Glu Ser Ser
            835                 840                 845

Met Pro Val Leu His Thr Leu Asp Ile Arg Asp Cys Arg Lys Leu Lys
850                 855                 860

Gln Leu Pro Asp Glu His Leu Pro Ser His Leu Thr Ser Ile Ser Leu
865                 870                 875                 880
```

```
Phe Phe Cys Cys Leu Glu Glu Asp Pro Met Pro Thr Leu Glu Arg Leu
                885                 890                 895

Val His Leu Lys Glu Leu Gln Leu Leu Phe Arg Ser Phe Ser Gly Arg
            900                 905                 910

Ile Met Val Cys Ala Gly Ser Gly Phe Pro Gln Leu His Lys Leu Lys
            915                 920                 925

Leu Ser Glu Leu Asp Gly Leu Glu Glu Trp Ile Val Glu Asp Gly Ser
        930                 935                 940

Met Pro Gln Leu His Thr Leu Glu Ile Arg Arg Cys Pro Lys Leu Lys
945                 950                 955                 960

Lys Leu Pro Asn Gly Phe Pro Gln Leu Gln Asn Leu Glu Leu Asn Glu
                965                 970                 975

Leu Glu Glu Trp Glu Glu Trp Ile Val Glu Asp Gly Ser Met Pro Leu
            980                 985                 990

Leu His Thr Leu Arg Ile Trp Asn Cys Pro Lys Leu Lys Gln Leu Pro
            995                 1000                1005

Asp Gly Leu Arg Phe Ile Tyr Ser Leu Lys Asn Leu Thr Val Pro
    1010                1015                1020

Lys Arg Trp Lys Lys Arg Leu Ser Lys Gly Gly Glu Asp Tyr Tyr
    1025                1030                1035

Lys Val Gln His Ile Pro Ser Val Glu Phe Tyr
    1040                1045

<210> SEQ ID NO 67
<211> LENGTH: 3757
<212> TYPE: DNA
<213> ORGANISM: Arabidopsis thaliana

<400> SEQUENCE: 67
cgtgtgctta tccaaagacg acgagaggag tcccaagaag tctagcggta tcaatcaaat        60
ctcttcttac tagaggagat tccttggaac catcaagagg aagcattatg gctggggaac       120
ttatttcgtt tggtatacaa aacctgtgga acctactgag tcaagaatgc gagctatttc       180
agggagtcga agatcaagta actgaactaa aagggatctt aaacttgtta agctcttttc       240
tgaaagatgc agatgcaaag aaacatacaa gtgcggtggt gaaaaactgt gttgaagaga       300
tcaaggaaat tatctatgat ggagaggata caatcgaaac atttgttctt gagcaaaacc       360
tgggaaaaac aagtggtatc aagaagagta tcagaagact tgcttgcatt attccagatc       420
gaaggagata tgcattaggt atcggaggct taagtaatag gatctccaag gtgatccgag       480
atatgcagag ttttggagtg caacaagcta tcgttgatgg tgggtataag caacctcaag       540
gtgataaaca aagggagatg cgaccaagat tttctaagga cgacgatagc gattttgtgg       600
ggttggaagc aaatgttaag aaattggttg gatatttggt ggacgaagca acgttcaag       660 tggtttccat aaccgggatg ggtggtctag gtaaaaccac acttgctaaa caggttttta       720
accatgagga tgttaaacat cagtttgatg ggctctcatg ggtgtgtgtt tcacaagatt       780
ttacccgaat gaatgtatgg caaaagatct tgagggacct caaacccaaa gaggaagaaa       840
agaaaatcat ggagatgaca caagatacac tccaaggtga actaattcga ttgttggaaa       900
cgtctaagtc attaattgtc ctcgatgaca tatgggaaaa agaagattgg gaactaatca       960
agccaatatt tccaccgacc aaaggttgga agtgttgct tacttctcga aacgagagtg      1020
tcgccatgcg tagaaataca tcatatatca actttaaacc agaatgccta accactgaag      1080
acagttggac actttttcag aggatagccc ttcctatgaa agatgcagct gaatttaaga      1140
```

```
ttgatgagga aaaggaagag ttgggtaagc taatgatcaa acactgtgga gggttaccat    1200
tggccatcag agtgttagga ggtatgttag ctgaaaaata cacatcgcat gattggagaa    1260
gattatctga gaatattgga tctcatctcg tgggaggaag aactaacttt aatgacgaca    1320
acaacaatac atgtaactat gtattgtctc taagctttga agaattgcca agttatttga    1380
agcattgttt cctctacttg gcccattttc cagatgatta tgagataaac gtaaagaatt    1440
tgtcatatta ctgggctgca gaaggaatat tccaacctag cattacgat ggagaaatca     1500 ttcgagatgt tggagatgtc tacatagagg agctggtgag gaggaatatg gtcatttccg    1560
aaagagatgt aaagacttcg agatttgaaa cttgtcattt gcatgacatg atgagagaag    1620
tttgtttgtt aaaagccaaa gaagagaact tcctacagat taccagtagc cgcacttcaa    1680
ctggaaactc tctgtctatt gtcacatctc gcaggcttgt ctaccaatat cctattacat    1740
tagatgttga gaaagatata aacgatccaa aacttcgatc tctcgtggtt gttgccaata    1800
cttatatgtt ttggggaggt tggagttgga tgctgttagg ttcaagcttt ataaggttag    1860
aactactgag ggtattagat atccatagag ccaagttgaa aggagggaag ttagcttctt    1920
ccattggaca gctcatccac ttaagatact tgaacttaaa gcatgctgag gtaactcata    1980
taccttattc actaggaaat ctgaagttgt tgatctatct gaatttagtc attttagtct    2040
ccggatctac attggtgccc aatgtcttga aggagatgca acaactgaga taccttgcgt    2100
taccaaaaga tatggggagg aagacaaaac tagaattgag taatctagta aaattggaga    2160
ctttgaaaaa tttctcaaca aagaattgca gcttggagga tcttcgtggt atggtcaggc    2220
tgagaacgct caccatcgaa ttacgtaagg agacgagtct agaaactcta gctgcatcta    2280
taggcggatt gaaataccct gaaagccttta caataactga tcttggttct gagatgagga    2340
cgaaggaagc gggaatcgta tttgatttcg tttatctcaa aacgctaacg ttgaaactgt    2400
atatgcctag gctttctaaa gaacaacact tcccttctca ccttacaacc ttatatctac    2460
aacattgtcg gttggaagag gatcccatgc cgattctaga gaagttgcat cagttgaaag    2520
agcttgaatt aaggcgtaaa tctttcagtg gaaaggaaat ggtttgctcg agcggtgggt    2580
ttcctcaatt gcagaagctt tcaataaaag gactagagga atgggaagat tggaaagtag    2640
aagaaagctc catgccagtt cttcatactc tcgatattcg ggattgtcga aaattaaagc    2700
agcttcctga tgaacacctt ccttctcacc ttacatccat atctctattt ttttgttgtt    2760
tggaggagga tccaatgccg actctagaga gattggttca cttgaaagag cttcaattat    2820
tgtttagatc tttcagtggg aggataatgg tttgcgctgg cagtgggttt cctcaactgc    2880
acaagctaaa attatctgaa ctagatgggt tggaagagtg gatagtagag gatggctcca    2940
tgccacagct tcatactctg gaattcgtc ggtgtccaaa gttaaagaag cttcctaatg     3000
ggtttccaca attgcagaat cttgagttaa atgagctaga ggaatgggaa gagtggatag    3060
tagaggatgg ctccatgcca cttcttcata ctctaagaat ttggaattgt ccaaagttaa    3120
agcagctgcc tgatgggttg cgatttatct attcattaaa gaatttgact gtaccaaaga    3180
gatggaagaa gagattgtcg aaaggaggag aagattatta caaagtccaa cacattcctt    3240
ctgttgaatt ctactaggaa tgctctcagc aatcacagac tatgtatata tatgtacaca    3300
taaagagctg cattgatggt gttcgatgaa ttgtctaact gtgactatcc ttgacgagat    3360
atgtaatcat aagcctctgt ttccacccaa aatcaggtcg gaagatagtt gcaggtagga    3420
agctaatcaa acaagacacc ttatttttca cgacgagatg ttgaacccct gaagaatgtt    3480
ggacaccatt ttgatggata aaacattttc ataggagaaa tgatagagtc gaggtgaaaa    3540
```

```
ggtgtctagc ttttgaagct tgctgtgta ctaagtggac aactttctta ttctctatct      3600
gtttttggtg tgtaataaga atctgaattt tatgcatggg tgaatttgta cgggttaata      3660
gagaagttca taacctaagt taagactagt ctgctaaatt cggacacaat gtgaaattct      3720
caagctcatc gtttaatcaa cagagagaat ttgattg                              3757
```

```
<210> SEQ ID NO 68
<211> LENGTH: 1049
<212> TYPE: PRT
<213> ORGANISM: Arabidopsis thaliana

<400> SEQUENCE: 68
```

| | | | | | | | | | | | | | | |
|---|---|---|---|---|---|---|---|---|---|---|---|---|---|---|
|Met|Ala|Gly|Glu|Leu|Ile|Ser|Phe|Gly|Ile|Gln|Asn|Leu|Trp|Asn|Leu|
|1| | | |5| | | | |10| | | | |15|

Leu Ser Gln Glu Cys Glu Leu Phe Gln Gly Val Glu Asp Gln Val Thr
             20                  25                  30

Glu Leu Lys Arg Asp Leu Asn Leu Leu Ser Ser Phe Leu Lys Asp Ala
         35                  40                  45

Asp Ala Lys Lys His Thr Ser Ala Val Val Lys Asn Cys Val Glu Glu
     50                  55                  60

Ile Lys Glu Ile Ile Tyr Asp Gly Glu Asp Thr Ile Glu Thr Phe Val
65                  70                  75                  80

Leu Glu Gln Asn Leu Gly Lys Thr Ser Gly Ile Lys Lys Ser Ile Arg
                 85                  90                  95

Arg Leu Ala Cys Ile Ile Pro Asp Arg Arg Tyr Ala Leu Gly Ile
            100                 105                 110

Gly Gly Leu Ser Asn Arg Ile Ser Lys Val Ile Arg Asp Met Gln Ser
        115                 120                 125

Phe Gly Val Gln Gln Ala Ile Val Asp Gly Gly Tyr Lys Gln Pro Gln
    130                 135                 140

Gly Asp Lys Gln Arg Glu Met Arg Pro Arg Phe Ser Lys Asp Asp
145                 150                 155                 160

Ser Asp Phe Val Gly Leu Glu Ala Asn Val Lys Lys Leu Val Gly Tyr
                165                 170                 175

Leu Val Asp Glu Ala Asn Val Gln Val Val Ser Ile Thr Gly Met Gly
            180                 185                 190

Gly Leu Gly Lys Thr Thr Leu Ala Lys Gln Val Phe Asn His Glu Asp
        195                 200                 205

Val Lys His Gln Phe Asp Gly Leu Ser Trp Val Cys Val Ser Gln Asp
    210                 215                 220

Phe Thr Arg Met Asn Val Trp Gln Lys Ile Leu Arg Asp Leu Lys Pro
225                 230                 235                 240

Lys Glu Glu Glu Lys Lys Ile Met Glu Met Thr Gln Asp Thr Leu Gln
                245                 250                 255

Gly Glu Leu Ile Arg Leu Leu Glu Thr Ser Lys Ser Leu Ile Val Leu
            260                 265                 270

Asp Asp Ile Trp Glu Lys Glu Asp Trp Glu Leu Ile Lys Pro Ile Phe
        275                 280                 285

Pro Pro Thr Lys Gly Trp Lys Val Leu Leu Thr Ser Arg Asn Glu Ser
    290                 295                 300

Val Ala Met Arg Arg Asn Thr Ser Tyr Ile Asn Phe Lys Pro Glu Cys
305                 310                 315                 320

Leu Thr Thr Glu Asp Ser Trp Thr Leu Phe Gln Arg Ile Ala Leu Pro
                325                 330                 335

```
Met Lys Asp Ala Ala Glu Phe Lys Ile Asp Glu Lys Glu Glu Leu
                340                 345                 350

Gly Lys Leu Met Ile Lys His Cys Gly Gly Leu Pro Leu Ala Ile Arg
            355                 360                 365

Val Leu Gly Gly Met Leu Ala Glu Lys Tyr Thr Ser His Asp Trp Arg
        370                 375                 380

Arg Leu Ser Glu Asn Ile Gly Ser His Leu Val Gly Gly Arg Thr Asn
385                 390                 395                 400

Phe Asn Asp Asp Asn Asn Thr Cys Asn Tyr Val Leu Ser Leu Ser
                405                 410                 415

Phe Glu Glu Leu Pro Ser Tyr Leu Lys His Cys Phe Leu Tyr Leu Ala
                420                 425                 430

His Phe Pro Asp Asp Tyr Glu Ile Asn Val Lys Asn Leu Ser Tyr Tyr
            435                 440                 445

Trp Ala Ala Glu Gly Ile Phe Gln Pro Arg His Tyr Asp Gly Glu Ile
        450                 455                 460

Ile Arg Asp Val Gly Asp Val Tyr Ile Glu Glu Leu Val Arg Arg Asn
465                 470                 475                 480

Met Val Ile Ser Glu Arg Asp Val Lys Thr Ser Arg Phe Glu Thr Cys
                485                 490                 495

His Leu His Asp Met Met Arg Glu Val Cys Leu Leu Lys Ala Lys Glu
                500                 505                 510

Glu Asn Phe Leu Gln Ile Thr Ser Ser Arg Thr Ser Thr Gly Asn Ser
                515                 520                 525

Leu Ser Ile Val Thr Ser Arg Arg Leu Val Tyr Gln Tyr Pro Ile Thr
        530                 535                 540

Leu Asp Val Glu Lys Asp Ile Asn Asp Pro Lys Leu Arg Ser Leu Val
545                 550                 555                 560

Val Val Ala Asn Thr Tyr Met Phe Trp Gly Gly Trp Ser Trp Met Leu
                565                 570                 575

Leu Gly Ser Ser Phe Ile Arg Leu Glu Leu Leu Arg Val Leu Asp Ile
            580                 585                 590

His Arg Ala Lys Leu Lys Gly Gly Lys Leu Ala Ser Ser Ile Gly Gln
        595                 600                 605

Leu Ile His Leu Arg Tyr Leu Asn Leu Lys His Ala Glu Val Thr His
            610                 615                 620

Ile Pro Tyr Ser Leu Gly Asn Leu Lys Leu Leu Ile Tyr Leu Asn Leu
625                 630                 635                 640

Val Ile Leu Val Ser Gly Ser Thr Leu Val Pro Asn Val Leu Lys Glu
                645                 650                 655

Met Gln Gln Leu Arg Tyr Leu Ala Leu Pro Lys Asp Met Gly Arg Lys
            660                 665                 670

Thr Lys Leu Glu Leu Ser Asn Leu Val Lys Leu Glu Thr Leu Lys Asn
        675                 680                 685

Phe Ser Thr Lys Asn Cys Ser Leu Glu Asp Leu Arg Gly Met Val Arg
            690                 695                 700

Leu Arg Thr Leu Thr Ile Glu Leu Arg Lys Glu Thr Ser Leu Glu Thr
705                 710                 715                 720

Leu Ala Ala Ser Ile Gly Gly Leu Lys Tyr Leu Glu Ser Leu Thr Ile
                725                 730                 735

Thr Asp Leu Gly Ser Glu Met Arg Thr Lys Glu Ala Gly Ile Val Phe
            740                 745                 750
```

```
Asp Phe Val Tyr Leu Lys Thr Leu Thr Leu Lys Leu Tyr Met Pro Arg
            755                 760                 765
Leu Ser Lys Glu Gln His Phe Pro Ser His Leu Thr Thr Leu Tyr Leu
        770                 775                 780
Gln His Cys Arg Leu Glu Glu Asp Pro Met Pro Ile Leu Glu Lys Leu
785                 790                 795                 800
His Gln Leu Lys Glu Leu Glu Leu Arg Arg Lys Ser Phe Ser Gly Lys
                805                 810                 815
Glu Met Val Cys Ser Ser Gly Gly Phe Pro Gln Leu Gln Lys Leu Ser
            820                 825                 830
Ile Lys Gly Leu Glu Glu Trp Glu Asp Trp Lys Val Glu Glu Ser Ser
        835                 840                 845
Met Pro Val Leu His Thr Leu Asp Ile Arg Asp Cys Arg Lys Leu Lys
850                 855                 860
Gln Leu Pro Asp Glu His Leu Pro Ser His Leu Thr Ser Ile Ser Leu
865                 870                 875                 880
Phe Phe Cys Cys Leu Glu Glu Asp Pro Met Pro Thr Leu Glu Arg Leu
            885                 890                 895
Val His Leu Lys Glu Leu Gln Leu Leu Phe Arg Ser Phe Ser Gly Arg
        900                 905                 910
Ile Met Val Cys Ala Gly Ser Gly Phe Pro Gln Leu His Lys Leu Lys
        915                 920                 925
Leu Ser Glu Leu Asp Gly Leu Glu Glu Trp Ile Val Glu Asp Gly Ser
    930                 935                 940
Met Pro Gln Leu His Thr Leu Glu Ile Arg Arg Cys Pro Lys Leu Lys
945                 950                 955                 960
Lys Leu Pro Asn Gly Phe Pro Gln Leu Gln Asn Leu Glu Leu Asn Glu
                965                 970                 975
Leu Glu Glu Trp Glu Glu Trp Ile Val Glu Asp Gly Ser Met Pro Leu
            980                 985                 990
Leu His Thr Leu Arg Ile Trp Asn Cys Pro Lys Leu Lys Gln Leu Pro
        995                 1000                1005
Asp Gly Leu Arg Phe Ile Tyr Ser Leu Lys Asn Leu Thr Val Pro
    1010                1015                1020
Lys Arg Trp Lys Lys Arg Leu Ser Lys Gly Gly Glu Asp Tyr Tyr
    1025                1030                1035
Lys Val Gln His Ile Pro Ser Val Glu Phe Tyr
    1040                1045

<210> SEQ ID NO 69
<211> LENGTH: 740
<212> TYPE: DNA
<213> ORGANISM: Arabidopsis thaliana

<400> SEQUENCE: 69
aaacatcatt attacatcaa aacaaaaaat gggaaagaga ggacaaaaac agaacaggtt      60
cttgagaatc gtcaccatgc ctcttaaagt tctatgcaaa gctcgtgatc tctacatgag     120
aagcatcaca ggttgtgcag ctcgaactca ctactcttca gccgtcgacg ccgcatccgt     180
tccatttccg agaagccgga gtacttcctc cgccttctct tcctctgcct cttctcggag     240
aagatcttcg gatttcactt tcgacgatga ttatagcgag ctgcttagag ctgcttccgt     300
taggagttta ggtcataaga atgagattga catgatcata caacaacagc aacagcagca     360
gcagcaacgg caggagaatc gcgttgcgat gggagcggtt acggttaaag gcggtttgcc     420
```

```
taagagctcg agtgttggga tgacaatggc taggattgat gaagaagatg aagaagaagg      480
atctgtaaag aatcaaaaga agggatctga tttcttatat cctcgtagca gatcacatgc      540
tgttactatt agaggatcca agttttaata tatactacta attaattgtc agttttattt      600 ttctttttgat ttaatttaaa agaatgttcc taattataca tgtttatgga attattttga     660
tgtaaagtta ctgtcatgga tttatacaaa aaaaagtta ctgtcaaatt tatttcaata       720
aaaattccta tatagattaa                                                  740
```

<210> SEQ ID NO 70
<211> LENGTH: 179
<212> TYPE: PRT
<213> ORGANISM: Arabidopsis thaliana

<400> SEQUENCE: 70

```
Met Gly Lys Arg Gly Gln Lys Gln Asn Arg Phe Leu Arg Ile Val Thr
1               5                   10                  15

Met Pro Leu Lys Val Leu Cys Lys Ala Arg Asp Leu Tyr Met Arg Ser
            20                  25                  30

Ile Thr Gly Cys Ala Ala Arg Thr His Tyr Ser Ser Ala Val Asp Ala
        35                  40                  45

Ala Ser Val Pro Phe Pro Arg Ser Arg Ser Thr Ser Ala Phe Ser
    50                  55                  60

Ser Ser Ala Ser Arg Arg Arg Ser Ser Asp Phe Thr Phe Asp Asp
65                  70                  75                  80

Asp Tyr Ser Glu Leu Leu Arg Ala Ala Ser Val Arg Ser Leu Gly His
                85                  90                  95

Lys Asn Glu Ile Asp Met Ile Ile Gln Gln Gln Gln Gln Gln Gln
            100                 105                 110

Gln Arg Gln Glu Asn Arg Val Ala Met Gly Ala Val Thr Val Lys Gly
        115                 120                 125

Gly Leu Pro Lys Ser Ser Ser Val Gly Met Thr Met Ala Arg Ile Asp
    130                 135                 140

Glu Glu Asp Glu Glu Glu Gly Ser Val Lys Asn Gln Lys Lys Gly Ser
145                 150                 155                 160

Asp Phe Leu Tyr Pro Arg Ser Arg Ser His Ala Val Thr Ile Arg Gly
                165                 170                 175

Ser Lys Phe
```

<210> SEQ ID NO 71
<211> LENGTH: 1313
<212> TYPE: DNA
<213> ORGANISM: Arabidopsis thaliana

<400> SEQUENCE: 71

```
tggttatata acactaatca ggagtgaaat tcatccaca aaattcctt ataaattcac        60 gaccaaacac acacatttct ttaattccat aaaaacaaaa acaaaaatat aatgtggact     120
tctaaaacca taagcttcac tctcttcatc acaacaacac ttctcgggtc ctgcaacgca    180
tctgcaaagg ccaaaacgca accgctattc ccagcgattc taatctttgg tgattcaaca    240
gtcgacacag gcaacaataa ttacccttca caaacaatct tcagagctaa acatgttcct    300
tacggaattg atctcccaaa ccactcacct aacggaagat tctcaaacgg gaaaattttc    360
tccgacataa tcgcaaccaa actcaacatc aaacagtttg ttcctccttt cttacaacca    420
aatctcaccg accaagaaat tgtaaccgga gtctgtttcg catcagcagg tgccggttac    480
```

```
gatgaccaaa ccagtctcac gacacaagcg attcgtgtct cggaacaacc aaatatgttc      540
aagagttaca ttgctcgtct taagagtatc gtaggagaca agaaagccat gaagatcata      600
aacaatgctt tggtggttgt gagtgcaggg cctaatgatt tcatcttgaa ttattacgag      660
gttccctcat ggcgtcgcat gtatcctagc atttctgatt accaagattt tgttcttagt      720
aggcttaaca atttcgtgaa ggagctttac agcctaggtt gccggaaaat tttggtcgga      780
ggtttaccgc caatgggatg tttaccgatt caaatgactg ctcaattccg caacgtccta      840
aggttttgct tggaacaaga gaacagagac tctgttttat acaatcagaa acttcagaag      900
ctcttacctc agacacaagc atctcttaca ggaagcaaga tcctttactc tgatgtctat      960
gaccctatga tggagatgct ccaaaacccct agcaaatacg gatttaaaga dacgacgaga     1020
ggatgttgtg aacagggtt cttggagacg agcttcatgt gtaatgctta ttcttccatg      1080
tgtcagaatc gctcggagtt tctgttcttt gactcgattc atccatctga agctacctac     1140
aattacattg gtaatgttct ggatactaag attcgtgggt ggcttaaggc ttaagttatc      1200
aagatttgca aagattgaac aaaattatct gtttcataat gtgactattt gtggacttcg     1260
tttgtttatc aactattaac tttggctctt actggcgctt taacttagcg aaa            1313
```

<210> SEQ ID NO 72
<211> LENGTH: 360
<212> TYPE: PRT
<213> ORGANISM: Arabidopsis thaliana

<400> SEQUENCE: 72

```
Met Trp Thr Ser Lys Thr Ile Ser Phe Thr Leu Phe Ile Thr Thr Thr
1               5                   10                  15

Leu Leu Gly Ser Cys Asn Ala Ser Ala Lys Ala Lys Thr Gln Pro Leu
            20                  25                  30

Phe Pro Ala Ile Leu Ile Phe Gly Asp Ser Thr Val Asp Thr Gly Asn
        35                  40                  45

Asn Asn Tyr Pro Ser Gln Thr Ile Phe Arg Ala Lys His Val Pro Tyr
    50                  55                  60

Gly Ile Asp Leu Pro Asn His Ser Pro Asn Gly Arg Phe Ser Asn Gly
65                  70                  75                  80

Lys Ile Phe Ser Asp Ile Ile Ala Thr Lys Leu Asn Ile Lys Gln Phe
                85                  90                  95

Val Pro Pro Phe Leu Gln Pro Asn Leu Thr Asp Gln Glu Ile Val Thr
            100                 105                 110

Gly Val Cys Phe Ala Ser Ala Gly Ala Gly Tyr Asp Asp Gln Thr Ser
        115                 120                 125

Leu Thr Thr Gln Ala Ile Arg Val Ser Glu Gln Pro Asn Met Phe Lys
    130                 135                 140

Ser Tyr Ile Ala Arg Leu Lys Ser Ile Val Gly Asp Lys Lys Ala Met
145                 150                 155                 160

Lys Ile Ile Asn Asn Ala Leu Val Val Val Ser Ala Gly Pro Asn Asp
                165                 170                 175

Phe Ile Leu Asn Tyr Tyr Glu Val Pro Ser Trp Arg Arg Met Tyr Pro
            180                 185                 190

Ser Ile Ser Asp Tyr Gln Asp Phe Val Leu Ser Arg Leu Asn Asn Phe
        195                 200                 205

Val Lys Glu Leu Tyr Ser Leu Gly Cys Arg Lys Ile Leu Val Gly Gly
    210                 215                 220

Leu Pro Pro Met Gly Cys Leu Pro Ile Gln Met Thr Ala Gln Phe Arg
```

Asn Val Leu Arg Phe Cys Leu Glu Gln Glu Asn Arg Asp Ser Val Leu
            245                 250                 255

Tyr Asn Gln Lys Leu Gln Lys Leu Leu Pro Gln Thr Gln Ala Ser Leu
            260                 265                 270

Thr Gly Ser Lys Ile Leu Tyr Ser Asp Val Tyr Asp Pro Met Met Glu
            275                 280                 285

Met Leu Gln Asn Pro Ser Lys Tyr Gly Phe Lys Glu Thr Thr Arg Gly
    290                 295                 300

Cys Cys Gly Thr Gly Phe Leu Glu Thr Ser Phe Met Cys Asn Ala Tyr
305                 310                 315                 320

Ser Ser Met Cys Gln Asn Arg Ser Glu Phe Leu Phe Phe Asp Ser Ile
            325                 330                 335

His Pro Ser Glu Ala Thr Tyr Asn Tyr Ile Gly Asn Val Leu Asp Thr
            340                 345                 350

Lys Ile Arg Gly Trp Leu Lys Ala
            355                 360

<210> SEQ ID NO 73
<211> LENGTH: 867
<212> TYPE: DNA
<213> ORGANISM: Arabidopsis thaliana

<400> SEQUENCE: 73
atcttcttca tcaattgatc tactctgctc tgctcaagat cagaaatcgt cggtttagtt      60
ctccggttaa aagtttcgtc tctgcgggaa ttggaacttc aatggaggga ttaaagctct     120
cagaagcgga attgatgatt tttattcatc cttcccagag cagaaacgtt tttcaaggaa     180
tttgtcgcga gctcagttct cttctattcc agtataatga aacctttgat ggagttctat     240
tggcttatga tgctactgtg aaaagcaaac aagctaaaat ccttacagga cttcatcctt     300
actttggcgt cagagttaac actagactac tcttatttga tcctaagccc aagagttttg     360
tagaagggaa aattgtgaag atttctccag agtcaatcca tgttattgtt cttggtttct     420
ctgctgctgt cattacagac gttgatatcc gggaagagtt caaatacaga gtgagagatg     480
gtgaaggttc tttcgtgagc agatcgcata acggcatgc actaaagctt ggaactatgt     540
tgcgccttca gtccaaagt tttgatgaag aggttatgca tatagctgga tctctacttc     600
cggaaaacac aggatgcgtt aagtggctcg aaaagaagtc tgaagaagct ttgcctacgg     660
atagggatca taaaggagg aaactcgcct gaggaatttt gaattacaa acagtagaa      720
gactcttgaa atgaagagaa gcagctatgc tgaaattttg ttgtatcaaa tccatttatg     780
taaacccttt tttttcatca taatactaac attaatgtcc tttaaaatct gaatgttctc     840
cttaatcaaa atcaaaaagt tatgagt                                          867

<210> SEQ ID NO 74
<211> LENGTH: 196
<212> TYPE: PRT
<213> ORGANISM: Arabidopsis thaliana

<400> SEQUENCE: 74

Met Glu Gly Leu Lys Leu Ser Glu Ala Glu Leu Met Ile Phe Ile His
1               5                   10                  15

Pro Ser Gln Ser Arg Asn Val Phe Gln Gly Ile Cys Arg Glu Leu Ser
            20                  25                  30

Ser Leu Leu Phe Gln Tyr Asn Glu Thr Phe Asp Gly Val Leu Leu Ala

```
                35                  40                  45
Tyr Asp Ala Thr Val Lys Ser Lys Gln Ala Lys Ile Leu Thr Gly Leu
 50                  55                  60

His Pro Tyr Phe Gly Val Arg Val Asn Thr Arg Leu Leu Leu Phe Asp
 65                  70                  75                  80

Pro Lys Pro Lys Ser Phe Val Glu Gly Lys Ile Val Lys Ile Ser Pro
                 85                  90                  95

Glu Ser Ile His Val Ile Val Leu Gly Phe Ser Ala Ala Val Ile Thr
            100                 105                 110

Asp Val Asp Ile Arg Glu Glu Phe Lys Tyr Arg Val Arg Asp Gly Glu
        115                 120                 125

Gly Ser Phe Val Ser Arg Ser His Lys Arg His Ala Leu Lys Leu Gly
130                 135                 140

Thr Met Leu Arg Leu Gln Val Gln Ser Phe Asp Glu Val Met His
145                 150                 155                 160

Ile Ala Gly Ser Leu Leu Pro Glu Asn Thr Gly Cys Val Lys Trp Leu
                165                 170                 175

Glu Lys Lys Ser Glu Glu Ala Leu Pro Thr Asp Arg Asp His Lys Arg
            180                 185                 190

Arg Lys Leu Ala
        195

<210> SEQ ID NO 75
<211> LENGTH: 887
<212> TYPE: DNA
<213> ORGANISM: Arabidopsis thaliana

<400> SEQUENCE: 75
ttgagactgt ttaattcgaa aaccctaagc tcattctcaa aagataaaac ttgccgctat      60
atagtttctc agaagtgaag ctttttttt atatatattt atgaacagga attggaactt     120
caatggaggg attaaagctc tcagaagcgg aattgatgat tttattcat ccttcccaga    180 gcagaaacgt ttttcaagga atttgtcgcg agctcagttc tcttctattc agtataatg    240 aaacctttga tggagttcta ttggcttatg atgctactgt gaaaagcaaa caagctaaaa    300
tccttacagg acttcatcct tactttggcg tcagagttaa cactagacta ctcttatttg    360
atcctaagcc caagagtttt gtagaaggga aaattgtgaa gatttctcca gagtcaatcc    420
atgttattgt tcttggtttc tctgctgctg tcattacaga cgttgatatc cgggaagagt    480
tcaaatacag agtgagagat ggtgaaggtt ctttcgtgag cagatcgcat aaacggcatg    540
cactaaagct tggaactatg ttgcgccttc aagtccaaag ttttgatgaa gaggttatgc    600
atatagctgg atctctactt ccggaaaaca caggatgcgt taagtggctc gaaaagaagt    660
ctgaagaagc tttgcctacg gatagggatc ataaaggag gaaactcgcc tgaggaattt    720
tgaaattaca aaacagtaga agactcttga aatgaagaga agcagctatg ctgaaatttt    780
gttgtatcaa atccattta gtaaacccttt tttttcatc ataatactaa cattaatgtc    840
ctttaaaatc tgaatgttct ccttaatcaa atcaaaaag ttatgag                   887

<210> SEQ ID NO 76
<211> LENGTH: 196
<212> TYPE: PRT
<213> ORGANISM: Arabidopsis thaliana

<400> SEQUENCE: 76

Met Glu Gly Leu Lys Leu Ser Glu Ala Glu Leu Met Ile Phe Ile His
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Pro | Ser | Gln | Ser | Arg | Asn | Val | Phe | Gln | Gly | Ile | Cys | Arg | Glu | Leu | Ser |
|   |   |   | 20 |   |   |   |   | 25 |   |   |   |   | 30 |   |
| Ser | Leu | Leu | Phe | Gln | Tyr | Asn | Glu | Thr | Phe | Asp | Gly | Val | Leu | Leu | Ala |
|   |   | 35 |   |   |   |   | 40 |   |   |   |   | 45 |   |   |
| Tyr | Asp | Ala | Thr | Val | Lys | Ser | Lys | Gln | Ala | Lys | Ile | Leu | Thr | Gly | Leu |
|   | 50 |   |   |   |   | 55 |   |   |   |   | 60 |   |   |   |
| His | Pro | Tyr | Phe | Gly | Val | Arg | Val | Asn | Thr | Arg | Leu | Leu | Leu | Phe | Asp |
| 65 |   |   |   |   | 70 |   |   |   |   | 75 |   |   |   |   | 80 |
| Pro | Lys | Pro | Lys | Ser | Phe | Val | Glu | Gly | Lys | Ile | Val | Lys | Ile | Ser | Pro |
|   |   |   |   | 85 |   |   |   |   | 90 |   |   |   |   | 95 |   |
| Glu | Ser | Ile | His | Val | Ile | Val | Leu | Gly | Phe | Ser | Ala | Ala | Val | Ile | Thr |
|   |   |   | 100 |   |   |   |   | 105 |   |   |   |   | 110 |   |   |
| Asp | Val | Asp | Ile | Arg | Glu | Glu | Phe | Lys | Tyr | Arg | Val | Arg | Asp | Gly | Glu |
|   |   | 115 |   |   |   |   | 120 |   |   |   |   | 125 |   |   |   |
| Gly | Ser | Phe | Val | Ser | Arg | Ser | His | Lys | Arg | His | Ala | Leu | Lys | Leu | Gly |
|   | 130 |   |   |   |   | 135 |   |   |   |   | 140 |   |   |   |   |
| Thr | Met | Leu | Arg | Leu | Gln | Val | Gln | Ser | Phe | Asp | Glu | Glu | Val | Met | His |
| 145 |   |   |   |   | 150 |   |   |   |   | 155 |   |   |   |   | 160 |
| Ile | Ala | Gly | Ser | Leu | Leu | Pro | Glu | Asn | Thr | Gly | Cys | Val | Lys | Trp | Leu |
|   |   |   | 165 |   |   |   |   | 170 |   |   |   |   | 175 |   |   |
| Glu | Lys | Lys | Ser | Glu | Glu | Ala | Leu | Pro | Thr | Arg | Asp | His | Lys | Arg |   |
|   |   |   | 180 |   |   |   |   | 185 |   |   |   |   | 190 |   |   |
| Arg | Lys | Leu | Ala |   |   |   |   |   |   |   |   |   |   |   |   |
|   |   |   | 195 |   |   |   |   |   |   |   |   |   |   |   |   |

<210> SEQ ID NO 77
<211> LENGTH: 2039
<212> TYPE: DNA
<213> ORGANISM: Arabidopsis thaliana

<400> SEQUENCE: 77

```
aagggaaaat cctaataaag gagaagaaaa acagatctga aatcccgctt gatactccac      60
cgactttaaa ctactggttt ttgtttgatt taagtatagt gttaatgact cctctctcca     120
ccttcctttg attctaccta tcacttccct tgccgttgct ccatcttcat cactagtcac     180
tatacaccaa tcttagatcc gggaagctaa tttctcttct ccgatcggtg aatgcagtta     240
cattgacctc ggatctaacc aagctcttct ggtttccagc tctctggaat tcaaaaaaat     300
ggaggagaaa tccaagtcaa gaggttggtg cggttggttc atcgccatta ttgtgctagc     360
ttctgttatc ctcgccgtcg tttacactgt taaattgaga acgaagaaat ccggtgacga     420
tgacggtggc ggtcccgttc ctggacctcc cggcgccatt gataagaaat acgccgacgc     480
tcttaagctc gctttgcagt tcttcgatat ccagaaatct ggtaaattgg agaacaataa     540
gataccttgg agaggagatt caggtcttaa agatggaagt gaagataatc tggatctttc     600
caaaggctta tatgatgctg agatcatat aaagtttggt tttccaatgg ctttcactgc     660
tacagttttg tcatggtcga ttcttgagta tggtgatcaa atgaatgcag tgaaccaatt     720
ggatcctgct aaagactctc tccggtggat cactgactat cttatcaaag ctcatccttc     780
tgacaatgtc ctctatatcc aggtgggaga tccaaaagta gatcatccat gctgggagag     840
accagaggat atgaaagaga agaccact tactaaaatt gatgtagata ctccagggac     900
agaggttgct gctgaaactg ctgcagctat ggcttcagcg tctttggtgt taaggatag     960
tgatcctaca tattcagcaa cgcttctgaa acatgcgaag cagttgttta attttgcaga    1020
```

```
tacaaagaga ggctcttaca gtgttaacat acctgaggtt cagaagtttt acaattcgac    1080
tggatatggt gatgagctac tatgggcagc tagttggttg tatcatgcaa cagaggataa    1140
aacttacctt gattatgtgt ctaatcatgg aaaagaattt gctagttttg gaaatcctac    1200
ttggtttagt tgggacaaca agcttgcagg aacacaggta ctattatcaa gattactctt    1260
ctttaagaaa gatttatcag gaagcaaggg acttggaaat tacaggaaca cagctaaagc    1320
tgtcatgtgt ggacttctac caaagtctcc aacatctaca gctagtagaa caaacggtgg    1380
tcttatatgg gttagtgaat ggaactcgat gcaacaatcc gtttcgtcag cgttttagc     1440 ctcgcttttc agtgattaca tgctcacttc ccgtatccat aaaatatctt gcgacgggaa    1500
aatcttcaaa gcaacagagc ttagagattt cgccaaatcg caggctgatt acatgctggg    1560
gaagaatccg ttgggaacga gcttcgtggt gggttatgga gacaaatacc cacaatttgt    1620
gcatcataga ggagcttcga tcccggcaga tgcaacaacg ggttgcttag atggattcaa    1680
atggtttaac tcgacgaaac caaacccaaa catagcatat ggtgcactcg taggtggacc    1740
tttcttcaat gagacgttca ctgactcacg agagaaccca atgcagaacg agccaaccac    1800
ttacaacaat gcactcctcg ttggtctctt gtctagtctt gtcactacat cttctacttt    1860
acagtcgttg aagtgagctt tgcgtgtttt agccttctta ttgaaaatca cattgcttca    1920
tttttatttg taatttttta aaaaaaatcg tgggtgtgtg tgtattcacg ttgtgtattg    1980
cttgatatgt tgatgcgtgt aaccaaacaa ttagttgctc tacgaatcca aaattgagg    2039
```

<210> SEQ ID NO 78
<211> LENGTH: 525
<212> TYPE: PRT
<213> ORGANISM: Arabidopsis thaliana

<400> SEQUENCE: 78

```
Met Glu Glu Lys Ser Lys Ser Arg Gly Trp Cys Gly Trp Phe Ile Ala
1               5                   10                  15

Ile Ile Val Leu Ala Ser Val Ile Leu Ala Val Val Tyr Thr Val Lys
            20                  25                  30

Leu Arg Thr Lys Lys Ser Gly Asp Asp Gly Gly Pro Val Pro
        35                  40                  45

Gly Pro Pro Gly Ala Ile Asp Lys Lys Tyr Ala Asp Ala Leu Lys Leu
    50                  55                  60

Ala Leu Gln Phe Phe Asp Ile Gln Lys Ser Gly Lys Leu Glu Asn Asn
65                  70                  75                  80

Lys Ile Pro Trp Arg Gly Asp Ser Gly Leu Lys Asp Gly Ser Glu Asp
                85                  90                  95

Asn Leu Asp Leu Ser Lys Gly Leu Tyr Asp Ala Gly Asp His Ile Lys
            100                 105                 110

Phe Gly Phe Pro Met Ala Phe Thr Ala Thr Val Leu Ser Trp Ser Ile
        115                 120                 125

Leu Glu Tyr Gly Asp Gln Met Asn Ala Val Asn Gln Leu Asp Pro Ala
    130                 135                 140

Lys Asp Ser Leu Arg Trp Ile Thr Asp Tyr Leu Ile Lys Ala His Pro
145                 150                 155                 160

Ser Asp Asn Val Leu Tyr Ile Gln Val Gly Asp Pro Lys Val Asp His
                165                 170                 175

Pro Cys Trp Glu Arg Pro Glu Asp Met Lys Glu Lys Arg Pro Leu Thr
            180                 185                 190
```

```
Lys Ile Asp Val Asp Thr Pro Gly Thr Glu Val Ala Glu Thr Ala
            195                 200                 205

Ala Ala Met Ala Ser Ala Ser Leu Val Phe Lys Asp Ser Asp Pro Thr
        210                 215                 220

Tyr Ser Ala Thr Leu Leu Lys His Ala Lys Gln Leu Phe Asn Phe Ala
225                 230                 235                 240

Asp Thr Lys Arg Gly Ser Tyr Ser Val Asn Ile Pro Glu Val Gln Lys
                245                 250                 255

Phe Tyr Asn Ser Thr Gly Tyr Gly Asp Glu Leu Leu Trp Ala Ala Ser
            260                 265                 270

Trp Leu Tyr His Ala Thr Glu Asp Lys Thr Tyr Leu Asp Tyr Val Ser
        275                 280                 285

Asn His Gly Lys Glu Phe Ala Ser Phe Gly Asn Pro Thr Trp Phe Ser
    290                 295                 300

Trp Asp Asn Lys Leu Ala Gly Thr Gln Val Leu Leu Ser Arg Leu Leu
305                 310                 315                 320

Phe Phe Lys Lys Asp Leu Ser Gly Ser Lys Gly Leu Gly Asn Tyr Arg
                325                 330                 335

Asn Thr Ala Lys Ala Val Met Cys Gly Leu Leu Pro Lys Ser Pro Thr
            340                 345                 350

Ser Thr Ala Ser Arg Thr Asn Gly Gly Leu Ile Trp Val Ser Glu Trp
        355                 360                 365

Asn Ser Met Gln Gln Ser Val Ser Ser Ala Phe Leu Ala Ser Leu Phe
    370                 375                 380

Ser Asp Tyr Met Leu Thr Ser Arg Ile His Lys Ile Ser Cys Asp Gly
385                 390                 395                 400

Lys Ile Phe Lys Ala Thr Glu Leu Arg Asp Phe Ala Lys Ser Gln Ala
                405                 410                 415

Asp Tyr Met Leu Gly Lys Asn Pro Leu Gly Thr Ser Phe Val Val Gly
            420                 425                 430

Tyr Gly Asp Lys Tyr Pro Gln Phe Val His His Arg Gly Ala Ser Ile
        435                 440                 445

Pro Ala Asp Ala Thr Thr Gly Cys Leu Asp Gly Phe Lys Trp Phe Asn
    450                 455                 460

Ser Thr Lys Pro Asn Pro Asn Ile Ala Tyr Gly Ala Leu Val Gly Gly
465                 470                 475                 480

Pro Phe Phe Asn Glu Thr Phe Thr Asp Ser Arg Glu Asn Pro Met Gln
                485                 490                 495

Asn Glu Pro Thr Thr Tyr Asn Asn Ala Leu Leu Val Gly Leu Leu Ser
            500                 505                 510

Ser Leu Val Thr Thr Ser Ser Thr Leu Gln Ser Leu Lys
        515                 520                 525

<210> SEQ ID NO 79
<211> LENGTH: 677
<212> TYPE: DNA
<213> ORGANISM: Arabidopsis thaliana

<400> SEQUENCE: 79
gcttaagcga ttctctgcaa agcttcatac caaacaaaga gaagtcgaaa tgccagtttc     60
agctccatct ccgcctcgtc ttcattctcc gttcattcac tgtcccatca atttcactcc    120
ttcttctttc tcggcgagga atctccggtc gccgtcaaca tcttatcccc gaatcaaagc    180
tgaactcgat cccaacacgg tagtcgcgat atctgtaggc gtagcaagcg tcgcattagg    240
```

```
aatcggaatc cctgtgttct acgagactca aatcgacaat gcggctaagc gagagaatac    300
tcaaccttgt tttccctgta atggcaccgg agctcagaaa tgcagattgt gtgtgggaag    360
tggtaatgtg accgtagagc ttggtggagg agagaaagaa gtctcaaact gtatcaactg    420
tgatggtgct ggttccttaa cttgcactac ttgtcaaggc tctggtgttc aacctcgata    480
ccttgatcga agggagttca aggacgatga ctaaatacct tgctctaagg aacatttctt    540
ttcttctccc ttctcacatt tcttcattgt acaatgctgt tttgttcacc aaacatgttg    600
agagaacatc atgacatgga tattgtaatt gtgaaagaaa accaccagag ttcaatcaaa    660
tgtttcttct tgtactt                                                    677
```

<210> SEQ ID NO 80
<211> LENGTH: 154
<212> TYPE: PRT
<213> ORGANISM: Arabidopsis thaliana

<400> SEQUENCE: 80

```
Met Pro Val Ser Ala Pro Ser Pro Pro Arg Leu His Ser Pro Phe Ile
1               5                   10                  15

His Cys Pro Ile Asn Phe Thr Pro Ser Ser Phe Ser Ala Arg Asn Leu
            20                  25                  30

Arg Ser Pro Ser Thr Ser Tyr Pro Arg Ile Lys Ala Glu Leu Asp Pro
        35                  40                  45

Asn Thr Val Val Ala Ile Ser Val Gly Val Ala Ser Val Ala Leu Gly
    50                  55                  60

Ile Gly Ile Pro Val Phe Tyr Glu Thr Gln Ile Asp Asn Ala Ala Lys
65                  70                  75                  80

Arg Glu Asn Thr Gln Pro Cys Phe Pro Cys Asn Gly Thr Gly Ala Gln
                85                  90                  95

Lys Cys Arg Leu Cys Val Gly Ser Gly Asn Val Thr Val Glu Leu Gly
            100                 105                 110

Gly Gly Glu Lys Glu Val Ser Asn Cys Ile Asn Cys Asp Gly Ala Gly
        115                 120                 125

Ser Leu Thr Cys Thr Thr Cys Gln Gly Ser Gly Val Gln Pro Arg Tyr
    130                 135                 140

Leu Asp Arg Arg Glu Phe Lys Asp Asp Asp
145                 150
```

<210> SEQ ID NO 81
<211> LENGTH: 501
<212> TYPE: DNA
<213> ORGANISM: Arabidopsis thaliana

<400> SEQUENCE: 81

```
atggtgtttg gatatgcata tcctgcttat gagtgcttca aaacggtcga actcaacaag     60
cctgaaattc aacaacttca gttctggtgc cagtattgga ttattgtagc tgctttgacg    120
attttcgaaa gaattggtga tgctcttgtt cttggttac caatgtatag cgaggcgaag    180
ttggctttct tcatttatct ctggtttcca agactaaag gaacaacata cgtttacgat    240
tctttcttca ggccatatat agcaaagcat gaaaatgaaa ttgaccgcaa cttggtgaag    300
gtaaagacta gagctaagga tatggcaatg atatatctcc aaaaagcaat caaccaaggg    360
cagaccaaat tctttgagat cttacagtat atcacagaac aatcaacacc aaaatctaag    420
gctgaggaaa agaaagagac aacaataacct aaactcgatg atccaattct taaggtgaaa    480
gaaaacgaag tcactaaatg a                                              501
```

<210> SEQ ID NO 82
<211> LENGTH: 166
<212> TYPE: PRT
<213> ORGANISM: Arabidopsis thaliana

<400> SEQUENCE: 82

Met Val Phe Gly Tyr Ala Tyr Pro Ala Tyr Glu Cys Phe Lys Thr Val
1               5                   10                  15

Glu Leu Asn Lys Pro Glu Ile Gln Gln Leu Gln Phe Trp Cys Gln Tyr
            20                  25                  30

Trp Ile Ile Val Ala Ala Leu Thr Ile Phe Glu Arg Ile Gly Asp Ala
        35                  40                  45

Leu Val Ser Trp Leu Pro Met Tyr Ser Glu Ala Lys Leu Ala Phe Phe
    50                  55                  60

Ile Tyr Leu Trp Phe Pro Lys Thr Lys Gly Thr Thr Tyr Val Tyr Asp
65                  70                  75                  80

Ser Phe Phe Arg Pro Tyr Ile Ala Lys His Glu Asn Glu Ile Asp Arg
                85                  90                  95

Asn Leu Val Lys Val Lys Thr Arg Ala Lys Asp Met Ala Met Ile Tyr
            100                 105                 110

Leu Gln Lys Ala Ile Asn Gln Gly Gln Thr Lys Phe Phe Glu Ile Leu
        115                 120                 125

Gln Tyr Ile Thr Glu Gln Ser Thr Pro Lys Ser Lys Ala Glu Glu Lys
    130                 135                 140

Lys Glu Thr Thr Ile Pro Lys Leu Asp Asp Pro Ile Leu Lys Val Lys
145                 150                 155                 160

Glu Asn Glu Val Thr Lys
                165

<210> SEQ ID NO 83
<211> LENGTH: 798
<212> TYPE: DNA
<213> ORGANISM: Arabidopsis thaliana

<400> SEQUENCE: 83
atgtcttctc cactcgccgc aaaatcaaac ctaaccacga ctcgatcggc ttcgttaaac      60
attccacatt cgacacgtac caatcacaac cacgatctcc ggtatagtct ttccgctggt     120
cctcgtacga acgaagatcg accagcttct gggaacggcg tcgccggaat cctctataaa     180
tgggtaaact acggccaagg atggaaacga cggtggttcg tactccagga cggtgttttg     240
tcgtattata gaatccatgg tcccgataaa atatctctct ccgttgagat ggatcggaga     300
tctaaactga tcgcggcga atctttacgg tttatttgcc gacatagcaa acgcggtgat      360
gttcatagcc ccgggaaacc tctcggccaa attcacctca aggtttcatc gattggacaa     420
agcatatcag atgcaagag attcactgta ttcacgggca cgaagagtct gcatttacga      480
gcagcaacga gcgaggatcg tgcctcttgg atcgaagcat tgaaagctgt taagaaaacg     540
tttccaagaa tgtcaaacga agaactaatg gcatcgacga ctaatgtctc agtctcgacc     600
gataagctaa ggcagagatt aatggaagaa gaggtagatg agacaatcat caaagattgc     660
gaagacataa tgaagaacaa tttcttagca ttgcatgatg aggttatgtc tctaaaacgg     720
taccaatatc atcttataga ttctctcaag aacgtcagta actcacctat aagacccagt     780
aaccaaagtt tttcatga                                                   798

<210> SEQ ID NO 84
<211> LENGTH: 265
<212> TYPE: PRT
<213> ORGANISM: Arabidopsis thaliana

<400> SEQUENCE: 84

Met Ser Ser Pro Leu Ala Ala Lys Ser Asn Leu Thr Thr Thr Arg Ser
1               5                   10                  15

Ala Ser Leu Asn Ile Pro His Ser Thr Arg Thr Asn His Asn His Asp
            20                  25                  30

Leu Arg Tyr Ser Leu Ser Ala Gly Pro Arg Thr Asn Glu Asp Arg Pro
        35                  40                  45

Ala Ser Gly Asn Gly Val Ala Gly Ile Leu Tyr Lys Trp Val Asn Tyr
    50                  55                  60

Gly Gln Gly Trp Lys Arg Arg Trp Phe Val Leu Gln Asp Gly Val Leu
65                  70                  75                  80

Ser Tyr Tyr Arg Ile His Gly Pro Asp Lys Ile Ser Leu Ser Val Glu
                85                  90                  95

Met Asp Arg Arg Ser Lys Leu Ile Gly Gly Glu Ser Leu Arg Phe Ile
            100                 105                 110

Cys Arg His Ser Lys Arg Gly Asp Val His Ser Pro Gly Lys Pro Leu
        115                 120                 125

Gly Gln Ile His Leu Lys Val Ser Ser Ile Gly Gln Ser Ile Ser Asp
    130                 135                 140

Gly Lys Arg Phe Thr Val Phe Thr Gly Thr Lys Ser Leu His Leu Arg
145                 150                 155                 160

Ala Ala Thr Ser Glu Asp Arg Ala Ser Trp Ile Glu Ala Leu Lys Ala
                165                 170                 175

Val Lys Glu Thr Phe Pro Arg Met Ser Asn Glu Glu Leu Met Ala Ser
            180                 185                 190

Thr Thr Asn Val Ser Val Ser Thr Asp Lys Leu Arg Gln Arg Leu Met
        195                 200                 205

Glu Glu Glu Val Asp Glu Thr Ile Ile Lys Asp Cys Glu Asp Ile Met
    210                 215                 220

Lys Asn Asn Phe Leu Ala Leu His Asp Glu Val Met Ser Leu Lys Arg
225                 230                 235                 240

Tyr Gln Tyr His Leu Ile Asp Ser Leu Lys Asn Val Ser Asn Ser Pro
                245                 250                 255

Ile Arg Pro Ser Asn Gln Ser Phe Ser
            260                 265

<210> SEQ ID NO 85
<211> LENGTH: 2339
<212> TYPE: DNA
<213> ORGANISM: Arabidopsis thaliana

<400> SEQUENCE: 85
accctaatcc gtaatcgaat gccatttcga agattgtaag aagactaaga agctagggtt      60
tctctgatga gtagatgatg cgtgaaccgc ttgttagcga agaagaagaa gaagaagcta     120
ctgaagtttt actagtggag aagacgaagt tgtgtaagag acgaggagac gaagaaaaaa     180
cggaagagag aagagacgat tgttgttgtt tagcttttaac gccgatggta cgatcgaaat     240
ctcaaggaac tactcggcgc gtcactccca cgccacctcc tgttgacgtg gagaaaccgt     300
taccaaacgg agatctctac atgggaacgt tttccggcgg gtttcccaac ggatccggta     360
agtatttgtg gaaggatggg tgtatgtacg aaggcgagtg gaaacgtggt aaagcgagtg     420

-continued

```
gtaaaggcaa gttttcgtgg ccgagtggtg cgacttatga aggagagttc aaatctggga    480
gaatggaagg atctgggact tttgttggtg ttgatggtga tacttatcgt ggctcttggg    540
ttgctgatcg gaaacaaggt catggtcaga agagatatgc caacggagat tactatgaag    600
gtacatggcg gcggaatctt caggatggga gagggagata tgtttggatg aatgggaatc    660
agtatacagg agagtggaga atggtgtgta tatgtggtaa aggtgtgctt gcttggccta    720
atgggaatag atatgaaggt caatgggaaa atggtgttcc taaaggaagt ggtgtgttta    780
cttgggctga tggaagttcg tggattggtt cttggaatga gagtagtaat ctcatgagga    840
atttctttga tgggattgag aagaatgagt tgattgttgc gactaggaag agatcttcgg    900
ttgatagtgg cgctggaagt ttgactgggg agaagatttt ccctaggata tgtatttggg    960
agtctgatgg agaagctggg gatattactt gtgatattgt tgataatgtg gaagcttctg   1020
tgatatacag agataggatt ctattgata aagatgggtt tcgtcagttt aggaagaatc   1080
cttgttgttt cagcggtgag gctaagaaac ctggagagac gatatctaaa gggcataaga   1140
aatatgattt gatgctcaac ctgcagcatg gaattaggta ctctgtcggc aaacacgctt   1200
ccgttgttcg agatctcaaa cagagtgatt ttgacccaag tgaaaagttc tggacaaggt   1260
tcccaccgga gggttctaag accacaccac cgcatctatc tgtggatttc cgctggaagg   1320
actattgccc tttggtgttt agacggctta gggagctatt cacggtggat cctgccgatt   1380
acatgctagc tatctgtgga aacgatgccc ttagggaatt gtcttcgcct ggaaagagtg   1440
gaagcttttt ttacttaact caagatgaca gatttatgat caagacggtg aagaaatctg   1500
aagtcaaggt gcttctacga atgcttccaa gttactacaa acacgtctgc cagtatgaaa   1560
atacacttgt gactaggttc tatggtgtgc attgtatcaa acctgttggt ggccagaaga   1620
ctcggtttat cgttatgggg aacttgttct gctccgaata tagaatccag agaaggtttg   1680
accttaaagg gtcttcccat ggacggtata cctccaaacc tgaaggggaa attgatgaga   1740
ccactactct taaggacctt gatctcaatt ttgctttccg tcttcagaga aattggtacc   1800
aagagcttat gacgcaaatt aaacgcgact gtgagttctt ggaagctgaa agaataatgg   1860
attatagtct tttggttggc gttcacttcc gtgatgacaa cacaggagac aaaatggggt   1920
tatctccatt tgtattgaga tctggtaaga tagagtcata ccaaagcgaa aaatttatgc   1980
gtggttgtcg gttcttggag gcggaacttc aagcatggga ccgcatttta gctggcagga   2040
aaccattgat tcgattaggc gcaaacatgc ctgcaagagc agaacgaatg gcgagaagaa   2100
gcgactatga tcagtattcc tcaggaggga ccaactacca atctcatgga gaggtctacg   2160
aagtggttct atattttgga atcattgaca ttttacaaga ttacgacata agcaagaaga   2220
tcgagcatgc ttacaagtct ctacaagctg acccggcttc aatctctgcc gttgatccca   2280
aactatactc aagaaggttt agagatttca tcagcagaat cttcatcgaa gacggctaa    2339
```

<210> SEQ ID NO 86
<211> LENGTH: 754
<212> TYPE: PRT
<213> ORGANISM: Arabidopsis thaliana

<400> SEQUENCE: 86

Met Met Arg Glu Pro Leu Val Ser Glu Glu Glu Glu Glu Ala Thr
1               5                   10                  15

Glu Val Leu Leu Val Glu Lys Thr Lys Leu Cys Lys Arg Arg Gly Asp
            20                  25                  30

-continued

Glu Glu Lys Thr Glu Glu Arg Arg Asp Asp Leu Leu Leu Leu Ala Leu
            35                  40                  45

Thr Pro Met Val Arg Ser Lys Ser Gln Gly Thr Thr Arg Arg Val Thr
 50                  55                  60

Pro Thr Pro Pro Val Asp Val Glu Lys Pro Leu Pro Asn Gly Asp
 65                  70                  75                  80

Leu Tyr Met Gly Thr Phe Ser Gly Gly Phe Pro Asn Gly Ser Gly Lys
                    85                  90                  95

Tyr Leu Trp Lys Asp Gly Cys Met Tyr Glu Gly Glu Trp Lys Arg Gly
                100                 105                 110

Lys Ala Ser Gly Lys Gly Lys Phe Ser Trp Pro Ser Gly Ala Thr Tyr
                115                 120                 125

Glu Gly Glu Phe Lys Ser Gly Arg Met Glu Gly Ser Gly Thr Phe Val
            130                 135                 140

Gly Val Asp Gly Asp Thr Tyr Arg Gly Ser Trp Val Ala Asp Arg Lys
145                 150                 155                 160

Gln Gly His Gly Gln Lys Arg Tyr Ala Asn Gly Asp Tyr Tyr Glu Gly
                165                 170                 175

Thr Trp Arg Arg Asn Leu Gln Asp Gly Arg Gly Arg Tyr Val Trp Met
            180                 185                 190

Asn Gly Asn Gln Tyr Thr Gly Glu Trp Arg Asn Gly Val Ile Cys Gly
                195                 200                 205

Lys Gly Val Leu Ala Trp Pro Asn Gly Asn Arg Tyr Glu Gly Gln Trp
            210                 215                 220

Glu Asn Gly Val Pro Lys Gly Ser Gly Val Phe Thr Trp Ala Asp Gly
225                 230                 235                 240

Ser Ser Trp Ile Gly Ser Trp Asn Glu Ser Ser Asn Leu Met Arg Asn
                245                 250                 255

Phe Phe Asp Gly Ile Glu Lys Asn Glu Leu Ile Val Ala Thr Arg Lys
                260                 265                 270

Arg Ser Ser Val Asp Ser Gly Ala Gly Ser Leu Thr Gly Glu Lys Ile
            275                 280                 285

Phe Pro Arg Ile Cys Ile Trp Glu Ser Asp Gly Glu Ala Gly Asp Ile
            290                 295                 300

Thr Cys Asp Ile Val Asp Asn Val Glu Ala Ser Val Ile Tyr Arg Asp
305                 310                 315                 320

Arg Ile Ser Ile Asp Lys Asp Gly Phe Arg Gln Phe Arg Lys Asn Pro
                325                 330                 335

Cys Cys Phe Ser Gly Glu Ala Lys Lys Pro Gly Glu Thr Ile Ser Lys
            340                 345                 350

Gly His Lys Lys Tyr Asp Leu Met Leu Asn Leu Gln His Gly Ile Arg
            355                 360                 365

Tyr Ser Val Gly Lys His Ala Ser Val Val Arg Asp Leu Lys Gln Ser
            370                 375                 380

Asp Phe Asp Pro Ser Glu Lys Phe Trp Thr Arg Phe Pro Pro Glu Gly
385                 390                 395                 400

Ser Lys Thr Thr Pro Pro His Leu Ser Val Asp Phe Arg Trp Lys Asp
                405                 410                 415

Tyr Cys Pro Leu Val Phe Arg Arg Leu Arg Glu Leu Phe Thr Val Asp
            420                 425                 430

Pro Ala Asp Tyr Met Leu Ala Ile Cys Gly Asn Asp Ala Leu Arg Glu
            435                 440                 445

Leu Ser Ser Pro Gly Lys Ser Gly Ser Phe Phe Tyr Leu Thr Gln Asp

|  | 450 | | | | 455 | | | | 460 | | |
|---|---|---|---|---|---|---|---|---|---|---|---|

Asp Arg Phe Met Ile Lys Thr Val Lys Ser Glu Val Lys Val Leu
465      470     475     480

Leu Arg Met Leu Pro Ser Tyr Tyr Lys His Val Cys Gln Tyr Glu Asn
      485     490     495

Thr Leu Val Thr Arg Phe Tyr Val His Cys Ile Lys Pro Val Gly
    500     505     510

Gly Gln Lys Thr Arg Phe Ile Val Met Gly Asn Leu Phe Cys Ser Glu
   515     520     525

Tyr Arg Ile Gln Arg Arg Phe Asp Leu Lys Gly Ser Ser His Gly Arg
530      535     540

Tyr Thr Ser Lys Pro Glu Gly Glu Ile Asp Glu Thr Thr Thr Leu Lys
545      550     555     560

Asp Leu Asp Leu Asn Phe Ala Phe Arg Leu Gln Arg Asn Trp Tyr Gln
     565     570     575

Glu Leu Met Thr Gln Ile Lys Arg Asp Cys Glu Phe Leu Glu Ala Glu
    580     585     590

Arg Ile Met Asp Tyr Ser Leu Leu Val Gly Val His Phe Arg Asp Asp
595      600     605

Asn Thr Gly Asp Lys Met Gly Leu Ser Pro Phe Val Leu Arg Ser Gly
610      615     620

Lys Ile Glu Ser Tyr Gln Ser Glu Lys Phe Met Arg Gly Cys Arg Phe
625      630     635     640

Leu Glu Ala Glu Leu Gln Asp Met Asp Arg Ile Leu Ala Gly Arg Lys
    645     650     655

Pro Leu Ile Arg Leu Gly Ala Asn Met Pro Ala Arg Ala Glu Arg Met
   660     665     670

Ala Arg Arg Ser Asp Tyr Asp Gln Tyr Ser Ser Gly Gly Thr Asn Tyr
   675     680     685

Gln Ser His Gly Glu Val Tyr Glu Val Val Leu Tyr Phe Gly Ile Ile
   690     695     700

Asp Ile Leu Gln Asp Tyr Asp Ile Ser Lys Lys Ile Glu His Ala Tyr
705      710     715     720

Lys Ser Leu Gln Ala Asp Pro Ala Ser Ile Ser Ala Val Asp Pro Lys
    725     730     735

Leu Tyr Ser Arg Arg Phe Arg Asp Phe Ile Ser Arg Ile Phe Ile Glu
   740     745     750

Asp Gly

<210> SEQ ID NO 87
<211> LENGTH: 1318
<212> TYPE: DNA
<213> ORGANISM: Arabidopsis thaliana

<400> SEQUENCE: 87

```
aaactctctc tacacagctc ataacagaaa gaagaaacac aaagtgagac agaactctct      60
aattagtccc gaaggtttca aagggtatt ttggtaaaat cgaaagagaa tcatggacgc     120
ttttgatgcg attccagatc ctgtggtcat cgacattttg aacagagtcg gtgacgtcaa     180
aacgttaata cgatgtcgtt ccgtttctaa acgattcaac tcgttagcca ctcagtctga     240
gtcgctcctt ctccaactcg atcagatcct cggagccacc gaatctgact ccgagatcga     300
ttctcctatc gctagcttct tccgatctct cttcaaatcc attcacggtc tccttcctcc     360
tatcttctcc aaaccagcta actctgacga aatcctaacc cgatctccga aaactccggc     420
```

```
tcagattctc tccggatttg aacggatccg aatctggag gtggaattat acggtggtga    480
tgtcaagctt gagaaaggcg ccgccgttaa gtggaaggct gagttcggga aaactctcaa    540
gagctgcgtc atcgtcgctt tccgttccgc gacggttaat acttcagcag ctacggaagc    600
tgccgccgtc gtcgacggtg ttgttgagtc agattcggag tttgtttgtg gattgaagac    660
gcgcgtggtg tggacgatca gcgcgttgat ggcggcttcc acgcgtcatt acttgatgag    720
agatttggtg aaagatcaca aggagatgga gaaattgatt gtgcgtgaca gtgatggtga    780
aggtacggtg gtgatggacg cggcgggat gaaagaatac agagagacgg aggtgcgtgg    840
ggataataaa gaatcagagc gcgtggggga acgaactgtg gtacctagcg tgaggatgag    900
tatgagacac gcgccgtcgc tgatgctgaa gagcgggatt tgtctcgaag cagcgacgct    960
ggtggtcgta aggccgactg tgtggcttc cgatgataac gatgttgagc tggtgacgga   1020
ggcgttcgcc ggagatggcg acgattgtat gtacggagaa gctgttacgg cgttgcttaa   1080
gcgtaggaga aatgtgttag agatgaattc tttctaaggc ctagtgggct ttttttgggc   1140
ttccgtttgt ttggccctt ttaatgtata tacatacgca tcgtacaaag ccaactgtac   1200
tattggcgta cgacttttgg gtcaaatgac atcaaatccg aattattcct ctaatatcat   1260
atgattacca cattaaatgc gttgcagcat ctaatattat acatagatat gattcgaa     1318
```

<210> SEQ ID NO 88
<211> LENGTH: 334
<212> TYPE: PRT
<213> ORGANISM: Arabidopsis thaliana

<400> SEQUENCE: 88

```
Met Asp Ala Phe Asp Ala Ile Pro Asp Pro Val Ile Asp Ile Leu
1               5                   10                  15

Asn Arg Val Gly Asp Val Lys Thr Leu Ile Arg Cys Arg Ser Val Ser
                20                  25                  30

Lys Arg Phe Asn Ser Leu Ala Thr Gln Ser Glu Ser Leu Leu Leu Gln
            35                  40                  45

Leu Asp Gln Ile Leu Gly Ala Thr Glu Ser Asp Ser Glu Ile Asp Ser
    50                  55                  60

Pro Ile Ala Ser Phe Phe Arg Ser Leu Phe Lys Ser Ile His Gly Leu
65                  70                  75                  80

Leu Pro Pro Ile Phe Ser Lys Pro Ala Asn Ser Asp Glu Ile Leu Thr
                85                  90                  95

Arg Ser Pro Lys Thr Pro Ala Gln Ile Leu Ser Gly Phe Glu Arg Ile
            100                 105                 110

Arg Asn Leu Glu Val Glu Leu Tyr Gly Gly Asp Val Lys Leu Glu Lys
        115                 120                 125

Gly Ala Ala Val Lys Trp Lys Ala Glu Phe Gly Lys Thr Leu Lys Ser
    130                 135                 140

Cys Val Ile Val Ala Phe Arg Ser Ala Thr Val Asn Thr Ser Ala Ala
145                 150                 155                 160

Thr Glu Ala Ala Ala Val Val Asp Gly Val Val Glu Ser Asp Ser Glu
                165                 170                 175

Phe Val Cys Gly Leu Lys Thr Arg Val Val Trp Thr Ile Ser Ala Leu
            180                 185                 190

Met Ala Ala Ser Thr Arg His Tyr Leu Met Arg Asp Leu Val Lys Asp
        195                 200                 205

His Lys Glu Met Glu Lys Leu Ile Val Arg Asp Ser Asp Gly Glu Gly
```

Thr Val Val Met Asp Ala Ala Gly Met Lys Glu Tyr Arg Glu Thr Glu
225                 230                 235                 240

Val Arg Gly Asp Asn Lys Glu Ser Glu Arg Val Gly Glu Arg Thr Val
            245                 250                 255

Val Pro Ser Val Arg Met Ser Met Arg His Ala Pro Ser Leu Met Leu
                260                 265                 270

Lys Ser Gly Ile Cys Leu Glu Ala Ala Thr Leu Val Val Val Arg Pro
            275                 280                 285

Thr Gly Val Ala Ser Asp Asp Asn Asp Val Glu Leu Val Thr Glu Ala
            290                 295                 300

Phe Ala Gly Asp Gly Asp Asp Cys Met Tyr Gly Glu Ala Val Thr Ala
305                 310                 315                 320

Leu Leu Lys Arg Arg Arg Asn Val Leu Glu Met Asn Ser Phe
                325                 330

<210> SEQ ID NO 89
<211> LENGTH: 1350
<212> TYPE: DNA
<213> ORGANISM: Arabidopsis thaliana

<400> SEQUENCE: 89

```
aaaccaaaca ccaagaaaac aaaagcagac ttaaaagaag ctatgatcaa aggaaacaat      60
ggaaacagag gatcttcttc ttctggttac tctgcagatt tgttggtttg tttcccttca     120
agaacccact tagctctgac tcctaagccc atttgtagcc catctcgtcc ctcagactct     180
tccactaacc gtcgtcctca ccaccgtcgc cagctcagta aactctccgg cggcggtgga     240
ggaggacacg gtagtcctgt tttgtgggct aaacaagcaa gtagtaagaa tatgggaggt     300
gacgaaatag cagaaccaac ttctcctaaa gtaacttgcg caggtcagat caaagtccgg     360
ccaagtaaat gcggagggag aggaaagaac tggcaatcgg tgatggaaga gattgagagg     420
atacatgata atagatcgca aagcaagttt tttggttga agaaagatgt gatgggtttc     480
ttgacttgtc ttagaaacat caaattcgat ttcaggtgtt ttggtgattt ccgacatgct     540
gatgtcacta gcgacgacga tgaggaagaa gatgatgatg atgatgagga agaagaggta     600
gtggaaggag aagaagaaga gaattcaaag actgttttct ctaaatggtt tatggtttta     660
caagaggaac agaacaacaa agatgacgac aagaacaaca acaagtgtga tgagaaacgc     720
gatcttgaag acacagagac agaaccagcg gttccgccgc caaacgcgct tttgttgatg     780
cggtgtagat cagctccagc gaagagttgg ttagaagaga gaatgaaagt aaaaacagag     840
caagaaaaga gagaagaaca aaaagaggaa aaagaaacag aggatcaaga acgagtatg     900
aagacaaaga agaaggattt gagatcatta atggaagaag agaagatgga attggtgttg    960
atgagatacg atactgagtt ttacagactc tcttcagaca tagctaagga aacttgggtt   1020
gtcggaggaa ttcaagatcc tctgtctcgg agtcgaagct ggaaaaattg attacacaga   1080
ttcatcgtta ctcatcagta aacatcgtat tttaaaaacc taatcaagcg ttttactat   1140
aatttgatta tctgttaatt aatttttgata cttacatttt tttttttttg ggtttcttga   1200
gttttttta atggttcttc tccctttttgt ttcgtatctc aaaggttttt ttttgtttac   1260
cttctttgtt ttgtgttttt catcacaacg tttgtaatgt aatgcaaaat atgtacaggc   1320
tttttacgtt ttacgcaaat ctgcttaata                                     1350
```

<210> SEQ ID NO 90

<211> LENGTH: 342
<212> TYPE: PRT
<213> ORGANISM: Arabidopsis thaliana

<400> SEQUENCE: 90

Met Ile Lys Gly Asn Asn Gly Asn Arg Gly Ser Ser Ser Gly Tyr
1               5                   10                  15

Ser Ala Asp Leu Leu Val Cys Phe Pro Ser Arg Thr His Leu Ala Leu
            20                  25                  30

Thr Pro Lys Pro Ile Cys Ser Pro Ser Arg Pro Ser Asp Ser Ser Thr
            35                  40                  45

Asn Arg Arg Pro His His Arg Arg Gln Leu Ser Lys Leu Ser Gly Gly
        50                  55                  60

Gly Gly Gly Gly His Gly Ser Pro Val Leu Trp Ala Lys Gln Ala Ser
65                  70                  75                  80

Ser Lys Asn Met Gly Gly Asp Glu Ile Ala Glu Pro Thr Ser Pro Lys
            85                  90                  95

Val Thr Cys Ala Gly Gln Ile Val Arg Pro Ser Lys Cys Gly Gly
            100                 105                 110

Arg Gly Lys Asn Trp Gln Ser Val Met Glu Glu Ile Glu Arg Ile His
        115                 120                 125

Asp Asn Arg Ser Gln Ser Lys Phe Phe Gly Leu Lys Lys Asp Val Met
130                 135                 140

Gly Phe Leu Thr Cys Leu Arg Asn Ile Lys Phe Asp Phe Arg Cys Phe
145                 150                 155                 160

Gly Asp Phe Arg His Ala Asp Val Thr Ser Asp Asp Glu Glu Glu
            165                 170                 175

Asp Asp Asp Asp Glu Glu Glu Val Val Glu Gly Glu Glu
            180                 185                 190

Glu Asn Ser Lys Thr Val Phe Ser Lys Trp Phe Met Val Leu Gln Glu
        195                 200                 205

Glu Gln Asn Asn Lys Asp Asp Lys Asn Asn Lys Cys Asp Glu
210                 215                 220

Lys Arg Asp Leu Glu Asp Thr Glu Thr Glu Pro Ala Val Pro Pro Pro
225                 230                 235                 240

Asn Ala Leu Leu Leu Met Arg Cys Arg Ser Ala Pro Ala Lys Ser Trp
            245                 250                 255

Leu Glu Glu Arg Met Lys Val Lys Thr Glu Gln Glu Lys Arg Glu Glu
            260                 265                 270

Gln Lys Glu Glu Lys Glu Thr Glu Asp Gln Glu Thr Ser Met Lys Thr
        275                 280                 285

Lys Lys Lys Asp Leu Arg Ser Leu Met Glu Glu Lys Met Glu Leu
290                 295                 300

Val Leu Met Arg Tyr Asp Thr Glu Phe Tyr Arg Leu Ser Ser Asp Ile
305                 310                 315                 320

Ala Lys Glu Thr Trp Val Val Gly Gly Ile Gln Asp Pro Leu Ser Arg
            325                 330                 335

Ser Arg Ser Trp Lys Asn
            340

<210> SEQ ID NO 91
<211> LENGTH: 1593
<212> TYPE: DNA
<213> ORGANISM: Arabidopsis thaliana

<400> SEQUENCE: 91

```
atggcaaaat cgaagaaaat ttctacaggt caaatatttg gttgtgagag tctccttggg    60
tgcattttcc agagctggag ccctcgccgt cgaaaaccct ctttaccgga aaaggatcat   120
cgggcaaaag ataacttgtc ttccaagtca tcaacaaccg ttacaaaccc taaaatcctc   180
ccaagaaaat ccaccgatac ttcttctcaa ccaaagaaat ctgactccca gaaccccaa    240
caaaagccaa aaccagatga gaatcacccg cgaaaatcat cggaatccgc cagaaaatca   300
tctgattccg caagaaaatc gatttcgtca ggctcatcaa gaacagagag caagagattc   360
tcacttaacg gcgttatggg aaacatcatc gtgaaaccac agccagccgt taaaactgac   420
gtgacacaga cgaaaagtcg gtgggagggt aaaccggtaa atcacagact cgatccagag   480
actctgaaga aaatgggaaa cgaagagtat tgtcgtggga ggtttggaca agctctcgtg   540
tttracgaga gagccattc agctgacccc aaaacgccga cgtattggtc taacaaatcc    600
gccgctttga tcagtctcgg tcgtcttctt gaagcttctg atgcttgtga gaagcttta    660
agactaaacc caacttacga gagagctcat cagagactag cttccctcca actcagattg   720
ggtgaggttg agaaagcttt gtgtcactat aatgaagctg aaaatatac agagacaaaa    780
catattgaac aagttgaaga tgttgttaaa tgcttaagga ggtgtgacga agctcgaaga   840
tcaaaggaat ggaatgttgc attgaaagag actcttttttg cgatatcata tggagcagat   900
tcttctcctc gggtctatgc actccaaacc gaggctttat tgcatcttca gcgacacgag   960
gaagcataca gcgtgtatca gaaaggaaca aaacgcttcg acatcgatag tttcataaag  1020
attttggtc tttccctcac ttcttacctc ttgatggtcg gagctcaggt ctacatagca   1080
gtaggaaggt ttgaagatgc agtaacggcg tcaaggcaag cggctcgact tgatccaagc   1140
agcgaagaag taaacgcggt ggctagaaaa gcgagagcgg ttgcttctgc aagactgagt  1200
ggaaatttgc ttttcaacgc atcaaaattt gaagggggcta gcgtggttta cacggaagga  1260
cttgagaacg atccatataa tgctctcttg ctctgtaaca gagctgcttc aagattcaag  1320
cttgatctgt tcgagaaagc tattgaagat tgcacattgg ctctcagtct ccagccatcg  1380
taccggaagg cgaggcggcg cagggcagat tcttatgcca agttggagaa atggcaacac  1440
gcgattcaag attatgagtt gttgatgatg agacacctg aagacgaaga gactagaaga   1500
gccttaactg aggtgaatgt ccggtttaag aaacagaccg gtggagatgt ccggtttaaa  1560
ggagtcggct cggaattggt tgtggctaat tga                               1593
```

<210> SEQ ID NO 92
<211> LENGTH: 530
<212> TYPE: PRT
<213> ORGANISM: Arabidopsis thaliana

<400> SEQUENCE: 92

Met Ala Lys Ser Lys Lys Ile Ser Thr Gly Gln Ile Phe Gly Cys Glu
1               5                   10                  15

Ser Leu Leu Gly Cys Ile Phe Gln Ser Trp Ser Pro Arg Arg Arg Lys
            20                  25                  30

Pro Ser Leu Pro Glu Lys Asp His Arg Ala Lys Asp Asn Leu Ser Ser
        35                  40                  45

Lys Ser Ser Thr Thr Val Thr Asn Pro Lys Ile Leu Pro Arg Lys Ser
    50                  55                  60

Thr Asp Thr Ser Ser Gln Pro Lys Lys Ser Asp Ser Gln Lys Pro Gln
65                  70                  75                  80

Gln Lys Pro Lys Pro Asp Glu Asn His Pro Arg Lys Ser Ser Glu Ser

```
                   85                  90                  95
Ala Arg Lys Ser Ser Asp Ser Ala Arg Lys Ser Ile Ser Ser Gly Ser
                100                 105                 110

Ser Arg Thr Glu Ser Lys Arg Phe Ser Leu Asn Gly Val Met Gly Asn
                115                 120                 125

Ile Ile Val Lys Pro Gln Pro Ala Val Lys Thr Asp Val Thr Gln Thr
130                 135                 140

Lys Ser Arg Trp Glu Gly Lys Pro Val Asn His Arg Leu Asp Pro Glu
145                 150                 155                 160

Thr Leu Lys Lys Met Gly Asn Glu Glu Tyr Cys Arg Gly Arg Phe Gly
                165                 170                 175

Gln Ala Leu Val Phe Tyr Glu Arg Ala Ile Ser Ala Asp Pro Lys Thr
                180                 185                 190

Pro Thr Tyr Trp Ser Asn Lys Ser Ala Ala Leu Ile Ser Leu Gly Arg
                195                 200                 205

Leu Leu Glu Ala Ser Asp Ala Cys Glu Glu Ala Leu Arg Leu Asn Pro
                210                 215                 220

Thr Tyr Glu Arg Ala His Gln Arg Leu Ala Ser Leu Gln Leu Arg Leu
225                 230                 235                 240

Gly Glu Val Glu Lys Ala Leu Cys His Tyr Asn Glu Ala Gly Lys Tyr
                245                 250                 255

Thr Glu Thr Lys His Ile Glu Gln Val Glu Asp Val Val Lys Cys Leu
                260                 265                 270

Arg Arg Cys Asp Glu Ala Arg Arg Ser Lys Glu Trp Asn Val Ala Leu
                275                 280                 285

Lys Glu Thr Leu Phe Ala Ile Ser Tyr Gly Ala Asp Ser Ser Pro Arg
                290                 295                 300

Val Tyr Ala Leu Gln Thr Glu Ala Leu Leu His Leu Gln Arg His Glu
305                 310                 315                 320

Glu Ala Tyr Ser Val Tyr Gln Lys Gly Thr Lys Arg Phe Asp Ile Asp
                325                 330                 335

Ser Phe Ile Lys Ile Phe Gly Leu Ser Leu Thr Ser Tyr Leu Leu Met
                340                 345                 350

Val Gly Ala Gln Val Tyr Ile Ala Val Gly Arg Phe Glu Asp Ala Val
                355                 360                 365

Thr Ala Ser Arg Gln Ala Ala Arg Leu Asp Pro Ser Ser Glu Glu Val
                370                 375                 380

Asn Ala Val Ala Arg Lys Ala Arg Ala Val Ala Ser Ala Arg Leu Ser
385                 390                 395                 400

Gly Asn Leu Leu Phe Asn Ala Ser Lys Phe Glu Gly Ala Ser Val Val
                405                 410                 415

Tyr Thr Glu Gly Leu Glu Asn Asp Pro Tyr Asn Ala Leu Leu Leu Cys
                420                 425                 430

Asn Arg Ala Ala Ser Arg Phe Lys Leu Asp Leu Phe Glu Lys Ala Ile
                435                 440                 445

Glu Asp Cys Thr Leu Ala Leu Ser Leu Gln Pro Ser Tyr Arg Lys Ala
                450                 455                 460

Arg Arg Arg Arg Ala Asp Ser Tyr Ala Lys Leu Glu Lys Trp Gln His
465                 470                 475                 480

Ala Ile Gln Asp Tyr Glu Leu Leu Met Met Glu Thr Pro Glu Asp Glu
                485                 490                 495

Glu Thr Arg Arg Ala Leu Thr Glu Val Asn Val Arg Phe Lys Lys Gln
                500                 505                 510
```

Thr Gly Gly Asp Val Arg Phe Lys Gly Val Gly Ser Glu Leu Val Val
        515                 520                 525

Ala Asn
    530

<210> SEQ ID NO 93
<211> LENGTH: 1287
<212> TYPE: DNA
<213> ORGANISM: Arabidopsis thaliana

<400> SEQUENCE: 93

| | | | | | |
|---|---|---|---|---|---|
| atggattggg | caacactgcc | aaaggatctc | ttagacctga | tctccaaatg | tctagaatct | 60 |
| tcctttgatc | tcatacagtt | ccgttctgta | tgttcttcat | ggcgatctgc | cgcggggcca | 120 |
| aagcgccttc | tctgggcaca | taacctcccg | ttcttcccct | ctgatgacaa | acccttctc | 180 |
| tccaatgtaa | tcctccgcgt | cgcgcaccag | agtatttac | ttatcaagcc | taatgaaccg | 240 |
| caatgcgagg | cggatctgtt | tggatggatt | gtcaaggttt | gggataacat | atatgtatct | 300 |
| cgtaagatga | cccttctcaa | accgttgagt | tcttcaagaa | actactttcc | tcagcattta | 360 |
| cctcgtattt | tcgatatgtc | taagtttacg | gttcgtgaat | tgtgtcggga | agtcaagctc | 420 |
| tatcatcctg | attactactg | tgtccctgga | cacacagctt | tagagttgga | gttggggaaa | 480 |
| actgttgtca | agtacctaaa | tgatgacaaa | ttcgtgttgc | ttacaattct | tgaatatgga | 540 |
| aagttagctg | tgtttaggtc | ttgggatcga | gaatggactg | tgatcaatga | ttacatacct | 600 |
| tctcgttgtc | aagatttgat | tatgttcgat | ggacgtttct | ttgctatcga | ctacaatggg | 660 |
| aggactgtag | ttgttgacta | ctcttctttc | aaattgacat | tggccgctaa | tcctttgatt | 720 |
| ggcggcggtg | acaagaagtt | tctgattgaa | tcttgtggtg | aaatgttct | ggtggatata | 780 |
| gagttttgcc | tgaatgaaaa | accggaattc | acaggggggtt | tctattcgta | ttttaatgag | 840 |
| accacggtca | gttacaaatt | taaattcttt | aaattagtgg | aaagagagaa | gagatgggtt | 900 |
| gaggttgagg | atcttgggga | taagatgttt | ttccttggtg | atgactccac | cttttccgct | 960 |
| tcaactgctg | atattatacc | tcgctgcgtg | ggaactggaa | gcttcgtgtt | cttctacacg | 1020 |
| catgaggaat | ccttggtggt | gatggatgat | cgaaacttgg | gagtgtttga | tttcaggagt | 1080 |
| gggaaaacag | agctggtaaa | caaactccct | gaatatgcca | agttgttttg | gcctccacct | 1140 |
| ccatggatta | ctacttctca | tgaggtcagt | ggtttccaat | ctctcaacca | cccgaataga | 1200 |
| gtagtgttga | aaattatact | ggagaaacat | catcacaatc | ccaatcttga | gtttaagacc | 1260 |
| ttggagatga | cacttcaact | tgaatga | | | | 1287 |

<210> SEQ ID NO 94
<211> LENGTH: 428
<212> TYPE: PRT
<213> ORGANISM: Arabidopsis thaliana

<400> SEQUENCE: 94

Met Asp Trp Ala Thr Leu Pro Lys Asp Leu Leu Asp Leu Ile Ser Lys
1               5                   10                  15

Cys Leu Glu Ser Ser Phe Asp Leu Ile Gln Phe Arg Ser Val Cys Ser
            20                  25                  30

Ser Trp Arg Ser Ala Ala Gly Pro Lys Arg Leu Leu Trp Ala His Asn
        35                  40                  45

Leu Pro Phe Phe Pro Ser Asp Asp Lys Pro Phe Leu Ser Asn Val Ile
    50                  55                  60

```
Leu Arg Val Ala His Gln Ser Ile Leu Ile Lys Pro Asn Glu Pro
 65                  70                  75                  80

Gln Cys Glu Ala Asp Leu Phe Gly Trp Ile Val Lys Val Trp Asp Asn
             85                  90                  95

Ile Tyr Val Ser Arg Lys Met Thr Leu Leu Lys Pro Leu Ser Ser Ser
            100                 105                 110

Arg Asn Tyr Phe Pro Gln His Leu Pro Arg Ile Phe Asp Met Ser Lys
        115                 120                 125

Phe Thr Val Arg Glu Leu Cys Arg Glu Val Lys Leu Tyr His Pro Asp
130                 135                 140

Tyr Tyr Cys Val Pro Gly His Thr Ala Leu Glu Leu Glu Leu Gly Lys
145                 150                 155                 160

Thr Val Val Lys Tyr Leu Asn Asp Asp Lys Phe Val Leu Leu Thr Ile
            165                 170                 175

Leu Glu Tyr Gly Lys Leu Ala Val Phe Arg Ser Trp Asp Arg Glu Trp
        180                 185                 190

Thr Val Ile Asn Asp Tyr Ile Pro Ser Arg Cys Gln Asp Leu Ile Met
    195                 200                 205

Phe Asp Gly Arg Phe Phe Ala Ile Asp Tyr Asn Gly Arg Thr Val Val
210                 215                 220

Val Asp Tyr Ser Ser Phe Lys Leu Thr Leu Ala Ala Asn Pro Leu Ile
225                 230                 235                 240

Gly Gly Gly Asp Lys Lys Phe Leu Ile Glu Ser Cys Gly Glu Met Phe
            245                 250                 255

Leu Val Asp Ile Glu Phe Cys Leu Asn Glu Lys Pro Glu Phe Thr Gly
        260                 265                 270

Gly Phe Tyr Ser Tyr Phe Asn Glu Thr Thr Val Ser Tyr Lys Phe Lys
    275                 280                 285

Phe Phe Lys Leu Val Glu Arg Glu Lys Arg Trp Val Glu Val Glu Asp
290                 295                 300

Leu Gly Asp Lys Met Phe Phe Leu Gly Asp Asp Ser Thr Phe Ser Ala
305                 310                 315                 320

Ser Thr Ala Asp Ile Ile Pro Arg Cys Val Gly Thr Gly Ser Phe Val
            325                 330                 335

Phe Phe Tyr Thr His Glu Glu Ser Leu Val Val Met Asp Asp Arg Asn
        340                 345                 350

Leu Gly Val Phe Asp Phe Arg Ser Gly Lys Thr Glu Leu Val Asn Lys
    355                 360                 365

Leu Pro Glu Tyr Ala Lys Leu Phe Trp Pro Pro Pro Trp Ile Thr
370                 375                 380

Thr Ser His Glu Val Ser Gly Phe Gln Ser Leu Asn His Pro Asn Arg
385                 390                 395                 400

Val Val Leu Lys Ile Ile Leu Glu Lys His His Asn Pro Asn Leu
            405                 410                 415

Glu Phe Lys Thr Leu Glu Met Thr Leu Gln Leu Glu
        420                 425
```

<210> SEQ ID NO 95
<211> LENGTH: 979
<212> TYPE: DNA
<213> ORGANISM: Arabidopsis thaliana

<400> SEQUENCE: 95
gggaaaagat attgagctcc cgggttttag gttccacccg actgaggaag agcttcttga    60

```
tttctacctc aagaacatgg tttacggtaa gagatcgagt gtcgaagtca ttggtttcct      120
taacatatac cgtcatgatc catgggactt acctggttta tcgagaatcg gggagaggga      180
atggtacttc tttgtaccaa gggaaaggaa gcatgggaac ggtgggaggc caagcaggac      240
aactgaaaaa ggatattgga aagcaactgg atccgatcgt aaaatcataa gcttgtctga      300
gccaaaacgt gttatagggc tcaagaagac gcttgtgttc tatagaggaa gagcaccagg      360
aggaagcaag actgattggg tgatgaacga gtttcggatg cccgataatt gctccttacc      420
aaaggatgtt gtgctttgta agatatatag aaaagctact tcattgaaag tattggagca      480
aagggcagag atggaagcta agatgaatca aacatgtcct aactctcctc tttcgtcttc      540
cgagacgatt tctttcgttg gtaaagaaga aaacatgatg acttcgttcc gtgctcctca      600
agtaatagct atggaagaag caaacaagat ccaaatgcat caagaaaacg cgaaaaccga      660
agagaaacaa agagaagcag agaccaaaga accttcttca tcactgaagc taccgtttgg      720
aagtttacca gagctacaat taccaaaacc aggagtagaa tgggaccagt tgttgagtat      780
aagcccatgg ctccagaatc ttacaccaat agttaacata tattggtagg atatgtaaag      840
aacaaataca tttaaatatt cttactctcg taaaaaacag agcttgtacc aaatagtatt      900
tactaaactt ttatgtatct tttgtaattt tgtaacataa gaaaatttgt aacactattt      960
atagtcatat ttgacgatc                                                  979

<210> SEQ ID NO 96
<211> LENGTH: 250
<212> TYPE: PRT
<213> ORGANISM: Arabidopsis thaliana

<400> SEQUENCE: 96

Met Val Tyr Gly Lys Arg Ser Val Glu Val Ile Gly Phe Leu Asn
1               5                   10                  15

Ile Tyr Arg His Asp Pro Trp Asp Leu Pro Gly Leu Ser Arg Ile Gly
                20                  25                  30

Glu Arg Glu Trp Tyr Phe Phe Val Pro Arg Glu Arg Lys His Gly Asn
            35                  40                  45

Gly Gly Arg Pro Ser Arg Thr Thr Glu Lys Gly Tyr Trp Lys Ala Thr
        50                  55                  60

Gly Ser Asp Arg Lys Ile Ile Ser Leu Ser Glu Pro Lys Arg Val Ile
65                  70                  75                  80

Gly Leu Lys Lys Thr Leu Val Phe Tyr Arg Gly Arg Ala Pro Gly Gly
                85                  90                  95

Ser Lys Thr Asp Trp Val Met Asn Glu Phe Arg Met Pro Asp Asn Cys
            100                 105                 110

Ser Leu Pro Lys Asp Val Val Leu Cys Lys Ile Tyr Arg Lys Ala Thr
        115                 120                 125

Ser Leu Lys Val Leu Glu Gln Arg Ala Glu Met Glu Ala Lys Met Asn
130                 135                 140

Gln Thr Cys Pro Asn Ser Pro Leu Ser Ser Ser Glu Thr Ile Ser Phe
145                 150                 155                 160

Val Gly Lys Glu Glu Asn Met Met Thr Ser Phe Arg Ala Pro Gln Val
                165                 170                 175

Ile Ala Met Glu Glu Ala Asn Lys Ile Gln Met His Gln Glu Asn Ala
            180                 185                 190

Lys Thr Glu Glu Lys Gln Arg Glu Ala Glu Thr Lys Glu Pro Ser Ser
        195                 200                 205
```

```
Ser Leu Lys Leu Pro Phe Gly Ser Leu Pro Glu Leu Gln Leu Pro Lys
    210                 215                 220

Pro Gly Val Glu Trp Asp Gln Leu Leu Ser Ile Ser Pro Trp Leu Gln
225                 230                 235                 240

Asn Leu Thr Pro Ile Val Asn Ile Tyr Trp
                245                 250

<210> SEQ ID NO 97
<211> LENGTH: 735
<212> TYPE: DNA
<213> ORGANISM: Arabidopsis thaliana

<400> SEQUENCE: 97
atgtcagatt ctgcagagat gcaacagccg gagttactgc tgaaatccat gaataaattg      60
aatgggtatc atccacaact aatcattcca agaagactc tcttcaagtg tgatctcgat      120
gacaaacagt cacgactcca agtttcttcc atgcatatgg aaaattcagg cttcttaacg     180
gaagatgaaa aacgaaccat agaggcacaa aagatgaaga acgacggac ggctggtttg      240 agagtagctt ttatagatcc tgaatcgcaa cagtacgtgc ttgagttaca aagtggacc      300 aagagctatg cctttgttaa aggttggaat aaggtggttg ataagaacga caaaacgttc     360
aaggtgggcg acgttttctc tctctgggtt ttccgttgcg gaggagtgaa ccctgttcac     420
gacggcgtca atctttcggg tggccacgcc gactctgttg ttgacggttt ggagcaaggt     480
agtctctgtt ttgttctggt tcctgcaaaa gtttctgttc acgacggcaa tcttcctcaa     540
gattctggtc acgacggcca caacgacaat cttcctcaag attctgttga acctagctct     600
tttttcgacg agtcttacga gttaaaccac ctgttctttg atcaagaaga cagtcaaggc     660
tatcttcccg acgaagatga agactttggc ttcaacgatg atggctcgat tcgtgattcc     720
ggtcactacc agtga                                                      735

<210> SEQ ID NO 98
<211> LENGTH: 244
<212> TYPE: PRT
<213> ORGANISM: Arabidopsis thaliana

<400> SEQUENCE: 98

Met Ser Asp Ser Ala Glu Met Gln Gln Pro Glu Leu Leu Leu Lys Ser
1               5                   10                  15

Met Asn Lys Leu Asn Gly Tyr His Pro Gln Leu Ile Ile Pro Lys Lys
                20                  25                  30

Thr Leu Phe Lys Cys Asp Leu Asp Lys Gln Ser Arg Leu Gln Val
            35                  40                  45

Ser Ser Met His Met Glu Asn Ser Gly Phe Leu Thr Glu Asp Glu Lys
    50                  55                  60

Arg Thr Ile Glu Ala Gln Lys Met Lys Lys Arg Thr Ala Gly Leu
65                  70                  75                  80

Arg Val Ala Phe Ile Asp Pro Glu Ser Gln Gln Tyr Val Leu Glu Leu
                85                  90                  95

His Lys Trp Thr Lys Ser Tyr Ala Phe Val Lys Gly Trp Asn Lys Val
                100                 105                 110

Val Asp Lys Asn Asp Lys Thr Phe Lys Val Gly Asp Val Phe Ser Leu
            115                 120                 125

Trp Val Phe Arg Cys Gly Gly Val Asn Pro Val His Asp Gly Val Asn
        130                 135                 140
```

| Leu | Ser | Gly | Gly | His | Ala | Asp | Ser | Val | Val | Asp | Gly | Leu | Glu | Gln | Gly |
| 145 | | | | 150 | | | | | 155 | | | | | 160 | |

| Ser | Leu | Cys | Phe | Val | Leu | Val | Pro | Ala | Lys | Val | Ser | Val | His | Asp | Gly |
| | | | 165 | | | | | 170 | | | | | 175 | | |

| Asn | Leu | Pro | Gln | Asp | Ser | Gly | His | Asp | Gly | His | Asn | Asp | Asn | Leu | Pro |
| | | | 180 | | | | 185 | | | | | 190 | | | |

| Gln | Asp | Ser | Val | Glu | Pro | Ser | Ser | Phe | Phe | Asp | Glu | Ser | Tyr | Glu | Leu |
| | | 195 | | | | | 200 | | | | | 205 | | | |

| Asn | His | Leu | Phe | Phe | Asp | Gln | Glu | Asp | Ser | Gln | Gly | Tyr | Leu | Pro | Asp |
| | 210 | | | | | 215 | | | | | 220 | | | | |

| Glu | Asp | Glu | Asp | Phe | Gly | Phe | Asn | Asp | Asp | Gly | Ser | Ile | Arg | Asp | Ser |
| 225 | | | | | 230 | | | | | 235 | | | | | 240 |

Gly His Tyr Gln

```
<210> SEQ ID NO 99
<211> LENGTH: 1164
<212> TYPE: DNA
<213> ORGANISM: Arabidopsis thaliana

<400> SEQUENCE: 99
atgaaatcac ggcgacagaa tgtgtccgtg gctcgacaaa ccatccttgg acgcgacgaa      60
aactttgaac caatcccaat tgatctcgtt atcgagatat tctcaaggtc gcctgtgaag     120
tctatagcaa gatgtcgttg cgtatcaaag ctttgggcct ccatactccg cctaccctat     180
ttcacggagt tgtacttgac caaatcttgt gctcgcccga ggctcttgtt cgcctgccaa     240
aaacacagag agttgttctt cttctcgaca cctcagcctc ataatcctaa tgagagctcg     300
tctcctttag ctgccagttt tcatatgaaa attccctttg atggtcgctt taatattatc     360
agtcctatcg gtggccttgt ctttgttaga tatgaacaga tcttaaaggg aaggaaaact     420
ccagaatttg tctcggcgat atgtaaccct agcacgggac aatccttaac cttaccaaaa     480
cctaagacaa ggaagaggat ttggggtaca agccattttg gtatgatcc tattgagaaa      540
caattcaagg tattgtcaat gaatataggt gatgggtct ataaagagca ttatgttctg      600
acattaggaa ctgagaacct ctcttggaga aggatcgaat gttctatacc ccatgttcat     660
ggttctaaag ggatatgcat caatggtgtt ttgtattatc gagcaaaggc tgacatgttt     720
tcaggtactt taatgatagt ttgctttgat gttaggtttg agaagttcag ctatattaaa     780
atcttgaaac ctacaacaac tctgattagc tacaacggta aattggcttc actagtgtgg     840
gaagggccta gttatatttg tggaaaacgt tttgaaatgt gggttttagg agaccccgaa     900
aaacatgaat ggttgaagca tacttacgaa ttgcgtcctc ggtggcagaa tgtacttgga     960
gaggacttgt taattttgc tggaatgact ggtacaaatg aaattgtgtt gtcgccaaag    1020
tatccatctc acccttttcta tgttttctac tacaatttgg agaggaatac tatcagaaga    1080
gttgaaatcc aaggaatggg agcgtttaag gttaatgaag attacatctt tctagaccat    1140
gtagaggatg tgaagcttat ataa                                            1164

<210> SEQ ID NO 100
<211> LENGTH: 387
<212> TYPE: PRT
<213> ORGANISM: Arabidopsis thaliana
```

```
<400> SEQUENCE: 100

Met Lys Ser Arg Arg Gln Asn Val Ser Val Ala Arg Gln Thr Ile Leu
1               5                   10                  15

Gly Arg Asp Glu Asn Phe Glu Pro Ile Pro Ile Asp Leu Val Ile Glu
            20                  25                  30

Ile Phe Ser Arg Ser Pro Val Lys Ser Ile Ala Arg Cys Arg Cys Val
        35                  40                  45

Ser Lys Leu Trp Ala Ser Ile Leu Arg Leu Pro Tyr Phe Thr Glu Leu
    50                  55                  60

Tyr Leu Thr Lys Ser Cys Ala Arg Pro Arg Leu Leu Phe Ala Cys Gln
65                  70                  75                  80

Lys His Arg Glu Leu Phe Phe Ser Thr Pro Gln Pro His Asn Pro
                85                  90                  95

Asn Glu Ser Ser Ser Pro Leu Ala Ala Ser Phe His Met Lys Ile Pro
                100                 105                 110

Phe Asp Gly Arg Phe Asn Ile Ile Ser Pro Ile Gly Gly Leu Val Phe
                115                 120                 125

Val Arg Tyr Glu Gln Ile Leu Lys Gly Arg Lys Thr Pro Glu Phe Val
            130                 135                 140

Ser Ala Ile Cys Asn Pro Ser Thr Gly Gln Ser Leu Thr Leu Pro Lys
145                 150                 155                 160

Pro Lys Thr Arg Lys Arg Ile Trp Gly Thr Ser His Phe Gly Tyr Asp
                165                 170                 175

Pro Ile Glu Lys Gln Phe Lys Val Leu Ser Met Asn Ile Gly Asp Gly
                180                 185                 190

Val Tyr Lys Glu His Tyr Val Leu Thr Leu Gly Thr Glu Asn Leu Ser
            195                 200                 205

Trp Arg Arg Ile Glu Cys Ser Ile Pro His Val His Gly Ser Lys Gly
            210                 215                 220

Ile Cys Ile Asn Gly Val Leu Tyr Tyr Arg Ala Lys Ala Asp Met Phe
225                 230                 235                 240

Ser Gly Thr Leu Met Ile Val Cys Phe Asp Val Arg Phe Glu Lys Phe
                245                 250                 255

Ser Tyr Ile Lys Ile Leu Lys Pro Thr Thr Thr Leu Ile Ser Tyr Asn
                260                 265                 270

Gly Lys Leu Ala Ser Leu Val Trp Glu Gly Pro Ser Tyr Ile Cys Gly
            275                 280                 285

Lys Arg Phe Glu Met Trp Val Leu Gly Asp Pro Glu Lys His Glu Trp
            290                 295                 300

Leu Lys His Thr Tyr Glu Leu Arg Pro Arg Trp Gln Asn Val Leu Gly
305                 310                 315                 320

Glu Asp Leu Leu Ile Phe Ala Gly Met Thr Gly Thr Asn Glu Ile Val
                325                 330                 335

Leu Ser Pro Lys Tyr Pro Ser His Pro Phe Tyr Val Phe Tyr Tyr Asn
                340                 345                 350

Leu Glu Arg Asn Thr Ile Arg Arg Val Glu Ile Gln Gly Met Gly Ala
                355                 360                 365

Phe Lys Val Asn Glu Asp Tyr Ile Phe Leu Asp His Val Glu Asp Val
            370                 375                 380

Lys Leu Ile
385
```